(12) United States Patent
Foletti et al.

(10) Patent No.: US 12,304,959 B2
(45) Date of Patent: May 20, 2025

(54) METHOD OF TREATING ASTHMA WITH ANTI-IL1RAP ANTIBODIES

(71) Applicant: 23andMe, Inc., Sunnyvale, CA (US)

(72) Inventors: Davide Foletti, Menlo Park, CA (US); Erik Karrer, Los Altos, CA (US); Germaine Fuh-Kelly, Pacifica, CA (US); Kristie Ibarra, San Jose, CA (US); Quan Zheng, Fremont, CA (US); Yao-ming Huang, San Mateo, CA (US); Lindsay Deis, San Bruno, CA (US); Christine Wolak, Burlingame, CA (US); Dominic Samuel Berns, Redwood City, CA (US)

(73) Assignee: 23andMe, Inc., Sunnyvale, CA (US)

( * ) Notice: Subject to any disclaimer, the term of this patent is extended or adjusted under 35 U.S.C. 154(b) by 824 days.

(21) Appl. No.: 17/486,864

(22) Filed: Sep. 27, 2021

(65) Prior Publication Data

US 2022/0106395 A1 Apr. 7, 2022

Related U.S. Application Data

(62) Division of application No. 16/541,990, filed on Aug. 15, 2019, now Pat. No. 11,168,140.

(60) Provisional application No. 62/719,397, filed on Aug. 17, 2018.

(51) Int. Cl.
*C07K 16/28* (2006.01)
*A61K 39/00* (2006.01)
*C12N 5/16* (2006.01)

(52) U.S. Cl.
CPC .......... *C07K 16/2866* (2013.01); *C12N 5/16* (2013.01); *A61K 2039/505* (2013.01); *C07K 2317/30* (2013.01); *C07K 2317/33* (2013.01); *C07K 2317/56* (2013.01); *C07K 2317/71* (2013.01); *C07K 2317/75* (2013.01); *C07K 2317/92* (2013.01)

(58) Field of Classification Search
CPC .......... C07K 16/2866; C07K 2317/56; C07K 2317/92; A61K 2039/505; C12N 5/16
See application file for complete search history.

(56) References Cited

U.S. PATENT DOCUMENTS

| | | |
|---|---|---|
| 6,280,955 B1 | 8/2001 | Cao |
| 6,326,472 B1 | 12/2001 | Timans |
| 7,049,095 B2 | 5/2006 | Sims |
| 8,187,596 B1 | 5/2012 | Chackerian |
| 8,709,715 B2 | 4/2014 | Karsunky |
| 8,715,619 B2 | 5/2014 | Karsunky |
| 9,796,783 B2 | 10/2017 | Fioretos |
| 10,005,841 B2 | 6/2018 | Fioretos |
| 10,005,842 B2 | 6/2018 | Fioretos |
| 10,100,119 B2 | 10/2018 | Fioretos |
| 11,639,392 B2 * | 5/2023 | Fischer ............ C07K 16/2866 424/133.1 |
| 2005/0129685 A1 | 6/2005 | Cao |
| 2008/0261252 A1 | 10/2008 | Bednarik |
| 2009/0048161 A1 | 2/2009 | Chemtob |
| 2010/0190652 A1 | 7/2010 | Nagalla |
| 2012/0171190 A1 | 7/2012 | Donndelinger |
| 2014/0030735 A1 | 1/2014 | Kelsen |
| 2014/0308294 A1 | 10/2014 | Seshire |
| 2015/0030586 A1 | 1/2015 | Warren |
| 2017/0121420 A1 | 5/2017 | Heidrich |
| 2018/0118836 A1 | 5/2018 | Bernett |
| 2018/0275123 A1 | 9/2018 | Steidl |

FOREIGN PATENT DOCUMENTS

| | | |
|---|---|---|
| CN | 107056946 | 8/2017 |
| WO | 1996023067 | 8/1996 |
| WO | 1998008969 | 3/1998 |
| WO | 2009120903 | 10/2009 |
| WO | 2013023015 | 2/2013 |
| WO | 2017011803 | 1/2014 |
| WO | 2014100772 | 6/2014 |
| WO | 2014174254 | 10/2014 |
| WO | 2015132602 A | 9/2015 |
| WO | 2016020502 A | 2/2016 |
| WO | 2016207304 | 12/2016 |
| WO | 2017191325 | 11/2017 |
| WO | 2018206565 | 11/2018 |
| WO | 2018231827 | 12/2018 |
| WO | 2019028190 | 2/2019 |

OTHER PUBLICATIONS

Ågerstam, "Antibodies targeting human IL1RAP (IL1R3) show therapeutic effects in xenograft models of acute myeloid leukemia", PNAS, 2015, 10786-10791, vol. 112, Issue 34.
Yoon, "Antibodies to Domains II and III of the IL-1 Receptor Accessory Protein Inhibit IL-1b Activity But Not Binding: Regulation of IL-1 Responses Is Via Type I Receptor, Not the Accessory", Protein J Immunol, 1998, 3170-3179, vol. 160.
Garlanda, "The Interleukin-1 Family: Back to the Future", Immunity, 2013, 1003-1018, vol. 39.
Greenfeder, "Molecular cloning and characterization of a second subunit of the interleukin 1 receptor complex", J Biol Chem, 1995, 13757-65, vol. 270, Issue 23.

(Continued)

*Primary Examiner* — Elly-Gerald Stoica

(74) *Attorney, Agent, or Firm* — FisherBroyles, LLP; Adam K. Whiting

(57) ABSTRACT

The present invention provides binding proteins, such as antibodies and antigen-binding fragments, which specifically bind to human interleukin-1 receptor accessory protein (hu-IL1RAP) and fully block the IL-1, IL-33, and IL-36 intracellular signaling pathways. Compositions comprising such binding proteins and methods of making and using such binding proteins are also provided.

19 Claims, 24 Drawing Sheets

Specification includes a Sequence Listing.

(56) References Cited

OTHER PUBLICATIONS

Smith, "The soluble form of IL-1 receptor accessory protein enhances the ability of soluble type II IL-1 receptor to Inhibit IL-1 action", Immunity, 2003, 87-96, vol. 18, Issue 1.
Wang, "Structural insights into the assembly and activation of IL-1B with its receptors", Nature Immunology, 2010, 905-911, vol. 11, Issue 10.
Gunther, "IL-1 Family Cytokines Use Distinct Molecular Mechanisms to Signal through Their Shared Co-receptor", Immunity, 2017, 510-523, vol. 47.
Järås, "Isolation and killing of candidate chronic myeloid leukemia stem cells by antibody targeting of IL-1 receptor accessory protein", PNAS, 2010, 16280-5, vol. 107, Issue 37.
Ali, "IL-1 receptor accessory protein is essential for IL-33-induced activation of T lymphocytes and mast cells", PNAS, 2007, 18660-5, vol. 104, Issue 47.
Towne, "Interleukin (IL)-1F6, IL-1F8, and IL-1F9 Signal through IL-1Rrp2 and IL-1RAcP to Activate the Pathway leading to NF-κB and MAPKs", J Biol Chem, 2004, 13677-13688, vol. 279, Issue 14.
Saluja, "The role of IL-33 and mast cells in allergy and inflammation", Clin Transl Allergy, 2015, 1-8, vol. 5, Issue 33.
Sims, "The IL-1 family: regulators of immunity", Nat. Rev. Immunol., 2010, 89-102, vol. 10, Issue 2.
Liew, "Interleukin-33 in health and disease", Nat. Rev. Immunol., 2016, 676-689, vol. 16, Issue 11.
Granzin, "Shaping of Natural Killer Cell Antitumor Activity by Ex Vivo Cultivation", Front. Immunol., 2017, 458, vol. 8.
Lambrecht, "The airway epithelium in asthma", Nat. Med., 2012, 684-692, vol. 18, No. 5.
Nowarski, "The Stromal Intervention: Regulation of Immunity and Inflammation at the Epithelial-Mesenchymal Barrier", Cell, 2017, 362-375, vol. 168, Issue 3.
Suwara, "IL-1α released from damaged epithelial cells is sufficient and essential to trigger inflammatory responses in human lung fibroblasts", Mucosal Immunol., 2014, 684-693, vol. 7, Issue 3.
Dall' Acqua, "Increasing the affinity of a human IgG1 for the neonatal Fc receptor: biological sequences", J Immunol., 2002, 5171-5180, vol. 169, Issue 9.
Ding, "IL-36 cytokines in autoimmunity and inflammatory disease", Oncotarget, 2017, 2895-2901, vol. 9, Issue 2.
Yi, "Structural and Functional Attributes of the Interleukin-36 Receptor", J Biol Chem, 2016, 16597-16609, vol. 291, Issue 32.
Højen, "IL-1R3 blockade broadly attenuates the functions of six members of the IL-1 family, revealing their contribution to models of disease", Nat Immunol, 2019, 1138-1149, vol. 20, Issue 9.
Doherty, "Autoinflammation translating mechanism to therapy", J. Leukoc. Biol., 2011, 37-47, vol. 90.
Evans, "Sputum cell IL-1 receptor expression level is a marker of airway neutrophilia and airflow obstruction in asthmatic patients", J Allergy Clin Immunol, 2018.
Dall' Acqua, "Properties of Human IgG1s Engineered for Enhanced Binding to the Neonatal Fc Receptor (FcRn)", J Biol Chem, 2006.
Bassoy et al., (2018) "Regulation and function of interleukin-36 cytokines," Immunol. Rev. 281(1): 169-178.
Barreyro (2013) "Molecular and functional characterization of stem and progenitor cells in acute myeloid leukemia," Doctoral Dissertation, Albert Einstein College of Medicine, Yeshiva University, New York.
Schwartz et al., (2016) "Basophils in inflammation," Eur. J. Pharma. 778: 90-95.
Mitchell et al., "IL1RAP potentiates multiple oncogenic signaling pathways in AML," The Journal of Experimental Medicine, vol. 215, No. 6, Jun. 4, 2018, pp. 1709-1727.
Agerstam et al., "IL1RAP antibodies block IL-1-induced expansion of candidate CML stem cells and mediate cell killing in xenograft models," Blood, vol. 128, No. 23, Jan. 1, 2016, pp. 2683-2693.
PCT/US2019/046711, "The International Search Report and The Written Opinoin of the International Searching Authority," date of mailing Nov. 25, 2019.
Fields et al., "Structural Basis of IL-1 Family Cytokine Signaling," Frontiers in Immunology 2019, vol. 10, 2019, p. 1412.
Boraschi et al., "The interleukin-1 receptor family," Seminars In Immunology, W.B. Saunders Company, PA, US, vol. 25, No. 6, Nov. 15, 2013, pp. 394-407.

* cited by examiner

FIG. 2

```
V_L domain sequence
Human germline    1  DIQMTQSPSSLSASVGDRVTITCRASQGISNSLAWYQQKPGKAPKLLLYAASRLESGVPS  60
Humanized h11C5   1  ............................EN.YSN.................V.G.KN.AD....  60
Murine 11C5(Hy)   1  ........A...V...ET..........EN.YSN.........Q.RS.Q..V.G.KN.AD....  60

Human germline   61  RFSGSGSGTDYTLTISSLQPEDFATYYCQQYYSTP-TFGGGTKVEIK  106
Humanized h11C5  61  ................................HFWT..R.......  107
Murine 11C5(Hy)  61  ......Q.S.N.N...S...G...........HFWT..R.....L..  107

V_H domain sequence
Human germline    1  EVQLVESGGGLVQPGGSLRLSCAASGFTFSSYWMSWVRQAPGKGLEWVANIKQDGSEKYY  60
Humanized h11C5   1  ........................................N.A..........TVTEG.DYN.C  60
Murine 11C5(Hy)   1  ...............K....K...........N.A.....T.E.R....TVTEG.DYN.C  60

Human germline   61  VDSVKGRFTISRDNAKNSLYLQMNSLRAEDTAVYYCAR-----YFDYWGQGTLVTVSS  113
Humanized h11C5  61  L.D.......................................DRWPYF..........  118
Murine 11C5(Hy)  61  L.D........NDN......SH.KS...S.R.....DRWPYF........TL.....  118
```

$$\frac{dA(1)}{dt} = -(CLt + CLd + \frac{Vmax}{Km + \frac{A(1)}{Vc}}) \times \frac{A(1)}{Vc} + CLd \times \frac{A(2)}{Vp} \quad (1)$$

$$\frac{dA(2)}{dt} = CLd \times \frac{A(1)}{Vc} - CLd \times \frac{A(2)}{Vp} \quad (2)$$

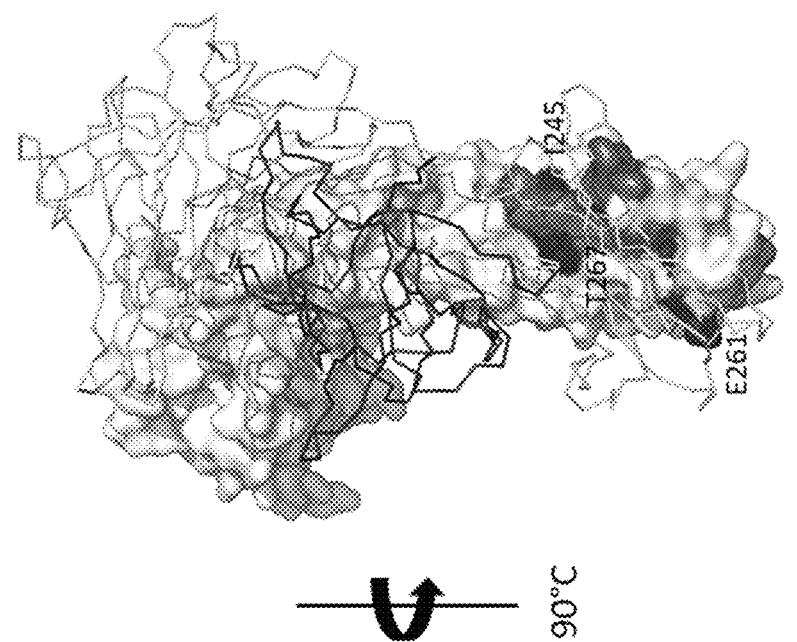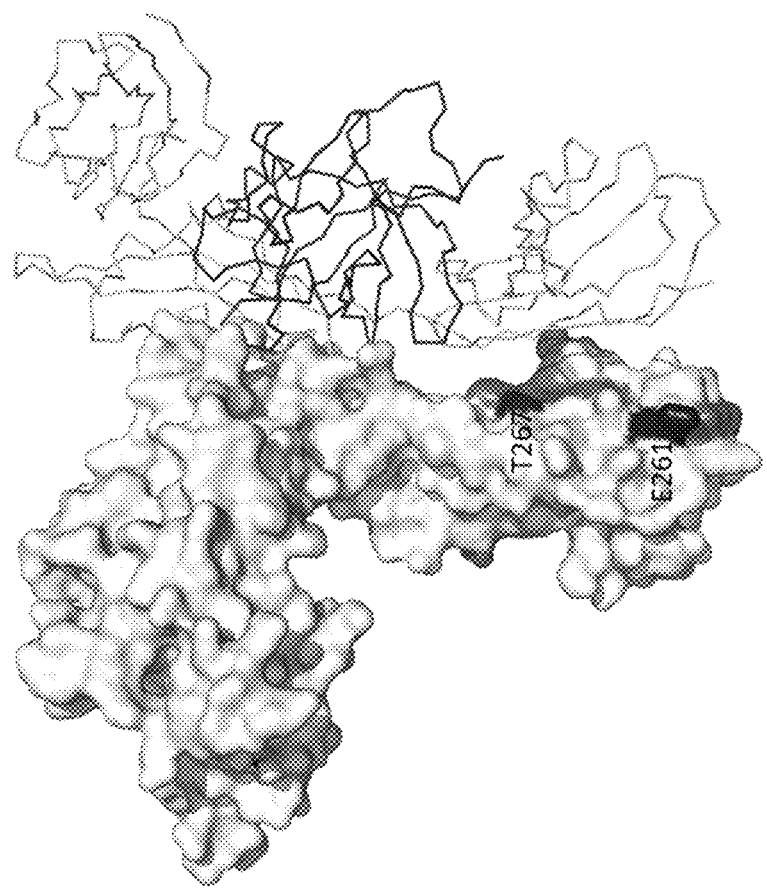
FIG. 15

METHOD OF TREATING ASTHMA WITH ANTI-IL1RAP ANTIBODIES

CROSS-REFERENCE

This application claims priority under 35 U.S.C. 120 as a divisional application of U.S. patent application Ser. No. 16/541,990, filed Aug. 15, 2019, and claims priority under 35 U.S.C. 119(e) from U.S. Provisional Patent Application No. 62/719,397, filed Aug. 17, 2018, each of which is hereby incorporated by reference herein for all purposes.

FIELD OF THE INVENTION

The present disclosure relates generally to binding proteins, such as antibodies and antigen-binding fragments, which bind to an interleukin-1 receptor accessory protein and methods of using such binding proteins.

REFERENCE TO SEQUENCE LISTING

The official copy of the Sequence Listing is submitted concurrently with the specification as an ASCII formatted text file via EFS-Web, with a file name of "09402-002US1_SeqListing_ST25. txt", a creation date of Aug. 15, 2019, and a size of 180,889 bytes. The Sequence Listing filed via EFS-Web is part of the specification and is incorporated in its entirety by reference herein.

BACKGROUND OF THE INVENTION

The interleukin-1 (IL-1) family of cytokine ligands and receptors is associated with inflammation, autoimmunity, immune regulation, cell proliferation, and host defense and contributes to the pathology of inflammatory, autoimmune, immune regulatory, degenerative, and cell proliferative (e.g., cancer) diseases and disorders and its cytokine and receptors serve as pathogenic mediators of such diseases and disorders. See, e.g., Garlanda et al., *Immunity*, 39:1003-1018 (2013).

The IL-1 family of cytokines includes interleukin-1 alpha (IL-1 alpha or IL-1a or IL-1α), interleukin-1 beta (IL-1β or IL-1b), interleukin-33 (IL-33), interleukin-36 alpha (IL-36 alpha or IL-36α), interleukin-36 beta (IL-36β or IL-36b), and interleukin-36 gamma (IL-36γ). Each of these cytokines serves as a ligand capable of binding a specific IL-1 family cell membrane receptor expressed on the surface of certain cells. Upon binding of an IL-1 family cytokine to its cognate receptor, a co-receptor is recruited to form a ternary complex comprising the cytokine, its cognate membrane receptor, and its co-receptor. The resulting ternary complex facilitates intracellular signal transduction and activation of a set of transcription factors, including NF-κB and AP-1, and mitogen-activated protein kinases, which triggers a cascade of inflammatory and immune responses, including the production of numerous cytokines, chemokines, enzymes, and adhesion molecules.

Interleukin-1 receptor accessory protein (IL1RAP) serves as the common cellular membrane co-receptor for several receptors in the IL-1 family, including interleukin-1 receptor 1 (IL1R1), ST2 (also known as interleukin-1 receptor-like 1 or IL1RL1), and interleukin-1 receptor-like 2 (IL1RL2). IL1RAP is a necessary component of the ternary signaling complex formed by one of the IL-1 family cytokines noted above, the cytokine's specific cognate receptor, and the IL1RAP co-receptor. Thus, IL1RAP serves an important function in the IL-1 family signal transduction pathways, since it is required to facilitate particular downstream signaling pathways stimulated by the IL-1 family cytokines IL-1α, IL-1β, IL-33, IL-36α, IL-36β, and IL-36γ.

WO2012098407A1 is directed to agents comprising a binding moiety, such as antibodies, with specificity for IL1RAP for use in inducing cell death and/or inhibiting growth and/or proliferation of cells associated with solid tumors that express IL1RAP. WO2012098407A1 discloses a mouse IgG2a monoclonal antibody to human IL1RAP, "mAb 81.2," that when administered in vivo resulted in statistically significant delay of tumor growth in a melanoma mouse model.

WO2015132602A1 is directed to antibodies with specificity for human IL1RAP and their use for treatment of solid tumors. WO2015132602A1 discloses a specific mouse-derived antibody "CAN04" that binds specifically to domain 2 of human IL1RAP with a $K_D$ of 200 pM, cross-reacts with cynomolgus monkey IL1RAP, capable of inducing ADCC in one or more cancer cell lines (such as CML) and has some inhibitory effect on IL-1α, IL-1β, and IL-33 stimulated signaling.

WO2016020502A1 discloses two specific mouse-derived antibodies "CAN01" and "CAN03" that bind specifically to domain 3 of human IL1RAP with a $K_D$ of 1.4 and 0.9 nM, respectively, cross-react with cynomolgus monkey IL1RAP, and are capable of inducing ADCC in one or more cancer cell lines (such as CML). CAN03 was determined to have some inhibitory effect on IL-1α, IL-1β, and IL-33 stimulated signaling, whereas CAN01 was found to lack appreciable inhibitory action on IL-1α, IL-1β, and IL-33 signaling.

WO2016207304A1 is directed to rabbit-derived antibodies that specifically bind human IL-1RAcP and have some inhibitory effect on NFkB activity stimulated by IL-1α, IL-1β, IL-33, and/or IL-36β.

WO2017191325A9 is directed to humanized IgG1 antibodies that specifically bind human IL-1R3 and have some inhibitory effect on NFkB activity stimulated by IL-1α, IL-1β, IL-33, and/or IL-36β.

There remains a need for therapies to treat, ameliorate, or prevent inflammatory, autoimmune, immune regulatory, degenerative, and cell proliferative diseases or disorders associated with the IL-1 family of cytokine ligands and receptors. The present disclosure fulfills these and other needs.

SUMMARY

The present disclosure provides antibodies that specifically bind human IL1RAP with high affinity. The antibodies are capable of decreasing, inhibiting, and/or fully-blocking IL-1, IL-33, and/or IL-36 signaling pathways, including signaling stimulated by binding of one or more of the following agonists: IL-1α, IL-1β, IL-33, IL-36α, IL-36β, and IL-36γ. The present disclosure also provides methods of treating diseases and conditions responsive to inhibition of IL-1, IL-33, and/or IL-36 signaling.

In some embodiments, the present disclosure provides an anti-IL1RAP antibody comprising (i) a first light chain hypervariable region (HVR-L1), a second light chain hypervariable region (HVR-L2), and a third light chain hypervariable region (HVR-L3), and/or (ii) a first heavy chain hypervariable region (HVR-H1), a second heavy chain hypervariable region (HVR-H2), and a third heavy chain hypervariable region (HVR-H3), wherein:

(a) HVR-L1 comprises an amino acid sequence RASENIXXNXX (SEQ ID NO: 10), wherein X at position 7 is Y or W, X at position 8 is S, H, K, L, M, N, Q, R, or Y, X at position 10 is L, A, G, I, M, N, Q, S, T, V, or Y, and X at position 11 is A, G, N, S, or T;

(b) HVR-L2 comprises an amino acid sequence GXXNXAD (SEQ ID NO: 36), wherein X at position 2 is A, D, E, F, G, H, I, K, L, M, N, Q, R, S, T, V, W, or Y, X at position 3 is K, G, or N, and X at position 5 is L, F, H, W, or Y;

(c) HVR-L3 comprises an amino acid sequence XXFXTXPRT (SEQ ID NO: 62), wherein X at position 1 is Q or S, X at position 2 is H or S, X at position 4 is W, A, F, G, H, I, K, L, M, V, or Y, and X at position 6 is T, I, or V;

(d) HVR-H1 comprises an amino acid sequence XXXXXXX (SEQ ID NO: 77), wherein X at position 1 is F, A, D, E, G, H, I, K, M, N, P, Q, R, S, T, W, or Y, X at position 2 is S, E, G, K, P, Q, R, or T, X at position 3 is N, D, E, G, K, Q, or R, X at position 4 is Y, A, D, E, H, S, or V, X at position 5 is A, N, or S, X at position 6 is M, V, or W, and X at position 7 is S, or G;

(e) HVR-H2 comprises an amino acid sequence TXXXXXXXXXYXLXDVKG (SEQ ID NO: 140), wherein X at position 2 is V, A, N, or S, X at position 3 is T or S, X at position 4 is E, D, N, T, or V, X at position 5 is G, I, P, T, or V, X at position 6 is G, D, E, F, H, I, K, L, M, N, P, Q, R, T, V, W, or Y, X at position 7 is D, A, E, G, H, K, N, P, Q, R, or S, X at position 8 is Y or W, X at position 9 is N, A, G, P, or R, X at position 11 is C, A, D, F, R, S, T, V, or Y, and X at position 13 is D, S, or W;

(f) HVR-H3 comprises an amino acid sequence XXDXXPYFXDY (SEQ ID NO: 202), wherein X at position 1 is A, G, S, or T, X at position 2 is H, I, L, M, N, Q, or V, X at position 4 is R, A, D, E, I, M, N, Q, or S, X at position 5 is W, or F, and X at position 9 is F, L, M, or W.

In some embodiments, the present disclosure provides an anti-IL1RAP antibody comprising (i) a first light chain hypervariable region (HVR-L1), a second light chain hypervariable region (HVR-L2), and a third light chain hypervariable region (HVR-L3), and/or (ii) a first heavy chain hypervariable region (HVR-H1), a second heavy chain hypervariable region (HVR-H2), and a third heavy chain hypervariable region (HVR-H3), wherein: (a) HVR-L1 comprises an amino acid sequence selected from SEQ ID NOs: 11-35; (b) HVR-L2 comprises an amino acid sequence selected from SEQ ID NOs: 37-61; (c) HVR-L3 comprises an amino acid sequence selected from SEQ ID NOs: 63-76; (d) HVR-H1 comprises an amino acid sequence selected from SEQ ID NOs: 78-120; (e) HVR-H2 comprises an amino acid sequence selected from SEQ ID NOs: 141-201; (f) HVR-H3 comprises an amino acid sequence selected from SEQ ID NOs: 203-225.

In some embodiments, the present disclosure provides an anti-IL1RAP antibody comprising (i) a first light chain hypervariable region (HVR-L1), a second light chain hypervariable region (HVR-L2), and a third light chain hypervariable region (HVR-L3), and/or (ii) a first heavy chain hypervariable region (HVR-H1), a second heavy chain hypervariable region (HVR-H2), and a third heavy chain hypervariable region (HVR-H3), wherein: (a) HVR-L1 comprises the amino acid sequence of SEQ ID NO: 11; (b) HVR-L2 comprises the amino acid sequence of SEQ ID NO: 37; (c) HVR-L3 comprises the amino acid sequence of SEQ ID NO: 63; (d) HVR-H1 comprises the amino acid sequence of SEQ ID NO: 78; (e) HVR-H2 comprises the amino acid sequence selected from SEQ ID NOs: 141, 184, 185, 186, 187, 188, 189, 190, and 191; (f) HVR-H3 comprises the amino acid sequence of SEQ ID NO: 203.

In some embodiments, the present disclosure provides an anti-IL1RAP antibody comprising (i) a first light chain hypervariable region (HVR-L1), a second light chain hypervariable region (HVR-L2), and a third light chain hypervariable region (HVR-L3), and/or (ii) a first heavy chain hypervariable region (HVR-H1), a second heavy chain hypervariable region (HVR-H2), and a third heavy chain hypervariable region (HVR-H3), wherein: (a) HVR-L1 comprises the amino acid sequence selected from SEQ ID NOs: 11, 13, and 23; (b) HVR-L2 comprises the amino acid sequence selected from SEQ ID NOs: 37, 38, 45, 49, 54, and 61; (c) HVR-L3 comprises the amino acid sequence selected from SEQ ID NOs: 63, 67, 69, 70, 71, 75, and 76; (d) HVR-H1 comprises the amino acid sequence selected from SEQ ID NOs: 78, 81, 90, 92, and 118; (e) HVR-H2 comprises the amino acid sequence selected from SEQ ID NOs: 141, 144, 149, 153, 172, 181, 191, 194, 195, 196, 197, 198, 199, 200, and 201; (f) HVR-H3 comprises the amino acid sequence selected from SEQ ID NOs: 203, 214, 215, 220, and 222.

In some embodiments, the anti-IL1RAP antibody of the present disclosure comprises complementarity determining regions CDR-L1, CDR-L2, CDR-L3, CDR-H1, CDR-H2, and CDR-H3, wherein:

(a) CDR-L1 comprises an amino acid sequence RASENIXXNXX (SEQ ID NO: 10), wherein X at position 7 is Y or W, X at position 8 is S, H, K, L, M, N, Q, R, or Y, X at position 10 is L, A, G, I, M, N, Q, S, T, V, or Y, and X at position 11 is A, G, N, S, or T;

(b) CDR-L2 comprises an amino acid sequence GXXNXAD (SEQ ID NO: 36), wherein X at position 2 is A, D, E, F, G, H, I, K, L, M, N, Q, R, S, T, V, W, or Y, X at position 3 is K, G, or N, and X at position 5 is L, F, H, W, or Y;

(c) CDR-L3 comprises an amino acid sequence XXFXTXPRT (SEQ ID NO: 62), wherein X at position 1 is Q or S, X at position 2 is H or S, X at position 4 is W, A, F, G, H, I, K, L, M, V, or Y, and X at position 6 is T, I, or V;

(d) CDR-H1 comprises an amino acid sequence XXXXX (SEQ ID NO: 121), wherein X at position 1 is N, D, E, G, K, Q, or R, X at position 2 is Y, A, D, E, H, S, or V, X at position 3 is A, N, or S, X at position 4 is M, V, or W, and X at position 5 is S, or G;

(e) CDR-H2 comprises an amino acid sequence TXXXXXXXXXYXLXDVKG (SEQ ID NO: 140), wherein X at position 2 is V, A, N, or S, X at position 3 is T or S, X at position 4 is E, D, N, T, or V, X at position 5 is G, I, P, T, or V, X at position 6 is G, D, E, F, H, I, K, L, M, N, P, Q, R, T, V, W, or Y, X at position 7 is D, A, E, G, H, K, N, P, Q, R, or S, X at position 8 is Y or W, X at position 9 is N, A, G, P, or R, X at position 11 is C, A, D, F, R, S, T, V, or Y, and X at position 13 is D, S, or W;

(f) CDR-H3 comprises an amino acid sequence DXXPYFXDY (SEQ ID NO: 226), wherein X at position 2 is R, A, D, E, I, M, N, Q, or S, X at position 3 is W, or F, and X at position 7 is F, L, M, or W.

In some embodiments, the anti-IL1RAP antibody of the present disclosure comprises complementarity determining regions CDR-L1, CDR-L2, CDR-L3, CDR-H1, CDR-H2, and CDR-H3, wherein: (a) CDR-L1 comprises an amino acid sequence selected from SEQ ID NOs: 11-35; (b) CDR-L2 comprises an amino acid sequence selected from SEQ ID NOs: 37-61; (c) CDR-L3 comprises an amino acid sequence selected from SEQ ID NOs: 63-76; (d) CDR-H1 comprises an amino acid sequence selected from SEQ ID NOs: 122-139; (e) CDR-H2 comprises an amino acid sequence selected from SEQ ID NOs: 141-201; (f) CDR-H3 comprises an amino acid sequence selected from SEQ ID NOs: 227-239.

In some embodiments, the anti-IL1RAP antibody of the present disclosure comprises a light chain variable domain ($V_L$) amino acid sequence having at least 90% identity to a sequence selected from SEQ ID NO: 257, 258, or 259; and/or a heavy chain variable domain ($V_H$) amino acid sequence having at least 90% identity to a sequence selected from SEQ ID NO: 279, 285, or 290. In some embodiments, the antibody comprises a light chain variable domain ($V_L$) amino acid sequence selected from SEQ ID NOs: 257-278. In some embodiments, the antibody comprises a heavy chain variable domain ($V_H$) amino acid sequence selected from SEQ ID NOs: 279-310.

In some embodiments, the present disclosure provides an anti-IL1RAP antibody wherein the antibody comprises:
  the light chain variable domain ($V_L$) amino acid sequence of SEQ ID NO: 259, and the heavy chain variable domain ($V_H$) amino acid sequence of SEQ ID NO: 290;
  the light chain variable domain ($V_L$) amino acid sequence of SEQ ID NO: 268, and the heavy chain variable domain ($V_H$) amino acid sequence of SEQ ID NO: 307;
  the light chain variable domain ($V_L$) amino acid sequence of SEQ ID NO: 268, and the heavy chain variable domain ($V_H$) amino acid sequence of SEQ ID NO: 298;
  the light chain variable domain ($V_L$) amino acid sequence of SEQ ID NO: 269, and the heavy chain variable domain ($V_H$) amino acid sequence of SEQ ID NO: 307;
  the light chain variable domain ($V_L$) amino acid sequence of SEQ ID NO: 269, and the heavy chain variable domain ($V_H$) amino acid sequence of SEQ ID NO: 298;
  the light chain variable domain ($V_L$) amino acid sequence of SEQ ID NO: 269, and the heavy chain variable domain ($V_H$) amino acid sequence of SEQ ID NO: 297;
  the light chain variable domain ($V_L$) amino acid sequence of SEQ ID NO: 270, and the heavy chain variable domain ($V_H$) amino acid sequence of SEQ ID NO: 307; or
  the light chain variable domain ($V_L$) amino acid sequence of SEQ ID NO: 270, and the heavy chain variable domain ($V_H$) amino acid sequence of SEQ ID NO: 298.

In some embodiments, the anti-IL1RAP antibody of the present disclosure comprises a light chain (LC) amino acid sequence having at least 90% identity to a sequence selected from SEQ ID NO: 328, 329, 330, or 331; and/or a heavy chain (HC) amino acid sequence having at least 90% identity to a sequence selected from SEQ ID NO: 332, 333, 334, 335, or 336. In some embodiments, the antibody comprises a light chain (LC) amino acid sequence selected from SEQ ID NOs: 328-331. In some embodiments, the antibody comprises a heavy chain (HC) amino acid sequence selected from SEQ ID NOs: 332-336.

In some embodiments, the present disclosure provides an anti-IL1RAP antibody wherein the antibody comprises:
  the light chain (LC) amino acid sequence of SEQ ID NO: 328, and the heavy chain (HC) amino acid sequence of SEQ ID NO: 332;
  the light chain (LC) amino acid sequence of SEQ ID NO: 329, and the heavy chain (HC) amino acid sequence of SEQ ID NO: 335;
  the light chain (LC) amino acid sequence of SEQ ID NO: 329, and the heavy chain (HC) amino acid sequence of SEQ ID NO: 336;
  the light chain (LC) amino acid sequence of SEQ ID NO: 329, and the heavy chain (HC) amino acid sequence of SEQ ID NO: 333;
  the light chain (LC) amino acid sequence of SEQ ID NO: 329, and the heavy chain (HC) amino acid sequence of SEQ ID NO: 334;
  the light chain (LC) amino acid sequence of SEQ ID NO: 330, and the heavy chain (HC) amino acid sequence of SEQ ID NO: 335;
  the light chain (LC) amino acid sequence of SEQ ID NO: 330, and the heavy chain (HC) amino acid sequence of SEQ ID NO: 336;
  the light chain (LC) amino acid sequence of SEQ ID NO: 330, and the heavy chain (HC) amino acid sequence of SEQ ID NO: 333;
  the light chain (LC) amino acid sequence of SEQ ID NO: 330, and the heavy chain (HC) amino acid sequence of SEQ ID NO: 334;
  the light chain (LC) amino acid sequence of SEQ ID NO: 331, and the heavy chain (HC) amino acid sequence of SEQ ID NO: 335;
  the light chain (LC) amino acid sequence of SEQ ID NO: 331, and the heavy chain (HC) amino acid sequence of SEQ ID NO: 336;
  the light chain (LC) amino acid sequence of SEQ ID NO: 331, and the heavy chain (HC) amino acid sequence of SEQ ID NO: 333; or
  the light chain (LC) amino acid sequence of SEQ ID NO: 331, and the heavy chain (HC) amino acid sequence of SEQ ID NO: 334.

In various embodiments of the anti-IL1RAP antibody provided by the present disclosure, the antibody is characterized by one or more of the following properties:
  (a) the antibody binds to human IL1RAP with a binding affinity of $1\times10^{-8}$ M or less, $1\times10^{-9}$ M or less, $1\times10^{-10}$ M or less, or $1\times10^{-11}$ M or less; optionally, wherein the binding affinity is measured by equilibrium dissociation constant ($K_D$) to hu-M-IL1RAP polypeptide of SEQ ID NO: 3;
  (b) the antibody decreases an IL-1 stimulated signal, an IL-33 stimulated signal, and/or an IL-36 stimulated signal by at least 90%, at least 95%, at least 99%, or 100%; optionally, wherein the decrease in signal is measured by a cell-based blocking assay; optionally, wherein the IL-1, IL-33, and/or IL-36 stimulated signals are stimulated by an agonist selected from IL-1α, IL-1β, IL-33, IL-36α, IL-36β, and IL-36γ; optionally, wherein at an agonist concentration of about EC50 the antibody has an $IC_{50}$ of 10 nM or less, 5 nM or less, or 1 nM or less.
  (c) the antibody decreases an intracellular signal initiated by one or more of IL-1α, IL-1β, IL-33, IL-36α, IL-36β, and IL-36γ agonist binding to its cognate receptor by at least 90%, at least 95%, at least 99%, or 100%; optionally, wherein the decrease in intracellular signal is measured by a cell-based blocking assay; optionally, wherein at an IL-1α, IL-1β, IL-33, IL-36α, IL-36β, and/or IL-36β concentration of about $EC_{50}$ the antibody decreases the intracellular signal initiated by the agonist with an $IC_{50}$ of 10 nM or less, 5 nM or less, or 1 nM;
  (d) the antibody inhibits IL-1α, IL-1β, and/or IL-36β stimulated release of IL8 from primary human lung fibroblasts (PHLF); optionally, wherein at an IL-1α, IL-1β, and/or IL-36β concentration of about $EC_{50}$ the antibody has an $IC_{50}$ of 10 nM or less, 5 nM or less, or 1 nM or less;

(e) the antibody inhibits IL-1β stimulated release of IL6 from primary human monocytes; optionally, wherein at an IL-1β concentration of about $EC_{50}$ the antibody has an $IC_{50}$ of 10 nM or less, 5 nM or less, or 1 nM or less;

(f) the antibody inhibits IL-33 stimulated release of INF-γ from human natural killer (NK) cells; optionally, wherein at an IL-33 concentration of about $EC_{50}$ the antibody has an $IC_{50}$ of 10 nM or less, 5 nM or less, or 1 nM or less;

(g) the antibody inhibits IL-36β stimulated release of IL8 from human epidermal keratinocytes (HEKn); optionally, wherein at an IL-36β concentration of about $EC_{60}$ the antibody has an $IC_{50}$ of 10 nM or less, 5 nM or less, or 2 nM or less;

(h) the antibody inhibits IL-33 stimulated phosphorylation in basophils; optionally, wherein at an IL-33 concentration of about $EC_{56}$ the antibody has an $IC_{50}$ of 75 nM or less, 50 nM or less, or 45 nM or less;

(i) the antibody inhibits IL-33 stimulated release of INF-γ from CD4+ T cells; optionally, wherein at an IL-33 concentration of about $EC_{34}$ the antibody has an $IC_{50}$ of 75 nM or less, 50 nM or less, or 45 nM or less;

(j) the antibody specifically binds to one or more amino acid residues within domain 3 of human IL1RAP, wherein domain 3 comprises positions 238-367 of the amino acid sequence of SEQ ID NO: 1 or 3;

(k) the antibody specifically binds to positions 243-255, positions 257-268, and/or positions 333-336 of the amino acid sequence of SEQ ID NO: 1 or 3;

(l) the antibody does not bind to amino acid residues within domain 1 or domain 2 of human IL1RAP; optionally, wherein domain 1 and domain 2 comprise positions 21-237 of the amino acid sequence of SEQ ID NO: 1 or 3;

(m) the antibody cross-reacts with a cynomolgus monkey IL1RAP polypeptide of SEQ ID NO: 8; and/or (n) the antibody cross-reacts with a mouse IL1RAP polypeptide of SEQ ID NO: 9.

The present disclosure also provides embodiments of the anti-IL1RAP antibody, wherein: (i) the antibody is a monoclonal antibody; (ii) the antibody is a human, humanized, or chimeric antibody; (iii) the antibody is a full length antibody of class IgG, optionally, wherein the class IgG antibody has an isotype selected from IgG1, IgG2, IgG3, and IgG4; (iv) the antibody is an Fc region variant, optionally an Fc region variant that alters effector function (e.g., a variant resulting in an effectorless antibody), an Fc region variant that exhibits decreased CDC activity, ADCC activity, and/or ADCP activity, an Fc region variant that exhibits decreased cytotoxic activity on human monocytes, neutrophils, and/or Jurkat cells, or an Fc region variant the alters antibody half-life; (v) the antibody is an antibody fragment, optionally selected from the group consisting of $F(ab')_2$, Fab', Fab, Fv, single domain antibody (VHH), and scFv; (vi) the antibody is an immunoconjugate, optionally, wherein the immunoconjugate comprises a therapeutic agent for treatment of an IL1RAP-mediated disease or condition; (vii) the antibody is a multi-specific antibody, optionally a bispecific antibody; and (viii) the antibody is a synthetic antibody, wherein the CDRs are grafted onto a scaffold or framework other than an immunoglobulin scaffold or framework; optionally, a scaffold selected from an alternative protein scaffold and an artificial polymer scaffold.

In other embodiments, the present disclosure provides isolated nucleic acids encoding the anti-IL1RAP antibodies disclosed herein.

In some embodiments, the present disclosure also provides a host cell comprising a nucleic acid encoding an anti-IL1RAP antibody as disclosed herein.

The disclosure also provides a method of producing an anti-IL1RAP antibody, wherein the method comprises culturing a host cell comprising a nucleic acid (or vector) encoding an anti-IL1RAP antibody so that an antibody is produced.

In some embodiments, the disclosure provides a pharmaceutical composition comprising an anti-IL1RAP antibody as disclosed herein and a pharmaceutically acceptable carrier. In some embodiments, the pharmaceutical composition further comprises a therapeutic agent for treatment of an IL-1, IL-33, IL-36, and/or IL1RAP-mediated disease or condition; optionally, wherein the therapeutic agent is a chemotherapeutic agent.

The present disclosure also provides a method of treating an IL1RAP-mediated disease in a subject, comprising administering to the subject a therapeutically effective amount of an anti-IL1RAP antibody as disclosed herein, or a therapeutically effective amount of a pharmaceutical formulation of an anti-IL1RAP antibody as disclosed herein.

The present disclosure also provides a method of treating a disease mediated by IL-1, IL-33, and/or IL-36 signaling in a subject, comprising administering to the subject a therapeutically effective amount of an anti-IL1RAP antibody as disclosed herein, or a therapeutically effective amount of a pharmaceutical composition of an anti-IL1RAP antibody as disclosed herein.

The present disclosure also provides a method of treating a disease mediated by IL-1α, IL-1β, IL-33, IL-36α, IL-36β, and/or IL-36γ stimulated signaling in a subject, comprising administering to the subject a therapeutically effective amount of an anti-IL1RAP antibody as disclosed herein, or a therapeutically effective amount of a pharmaceutical composition of an anti-IL1RAP antibody as disclosed herein.

In the various embodiments of the methods of treatment disclosed herein, the IL1RAP-mediated diseases and conditions, or the diseases mediated by IL-1, IL-33, and/or IL-36 signaling, include inflammatory diseases, autoimmune diseases, respiratory diseases, metabolic disorders, infections, and cancers. In some embodiments, the IL1RAP-mediated diseases and conditions can be selected from: acne, acute pancreatitis, acute severe ulcerative colitis, adult-onset Still's disease, age-related macular degeneration (AMD), airway hyperresponsiveness, airway inflammation, allergic conjunctivitis, allergic rhinitis, allergy, Alzheimer's disease, amyotrophic lateral sclerosis (ALS), anaphylaxis, arthritis pain, asthma, atherosclerosis, atopic dermatitis, atopic eczema, autoimmune vasculitis, Behcet's disease, bone cancer, brain cancer, breast cancer, cachexia/anorexia, cartilage damage, cerebral ischemia, chronic fatigue syndrome, chronic obstructive pulmonary disease, *Clostridium* associated illnesses, colon cancer, congestive heart failure, conjunctivitis, coronary artery bypass graft, coronary restenosis, Crohn's disease, diabetes, diabetic macular edema, diabetic retinopathy, dry eye disease, endometriosis, eosinophil-associated gastrointestinal disorder, eosinophilic esophagitis, familial cold autoinflammatory syndrome, familial Mediterranean fever, fever, fibromyalgia, fibrotic disorder, food allergy, generalized pustular psoriasis, glaucoma, glomerulonephritis, gouty arthritis, graft versus host disease, helminth infection, hemorrhagic shock, hidradenitis suppurativa, hyperalgesia, hyper-IgD syndrome, hyperuricemia, idiopathic pulmonary fibrosis (IPF), cancer-related pain, infection, inflammatory bowel disease (IBD), inflammatory conditions resulting from strain, inflammatory eye disease associated with corneal transplant, inflammatory pain, influenza, intestinal cancer, ischemia, juvenile arthritis, Kawasaki's disease, kidney cancer, Leber's congenital amaurosis, liver cancer, liver disease, lung cancer, Muckle-Wells syndrome, multiple myeloma, multiple sclerosis, musculoskeletal pain, myelogenous and other leukemias, myocardial dysfunction, myopathies, nasal polyp, neonatal onset multisystem inflammatory disease, neurotoxicity, non-infectious conjunctivitis, non-small cell lung cancer, orthopedic surgery, osteoarthritis, osteoporosis, pain, palmoplantar pustulosis, pancreas cancer, Parkinson's disease, periodontal disease, peripheral vascular disease, polymyalgia rheumatica, polypoidal choroidal vasculopathy (PCV), pre-term labor, prostate cancer, protozoan infection, psoriasis, psoriatic arthritis, pyoderma gangrenosum, reperfusion injury, respiratory syncytial virus (RSV), restenosis, retinal detachment, retinitis pigmentosa, retinopathy of prematurity (ROP), rheumatoid arthritis, septic shock, sickle-cell anemia, side effects from radiation therapy, sinusitis, skin cancer, sleep disturbance, sprain, Stargardt's disease, stomach cancer, temporal mandibular joint disease, TNF receptor associated periodic syndrome, transplant rejection, trauma, traumatic eye injury, type-2 diabetes, ulcerative colitis, and uveitis.

In some embodiments, the present disclosure also provides a method of treating cancer in a subject, the method comprising administering to the subject a therapeutically effective amount of an antibody of an anti-IL1RAP antibody as disclosed herein, or a therapeutically effective amount of a pharmaceutical formulation of an anti-IL1RAP antibody as disclosed herein. In embodiments, the cancer is selected from breast cancer, colorectal cancer, non-small cell lung cancer, pancreatic cancer.

In some embodiments, the present disclosure also provides a method of treating asthma in a subject, the method comprising administering to the subject a therapeutically effective amount of an antibody of an anti-IL1RAP antibody as disclosed herein, or a therapeutically effective amount of a pharmaceutical formulation of an anti-IL1RAP antibody as disclosed herein.

In some embodiments, the present disclosure also provides a method for detecting the level of IL1RAP in a biological sample, comprising the step of contacting the sample with an anti-IL1RAP antibody as disclosed herein. The anti-IL1RAP antibodies of the present disclosure may be employed in any known assay method, such as competitive binding assays, direct and indirect sandwich assays, immunoprecipitation assays and enzyme-linked immunosorbent assays (ELISA) (See, Sola, 1987, Monoclonal Antibodies: A Manual of Techniques, pp. 147-158, CRC Press, Inc.) for the detection and quantitation of IL1RAP. The antibodies bind hu-IL1RAP with high affinity appropriate for a wide range of assays.

BRIEF DESCRIPTION OF THE DRAWINGS

FIG. 1A: 11C5(Hy) inhibition of IL-1α stimulation ([IL-1α]=35 pM) of HEK-BLUE™ IL-1/IL-33 responsive cells; $IC_{50}$=4.70 nM. FIG. 1B: 11C5(Hy) inhibition of IL-1β stimulation ([IL-1β]=7 pM) of HEK-BLUE™ IL-1/IL-33 responsive cells; $IC_{50}$=1.00 nM. FIG. 1C: 11C5(Hy) inhibition of IL-33 stimulation ([IL-33]=60 pM) of HEK-BLUE™ IL-1/IL-33 responsive cells; $IC_{50}$=3.71 nM. FIG. 1D: 11C5(Hy) inhibition of IL-36α stimulation ([IL-36α]=10 pM) of HEK-BLUE™ IL-36 responsive cells; $IC_{50}$=2.52 nM. FIG. 1E: 11C5(Hy) inhibition of IL-36β stimulation ([IL-36β]=5 pM) of HEK-BLUE™ IL-36 responsive cells; $IC_{50}$=0.98 nM. FIG. 1F: 11C5(Hy) inhibition of IL-36γ stimulation ([IL-36γ]=7 pM) of HEK-BLUE™ IL-36 responsive cells; $IC_{50}$=0.67 nM. All assays were performed at an agonist concentration of about $EC_{50}$ to $EC_{70}$; error bars shown are representative of the standard deviation from duplicate samples; and positive control (PC) is represented by a black, dashed line, while the negative control (NC) is represented by a grey, dashed line.

FIG. 2 depicts the amino acid sequence alignment of the closest human germline kappa light chain $V_L$ region (Gene ID—V gene: IGKV1-NL1*01, J gene: IGKJ4*02) and heavy chain $V_H$ region (Gene ID—V gene: IGHV3-7*03, J gene: IGHJ4*03) against the $V_L$ and $V_H$ regions of the hybridoma-derived murine anti-hu-IL1RAP antibody, 11C5 (Hy), and the humanized version of this antibody, h11C5.

FIG. 4A: 11C5(Hy), m11C5 and h11C5 inhibition of IL-1β stimulation ([IL-1β]=7 pM) of HEK-BLUE™ IL-1/IL-33 responsive cells. FIG. 4B: 11C5(Hy), m11C5 and h11C5 inhibition of IL-33 stimulation ([IL-33]=60 pM) of HEK-BLUE™ IL-1/IL-33 responsive cells. FIG. 4C: h11C5 and h11C5_C59Y inhibition of IL-1β stimulation ([IL-1β]=7 pM) of HEK-BLUE™ IL-1/IL-33 responsive cells. FIG. 4D: h11C5 and h11C5_C59Y inhibition of IL-33 stimulation ([IL-33]=60 pM) of HEK-BLUE™ IL-1/IL-33 responsive cells. FIG. 4E: c11C5_C59Y inhibition of IL-1α stimulation ([IL-1α]=10 pM) of primary human lung fibroblasts (PHLFs); $IC_{50}$=3.96 nM. FIG. 4F: c11C5_C59Y inhibition of IL-1β stimulation ([IL-1β]=0.925 nM) of primary human monocytes (PHMs); $IC_{50}$=0.74 nM. FIG. 4G: c11C5_C59Y inhibition of IL-33 stimulation ([IL-33]=1 nM, [IL-12]=0.1 ng/mL) of primary human NK (PHNK) cells; $IC_{50}$=2.90 nM. FIG. 4H: c11C5_C59Y inhibition of IL-36β stimulation ([IL-36β]=2 nM) of PHLFs; $IC_{50}$=0.28 nM. All recombinant antibodies also contain the N297G mutation conferring effectorless function; agonists were used at an effective concentration of about $EC_{50}$ to $EC_{70}$; error bars are representative of the standard deviation from duplicate samples; positive control (PC) is represented by a black, dashed line, while the negative control (NC) is represented by a grey, dashed line.

FIG. 5A: inhibition of IL-1β stimulation ([IL-1β]=7 pM) of HEK-BLUE™ IL-1/IL-33 responsive cells. FIG. 5B: inhibition of IL-33 stimulation ([IL-33]=40 pM) of HEK-BLUE™ IL-1/IL-33 responsive cells. FIG. 5C: inhibition of IL-36α stimulation ([IL-36α]=60 pM) of HEK-BLUE™ IL-36 responsive cells. FIG. 1D: inhibition of IL-1β stimulation ([IL-1β]=9 pM) of HEK-BLUE™ IL-1/IL-33 responsive cells. FIG. 5E: inhibition of IL-33 stimulation ([IL-33]=60 pM) of HEK-BLUE™ IL-1/IL-33 responsive cells. FIG. 5F: inhibition of IL-36α stimulation ([IL-36α]=50 pM) of HEK-BLUE™ IL-36 responsive cells. The $V_L$ and $V_H$ region mutations corresponding to the identifiers for the variants used in the figure are explained in Example 9. FIGS. 5A-C depict results for the Fab versions of the affinity matured variants, including the Fab version of the non-affinity matured parental antibody, "h11C5_AC59Y/A43S," and the IgG control, "Fab Ctrl. " FIGS. 5D-F depict results for the full-length IgG antibody versions of the affinity-matured variants and include the full-length IgG antibody version of the non-affinity matured parental antibody, "h11C5_AC59Y/A43S" and the IgG control. All full-length IgG antibodies tested, including the isotype IgG control antibody, contained the N297G mutation conferring effectorless function. Assays of IL-1β or IL-36α stimulation were performed at an agonist concentration of about $EC_{50}$ to $EC_{60}$. Assays of IL-33 stimulation were performed at an agonist concentration of about $EC_{35}$ to $EC_{45}$. Error bars shown are representative of the standard deviation from duplicate samples. Positive control (PC) is represented by a black, dashed line, while the negative control (NC) is represented by a grey, dashed line.

FIG. 6A shows assay results for HEK-Blue cells stimulated with IL-1β; FIG. 6B shows assay results for HEK-Blue cells stimulated with IL-33; and FIG. 6C shows assay results for HEK-Blue cells stimulated with IL-36β. In each assay the agonist concentration is near or greater than $EC_{55}$. The error bars shown are representative of the standard error of the mean from duplicate samples. The positive control (PC) is represented by a black, dashed line, while the negative control (NC) is represented by a grey, dashed line.

FIG. 14B: YKD doses of 40 mg/kg (shown as closed circles), 20 mg/kg (open circles), 10 mg/kg (closed squares), 3 mg/kg (open squares) and 1 mg/kg (closed triangles). FIG. 14C: YKD/YTE doses of 40 mg/kg (shown as closed circles), 10 mg/kg (open squares) and 3 mg/kg (closed triangles). Error bars are representative of the standard deviation.

FIG. 15 depicts a molecular surface and ribbon representation of the crystal structure (PDB code: 3O4O) of a ternary complex of human IL1RAP (molecular surface), IL-1β (dark gray ribbon), and IL-1R1 (light gray ribbon). The representation depicts the spatial distribution of IL1RAP amino acid residues identified as deleterious for binding of the anti-hu-IL1RAP antibodies, YIS and YKS, but not deleterious for the binding of a reference antibody if mutated, as described in Example 15. The IL1RAP residues, I245, E261, and T267, which were observed with 9 or more flagged substitutions are colored in black, and other residues in the epitope with 6-8 flagged substitutions are colored in dark gray.

Figure 16A:
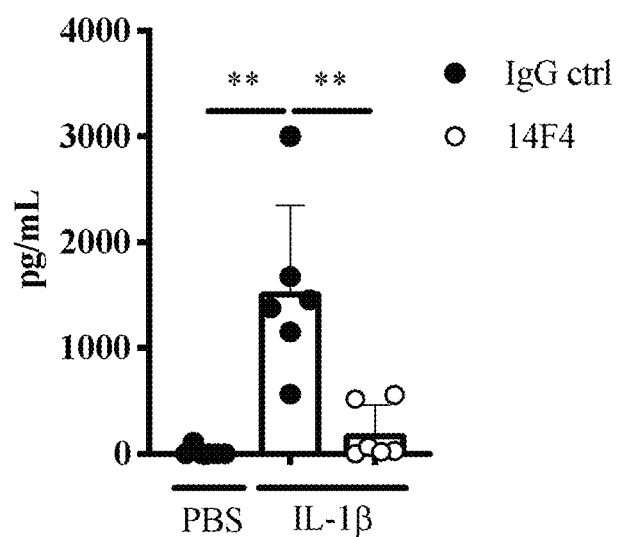
Figure 16B:
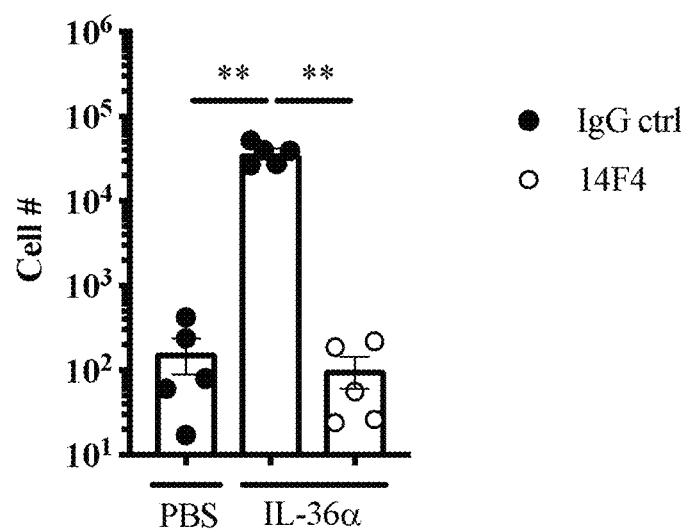

FIGS. 16A and 16B depict plots blocking efficacy of 14F4 or an isotype control (IgG Ctrl) as determined in the single IL-1β challenge model (FIG. 16A) or the single IL-36α challenge model (FIG. 16B) as described in Example 18. FIG. 16A: mice were dosed with 14F4 or the IgG Ctrl, and one day later challenged i.p. with D-PBS or 50 ng of IL-1β; two hours after challenge, blood was collected, and serum IL-6 levels were determined; data is from 5 mice per group and is representative of two independent experiments; bar graphs indicate mean+/−SEM; individual circles indicate data from one individual mouse; mice dosed with 14F4 or IgG Ctrl are indicated with the white or black circles, respectively; $p \leq 0.01$ using Mann-Whitney test comparing isotype/PBS and isotype/IL-1β-challenged mice or comparing isotype/IL-1β-challenged and 14F4/IL-1β-challenged mice. FIG. 16B: mice were dosed with 14F4 or the IgG Ctrl, and one day later challenged i.n. with D-PBS or 10 ng of IL-36α; one day after challenge, cellular inflammation in the lung airspace was determined; data is from 5 mice per group and is representative of two independent experiments; bar graphs indicate mean+/−SEM; individual circles indicate data from one individual mouse; mice dosed with 14F4 or IgG Ctrl are indicated with the white or black circles, respectively; $p \leq 0.01$ using Mann-Whitney test comparing isotype/PBS and isotype/IL-36α-challenged mice or comparing isotype/IL-36α-challenged and 14F4/IL-36α-challenged mice.

Figure 17A:
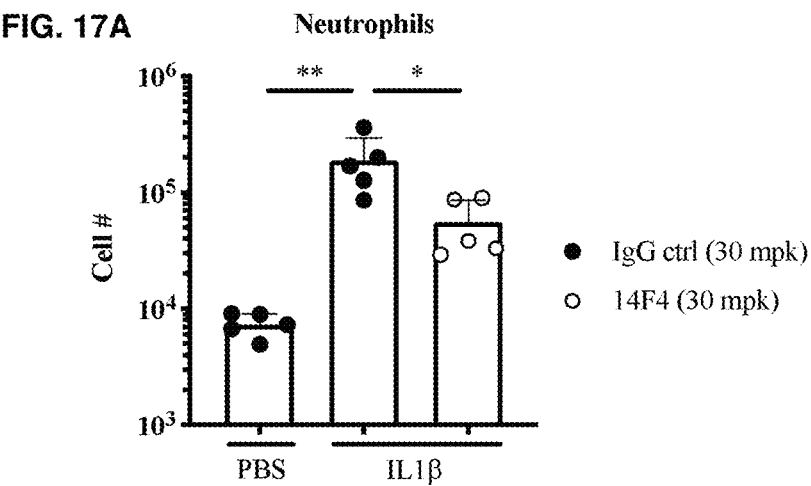
Figure 17B:
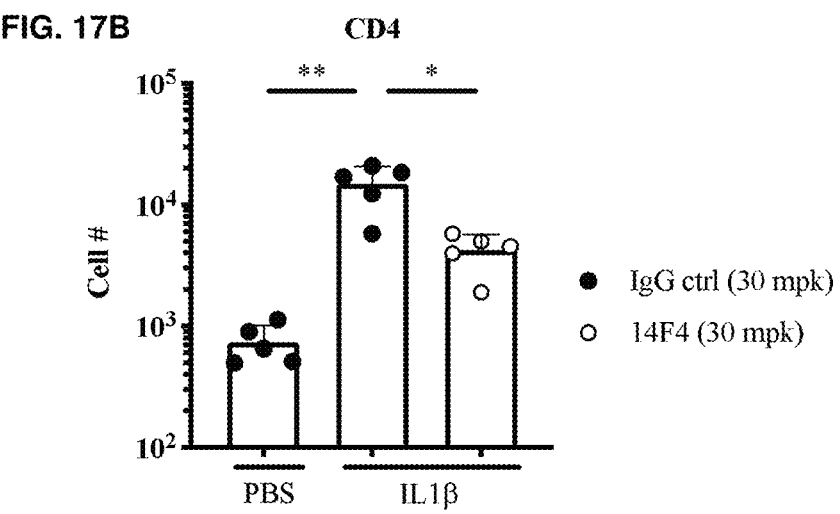
Figure 17C:
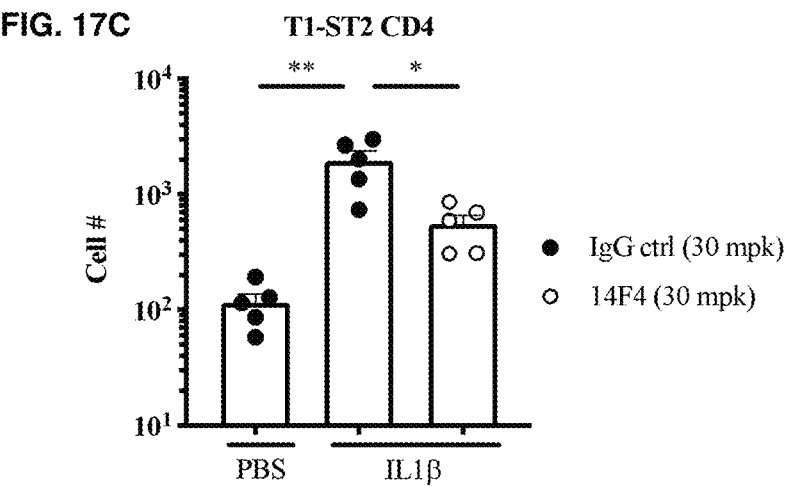
Figure 17D:
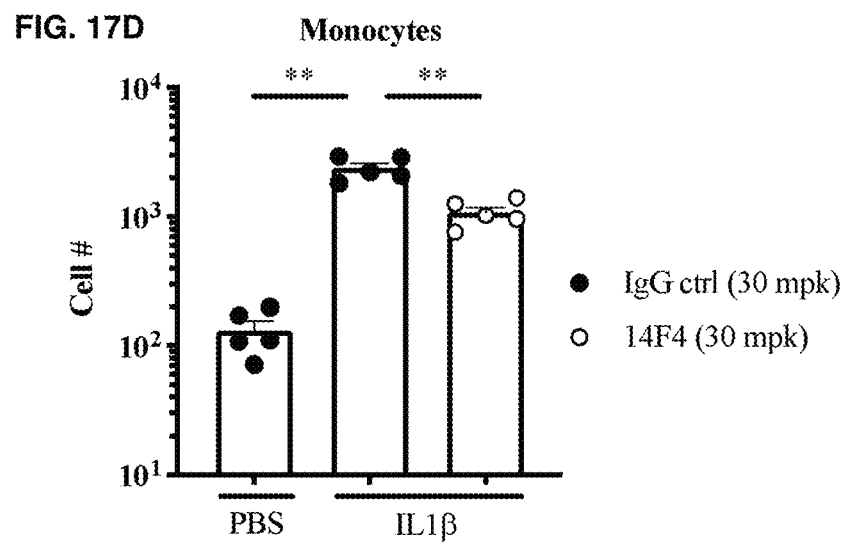
Figure 17E:
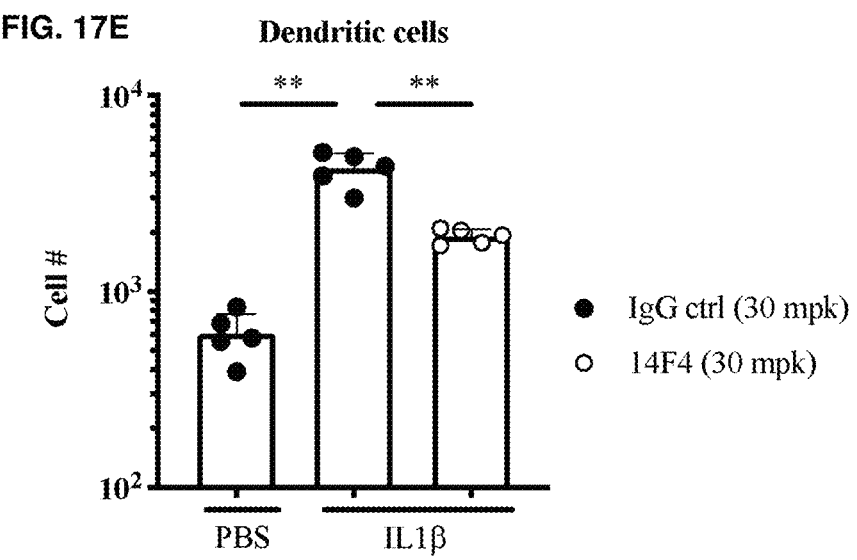

FIGS. 17A, 17B, 17C, 17D, and 17E depict plots of blocking efficacy of 14F4 or an isotype control (IgG Ctrl) as determined in the multiple IL-1β challenge model that assays immune cell infiltration in the lung airspace as described in Example 18. Blocking efficacy was measured for the infiltration of five different cell types in the lung airspace: neutrophils (FIG. 17A); CD4 T cells (FIG. 17B); T1-ST2$^+$ CD4 T cells (FIG. 17C); monocytes (FIG. 17D); and dendritic cells (FIG. 17E). Mice were dosed with 14F4, or the IgG Ctrl on Day −1 and Day 2, and challenged i.n. with D-PBS or 30 ng of IL-1β on Day 0, 1, and 2; on Day 3, cellular inflammation in the lung airspace was determined; data is from 5 mice per group and is representative of two independent experiments; bar graphs indicate mean+/−SEM. Individual circles indicate data from one individual mouse; the mice dosed with 14F4 or IgG Ctrl are indicated with the white or black circles, respectively; *$p \leq 0.05$ and **$p \leq 0.01$ using Mann-Whitney test comparing isotype/PBS and isotype/IL-1β-challenged mice or comparing isotype/IL-1β-challenged and 14F4/IL-1β-challenged mice.

Figure 18A:
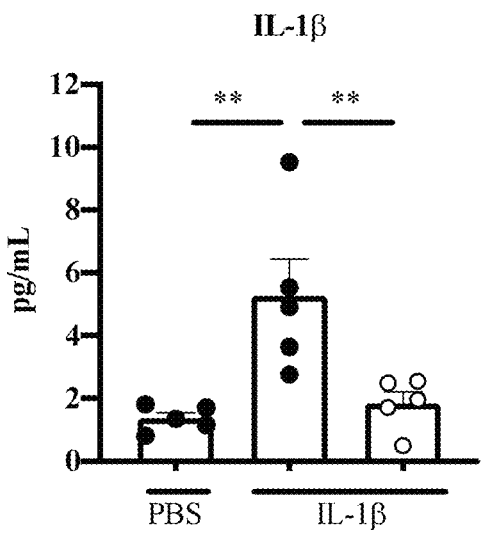
Figure 18B:
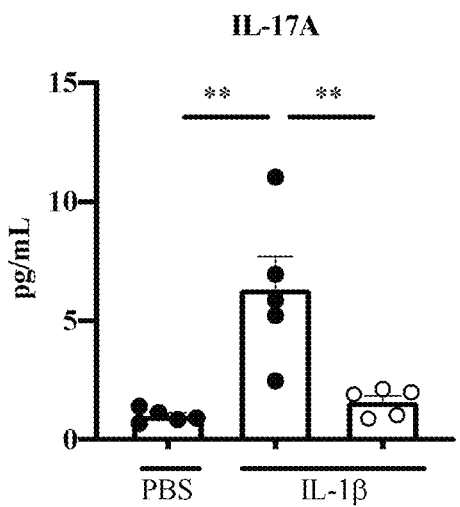
Figure 18C:
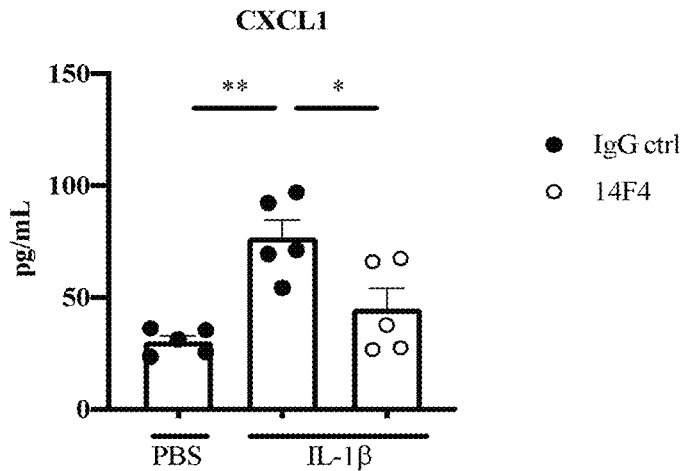

FIGS. 18A, 18B, and 18C depict plots of blocking efficacy of 14F4 or an isotype control (IgG Ctrl) as determined in the multiple IL-1β challenge model that assays chemokine and cytokine levels in lung tissue as described in Example 18. Blocking efficacy was determined based on the levels of three different chemokines and cytokines as measured from lung tissue samples: IL-1β (FIG. 18A); IL-17A (FIG. 18B); and CXCL1 (FIG. 18C). Mice were dosed with 14F4, or the IgG Ctrl on Day −1 and Day 2, and challenged i.n. with D-PBS or 30 ng of IL-1β on Day 0, 1, and 2; on Day 3, lung tissue was collected for protein chemokine and cytokine analysis; data is from 5 mice per group and is representative of two independent experiments; bar graphs indicate mean+/−SEM; individual circles indicate data from one individual mouse; mice dosed with 14F4 or IgG Ctrl are indicated with the white or black circles, respectively; *$p \leq 0.05$ and **$p \leq 0.01$ using Mann-Whitney test comparing isotype/PBS and isotype/IL-1β-challenged mice or comparing isotype/IL-1β-challenged and 14F4/IL-1β-challenged mice.

Figure 19A:
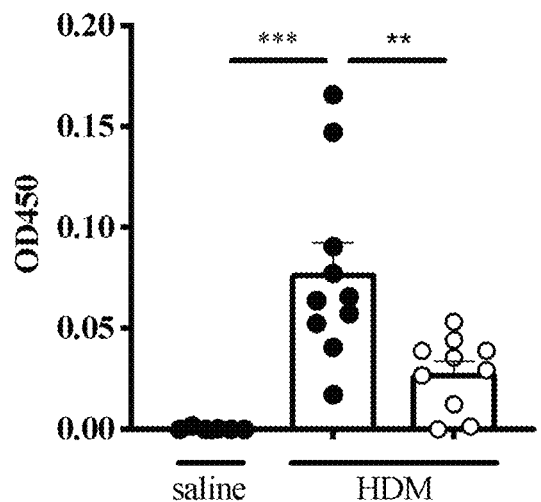
Figure 19B:
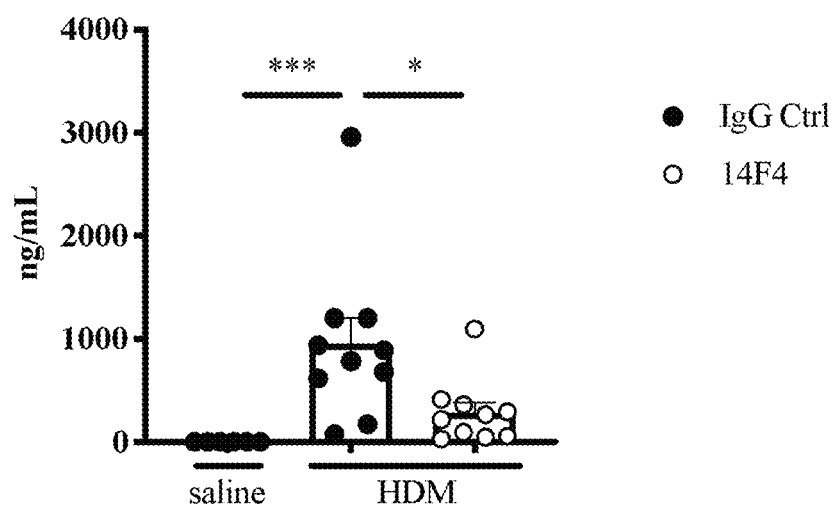

FIGS. 19A and 19B depict plots of blocking efficacy of 14F4 or an isotype control (IgG Ctrl) as determined in the acute HDM asthma model that assays serum antibody levels as described in Example 18. FIG. 19A: assay for HDM-specific IgE; FIG. 19B: assay for HDM-specific IgG1. Mice were dosed i.p. with 14F4, or IgG control, on Days −1, 2, 6, 9, and 13; on Days 0-3, 6-10, 13 and 14, mice were challenged i.n. with saline or 25 µg HDM; one day after the last challenge, blood was collected, and serum HDM-specific IgE and IgG1 levels were determined; data is from 6-10 mice per group and is representative of two independent experiments; bar graphs indicate mean+/−SEM; individual circles indicate data from one individual mouse; mice dosed with 14F4 or IgG Ctrl are indicated with the white or black circles, respectively; *$p \leq 0.05$, $p \leq 0.01$, *$p \leq 0.001$ using Mann-Whitney test comparing isotype/saline and isotype/HDM-challenged mice or comparing isotype/HDM-challenged and 14F4/HDM-challenged mice.

DETAILED DESCRIPTION

The present disclosure provides antibodies, including humanized antibodies, that specifically bind human IL1RAP with high affinity. The disclosed anti-IL1RAP antibodies are capable of decreasing, inhibiting, and/or fully-blocking intracellular signaling by IL1RAP-mediated pathways, including the IL-1, IL-33, and/or IL-36 signaling pathways. More specifically, the anti-IL1RAP antibodies disclosed herein are capable of decreasing, inhibiting, and/or fully-blocking signaling stimulated by binding of one or more of the following agonists: IL-1α, IL-1β, IL-33, IL-36α, IL-36β, and IL-36γ. The present disclosure also provides uses of the anti-IL1RAP antibodies in methods of treating IL1RAP-mediated diseases, including diseases and conditions responsive to inhibition of IL-1, IL-33, and/or IL-36 signaling, including, but not limited to, various cancers (e.g., breast, colorectal, non-small cell lung, pancreatic), as well as inflammatory, infectious, and autoimmune diseases, including arthritis, asthma, and ulcerative colitis.

Overview of Terminology and Techniques

For the descriptions herein and the appended claims, the singular forms "a", and "an" include plural referents unless the context clearly indicates otherwise. Thus, for example, reference to "a protein" includes more than one protein, and reference to "a compound" refers to more than one compound. The use of "comprise," "comprises," "comprising" "include," "includes," and "including" are interchangeable and not intended to be limiting. It is to be further understood that where descriptions of various embodiments use the term "comprising," those skilled in the art would understand that in some specific instances, an embodiment can be alternatively described using language "consisting essentially of" or "consisting of."

Where a range of values is provided, unless the context clearly dictates otherwise, it is understood that each intervening integer of the value, and each tenth of each intervening integer of the value, unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of these limits, ranges excluding (i) either or (ii) both of those included limits are also included in the invention. For example, "1 to 50," includes "2 to 25," "5 to 20," "25 to 50," "1 to 10," etc.

Generally, the nomenclature used herein and the techniques and procedures described herein include those that are well understood and commonly employed by those of ordinary skill in the art, such as the common techniques and methodologies described in Sambrook et al., *Molecular Cloning-A Laboratory Manual* (2nd Ed.), Vols. 1-3, Cold Spring Harbor Laboratory, Cold Spring Harbor, N.Y., 1989 (hereinafter "Sambrook"); *Current Protocols in Molecular Biology*, F. M. Ausubel et al., eds., Current Protocols, a joint venture between Greene Publishing Associates, Inc. and John Wiley & Sons, Inc. (supplemented through 2011) (hereinafter "Ausubel"); *Antibody Engineering*, Vols. 1 and 2, R. Kontermann and S. Dubel, eds., Springer-Verlag, Berlin and Heidelberg (2010); *Monoclonal Antibodies: Methods and Protocols*, V. Ossipow and N. Fischer, eds., 2nd Ed., Humana Press (2014); *Therapeutic Antibodies: From Bench to Clinic*, Z. An, ed., J. Wiley & Sons, Hoboken, N.J. (2009); and *Phage Display*, Tim Clackson and Henry B. Lowman, eds., Oxford University Press, United Kingdom (2004).

All publications, patents, patent applications, and other documents referenced in this disclosure are hereby incorporated by reference in their entireties for all purposes to the same extent as if each individual publication, patent, patent application or other document were individually indicated to be incorporated by reference herein for all purposes.

Unless defined otherwise, all technical and scientific terms used herein have the same meaning as commonly understood by one of ordinary skill in the art to which the present invention pertains. It is to be understood that the terminology used herein is for describing particular embodiments only and is not intended to be limiting. For purposes of interpreting this disclosure, the following description of terms will apply and, where appropriate, a term used in the singular form will also include the plural form and vice versa.

"IL1RAP," as used herein, refers to the interleukin-1 receptor accessory protein that is the cellular membrane co-receptor for several receptors in the IL-1 family, including interleukin-1 receptor 1 (IL1R1), ST2 (also known as interleukin-1 receptor-like 1 or IL1RL1), and interleukin-1 receptor-like protein 2 (IL1RL2). It is noted that the interleukin-1 receptor accessory protein, or IL1RAP, is sometimes referred to in the art as "IL-1RAP," "IL-1RAcP," "IL1 RAcP" or "IL-1R3." The terms "IL1RAP," "IL1RAP polypeptide," and "IL1RAP protein" are used herein interchangeably.

"IL1RAP mediated condition" or "IL1RAP mediated disease," as used herein, encompasses any medical condition associated with aberrant function of the signaling pathways mediated by IL-1 family of cytokines together with IL1RAP acting as a co-receptor, including but not limited to, the downstream signaling pathways stimulated by the IL-1 family cytokines IL-1α, IL-1β, IL-33, IL-36α, IL-36β, and IL-36γ. For example, IL1RAP mediated diseases can include, but are not limited to, diseases mediated by and/or responsive to antagonists or inhibitors of the IL-1, IL-33, and/or IL-36 signaling pathways including cancer, inflammatory, infectious, and autoimmune diseases. More specifically, IL1RAP mediated disease can include but are not limited to acne, acute severe ulcerative colitis, adult-onset Still's disease, allergic rhinitis, gouty arthritis, juvenile arthritis, osteo arthritis, rheumatoid arthritis, arthritis pain, asthma, atherosclerosis, atopic eczema, Behcet's disease, cachexia, breast cancer, colorectal cancer, non-small cell lung cancer, pancreatic cancer, chronic obstructive pulmonary disease, dry eye syndrome, familial cold autoinflammatory syndrome, familial Mediterranean fever, food allergy, generalized pustular psoriasis, hidradenitis suppurativa, hyper-IgD syndrome, hyperuricemia, Muckle-Wells syndrome, neonatal onset multisystem inflammatory disease, musculoskeletal pain, palmoplantar pustulosis, peripheral vascular disease, polymyalgia rheumatica, nasal polyp, psoriasis, pyoderma gangrenosum, restenosis, sickle-cell anemia, sinusitis, TNF receptor associated periodic syndrome, type-2 diabetes, and ulcerative colitis.

"IL-1 stimulated signal," as used herein, refers to an intracellular signal initiated by binding of an IL-1 cytokine, such as IL-1α or IL-1β, to its cognate cell surface receptor, IL1R1. Exemplary IL-1 stimulated signals include those measurable using a cell-based blocking assay, such as a HEK-BLUE™ IL-1 responsive cell-based assay as disclosed in the Examples herein.

"IL-33 stimulated signal," as used herein, refers to an intracellular signal initiated by binding of an IL-33 cytokine, such as IL-33, to its cognate cell surface receptor, IL1RL1 (also known as ST2). Exemplary IL-33 stimulated signals include those measurable using a cell-based blocking assay, such as a HEK-BLUE™ IL-33 responsive cell-based assay as disclosed in the Examples herein.

"IL-36 stimulated signal," as used herein, refers to an intracellular signal initiated by binding of an IL-36 cytokine, such as IL-36α, IL-36β, or IL-36γ, to its cognate cell surface receptor, IL1RL2. Exemplary IL-36 stimulated signals include those measured by surrogate cell-based blocking assays, such as a HEK-BLUE™ IL-36 responsive cell-based assay as disclosed in the Examples herein.

"Cell-based blocking assay" refers to an assay in which the ability of an antibody to inhibit or reduce the biological activity of the antigen it binds can be measured. For example, a cell-based blocking assay can be used to measure the concentration of antibody required to inhibit a specific biological or biochemical function, such as IL1RAP-mediated intracellular signaling via the IL-1, IL-33, and IL-36 signaling pathways. In some embodiments, the half maximal inhibitory concentration ($IC_{50}$) and/or 90% inhibitory concentration ($IC_{90}$) of an antibody (e.g., an anti-IL1RAP antibody of the disclosure) is measured using a cell-based blocking assay. In some embodiments, the cell-based blocking assay is used to determine whether an antibody blocks the interaction between an agonist (e.g., IL-1α, IL-1β, IL-33, IL-36α, IL-36β, IL-36γ) and its cognate receptor. Cell-based blocking assays useful with the antibodies of the present disclosure can include primary cell assays (e.g., PHLF cells) as well as reporter or sensor cell assays (e.g., a HEK-BLUE™ reporter cell assay). Exemplary cell-based blocking assays for the IL-1, IL-33, and IL-36 signaling pathways, such as suitable HEK-BLUE™ specific cytokine-responsive reporter cell-based assays, are described in the Examples provided herein.

"Antibody," as used herein, refers to a molecule comprising one or more polypeptide chains that specifically binds to, or is immunologically reactive with, a particular antigen. Exemplary antibodies of the present disclosure include monoclonal antibodies, polyclonal antibodies, chimeric antibodies, humanized antibodies, human antibodies, multispecific (or heteroconjugate) antibodies (e.g., bispecific antibodies), monovalent antibodies (e.g., single-arm antibodies), multivalent antibodies, antigen-binding fragments (e.g., Fab', F(ab')$_2$, Fab, Fv, rIgG, and scFv fragments), antibody fusions, and synthetic antibodies (or antibody mimetics).

"Anti-IL1RAP antibody" or "antibody that binds IL1RAP" refers to an antibody that binds IL1RAP with sufficient affinity such that the antibody is useful as a diagnostic and/or therapeutic agent in targeting IL1RAP. In some embodiments, the extent of binding of an anti-IL1RAP antibody to an unrelated, non-IL1RAP antigen is less than about 10% of the binding of the antibody to IL1RAP as measured, e.g., by a radioimmunoassay (RIA). In some embodiments, an antibody that binds to IL1RAP has a dissociation constant ($K_D$) of <1 µM, <100 nM, <10 nM, <1 nM, <0.1 nM, <0.01 nM, or <1 pM (e.g., $10^{-8}$ M or less, e.g., from $10^{-8}$ M to $10^{-13}$ M, e.g., from $10^{-9}$ M to $10^{-13}$ M).

"Full-length antibody," "intact antibody," or "whole antibody" are used herein interchangeably to refer to an antibody having a structure substantially similar to a native antibody structure or having heavy chains that contain an Fc region as defined herein.

"Antibody fragment" refers to a portion of a full-length antibody which is capable of binding the same antigen as the full-length antibody. Examples of antibody fragments include, but are not limited to, Fv, Fab, Fab', Fab'-SH, F(ab')$_2$; diabodies; linear antibodies; monovalent, or single-armed antibodies; single-chain antibody molecules (e.g., scFv); and multispecific antibodies formed from antibody fragments.

"Class" of an antibody refers to the type of constant domain or constant region possessed by its heavy chain. There are five major classes of antibodies: IgA, IgD, IgE, IgG, and IgM, and several of these are further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and µ, respectively.

"Variable region" or "variable domain" refers to the domain of an antibody heavy or light chain that is involved in binding the antibody to antigen. The variable domains of the heavy chain and light chain ($V_H$ and $V_L$, respectively) of a native antibody generally have similar structures, with each domain comprising four conserved framework regions (FRs) and three hypervariable regions (HVRs) (see, e.g., Kindt et al., Kuby Immunology, 6$^{th}$ ed., W.H. Freeman and Co., page 91). A single $V_H$ or $V_L$ domain may be sufficient to confer antigen-binding specificity. Furthermore, antibodies that bind a particular antigen may be isolated using a $V_H$ or $V_L$ domain from an antibody that binds the antigen to screen a library of complementary $V_L$ or $V_H$ domains, respectively (see, e.g., Portolano et al., J. Immunol., 150: 880-887 (1993); Clarkson et al., Nature, 352:624-628 (1991)).

"Hypervariable region" or "HVR," as used herein, refers to each of the regions of an antibody variable domain which are hypervariable in sequence and/or form structurally defined loops ("hypervariable loops"). Generally, native antibodies comprise four chains with six HVRs; three in the heavy chain variable domain, $V_H$ (HVR-H1, HVR-H2, HVR-H3), and three in the light chain variable domain, $V_L$ (HVR-L1, HVR-L2, HVR-L3). The HVRs generally comprise amino acid residues from the hypervariable loops and/or from the "complementarity determining regions" (CDRs). Unless otherwise indicated, HVR residues and other residues in the variable domain (e.g., FR residues) are numbered herein according to Kabat et al., Sequences of Proteins of Immunological Interest, 5th Ed. Public Health Service, National Institutes of Health, Bethesda, MD (1991).

"Complementarity determining region," or "CDR," as used herein, refers to the regions within the HVRs of the variable domain which have the highest sequence variability and/or are involved in antigen recognition. Generally, native antibodies comprise four chains with six CDRs; three in the heavy chain variable domains, $V_H$ (H1, H2, H3), and three in the light chain variable domains, $V_L$ (L1, L2, L3). Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., supra).

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in $V_H$ (or $V_L$): FR1-H1(L1)-FR2-H2(L2)-FR3-H3(L3)-FR4.

"Native antibody" refers to a naturally occurring immunoglobulin molecule. For example, native IgG antibodies are heterotetrameric glycoproteins of about 150,000 Daltons, composed of two identical light chains and two identical heavy chains that are disulfide-bonded. From N- to C-terminus, each heavy chain has a variable region ($V_H$), also called a variable heavy domain or a heavy chain variable domain, followed by three constant domains (CH1, CH2, and CH3). Similarly, from N- to C-terminus, each light chain has a variable region ($V_L$), also called a variable light domain or a light chain variable domain, followed by a constant light (CL) domain. The light chain of an antibody may be assigned to one of two types, called kappa (κ) and lambda (λ), based on the amino acid sequence of its constant domain.

"Monoclonal antibody" as used herein refers to an antibody obtained from a substantially homogeneous population of antibodies, i.e., the individual antibodies comprising the population are identical and/or bind the same epitope, except for possible variant antibodies (e.g., variant antibodies contain mutations that occur naturally or arise during production of a monoclonal antibody, and generally are present in minor amounts). In contrast to polyclonal antibody preparations, which typically include different antibodies directed against different determinants (epitopes), each monoclonal antibody of a monoclonal antibody preparation is directed against a single determinant on an antigen. Thus, the term "monoclonal" indicates the character of the antibody as being obtained from a substantially homogeneous population of antibodies and is not to be construed as requiring production of the antibody by any particular method. For example, the monoclonal antibodies to be used may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

"Chimeric antibody" refers to an antibody in which a portion of the heavy and/or light chain is derived from a particular source or species, while the remainder of the heavy and/or light chain is derived from a different source or species.

"Humanized antibody" refers to a chimeric antibody comprising amino acid sequences from non-human HVRs and amino acid sequences from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

"Human antibody" refers to an antibody which possesses an amino acid sequence corresponding to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

"Human consensus framework" is a framework which represents the most commonly occurring amino acid residues in a selection of human immunoglobulin $V_L$ or $V_H$ framework sequences. Generally, the selection of human immunoglobulin $V_L$ or $V_H$ sequences is from a subgroup of variable domain sequences. Generally, the subgroup of sequences is a subgroup as in Kabat et al., Sequences of Proteins of Immunological Interest, Fifth Edition, NIH Publication 91-3242, Bethesda MD (1991), vols. 1-3. In one embodiment, for the $V_L$, the subgroup is subgroup kappa I as in Kabat et al., supra. In one embodiment, for the $V_H$, the subgroup is subgroup III as in Kabat et al., supra.

"Acceptor human framework" as used herein is a framework comprising the amino acid sequence of a light chain variable domain ($V_L$) framework or a heavy chain variable domain ($V_H$) framework derived from a human immunoglobulin framework or a human consensus framework. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the $V_L$ acceptor human framework is identical in sequence to the $V_L$ human immunoglobulin framework sequence or human consensus framework sequence.

"Fc region," refers to a dimer complex comprising the C-terminal polypeptide sequences of an immunoglobulin heavy chain, wherein a C-terminal polypeptide sequence is that which is obtainable by papain digestion of an intact antibody. The Fc region may comprise native or variant Fc sequences. Although the boundaries of the Fc sequence of an immunoglobulin heavy chain may vary, the human IgG heavy chain Fc sequence is usually defined to stretch from an amino acid residue at about position Cys226, or from about position Pro230, to the carboxyl-terminus of the Fc sequence at Lys447. However, the C-terminal lysine (Lys447) of the Fc sequence may or may not be present in the Fc region of recombinant antibodies due to enzymatic cleavage that can occur in cell culture systems used for recombinant production (e.g., production in CHO cells). The Fc sequence of an immunoglobulin generally comprises two constant domains, a CH2 domain and a CH3 domain, and optionally comprises a CH4 domain.

"Fc receptor" or "FcR," refers to a receptor that binds to the Fc region of an antibody. In some embodiments, an FcR is a native human FcR. In some embodiments, an FcR is one which binds an IgG antibody (a gamma receptor) and includes receptors of the FcγRI, FcγRII, and FcγRIII subclasses, including allelic variants and alternatively spliced forms of those receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain, (see, e.g., Daeron, *Annu. Rev. Immunol.,* 15:203-234 (1997)). FcR, as used herein, also includes the neonatal receptor, FcRn, which is responsible for the transfer of maternal IgGs to the fetus (Guyer et al., *J. Immunol.,* 1 17:587 (1976) and Kim et al., *Eur. J. Immunol.,* 24:2429-2434 (1994)) and regulation of homeostasis of immunoglobulins. FcRs are reviewed, for example, in Ravetch and Kinet, *Annu. Rev. Immunol,* 9:457-92 (1991); Capel et al., *Immunomethods* 4:25-34 (1994); and de Haas et al., *J. Lab. Clin. Med.,* 126:330-41 (1995).

"Multivalent antibody," as used herein, is an antibody comprising three or more antigen binding sites. The multivalent antibody is preferably engineered to have the three or more antigen binding sites and is generally not a native sequence IgM or IgA antibody.

"Multispecific antibody" is an antibody having at least two different binding sites, each site with a different binding specificity. A multispecific antibody can be a full-length antibody or an antibody fragment, and the different binding sites may bind each to a different antigen or the different binding sites may bind to two different epitopes of the same antigen.

"Fv fragment" refers to an antibody fragment which contains a complete antigen recognition and binding site. This region consists of a dimer of one heavy and one light chain variable domain in tight association, which can be covalent in nature, for example in scFv. It is in this configuration that the three HVRs of each variable domain interact to define an antigen binding site on the surface of the $V_H$-$V_L$ dimer. Collectively, the six HVRs or a subset thereof confer antigen binding specificity to the antibody. However, even a single variable domain (or half of an Fv comprising only three HVRs specific for an antigen) has the ability to recognize and bind antigen, although usually at a lower affinity than the entire binding site.

"Fab fragment" refers to an antibody fragment that contains a variable and constant domain of the light chain and a variable domain and the first constant domain (CH1) of the heavy chain. "F(ab')$_2$ fragments" comprise a pair of Fab fragments which are generally covalently linked near their carboxy termini by hinge cysteines between them. Other chemical couplings of antibody fragments also are known in the art.

"Antigen binding arm," as used herein, refers to a component of an antibody that has an ability to specifically bind a target molecule of interest. Typically, the antigen binding arm is a complex of immunoglobulin polypeptide sequences, e.g., HVR and/or variable domain sequences of an immunoglobulin light and heavy chain.

"Single-chain Fv" or "scFv" refer to antibody fragments comprising the $V_H$ and $V_L$ domains of an antibody, wherein these domains are present in a single polypeptide chain. Generally, an Fv polypeptide further comprises a polypeptide linker between the $V_H$ and $V_L$ domains which enables the scFv to form the desired antigen binding structure.

"Diabodies" refers to small antibody fragments with two antigen-binding sites, which fragments comprise a heavy chain variable domain ($V_H$) connected to a light chain variable domain ($V_L$) in the same polypeptide chain ($V_H$ and $V_L$). By using a linker that is too short to allow pairing between the two domains on the same chain, the domains are forced to pair with the complementary domains of another chain and create two antigen-binding sites.

"Linear antibodies" refers to the antibodies described in Zapata et al., *Protein Eng.*, 8(10): 1057-1062 (1995). Briefly, these antibodies comprise tandem repeats of a heavy chain fragment (VH-CH1-VH-CH1) which, together with complementary light chain polypeptides, form a pair of antigen binding regions. Linear antibodies can be bispecific or monospecific.

"Naked antibody" refers to an antibody that is not conjugated to a heterologous moiety (e.g., a cytotoxic moiety) or radiolabel.

"Affinity" refers to the strength of the total of noncovalent interactions between a single binding site of a molecule (e.g., an antibody) and its binding partner (e.g., an antigen). "Binding affinity" refers to intrinsic binding affinity which reflects a 1:1 interaction between members of a binding pair (e.g., antibody and antigen). The affinity of a molecule X for its partner Y can generally be represented by the equilibrium dissociation constant ($K_D$). Affinity can be measured by common methods known in the art, including those described herein. Specific illustrative and exemplary embodiments for measuring binding affinity are described in the following.

"Binds specifically" or "specific binding" refers to binding of an antibody to an antigen with an affinity value of no more than about $1 \times 10^{-7}$ M.

"Affinity matured" antibody refers to an antibody with one or more alterations in one or more HVRs, compared to a parent antibody which does not possess such alterations, such alterations resulting in an improvement in the affinity of the antibody for antigen.

"Functional antigen binding site" of an antibody is one which is capable of binding a target antigen. The antigen binding affinity of the antigen binding site is not necessarily as strong as the parent antibody from which the antigen binding site is derived, but the ability to bind antigen must be measurable using any one of a variety of methods known for evaluating antibody binding to an antigen.

"Isolated antibody" refers to an antibody which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic methods (e.g., ion exchange or reverse phase HPLC). For review of methods for assessment of antibody purity, see, e.g., Flatman et al., *J. Chromatogr. B Analyt. Technol Biomed Life Sci*, 848:79-87.

"Substantially similar" or "substantially the same," as used herein, refers to a sufficiently high degree of similarity between two numeric values (for example, one associated with a test antibody and the other associated with a reference antibody), such that one of skill in the art would consider the difference between the two values to be of little or no biological and/or statistical significance within the context of the biological characteristic measured by said values (e.g., $K_D$ values).

"Substantially different," as used herein, refers to a sufficiently high degree of difference between two numeric values (generally one associated with a molecule and the other associated with a reference molecule) such that one of skill in the art would consider the difference between the two values to be of statistical significance within the context of the biological characteristic measured by said values (e.g., $K_D$ values).

"Effector functions" refer to those biological activities attributable to the Fc region of an antibody, which vary with the antibody isotype. Examples of antibody effector functions include: Clq binding and complement dependent cytotoxicity (CDC); Fc receptor binding; antibody-dependent cell-mediated cytotoxicity (ADCC); phagocytosis; down regulation of cell surface receptors (e.g., B cell receptor); and B cell activation.

"Immunoconjugate" refers to an antibody conjugated to one or more heterologous molecule(s), including but not limited to a cytotoxic agent.

"Treatment," "treat" or "treating" refers to clinical intervention in an attempt to alter the natural course of a disorder in the individual being treated and can be performed either for prophylaxis or during the course of clinical pathology. Desired results of treatment can include, but are not limited to, preventing occurrence or recurrence of the disorder, alleviation of symptoms, diminishment of any direct or indirect pathological consequences of the disorder, preventing metastasis, decreasing the rate of progression, amelioration or palliation of a disease state, and remission or improved prognosis. For example, treatment can include administration of a therapeutically effective amount of pharmaceutical formulation comprising an anti-IL1RAP antibody to a subject to delay development or slow progression of a disease or condition mediated by IL1RAP.

"Pharmaceutical formulation" refers to a preparation in a form that allows the biological activity of the active ingredient(s) to be effective, and which contain no additional components which are toxic to the subjects to which the formulation is administered.

"Pharmaceutically acceptable carrier" refers to an ingredient in a pharmaceutical formulation, other than an active ingredient, which is nontoxic to the subject to whom it is administered. A pharmaceutically acceptable carrier includes, but is not limited to, a buffer, excipient, stabilizer, or preservative.

"Therapeutically effective amount" refers to the amount of an active ingredient or agent (e.g., a pharmaceutical formulation) to achieve a desired therapeutic or prophylactic result, e.g., to treat or prevent a disease, disorder, or condition in a subject. In the case of a IL1RAP mediated disease or condition, the therapeutically effective amount of the therapeutic agent is an amount that reduces, prevents, inhibits, and/or relieves to some extent one or more of the symptoms associated with the disease, disorder, or condition. For asthma therapy, efficacy in vivo can, for example, be measured by assessing the duration, severity, and/or recurrence of symptoms, the response rate (RR), duration of response, and/or quality of life.

"Concurrently," as used herein to, refers to administration of two or more therapeutic agents, where at least part of the administration overlaps in time. Accordingly, concurrent administration includes a dosing regimen when the administration of one or more agent(s) continues after discontinuing the administration of one or more other agent(s).

"Individual" or "subject" refers to a mammal, including but not limited to, domesticated animals (e.g., cows, sheep, cats, dogs, and horses), primates (e.g., humans and non-human primates such as monkeys), rabbits, and rodents (e.g., mice and rats).

Detailed Description of Various Embodiments

I. The IL-1 Family of Cytokines

The IL-1 family comprises a number of agonist cytokines, including IL-1α, IL-1β, IL-33, IL-36α, IL-36β, and IL-36γ, that serve as pathogenic mediators and regulators of immunity, cell proliferation, and inflammation. The binding of each such cytokine to its respective cognate cell membrane receptor results in the recruitment of the IL1RAP co-receptor and the formation of a signaling complex that triggers intracellular signal transduction.

For example, IL-1α acts as an agonist cytokine, initiating intracellular signaling through its binding to its cognate receptor, IL1R1. Upon binding of IL-1α to IL1R1, the co-receptor accessory protein IL1RAP is recruited and engaged to form a ternary signaling complex comprising IL-1α, IL1R1, and IL1RAP. Signal transduction stimulated by IL-1 alpha leads to activation of the nuclear factor kappa B (NF-κB) transcription factor pathway and mitogen-activated protein kinase (MAPK) pathways in target cells and triggers a cascade of pathogenic inflammatory, cell proliferative, and immune responses. The ensuing signaling cascade results in the expression of several proteins associated with pathogenic inflammatory, cell proliferative, and immune responses. See, e.g., Garlanda et al., *Immunity,* 39:1003-1018 (2013).

Similarly, IL-1β acts as an agonist cytokine, initiating intracellular signaling by binding to its cognate receptor, IL1R1. Upon binding of IL-1β to IL1R1, co-receptor IL1RAP is recruited and engaged, resulting in the formation of a ternary signaling complex comprising IL-1β, IL1R1, and IL1RAP. Signal transduction mediated by IL-1β results in activation of the NF-κB transcription factor pathway and mitogen-activated protein kinase pathway in target cells, which precipitates a signaling cascade resulting in the expression a number of proteins associated with pathogenic inflammatory, cell proliferative, and immune responses. See, e.g., Wang et al., *Nature Immunol.,* 11(1):905-912 (2010); Saluja et al., *Clin. Transl. Allergy,* 5:33 (2015).

The agonist cytokine IL-33 mediates its functional intracellular signaling effects by binding to its cognate receptor ST2 (also known as IL1RL1), which is followed by subsequent recruitment and engagement of co-receptor IL1RAP to form a ternary signaling complex comprising IL-33, ST2, and IL1RAP. Signal transduction mediated by IL-33 leads to the activation of the NF-κB transcription factor pathway and AP-1 pathway and produces a range of immune and inflammatory responses. See, e.g., Sebastian Gunther et al., *Immunity,* 47:510-523 (2017). The signaling cascade results in the expression a number of proteins associated with pathogenic inflammatory, cell proliferative, and immune responses. Shafaqat Ali et al., *PNAS,* 104(47):18660-18665 (2007).

Each of the agonist cytokines IL-36α, IL-36β, and IL-36γ induces intracellular signaling by binding to the cognate receptor, IL1RL2. Binding by any of these IL-36 cytokines to IL1RL2 causes recruitment and engagement of co-receptor IL1RAP, resulting in the formation of a ternary signaling complex comprising IL1RL2, IL1RAP, and the respective IL-36 cytokine that initiated the signaling event. Signal transduction stimulated by IL-36α, IL-36β, or IL-36γ leads to activation of the NK-κB transcription factor and AP-1 pathways in target cells and induces various inflammatory, proliferative, and pathogenic immune responses. See, e.g., Jennifer Towne et al., *J. Biol. Chem.,* 279(14):13677-13688 (2004); Sebastian Gunther et al., *J. Immunol.,* 193(2):921-930 (2014).

II. IL1RAP

IL1RAP is a membrane protein expressed on the surface of certain cells. The sequence and annotation of human IL1RAP (also referred to herein as "hu-IL1RAP") can be found with the GenBank Accession No. AAB84059.1 or UniProt entry Q9NPH3. The amino acid sequence of the full-length hu-IL1RAP precursor protein is set forth herein as SEQ ID NO: 1. An exemplary 1740 nucleotide sequence encoding the full-length hu-IL1RAP is set forth herein as SEQ ID NO: 2.

The amino acid sequence of full-length hu-IL1RAP comprises in consecutive order a signal peptide, extracellular domain, transmembrane domain, and cytoplasmic domain. The signal sequence comprises amino acids 1-20 of SEQ ID NO: 1. The mature form of hu-IL1RAP comprises amino acids 21-570 of SEQ ID NO: 1. The extracellular domain of hu-IL1RAP comprises amino acids 21-367 of SEQ ID NO: 1. The extracellular domain of hu-IL1RAP further comprises three distinct domains. Domain 1 ("D1") comprises amino acids 21-133 of SEQ ID NO: 1. Domain 2 ("D2") comprises amino acids 134-237 of SEQ ID NO: 1. Domain 3 ("D3") comprises amino acids 238-367 of SEQ ID NO: 1. The transmembrane domain and cytoplasmic domain of hu-IL1RAP comprise amino acids 368-388, and amino acids 389-570, respectively, of SEQ ID NO: 1.

Polypeptide constructs corresponding to portions of the full-length hu-IL1RAP protein can be used as antigens to elicit anti-IL1RAP antibodies with high binding affinity. As disclosed elsewhere herein, these anti-IL1RAP antibodies are capable of decreasing intracellular signals initiated by binding of one or more of IL-1α, IL-1β, IL-33, IL-36α, IL-36β, and IL-36γ to its cognate receptor. The polypeptide constructs corresponding to portions of hu-IL1RAP protein useful as antigens include polypeptides corresponding to the extracellular domain, and the domains D1, D2, D1+D2, and D3, of the hu-IL1RAP.

Table 1 below provides a summary description of the sequences of the hu-IL1RAP polypeptide constructs of the present disclosure, and their sequence identifiers. Additionally, abbreviated polypeptide constructs corresponding to the mouse and cynomolgus monkey IL1RAP proteins are provided, as these are useful in determining cross-reactivity of the anti-hu-IL1RAP antibodies. The sequences also are included in the accompanying Sequence Listing.

TABLE 1

IL1RAP construct sequences

| Description | Sequence | SEQ ID NO: |
|---|---|---|
| hu-IL1RAP (aa) (GenBank Acc. No. AAB84059.1) | MTLLWCVVSLYFYGILQSDASERCDDWGLDTMRQIQVFEDEPARI KCPLFEHFLKFNYSTAHSAGLTLIWYWTRQDRDLEEPINFRLPEN RISKEKDVLWFRPTLLNDTGNYTCMLRNTTYCSKVAFPLEVVQKD SCFNSPMKLPVHKLYIEYGIQRITCPNVDGYFPSSVKPTITWYMG CYKIQNFNNVIPEGMNLSFLIALISNNGNYTCVVTYPENGRTFHL TRTLTVKVVGSPKNAVPPVIHSPNDHVVYEKEPGEELLIPCTVYF SFLMDSRNEVWWTIDGKKPDDITIDVTINESISHSRTEDETRTQI LSIKKVTSEDLKRSYVCHARSAKGEVAKAAKVKQKVPAPRYTVEL ACGFGATVLLVVILIVVYHVYWLEMVLFYRAHFGTDETILDGKEY DIYVSYARNAEEEEFVLLTLRGVLENEFGYKLCIFDRDSLPGGIV TDETLSFIQKSRRLLVVLSPNYVLQGTQALLELKAGLENMASRGN INVILVQYKAVKETKVKELKRAKTVLTVIKWKGEKSKYPQGRFWK QLQVAMPVKKSPRRSSSDEQGLSYSSLKNV | 1 |
| hu-IL1RAP (nt) (GenBank Acc. No. AF029213.1) | TCTCAAAGGATGACACTTCTGTGGTGTGTAGTGAGTCTCTACTTT TATGGAATCCTGCAAAGTGATGCCTCAGAACGCTGCGATGACTGG GGACTAGACACCATGAGGCAAATCCAAGTGTTTGAAGATGAGCCA GCTCGCATCAAGTGCCCACTCTTTGAACACTTCTTGAAATTCAAC TACAGCACAGCCCATTCAGCTGGCCTTACTCTGATCTGGTATTGG ACTAGGCAGGACCGGGACCTTGAGGAGCCAATTAACTTCCGCCTC CCCGAGAACCGCATTAGTAAGGAGAAAGATGTGCTGTGGTTCCGG CCCACTCTCCTCAATGACACTGGCAACTATACCTGCATGTTAAGG AACACTACATATTGCAGCAAAGTTGCATTTCCCTTGGAAGTTGTT CAAAAAGACAGCTGTTTCAATTCCCCCATGAAACTCCCAGTGCAT AAACTGTATATAGAATATGGCATTCAGAGGATCACTTGTCCAAAT GTAGATGGATATTTTCCTTCCAGTGTCAAACCGACTATCACTTGG TATATGGGCTGTTATAAAATACAGAATTTTAATAATGTAATACCC GAAGGTATGAACTTGAGTTTCCTCATTGCCTTAATTTCAAATAAT GGAAATTACACATGTGTTGTTACATATCCAGAAAATGGACGTACG TTTCATCTCACCAGGACTCTGACTGTAAAGGTAGTAGGCTCTCCA AAAAATGCAGTGCCCCCTGTGATCCATTCACCTAATGATCATGTG GTCTATGAGAAAGAACCAGGAGAGGAGCTACTCATTCCCTGTACG GTCTATTTTAGTTTTCTGATGGATTCTCGCAATGAGGTTTGGTGG ACCATTGATGGAAAAAAACCTGATGACATCACTATTGATGTCACC ATTAACGAAAGTATAAGTCATAGTAGAACAGAAGATGAAACAAGA ACTCAGATTTTGAGCATCAAGAAAGTTACCTCTGAGGATCTCAAG CGCAGCTATGTCTGTCATGCTAGAAGTGCCAAAGGCGAAGTTGCC AAAGCAGCCAAGGTGAAGCAGAAAGTGCCAGCTCCAAGATACACA GTGGAACTGGCTTGTGGTTTTGGAGCCACAGTCCTGCTAGTGGTG ATTCTCATTGTTGTTTACCATGTTTACTGGCTAGAGATGGTCCTA TTTTACCGGGCTCATTTTGGAACAGATGAAACCATTTTAGATGGA AAAGAGTATGATATTTATGTATCCTATGCAAGGAATGCGGAAGAA GAAGAATTTGTATTACTGACCCTCCGTGGAGTTTTGGAGAATGAA TTTGGATACAAGCTGTGCATCTTTGACCGAGACAGTCTGCCTGGG GGAATTGTCACAGATGAGACTTTGAGCTTCATTCAGAAAAGCAGA CGCCTCCTGGTTGTTCTAAGCCCCAACTACGTGCTCCAGGGAACC CAAGCCCTCCTGGAGCTCAAGGCTGGCCTAGAAAATATGGCCTCT CGGGGCAACATCAACGTCATTTTAGTACAGTACAAAGCTGTGAAG GAAACGAAGGTGAAAGAGCTGAAGAGGGCTAAGACGGTGCTCACG GTCATTAAATGGAAAGGGGAAAAATCCAAGTATCCACAGGGCAGG TTCTGGAAGCAGCTGCAGGTGGCCATGCCAGTGAAGAAAAGTCCC AGGCGGTCTAGCAGTGATGAGCAGGGCCTCTCGTATTCATCTTTG AAAAATGTATGAAAGGAATAATGAAAAGGA | 2 |
| hu-M-IL1RAP construct, positions S21-1367 | SERCDDWGLDTMRQIQVFEDEPARIKCPLFEHFLKFNYSTAHSAG LTLIWYWTRQDRDLEEPINFRLPENRISKEKDVLWFRPTLLNDTG NYTCMLRNTTYCSKVAFPLEVVQKDSCFNSPMKLPVHKLYIEYGI QRITCPNVDGYFPSSVKPTITWYMGCYKIQNFNNVIPEGMNLSFL TALISNNGNYTCVVTYPENGRTFHLTRTLTVKVVGSPKNAVPPVI HSPNDHVVYEKEPGEELLIPCTVYFSFLMDSRNEVWWTIDGKKPD DITIDVTINESISHSRTEDETRTQILSIKKVTSEDLKRSYVCHAR SAKGEVAKAAKVKQKVPAPRYTVELACGFGAT | 3 |
| hu-M-IL1RAP-D1 construct, positions S21-Q133 | SERCDDWGLDTMRQIQVFEDEPARIKCPLFEHFLKFNYSTAHSAG LTLIWYWTRQDRDLEEPINFRLPENRISKEKDVLWFRPTLLNDTG NYTCMLRNTTYCSKVAFPLEVVQ | 4 |
| hu-M-IL1RAP-D1D2 construct, positions S21-P237 | SERCDDWGLDTMRQIQVFEDEPARIKCPLFEHFLKFNYSTAHSAG LTLIWYWTRQDRDLEEPINFRLPENRISKEKDVLWFRPTLLNDTG NYTCMLRNTTYCSKVAFPLEVVQKDSCFNSPMKLPVHKLYIEYGI QRITCPNVDGYFPSSVKPTITWYMGCYKIQNFNNVIPEGMNLSFL TALISNNGNYTCVVTYPENGRTFHLTRTLTVKVVGSP | 5 |

TABLE 1-continued

IL1RAP construct sequences

| Description | Sequence | SEQ ID NO: |
|---|---|---|
| hu-M-IL1RAP-D3 construct, positions K238-T367 | KNAVPPVIHSPNDHVVYEKEPGEELLIPCTVYFSFLMDSRNEVWW TIDGKKPDDITIDVTINESISHSRTEDETRTQILSIKKVTSEDLK RSYVCHARSAKGEVAKAAKVKQKVPAPRYTVELACGFGAT | 6 |
| hu-S-IL1RAP construct, positions S21-Q356 | SERCDDWGLDTMRQIQVFEDEPARIKCPLFEHFLKFNYSTAHSAG LTLIWYWTRQDRDLEEPINFRLPENRISKEKDVLWFRPTLLNDTG NYTCMLRNTTYCSKVAFPLEVVQKDSCFNSPMKLPVHKLYIEYGI QRITCPNVDGYFPSSVKPTITWYMGCYKIQNFNNVIPEGMNLSFL TALISNNGNYTCVVTYPENGRTFHLTRTLTVKVVGSPKNAVPPVI HSPNDHVVYEKEPGEELLIPCTVYFSFLMDSRNEVWWTIDGKKPD DITIDVTINESISHSRTEDETRTQILSIKKVTSEDLKRSYVCHAR SAKGEVAKAAKVKQKGNRCGQ | 7 |
| cyno-M-IL1RAP construct, positions S21-I367 | SERCDDWGLDTMRQIQVFEDEPARIKCPLFEHFLKFNYSTAHSAG LTLIWYWTRQDRDLEEPINFRLPENRISKEKDVLWFRPTLLNDTG NYTCMLRNTTYCSKVAFPLEVVQKDSCFNSPMKLPVHKLYIEYGI QRITCPNVDGYFPSSVKPTITWYMGCYKIQNFNNVIPEGMNLSFL TAFTSNNGNYTCVVTYPENGRTFHLTRTLTVKVVGSPKNAVPPVI HSPNDHVVYEKEPGEELLIPCTVYFSFLMDSRNEVWWTIDGKKPD DIPIDVTINESISHSRTEDETRTQILSIKKVTSEDLKRSYVCHAR SAKGEVAKAATVKQKVPAPRYTVELACGFGAT | 8 |
| mu-M-IL1RAP construct, positions S21-T367 | SERCDDWGLDTMRQIQVFEDEPARIKCPLFEHFLKYNYSTAHSSG LTLIWYWTRQDRDLEEPINFRLPENRISKEKDVLWFRPTLLNDTG NYTCMLRNTTYCSKVAFPLEVVQKDSCFNSAMRFPVHKMYIEHGI HKITCPNVDGYFPSSVKPSVTWYKGCTEIVDFHNVLPEGMNLSFF IPLVSNNGNYTCVVTYPENGRLFHLTRTVTVKVVGSPKDALPPQI YSPNDRVVYEKEPGEELVIPCKVYFSFIMDSHNEVWWTIDGKKPD DVTVDITINESVSYSSTEDETRTQILSIKKVTPEDLRRNYVCHAR NTKGEAEQAAKVKQKVIPPRYTVELACGFGAT | 9 |
| mu-M-IL1RAP-D3 construct, positions K239-T368 | KDALPPQIYSPNDRVVYEKEPGEELVIPCKVYFSFIMDSHNEVWW TIDGKKPDDVTVDITINESVSYSSTEDETRTQILSIKKVTPEDLR RNYVCHARNTKGEAEQAAKVKQKVIPPRYTVELACGFGAT | 337 |
| mu-M-IL1RAP-D1D2 construct, positions S21-P237 | SERCDDWGLDTMRQIQVFEDEPARIKCPLFEHFLKYNYSTAHSSG LTLIWYWTRQDRDLEEPINFRLPENRISKEKDVLWFRPTLLNDTG NYTCMLRNTTYCSKVAFPLEVVQKDSCFNSAMRFPVHKMYIEHGI HKITCPNVDGYFPSSVKPSVTWYKGCTEIVDFHNVLPEGMNLSFF IPLVSNNGNYTCVVTYPENGRLFHLTRTVTVKVVGSP | 338 |

III. Anti-IL1RAP Antibodies

In some embodiments, the present disclosure provides structures of anti-IL1RAP antibodies in terms on the amino acid and encoding nucleotide sequences of the various well-known immunoglobulin features (e.g., CDRs, HVRs, FRs, $V_H$, and $V_L$ domains). Table 2 below provides a summary description of the anti-IL1RAP antibody sequences of the present disclosure, and their sequence identifiers. The sequences are included in the accompanying Sequence Listing.

TABLE 2

Anti-IL1RAP antibody sequences

| Description[1] | Sequence | SEQ ID NO: |
|---|---|---|
| CDR-L1-generic | RASENIXXNXX X at 7 is Y or W; X at 8 is S, H, K, L, M, N, Q, R, or Y; X at 10 is L, A, G, I, M, N, Q, S, T, V, or Y; X at 11 is A, G, N, S, or T | 10 |
| CDR-L1-wild-type | RASENIYSNLA | 11 |
| CDR-L1-Y30F | RASENIFSNLA | 12 |
| CDR-L1-Y30W | RASENIWSNLA | 13 |
| CDR-L1-S31H | RASENIYHNLA | 14 |
| CDR-L1-S31K | RASENIYKNLA | 15 |

TABLE 2-continued

Anti-IL1RAP antibody sequences

| Description[1] | Sequence | SEQ ID NO: |
|---|---|---|
| CDR-L1-S31L | RASENIYLNLA | 16 |
| CDR-L1-S31M | RASENIYMNLA | 17 |
| CDR-L1-S31N | RASENIYNNLA | 18 |
| CDR-L1-S31Q | RASENIYQNLA | 19 |
| CDR-L1-S31R | RASENIYRNLA | 20 |
| CDR-L1-S31Y | RASENIYYNLA | 21 |
| CDR-L1-L33A | RASENIYSNAA | 22 |
| CDR-L1-L33G | RASENIYSNGA | 23 |
| CDR-L1-L33I | RASENIYSNIA | 24 |
| CDR-L1-L33M | RASENIYSNMA | 25 |
| CDR-L1-L33N | RASENIYSNNA | 26 |
| CDR-L1-L33Q | RASENIYSNQA | 27 |
| CDR-L1-L33S | RASENIYSNSA | 28 |
| CDR-L1-L33T | RASENIYSNTA | 29 |
| CDR-L1-L33V | RASENIYSNVA | 30 |
| CDR-L1-L33Y | RASENIYSNYA | 31 |
| CDR-L1-A34G | RASENIYSNLG | 32 |
| CDR-L1-A34N | RASENIYSNLN | 33 |
| CDR-L1-A34S | RASENIYSNLS | 34 |
| CDR-L1-A34T | RASENIYSNLT | 35 |
| CDR-L2-generic | GXXNXAD<br>X at 2 is A, D, E, F, G, H, I, K, L, M, N, Q, R, S, T, V, W, or Y; X at 3 is K, G, or N; X at 5 is L, F, H, W, or Y | 36 |
| CDR-L2-wild-type | GAKNLAD | 37 |
| CDR-L2-A51D | GDKNLAD | 38 |
| CDR-L2-A51E | GEKNLAD | 39 |
| CDR-L2-A51F | GFKNLAD | 40 |
| CDR-L2-A51G | GGKNLAD | 41 |
| CDR-L2-A51H | GHKNLAD | 42 |
| CDR-L2-A51I | GIKNLAD | 43 |
| CDR-L2-A51K | GKKNLAD | 44 |
| CDR-L2-A51L | GLKNLAD | 45 |
| CDR-L2-A51M | GMKNLAD | 46 |
| CDR-L2-A51N | GNKNLAD | 47 |
| CDR-L2-A51Q | GQKNLAD | 48 |
| CDR-L2-A51R | GRKNLAD | 49 |
| CDR-L2-A51S | GSKNLAD | 50 |
| CDR-L2-A51T | GTKNLAD | 51 |

TABLE 2-continued

Anti-IL1RAP antibody sequences

| Description[1] | Sequence | SEQ ID NO: |
|---|---|---|
| CDR-L2-A51V | GVKNLAD | 52 |
| CDR-L2-A51W | GWKNLAD | 53 |
| CDR-L2-A51Y | GYKNLAD | 54 |
| CDR-L2-K52G | GAGNLAD | 55 |
| CDR-L2-K52N | GANNLAD | 56 |
| CDR-L2-L54F | GAKNFAD | 57 |
| CDR-L2-L54H | GAKNHAD | 58 |
| CDR-L2-L54W | GAKNWAD | 59 |
| CDR-L2-L54Y | GAKNYAD | 60 |
| CDR-L2-A51R/K52G | GRGNLAD | 61 |
| CDR-L3-generic | XXFXTXPRT<br>X at 1 is Q or S; X at 2 is H or S; X at 4 is W, A, F, G, H, I, K, L, M, V, or Y; X at 6 is T, I, or V | 62 |
| CDR-L3-wild-type | QHFWTTPRT | 63 |
| CDR-L3-Q89S | SHFWTTPRT | 64 |
| CDR-L3-H90S | QSFWTTPRT | 65 |
| CDR-L3-W92A | QHFATTPRT | 66 |
| CDR-L3-W92F | QHFFTTPRT | 67 |
| CDR-L3-W92G | QHFGTTPRT | 68 |
| CDR-L3-W92I | QHFITTPRT | 69 |
| CDR-L3-W92K | QHFKTTPRT | 70 |
| CDR-L3-W92L | QHFLTTPRT | 71 |
| CDR-L3-W92M | QHFMTTPRT | 72 |
| CDR-L3-W92V | QHFVTTPRT | 73 |
| CDR-L3-W92Y | QHFYTTPRT | 74 |
| CDR-L3-I94I | QHFWTIPRT | 75 |
| CDR-L3 T94V | QHFWTVPRT | 76 |
| HVR-H1-generic | XXXXXXX<br>X at 1 is F, A, D, E, G, H, I, K, M, N, P, Q, R, S, T, W, or Y; X at 2 is S, E, G, K, P, Q, R, or T; X at 3 is N, D, E, G, K, Q, or R; X at 4 is Y, A, D, E, H, S, or V; X at 5 is A, N, or S; X at 6 is M, V, or W; X at 7 is S, or G | 77 |
| HVR-H1-wild-type | FSNYAMS | 78 |
| HVR-H1-F29A | ASNYAMS | 79 |
| HVR-H1-F29D | DSNYAMS | 80 |
| HVR-H1-F29E | ESNYAMS | 81 |
| HVR-H1-F29G | GSNYAMS | 82 |

TABLE 2-continued

Anti-IL1RAP antibody sequences

| Description[1] | Sequence | SEQ ID NO: |
|---|---|---|
| HVR-H1-F29H | HSNYAMS | 83 |
| HVR-H1-F29I | ISNYAMS | 84 |
| HVR-H1-F29K | KSNYAMS | 85 |
| HVR-H1-F29L | LSNYAMS | 86 |
| HVR-H1-F29M | MSNYAMS | 87 |
| HVR-H1-F29N | NSNYAMS | 88 |
| HVR-H1-F29P | PSNYAMS | 89 |
| HVR-H1-F29Q | QSNYAMS | 90 |
| HVR-H1-F29R | RSNYAMS | 91 |
| HVR-H1-F29S | SSNYAMS | 92 |
| HVR-H1-F29T | TSNYAMS | 93 |
| HVR-H1-F29V | VSNYAMS | 94 |
| HVR-H1-F29W | WSNYAMS | 95 |
| HVR-H1-F29Y | YSNYAMS | 96 |
| HVR-H1-S30E | FENYAMS | 97 |
| HVR-H1-S30G | FGNYAMS | 98 |
| HVR-H1-S30K | FKNYAMS | 99 |
| HVR-H1-S30P | FPNYAMS | 100 |
| HVR-H1-S30Q | FQNYAMS | 101 |
| HVR-H1-S30R | FRNYAMS | 102 |
| HVR-H1-S30T | FTNYAMS | 103 |
| HVR-H1-N31D | FSDYAMS | 104 |
| HVR-H1-N31E | FSEYAMS | 105 |
| HVR-H1-N31G | FSGYAMS | 106 |
| HVR-H1-N31K | FSKYAMS | 107 |
| HVR-H1-N31Q | FSQYAMS | 108 |
| HVR-H1-N31R | FSRYAMS | 109 |
| HVR-H1-Y32A | FSNAAMS | 110 |
| HVR-H1-Y32D | FSNDAMS | 111 |
| HVR-H1-Y32E | FSNEAMS | 112 |
| HVR-H1-Y32H | FSNHAMS | 113 |
| HVR-H1-Y32S | FSNSAMS | 114 |
| HVR-H1-Y32V | FSNVAMS | 115 |
| HVR-H1-A33N | FSNYNMS | 116 |
| HVR-H1-A33S | FSNYSMS | 117 |
| HVR-H1-M34V | FSNYAVS | 118 |
| HVR-H1-M34W | FSNYAWS | 119 |

TABLE 2-continued

Anti-IL1RAP antibody sequences

| Description[1] | Sequence | SEQ ID NO: |
|---|---|---|
| HVR-H1-S35G | FSNYAMG | 120 |
| CDR-H1-generic | XXXXX<br>X at 1 is N, D, E, G, K, Q, or R; X at 2 is Y, A, D, E, H, S, or V; X at 3 is A, N, or S; X at 4 is M, V, or W; X at 5 is S, or G | 121 |
| CDR-H1-wild-type | NYAMS | 122 |
| CDR-H1-N31D | DYAMS | 123 |
| CDR-H1-N31E | EYAMS | 124 |
| CDR-H1-N31G | GYAMS | 125 |
| CDR-H1-N31K | KYAMS | 126 |
| CDR-H1-N31Q | QYAMS | 127 |
| CDR-H1-N31R | RYAMS | 128 |
| CDR-H1-Y32A | NAAMS | 129 |
| CDR-H1-Y32D | NDAMS | 130 |
| CDR-H1-Y32E | NEAMS | 131 |
| CDR-H1-Y32H | NHAMS | 132 |
| CDR-H1-Y32S | NSAMS | 133 |
| CDR-H1-Y32V | NVAMS | 134 |
| CDR-H1-A33N | NYNMS | 135 |
| CDR-H1-A33S | NYSMS | 136 |
| CDR-H1-M34V | NYAVS | 137 |
| CDR-H1-M34W | NYAWS | 138 |
| CDR-H1-S35G | NYAMG | 139 |
| CDR-H2-generic | TXXXXXXXXYXLXDVKG<br>X at 2 is V, A, N, or S; X at 3 is T or S; X at 4 is E, D, N, T, or V; X at 5 is G, I, P, T, or V; X at 6 is G, D, E, F, H, I, K, L, M, N, P, Q, R, T, V, W, or Y; X at 7 is D, A, E, G, H, K, N, P, Q, R, or S; X at 8 is Y or W; X at 9 is N, A, G, P, or R; X at 11 is C, A, D, F, R, S, T, V, or Y; X at 13 is D, S, or W | 140 |
| CDR-H2-wild-type | TVTEGGDYNYCLDDVKG | 141 |
| CDR-H2-V51A | TATEGGDYNYCLDDVKG | 142 |
| CDR-H2-V51N | TNTEGGDYNYCLDDVKG | 143 |
| CDR-H2-V51S | TSTEGGDYNYCLDDVKG | 144 |
| CDR-H2-T52S | TVSEGGDYNYCLDDVKG | 145 |
| CDR-H2-E52aD | TVTDGGDYNYCLDDVKG | 146 |
| CDR-H2-E52aN | TVTNGGDYNYCLDDVKG | 147 |
| CDR-H2-E52aT | TVTTGGDYNYCLDDVKG | 148 |
| CDR-H2-E52aV | TVTVGGDYNYCLDDVKG | 149 |
| CDR-H2-G53I | TVTEIGDYNYCLDDVKG | 150 |
| CDR-H2-G53P | TVTEPGDYNYCLDDVKG | 151 |

TABLE 2-continued

Anti-IL1RAP antibody sequences

| Description[1] | Sequence | SEQ ID NO: |
|---|---|---|
| CDR-H2-G53T | TVTETGDYNYCLDDVKG | 152 |
| CDR-H2-G53V | TVTEVGDYNYCLDDVKG | 153 |
| CDR-H2-G54D | TVTEGDDYNYCLDDVKG | 154 |
| CDR-H2-G54E | TVTEGEDYNYCLDDVKG | 155 |
| CDR-H2-G54F | TVTEGFDYNYCLDDVKG | 156 |
| CDR-H2-G54H | TVTEGHDYNYCLDDVKG | 157 |
| CDR-H2-G54I | TVTEGIDYNYCLDDVKG | 158 |
| CDR-H2-G54K | TVTEGKDYNYCLDDVKG | 159 |
| CDR-H2-G54L | TVTEGLDYNYCLDDVKG | 160 |
| CDR-H2-G54M | TVTEGMDYNYCLDDVKG | 161 |
| CDR-H2-G54N | TVTEGNDYNYCLDDVKG | 162 |
| CDR-H2-G54P | TVTEGPDYNYCLDDVKG | 163 |
| CDR-H2-G54Q | TVTEGQDYNYCLDDVKG | 164 |
| CDR-H2-G54R | TVTEGRDYNYCLDDVKG | 165 |
| CDR-H2-G54T | TVTEGTDYNYCLDDVKG | 166 |
| CDR-H2-G54V | TVTEGVDYNYCLDDVKG | 167 |
| CDR-H2-G54W | TVTEGWDYNYCLDDVKG | 168 |
| CDR-H2-G54Y | TVTEGYDYNYCLDDVKG | 169 |
| CDR-H2-D55A | TVTEGGAYNYCLDDVKG | 170 |
| CDR-H2-D55E | TVTEGGEYNYCLDDVKG | 171 |
| CDR-H2-D55G | TVTEGGGYNYCLDDVKG | 172 |
| CDR-H2-D55H | TVTEGGHYNYCLDDVKG | 173 |
| CDR-H2-D55K | TVTEGGKYNYCLDDVKG | 174 |
| CDR-H2-D55N | TVTEGGNYNYCLDDVKG | 175 |
| CDR-H2-D55Q | TVTEGGQYNYCLDDVKG | 176 |
| CDR-H2-D55P | TVTEGGPYNYCLDDVKG | 177 |
| CDR-H2-D55R | TVTEGGRYNYCLDDVKG | 178 |
| CDR-H2-D55S | TVTEGGSYNYCLDDVKG | 179 |
| CDR-H2-N57A | TVTEGGDYAYCLDDVKG | 180 |
| CDR-H2-N57G | TVTEGGDYGYCLDDVKG | 181 |
| CDR-H2-N57P | TVTEGGDYPYCLDDVKG | 182 |
| CDR-H2-N57R | TVTEGGDYRYCLDDVKG | 183 |
| CDR-H2-C59A | TVTEGGDYNYALDDVKG | 184 |
| CDR-H2-C59D | TVTEGGDYNYDLDDVKG | 185 |
| CDR-H2-C59F | TVTEGGDYNYFLDDVKG | 186 |
| CDR-H2-C59R | TVTEGGDYNYRLDDVKG | 187 |
| CDR-H2-C59S | TVTEGGDYNYSLDDVKG | 188 |

TABLE 2-continued

Anti-IL1RAP antibody sequences

| Description¹ | Sequence | SEQ ID NO: |
|---|---|---|
| CDR-H2-C59T | TVTEGGDYNYTLDDVKG | 189 |
| CDR-H2-C59V | TVTEGGDYNYVLDDVKG | 190 |
| CDR-H2-C59Y | TVTEGGDYNYYLDDVKG | 191 |
| CDR-H2-D61S | TVTEGGDYNYCLSDVKG | 192 |
| CDR-H2-D61W | TVTEGGDYNYCLWDVKG | 193 |
| CDR-H2-V51S/G54H | TSTEGHDYNYCLDDVKG | 194 |
| CDR-H2-V51S/C59Y | TSTEGGDYNYYLDDVKG | 195 |
| CDR-H2-E52aV/C59Y | TVTVGGDYNYYLDDVKG | 196 |
| CDR-H2-G54H/C59Y | TVTEGHDYNYYLDDVKG | 197 |
| CDR-H2-G54V/C59Y | TVTEGVDYNYYLDDVKG | 198 |
| CDR-H2-D55G/C59Y | TVTEGGGYNYYLDDVKG | 199 |
| CDR-H2-N57G/C59Y | TVTEGGDYGYYLDDVKG | 200 |
| CDR-H2-V51S/G54H/C59Y | TSTEGHDYNYYLDDVKG | 201 |
| HVR-H3-generic | XXDXXPYFXDY<br>X at 1 is A, G, S, or T; X at 2 is H, I, L, M, N, Q, or V; X at 4 is R, A, D, E, I, M, N, Q, or S; X at 5 is W, or F; X at 9 is F, L, M, or W | 202 |
| HVR-H3-wild-type | ARDRWPYFFDY | 203 |
| HVR-H3-A93G | GRDRWPYFFDY | 204 |
| HVR-H3-A93S | SRDRWPYFFDY | 205 |
| HVR-H3-A93T | TRDRWPYFFDY | 206 |
| HVR-H3-R94H | AHDRWPYFFDY | 207 |
| HVR-H3-R94I | AIDRWPYFFDY | 208 |
| HVR-H3-R94L | ALDRWPYFFDY | 209 |
| HVR-H3-R94M | AMDRWPYFFDY | 210 |
| HVR-H3-R94N | ANDRWPYFFDY | 211 |
| HVR-H3-R94Q | AQDRWPYFFDY | 212 |
| HVR-H3-R94V | AVDRWPYFFDY | 213 |
| HVR-H3-R96A | ARDAWPYFFDY | 214 |
| HVR-H3-R96D | ARDDWPYFFDY | 215 |
| HVR-H3-R96E | ARDEWPYFFDY | 216 |
| HVR-H3-R96I | ARDIWPYFFDY | 217 |
| HVR-H3-R96M | ARDMWPYFFDY | 218 |
| HVR-H3-R96N | ARDNWPYFFDY | 219 |

TABLE 2-continued

Anti-IL1RAP antibody sequences

| Description[1] | Sequence | SEQ ID NO: |
|---|---|---|
| HVR-H3-R96Q | ARDQWPYFFDY | 220 |
| HVR-H3-R96S | ARDSWPYFFDY | 221 |
| HVR-H3-W97F | ARDRFPYFFDY | 222 |
| HVR-H3-F100aL | ARDRWPYFLDY | 223 |
| HVR-H3-F100aM | ARDRWPYFMDY | 224 |
| HVR-H3-F100aW | ARDRWPYFWDY | 225 |
| CDR-H3-generic | DXXPYFXDY<br>X at 2 is R, A, D, E, I, M, N, Q, or S; X at 3 is W, or F; X at 7 is F, L, M, or W | 226 |
| CDR-H3-wild-type | DRWPYFFDY | 227 |
| CDR-H3-R96A | DAWPYFFDY | 228 |
| CDR-H3-R96D | DDWPYFFDY | 229 |
| CDR-H3-R96E | DEWPYFFDY | 230 |
| CDR-H3-R96I | DIWPYFFDY | 231 |
| CDR-H3-R96M | DMWPYFFDY | 232 |
| CDR-H3-R96N | DNWPYFFDY | 233 |
| CDR-H3-R96O | DQWPYFFDY | 234 |
| CDR-H3-R96S | DSWPYFFDY | 235 |
| CDR-H3-W97F | DRFPYFFDY | 236 |
| CDR-H3-F100aL | DRWPYFLDY | 237 |
| CDR-H3-F100aM | DRWPYFMDY | 238 |
| CDR-H3-F100aW | DRWPYFWDY | 239 |
| 11C5-FR-L1 | DIQMTQSPASLSVSVGETVTITC | 240 |
| 11C5-FR-L2 | WYQQKQGRSPQLLVY | 241 |
| 11C5-FR-L3 | GVPSRFSGSGSGTQYSLNINSLQSEDFGTYYC | 242 |
| h11C5-FR-L4 | FGGGTKLEIK | 243 |
| h11C5-FR-L1 | DIQMTQSPSSLSASVGDRVTITC | 244 |
| h11C5-FR-L2 | WYQQKPGKAPKLLVY | 245 |
| h11C5-FR-L2-A43S | WYQQKPGKSPKLLVY | 246 |
| h11C5-FR-L3 | GVPSRFSGSGSGTDYTLTISSLQPEDFATYYC | 247 |
| h11C5-FR-L4 | FGGGTKVEIK | 248 |
| 11C5-FR-H1 | EVQLVESGGGLVKPGGSLKLSCAASGFT | 249 |
| 11C5-FR-H2 | WVRQTPEKRLEWVA | 250 |
| 11C5-FR-H3 | RFTISRDNANDNLYLQMSHLKSEDSARYYCAR | 251 |
| 11C5-FR-H4 | YWGQGTTLTVSS | 252 |
| h11C5-FR-H1 | EVQLVESGGGLVQPGGSLRLSCAASGFT | 253 |
| h11C5-FR-H2 | WVRQAPGKGLEWVA | 254 |

TABLE 2-continued

Anti-IL1RAP antibody sequences

| Description | Sequence | SEQ ID NO: |
|---|---|---|
| h11C5-FR-H3 | RFTISRDNAKNSLYLQMNSLRAEDTAVYYCAR | 255 |
| h11C5-FR-H4 | YWGQGTLVTVSS | 256 |
| 11C5-V$_L$-wild-type | DIQMTQSPASLSVSVGETVTITCRASENIYSNLAWYQQKQGRSPQ LLVYGAKNLADGVPSRFSGSGSGTQYSLNINSLQSEDFGTYYCQH FWTTPRTFGGGTKLEIK | 257 |
| h11C5-V$_L$-wild-type | DIQMTQSPSSLSASVGDRVTITCRASENIYSNLAWYQQKPGKAPK LLVYGAKNLADGVPSRFSGSGSGTDYTLTISSLQPEDFATYYCQH FWTTPRTFGGGTKVEIK | 258 |
| h11C5-V$_L$-A43S | DIQMTQSPSSLSASVGDRVTITCRASENIYSNLAWYQQKPGKSPK LLVYGAKNLADGVPSRFSGSGSGTDYTLTISSLQPEDFATYYCQH FWTTPRTFGGGTKVEIK | 259 |
| h11C5-V$_L$-Y30W/A43S | DIQMTQSPSSLSASVGDRVTITCRASENIWSNLAWYQQKPGKSPK LLVYGAKNLADGVPSRFSGSGSGTDYTLTISSLQPEDFATYYCQH FWTTPRTFGGGTKVEIK | 260 |
| h11C5-V$_L$-Y30W/A43S/W92L | DIQMTQSPSSLSASVGDRVTITCRASENIWSNLAWYQQKPGKSPK LLVYGAKNLADGVPSRFSGSGSGTDYTLTISSLQPEDFATYYCQH FLTTPRTFGGGTKVEIK | 261 |
| h11C5-V$_L$-Y30W/A43S/W92F | DIQMTQSPSSLSASVGDRVTITCRASENIWSNLAWYQQKPGKSPK LLVYGAKNLADGVPSRFSGSGSGTDYTLTISSLQPEDFATYYCQH FFTTPRTFGGGTKVEIK | 262 |
| h11C5-V$_L$-L33G/A43S | DIQMTQSPSSLSASVGDRVTITCRASENIYSNGAWYQQKPGKSPK LLVYGAKNLADGVPSRFSGSGSGTDYTLTISSLQPEDFATYYCQH FWTTPRTFGGGTKVEIK | 263 |
| h11C5-V$_L$-L33G/A43S/A51Y | DIQMTQSPSSLSASVGDRVTITCRASENIYSNGAWYQQKPGKSPK LLVYGYKNLADGVPSRFSGSGSGTDYTLTISSLQPEDFATYYCQH FWTTPRTFGGGTKVEIK | 264 |
| h11C5-V$_L$-A43S/A51D | DIQMTQSPSSLSASVGDRVTITCRASENIYSNLAWYQQKPGKSPK LLVYGDKNLADGVPSRFSGSGSGTDYTLTISSLQPEDFATYYCQH FWTTPRTFGGGTKVEIK | 265 |
| h11C5-V$_L$-A43S/A51L | DIQMTQSPSSLSASVGDRVTITCRASENIYSNLAWYQQKPGKSPK LLVYGLKNLADGVPSRFSGSGSGTDYTLTISSLQPEDFATYYCQH FWTTPRTFGGGTKVEIK | 266 |
| h11C5-V$_L$-A43S/A51R | DIQMTQSPSSLSASVGDRVTITCRASENIYSNLAWYQQKPGKSPK LLVYGRKNLADGVPSRFSGSGSGTDYTLTISSLQPEDFATYYCQH FWTTPRTFGGGTKVEIK | 267 |
| h11C5-V$_L$-A43S/A51Y | DIQMTQSPSSLSASVGDRVTITCRASENIYSNLAWYQQKPGKSPK LLVYGYKNLADGVPSRFSGSGSGTDYTLTISSLQPEDFATYYCQH FWTTPRTFGGGTKVEIK | 268 |
| h11C5-V$_L$-A43S/A51Y/W92I | DIQMTQSPSSLSASVGDRVTITCRASENIYSNLAWYQQKPGKSPK LLVYGYKNLADGVPSRFSGSGSGTDYTLTISSLQPEDFATYYCQH FITTPRTFGGGTKVEIK | 269 |
| h11C5-V$_L$-A43S/A51Y/W92K | DIQMTQSPSSLSASVGDRVTITCRASENIYSNLAWYQQKPGKSPK LLVYGYKNLADGVPSRFSGSGSGTDYTLTISSLQPEDFATYYCQH FKTTPRTFGGGTKVEIK | 270 |
| 9h11C5-V$_L$-A43S/K52G | DIQMTQSPSSLSASVGDRVTITCRASENIYSNLAWYQQKPGKSPK LLVYGAGNLADGVPSRFSGSGSGTDYTLTISSLQPEDFATYYCQH FWTTPRTFGGGTKVEIK | 271 |
| h11C5-V$_L$-A43S/A51R/K52G | DIQMTQSPSSLSASVGDRVTITCRASENIYSNLAWYQQKPGKSPK LLVYGRGNLADGVPSRFSGSGSGTDYTLTISSLQPEDFATYYCQH FWTTPRTFGGGTKVEIK | 272 |
| h11C5-V$_L$-A43S/W92F | DIQMTQSPSSLSASVGDRVTITCRASENIYSNLAWYQQKPGKSPK LLVYGAKNLADGVPSRFSGSGSGTDYTLTISSLQPEDFATYYCQH FFTTPRTFGGGTKVEIK | 273 |

TABLE 2-continued

Anti-IL1RAP antibody sequences

| Description[1] | Sequence | SEQ ID NO: |
|---|---|---|
| h11C5-V$_L$-A43S/W92I | DIQMTQSPSSLSASVGDRVTITCRASENIYSNLAWYQQKPGKSPK LLVYGAKNLADGVPSRFSGSGSGTDYTLTISSLQPEDFATYYCQH FITTPRTFGGGTKVEIK | 274 |
| h11C5-V$_L$-A43S/W92K | DIQMTQSPSSLSASVGDRVTITCRASENIYSNLAWYQQKPGKSPK LLVYGAKNLADGVPSRFSGSGSGTDYTLTISSLQPEDFATYYCQH FKTTPRTFGGGTKVEIK | 275 |
| h11C5-V$_L$-A43S/W92L | DIQMTQSPSSLSASVGDRVTITCRASENIYSNLAWYQQKPGKSPK LLVYGAKNLADGVPSRFSGSGSGTDYTLTISSLQPEDFATYYCQH FLTTPRTFGGGTKVEIK | 276 |
| h11C5-V$_L$-A43S/T94I | DIQMTQSPSSLSASVGDRVTITCRASENIYSNLAWYQQKPGKSPK LLVYGAKNLADGVPSRFSGSGSGTDYTLTISSLQPEDFATYYCQH FWTIPRTFGGGTKVEIK | 277 |
| h11C5-V$_L$-A43S/I94V | DIQMTQSPSSLSASVGDRVTITCRASENIYSNLAWYQQKPGKSPK LLVYGAKNLADGVPSRFSGSGSGTDYTLTISSLQPEDFATYYCQH FWTVPRTFGGGTKVEIK | 278 |
| 11C5-V$_H$-wild-type | EVQLVESGGGLVKPGGSLKLSCAASGFTFSNYAMSWVRQTPEKRL EWVATVTEGGDYNYCLDDVKGRFTISRDNANDNLYLQMSHLKSED SARYYCARDRWPYFFDYWGQGTTLTVSS | 279 |
| 11C5-V$_H$-C59A | EVQLVESGGGLVKPGGSLKLSCAASGFTFSNYAMSWVRQTPEKRL EWVATVTEGGDYNYALDDVKGRFTISRDNANDNLYLQMSHLKSED SARYYCARDRWPYFFDYWGQGTTLTVSS | 280 |
| 11C5-V$_H$-C59S | EVQLVESGGGLVKPGGSLKLSCAASGFTFSNYAMSWVRQTPEKRL EWVATVTEGGDYNYSLDDVKGRFTISRDNANDNLYLQMSHLKSED SARYYCARDRWPYFFDYWGQGTTLTVSS | 281 |
| 11C5-V$_H$-C59T | EVQLVESGGGLVKPGGSLKLSCAASGFTFSNYAMSWVRQTPEKRL EWVATVTEGGDYNYTLDDVKGRFTISRDNANDNLYLQMSHLKSED SARYYCARDRWPYFFDYWGQGTTLTVSS | 282 |
| 11C5-V$_H$-C59V | EVQLVESGGGLVKPGGSLKLSCAASGFTFSNYAMSWVRQTPEKRL EWVATVTEGGDYNYVLDDVKGRFTISRDNANDNLYLQMSHLKSED SARYYCARDRWPYFFDYWGQGTTLTVSS | 283 |
| 11C5-V$_H$-C59Y | EVQLVESGGGLVKPGGSLKLSCAASGFTFSNYAMSWVRQTPEKRL EWVATVTEGGDYNYYLDDVKGRFTISRDNANDNLYLQMSHLKSED SARYYCARDRWPYFFDYWGQGTTLTVSS | 284 |
| h11C5-V$_H$-wild-type | EVQLVESGGGLVQPGGSLRLSCAASGFTFSNYAMSWVRQAPGKGL EWVATVTEGGDYNYCLDDVKGRFTISRDNAKNSLYLQMNSLRAED TAVYYCARDRWPYFFDYWGQGTLVTVSS | 285 |
| h11C5-V$_H$-C59A | EVQLVESGGGLVQPGGSLRLSCAASGFTFSNYAMSWVRQAPGKGL EWVATVTEGGDYNYALDDVKGRFTISRDNAKNSLYLQMNSLRAED TAVYYCARDRWPYFFDYWGQGTLVTVSS | 286 |
| h11C5-V$_H$-C59S | EVQLVESGGGLVQPGGSLRLSCAASGFTFSNYAMSWVRQAPGKGL EWVATVTEGGDYNYSLDDVKGRFTISRDNAKNSLYLQMNSLRAED TAVYYCARDRWPYFFDYWGQGTLVTVSS | 287 |
| h11C5-V$_H$-C59T | EVQLVESGGGLVQPGGSLRLSCAASGFTFSNYAMSWVRQAPGKGL EWVATVTEGGDYNYTLDDVKGRFTISRDNAKNSLYLQMNSLRAED TAVYYCARDRWPYFFDYWGQGTLVTVSS | 288 |
| h11C5-V$_H$-C59V | EVQLVESGGGLVQPGGSLRLSCAASGFTFSNYAMSWVRQAPGKGL EWVATVTEGGDYNYVLDDVKGRFTISRDNAKNSLYLQMNSLRAED TAVYYCARDRWPYFFDYWGQGTLVTVSS | 289 |
| h11C5-V$_H$-C59Y | EVQLVESGGGLVQPGGSLRLSCAASGFTFSNYAMSWVRQAPGKGL EWVATVTEGGDYNYYLDDVKGRFTISRDNAKNSLYLQMNSLRAED TAVYYCARDRWPYFFDYWGQGTLVTVSS | 290 |
| h11C5-V$_H$-F29E/C59Y | EVQLVESGGGLVQPGGSLRLSCAASGFTESNYAMSWVRQAPGKGL EWVATVTEGGDYNYYLDDVKGRFTISRDNAKNSLYLQMNSLRAED TAVYYCARDRWPYFFDYWGQGTLVTVSS | 291 |

TABLE 2-continued

Anti-IL1RAP antibody sequences

| Description[1] | Sequence | SEQ ID NO: |
|---|---|---|
| h11C5-V$_H$-F29E/N57G/C59Y/R96A | EVQLVESGGGLVQPGGSLRLSCAASGFTESNYAMSWVRQAPGKGL EWVATVTEGGDYGYYLDDVKGRFTISRDNAKNSLYLQMNSLRAED TAVYYCARDAWPYFFDYWGQGTLVTVSS | 292 |
| h11C5-V$_H$-F29O/C59Y | EVQLVESGGGLVQPGGSLRLSCAASGFTQSNYAMSWVRQAPGKGL EWVATVTEGGDYNYYLDDVKGRFTISRDNAKNSLYLQMNSLRAED TAVYYCARDRWPYFFDYWGQGTLVTVSS | 293 |
| h11C5-V$_H$-F29S/C59Y | EVQLVESGGGLVQPGGSLRLSCAASGFTSSNYAMSWVRQAPGKGL EWVATVTEGGDYNYYLDDVKGRFTISRDNAKNSLYLQMNSLRAED TAVYYCARDRWPYFFDYWGQGTLVTVSS | 294 |
| h11C5-V$_H$-F29S/E52aV/C59Y/R96A | EVQLVESGGGLVQPGGSLRLSCAASGFTSSNYAMSWVRQAPGKGL EWVATVTVGGDYNYYLDDVKGRFTISRDNAKNSLYLQMNSLRAED TAVYYCARDAWPYFFDYWGQGTLVTVSS | 295 |
| h11C5-V$_H$-F29S/D55G/C59Y/R96S | EVQLVESGGGLVQPGGSLRLSCAASGFTSSNYAMSWVRQAPGKGL EWVATVTEGGGYNYYLDDVKGRFTISRDNAKNSLYLQMNSLRAED TAVYYCARDSWPYFFDYWGQGTLVTVSS | 296 |
| h11C5-V$_H$-M34V/C59Y | EVQLVESGGGLVQPGGSLRLSCAASGFTFSNYAVSWVRQAPGKGL EWVATVTEGGDYNYYLDDVKGRFTISRDNAKNSLYLQMNSLRAED TAVYYCARDRWPYFFDYWGQGTLVTVSS | 297 |
| h11C5-V$_H$-V51S/C59Y | EVQLVESGGGLVQPGGSLRLSCAASGFTFSNYAMSWVRQAPGKGL EWVATSTEGGDYNYYLDDVKGRFTISRDNAKNSLYLQMNSLRAED TAVYYCARDRWPYFFDYWGQGTLVTVSS | 298 |
| h11C5-V$_H$-E52aV/C59Y | EVQLVESGGGLVQPGGSLRLSCAASGFTFSNYAMSWVRQAPGKGL EWVATVTVGGDYNYYLDDVKGRFTISRDNAKNSLYLQMNSLRAED TAVYYCARDRWPYFFDYWGQGTLVTVSS | 299 |
| h11C5-V$_H$-G54H/C59Y | EVQLVESGGGLVQPGGSLRLSCAASGFTFSNYAMSWVRQAPGKGL EWVATVTEGHDYNYYLDDVKGRFTISRDNAKNSLYLQMNSLRAED TAVYYCARDRWPYFFDYWGQGTLVTVSS | 300 |
| h11C5-V$_H$-G54V/C59Y | EVQLVESGGGLVQPGGSLRLSCAASGFTFSNYAMSWVRQAPGKGL EWVATVTEGVDYNYYLDDVKGRFTISRDNAKNSLYLQMNSLRAED TAVYYCARDRWPYFFDYWGQGTLVTVSS | 301 |
| h11C5-V$_H$-G54V/C59Y/R96A | EVQLVESGGGLVQPGGSLRLSCAASGFTFSNYAMSWVRQAPGKGL EWVATVTEGVDYNYYLDDVKGRFTISRDNAKNSLYLQMNSLRAED TAVYYCARDAWPYFFDYWGQGTLVTVSS | 302 |
| h11C5-V$_H$-D55G/C59Y | EVQLVESGGGLVQPGGSLRLSCAASGFTFSNYAMSWVRQAPGKGL EWVATVTEGGGYNYYLDDVKGRFTISRDNAKNSLYLQMNSLRAED TAVYYCARDRWPYFFDYWGQGTLVTVSS | 303 |
| h11C5-V$_H$-N57G/C59Y | EVQLVESGGGLVQPGGSLRLSCAASGFTFSNYAMSWVRQAPGKGL EWVATVTEGGDYGYYLDDVKGRFTISRDNAKNSLYLQMNSLRAED TAVYYCARDRWPYFFDYWGQGTLVTVSS | 304 |
| h11C5-V$_H$-V51S/G54H/C59Y | EVQLVESGGGLVQPGGSLRLSCAASGFTFSNYAMSWVRQAPGKGL EWVATSTEGHDYNYYLDDVKGRFTISRDNAKNSLYLQMNSLRAED TAVYYCARDRWPYFFDYWGQGTLVTVSS | 305 |
| h11C5-V$_H$-C59Y/R96A | EVQLVESGGGLVQPGGSLRLSCAASGFTFSNYAMSWVRQAPGKGL EWVATVTEGGDYNYYLDDVKGRFTISRDNAKNSLYLQMNSLRAED TAVYYCARDAWPYFFDYWGQGTLVTVSS | 306 |
| h11C5-VH-C59Y/R96D | EVQLVESGGGLVQPGGSLRLSCAASGFTFSNYAMSWVRQAPGKGL EWVATVTEGGDYNYYLDDVKGRFTISRDNAKNSLYLQMNSLRAED TAVYYCARDDWPYFFDYWGQGTLVTVSS | 307 |
| h11C5-V$_H$-C59Y/R96O | EVQLVESGGGLVQPGGSLRLSCAASGFTFSNYAMSWVRQAPGKGL EWVATVTEGGDYNYYLDDVKGRFTISRDNAKNSLYLQMNSLRAED TAVYYCARDQWPYFFDYWGQGTLVTVSS | 308 |
| h11C5-V$_H$-C59Y/R96S | EVQLVESGGGLVQPGGSLRLSCAASGFTFSNYAMSWVRQAPGKGL EWVATVTEGGDYNYYLDDVKGRFTISRDNAKNSLYLQMNSLRAED TAVYYCARDSWPYFFDYWGQGTLVTVSS | 309 |

TABLE 2-continued

Anti-IL1RAP antibody sequences

| Description[1] | Sequence | SEQ ID NO: |
|---|---|---|
| h11C5-$V_H$-C59Y/W97F | EVQLVESGGGLVQPGGSLRLSCAASGFTFSNYAMSWVRQAPGKGL EWVATVTEGGDYNYYLDDVKGRFTISRDNAKNSLYLQMNSLRAED TAVYYCARDRFPYFFDYWGQGTLVTSS | 310 |
| 10A11-$V_L$ | DIQMTQTTSSLSASLGDRVTISCRASQDISNYLNWYQQKPDGTVK LLIYYTSTLHSGVPSRFSGSGSGTDYSLTISNLEPEDIATYYCHQ YSKFPPTFGSGTKLEIK | 311 |
| 10A11-$V_H$ | EVQLQQSGAELVKPGASVRLSCTSSGFNIKDYFMHWVKQRTEQGL EWVGRIDPEDGETQYAPNFQDKATITVDTSSNTVYLQLSSLTSED TAVYYCFRPLYYGNSPWFAYWGQGTLVTVP | 312 |
| 9D5-$V_L$ | DIKMTQSPSSMYASLGERVTITCKASQDINTYLSWFLQKPGKSPK TLIYRADRLVDGVPSRFSGGGSGQDYSLTISSLEYEDLGIYYCLQ YDEFPYTFGSGTKLEIK | 313 |
| 9D5-$V_H$ | QVQLQQSGAELARPGASVKFSCKASGYTFTSYWMQWVKQRPGQGL EWIGTIYPGDGNTRYTQKFKGKATLTADKSSSTAYMQLSGLASED SAVYYCARGYFGNLVFDVWGAGTTVTVSS | 314 |
| 8H1-$V_L$ | NIVMTQTPKFLPVAAEDRVIITCKASQDVSNEVAWYQQKPGQSPK LLMYYASNRYTGVPDRFTGSGSGTDFTFTISSVQVEDLAVYFCQQ HYSSPLTFGAGTKLELK | 315 |
| 8H1-$V_H$ | QVQLQQSGPELVKSGASVRISCKASGYAFSGSWMNWVKQRPGKGL EWIGRIYPGDGNTNYNGKFKDKATLTADKSSSTAFMQLSSLTSED SAVYFCARDYYLFYFDYWGQGTTLTVSS | 316 |
| 13D8-$V_L$ | DIQMTQSPASLSVSVGETVTITCRASDNIYSNLAWYQEKQGKSPQ LLVYGATNLADGVPSRFSGSGSGTQYSLKINSLQSEDFGSYYCQH FWTTPRSFGGGTKLELK | 317 |
| 13D8-$V_H$ | EVQLVESGGGLVKPGGSLKLSCTASGFTFSNYAMSWVRQTPEKRL EWVATISDGGNYTYYPDNVKGRFTISRDIAKNNLYLQMSHLKSED TAMYYCARDRWPYFFDFWGQGTTLTVSS | 318 |
| Fc-YTE | ASTKGPSVFPLAPSSKSTSGGTAALGCLVKDYFPEPVTVSWNSGA LTSGVHTFPAVLQSSGLYSLSSVVTVPSSSLGTQTYICNVNHKPS NTKVDKKVEPKSCDKTHTCPPCPAPELLGGPSVFLFPPKPKDTLY ITREPEVTCVVVDVSHEDPEVKFNWYVDGVEVHNAKTKPREEQYG STYRVVSVLTVLHQDWLNGKEYKCKVSNKALPAPIEKTISKAKGQ PREPQVYTLPPSRDELTKNQVSLTCLVKGFYPSDIAVEWESNGQP ENNYKTTPPVLDSDGSFFLYSKLTVDKSRWQQGNVFSCSVMHEAL HNHYTQKSLSLSPGK | 327 |
| h11C5-LC-wild-type | DIQMTQSPSSLSASVGDRVTITC<u>RASENIYSNLA</u>WYQQKPGKAPK LLVY<u>GAKNLAD</u>GVPSRFSGSGSG<u>T</u>DYTLTISSLQPEDFATYYC<u>QH FWTTPRT</u>FGGGTKVEIKRTVAAPSVFIFPPSDEQLKSGTASVVCL LNNFYPREAKVQWKVDNALQSGNSQESVTEQDSKDSTYSLSSTLT LSKADYEKHKVYACEVTHQGLSSPVTKSFNRGEC | 328 |
| h11C5-LC-YD or YS | DIQMTQSPSSLSASVGDRVTITC<u>RASENIYSNLA</u>WYQQKPGKSPK LLVYG<u>Y</u>KNLADGVPSRFSGSGSG<u>T</u>DYTLTISSLQPEDFATYYC<u>QH FWTTPRT</u>FGGGTKVEIKRTVAAPSVFIFPPSDEQLKSGTASVVCL LNNFYPREAKVQWKVDNALQSGNSQESVTEQDSKDSTYSLSSTLT LSKADYEKHKVYACEVTHQGLSSPVTKSFNRGEC | 329 |
| h11C5-LC-YIS or YID | DIQMTQSPSSLSASVGDRVTITC<u>RASENIYSNLA</u>WYQQKPGKSPK LLVYG<u>Y</u>KNLADGVPSRFSGSGSG<u>T</u>DYTLTISSLQPEDFATYYC<u>QH F</u>I<u>TTPRT</u>FGGGTKVEIKRTVAAPSVFIFPPSDEQLKSGTASVVCL LNNFYPREAKVQWKVDNALQSGNSQESVTEQDSKDSTYSLSSTLT LSKADYEKHKVYACEVTHQGLSSPVTKSFNRGEC | 330 |
| h11C5-LC-YKD or YKS | DIQMTQSPSSLSASVGDRVTITC<u>RASENIYSNLA</u>WYQQKPGKSPK LLVYG<u>YK</u>NLADGVPSRFSGSGSG<u>T</u>DYTLTISSLQPEDFATYYC<u>QH F</u>K<u>TTPRT</u>FGGGTKVEIKRTVAAPSVFIFPPSDEQLKSGTASVVCL LNNFYPREAKVQWKVDNALQSGNSQESVTEQDSKDSTYSLSSTLT LSKADYEKHKVYACEVTHQGLSSPVTKSFNRGEC | 331 |
| h11C5-HC-wild-type | EVQLVESGGGLVQPGGSLRLSCAASGFTFS<u>NYAMS</u>WVRQAPGKGL EWVA<u>T</u>VTEGGDYNYCLDDVKGRFTISRDNA<u>K</u>NSLYLQMNSLRAED TAVYYCAR<u>DRWPYFFDY</u>WGQGTLVTVSSASTKGPSVFPLAPSSKS TSGGTAALGCLVKDYFPEPVTVSWNSGALTSGVHTFPAVLQSSGL | 332 |

TABLE 2-continued

Anti-IL1RAP antibody sequences

| Description[1] | Sequence | SEQ ID NO: |
|---|---|---|
| | YSLSSVVTVPSSSLGTQTYICNVNHKPSNTKVDKKVEPKSCDKTH<br>TCPPCPAPELLGGPSVFLFPPKPKDTLMISRTPEVTCVVVDVSHE<br>DPEVKFNWYVDGVEVHNAKTKPREEQYGSTYRVVSVLTVLHQDWL<br>NGKEYKCKVSNKALPAPIEKTISKAKGQPREPQVYTLPPSRDELT<br>KNQVSLTCLVKGFYPSDIAVEWESNGQPENNYKTTPPVLDSDGSF<br>FLYSKLTVDKSRWQQGNVFSCSVMHEALHNHYTQKSLSLSPG | |
| h11C5-HC-<br>YS, YKS, or YIS | EVQLVESGGGLVQPGGSLRLSCAASGFTFSNYAMSWVRQAPGKGL<br>EWVATSTEGGDYNYYLDDVKGRFTISRDNAKNSLYLQMNSLRAED<br>TAVYYCARDRWPYFFDYWGQGTLVTVSSASTKGPSVFPLAPSSKS<br>TSGGTAALGCLVKDYFPEPVTVSWNSGALTSGVHTFPAVLQSSGL<br>YSLSSVVTVPSSSLGTQTYICNVNHKPSNTKVDKKVEPKSCDKTH<br>TCPPCPAPELLGGPSVFLFPPKPKDTLMISRTPEVTCVVVDVSHE<br>DPEVKFNWYVDGVEVHNAKTKPREEQYGSTYRVVSVLTVLHQDWL<br>NGKEYKCKVSNKALPAPIEKTISKAKGQPREPQVYTLPPSRDELT<br>KNQVSLTCLVKGFYPSDIAVEWESNGQPENNYKTTPPVLDSDGSF<br>FLYSKLTVDKSRWQQGNVFSCSVMHEALHNHYTQKSLSLSPG | 333 |
| h11C5-HC-<br>YS/YTE, YKS/YTE,<br>or YIS/YTE | EVQLVESGGGLVQPGGSLRLSCAASGFTFSNYAMSWVRQAPGKGL<br>EWVATSTEGGDYNYYLDDVKGRFTISRDNAKNSLYLQMNSLRAED<br>TAVYYCARDRWPYFFDYWGQGTLVTVSSASTKGPSVFPLAPSSKS<br>TSGGTAALGCLVKDYFPEPVTVSWNSGALTSGVHTFPAVLQSSGL<br>YSLSSVVTVPSSSLGTQTYICNVNHKPSNTKVDKKVEPKSCDKTH<br>TCPPCPAPELLGGPSVFLFPPKPKDTLYITREPEVTCVVVDVSHE<br>DPEVKFNWYVDGVEVHNAKTKPREEQYGSTYRVVSVLTVLHQDWL<br>NGKEYKCKVSNKALPAPIEKTISKAKGQPREPQVYTLPPSRDELT<br>KNQVSLTCLVKGFYPSDIAVEWESNGQPENNYKTTPPVLDSDGSF<br>FLYSKLTVDKSRWQQGNVFSCSVMHEALHNHYTQKSLSLSPGK | 334 |
| h11C5-HC-<br>YD, YKD, or YID | EVQLVESGGGLVQPGGSLRLSCAASGFTFSNYAMSWVRQAPGKGL<br>EWVATVTEGGDYNYYLDDVKGRFTISRDNAKNSLYLQMNSLRAED<br>TAVYYCARDDWPYFFDYWGQGTLVTVSSASTKGPSVFPLAPSSKS<br>TSGGTAALGCLVKDYFPEPVTVSWNSGALTSGVHTFPAVLQSSGL<br>YSLSSVVTVPSSSLGTQTYICNVNHKPSNTKVDKKVEPKSCDKTH<br>TCPPCPAPELLGGPSVFLFPPKPKDTLMISRTPEVTCVVVDVSHE<br>DPEVKFNWYVDGVEVHNAKTKPREEQYGSTYRVVSVLTVLHQDWL<br>NGKEYKCKVSNKALPAPIEKTISKAKGQPREPQVYTLPPSRDELT<br>KNQVSLTCLVKGFYPSDIAVEWESNGQPENNYKTTPPVLDSDGSF<br>FLYSKLTVDKSRWQQGNVFSCSVMHEALHNHYTQKSLSLSPG | 335 |
| h11C5-HC-<br>YD/YTE, YKD/YTE,<br>or YID/YTE | EVQLVESGGGLVQPGGSLRLSCAASGFTFSNYAMSWVRQAPGKGL<br>EWVATVTEGGDYNYYLDDVKGRFTISRDNAKNSLYLQMNSLRAED<br>TAVYYCARDDWPYFFDYWGQGTLVTVSSASTKGPSVFPLAPSSKS<br>TSGGTAALGCLVKDYFPEPVTVSWNSGALTSGVHTFPAVLQSSGL<br>YSLSSVVTVPSSSLGTQTYICNVNHKPSNTKVDKKVEPKSCDKTH<br>TCPPCPAPELLGGPSVFLFPPKPKDTLYITREPEVTCVVVDVSHE<br>DPEVKFNWYVDGVEVHNAKTKPREEQYGSTYRVVSVLTVLHQDWL<br>NGKEYKCKVSNKALPAPIEKTISKAKGQPREPQVYTLPPSRDELT<br>KNQVSLTCLVKGFYPSDIAVEWESNGQPENNYKTTPPVLDSDGSF<br>FLYSKLTVDKSRWQQGNVFSCSVMHEALHNHYTQKSLSLSPGK | 336 |

[1]The sequences described as HVR-H1 and HVR-H3 correspond to a slightly extended portion of the hypervariable region relative to the CDR sequences, CDR-H1 and CDR-H3, and therefore have different sequence identifiers listed in Table 2 and the accompanying Sequence Listing. The HVR sequences, HVR-L1, HVR-L2, HVR-L3, and HVR-H2, however, are identical to the corresponding CDR sequences, CDR-L1, CDR-L2, CDR-L3, and CDR-H2, and therefore do not have separate sequence identifiers (i.e., HVR-L1, HVR-L2, HVR-L3, and HVR-H2 are identical to CDR-L1, CDR-L2, CDR-L3, and CDR-H2, respectively).

1. Binding Affinity and Cell-Signaling Inhibition of Anti-IL1RAP Antibodies

In some embodiments, the anti-IL1RAP antibodies provided herein have an equilibrium dissociation constant ($K_D$) for binding to human IL1RAP of <100 nM, <10 nM, <1 nM, <0.1 nM, <0.01 nM, or <0.001 nM (e.g., $10^{-8}$ M or less, from $10^{-8}$ M to $10^{-13}$ M, e.g., from $10^{-9}$ M to $10^{-13}$ M). More specifically, in some embodiments, the anti-IL1RAP antibodies of the present disclosure bind to human IL1RAP with a binding affinity of $1\times10^{-8}$ M or less, $1\times10^{-9}$ M or less, $1\times10^{-10}$ M or less, or $1\times10^{-11}$ M or less. In some embodiments, the binding affinity is measured as the equilibrium dissociation constant ($K_D$) for binding to the hu-M-IL1RAP polypeptide of SEQ ID NO: 3. Generally, binding affinity of a ligand to its receptor can be determined using any of a variety of assays and expressed in terms of a variety of quantitative values. Specific IL1RAP binding assays useful in determining affinity of the antibodies are disclosed in the Examples herein. Additionally, antigen binding assays are known in the art and can be used herein including without limitation any direct or competitive binding assays using techniques such as western blots, radioimmunoassays, enzyme-linked immunoabsorbent assay (ELISA), "sandwich" immunoassays, surface plasmon resonance based assay (such as the BIAcore assay as described in WO2005/

012359), immunoprecipitation assays, fluorescent immunoassays, and protein A immunoassays.

Accordingly, in some embodiments, the binding affinity is expressed as $K_D$ values and reflects intrinsic binding affinity (e.g., with minimized avidity effects). The anti-IL1RAP antibodies of the present disclosure exhibit strong binding affinities for hu-M-IL1RAP polypeptide (SEQ ID NO: 3), for example, exhibiting $K_D$ values of between 10 nM and 1 pM.

In some embodiments, the anti-IL1RAP antibodies provided herein decrease, inhibit, and/or fully-block intracellular signaling by IL1RAP-mediated pathways, including the IL-1, IL-33, and/or IL-36 signaling pathways, and more specifically, the signaling pathways that are stimulated by binding of one or more of the following agonists: IL-1α, IL-1β, IL-33, IL-36α, IL-36β, and IL-36γ. The ability of the antibodies to inhibit these IL1RAP-mediated signaling pathways can be assayed in vitro using known cell-based blocking assays including the HEK-BLUE™ reporter cell assays and primary cell-based blocking assays described in the Examples of the present disclosure. In some embodiments, the ability of the antibody to decrease, inhibit, and/or fully-block intracellular signaling is determined as $IC_{50}$ of the antibody using a reporter cell-based blocking assay with the agonist(s) IL-1α, IL-1β, IL-33, IL-36α, IL-36β, and/or IL-36γ at concentration of about $EC_{50}$. The agonist $EC_{50}$ often can only be estimated prior to the assay and is determined after the assay is completed using nonlinear regression analysis of the data. In such assays, a value of about $EC_{50}$ typically will be in the range of from $EC_{40-45}$ to $EC_{55-60}$.

Accordingly, in some embodiments, the IL1RAP antibodies of the present disclosure are characterized by one or more of following functional properties based on the ability to decrease, inhibit, and/or fully-block intracellular signaling by IL1RAP-mediated pathways.

In some embodiments the anti-IL1RAP antibody decreases an IL-1 stimulated signal, an IL-33 stimulated signal, and/or an IL-36 stimulated signal by at least 90%, at least 95%, at least 99%, or 100%. In some embodiments, the decrease in signal can be measured using a reporter cell-based blocking assay (e.g., HEK-BLUE™ reporter cell assay). One of ordinary skill can select any of the known reporter cell assays known for use in determining inhibition of cell-signaling in an IL-1 stimulated, an IL-33 stimulated, and/or an IL-36 stimulated pathway. Generally, the anti-IL1RAP antibodies of the present disclosure decrease the IL1RAP-mediated intracellular signal initiated by binding of an agonist at a concentration of about $EC_{50}$ (e.g., $EC_{40}$ to $EC_{60}$) with an $IC_{50}$ value for the antibody of 10 nM or less, 5 nM or less, or 1 nM.

In some embodiments the anti-IL1RAP antibody decreases an IL-1 stimulated signal, an IL-33 stimulated signal, and an IL-36 stimulated signal by at least 95%, or at least 99%; optionally, wherein the IL-1, IL-33, and/or IL-36 stimulated signals are stimulated by an agonist selected from IL-1α, IL-1β, IL-33, IL-36α, IL-36β, and IL-36γ; optionally, wherein at an agonist concentration of about $EC_{50}$ the antibody has an $IC_{50}$ of 10 nM or less, 5 nM or less, or 1 nM or less.

In some embodiments the anti-IL1RAP antibody decreases an intracellular signal initiated by one or more of IL-1α, IL-1β, IL-33, IL-36α, IL-36β, and IL-36γ agonist binding to its cognate receptor by at least 90%, at least 95%, at least 99%, or 100%. In some embodiments the anti-IL1RAP antibody inhibits IL-1α, IL-1β, and/or IL-36β stimulated release of IL8 from primary human lung fibroblasts (PHLF); optionally, wherein at an IL-1α, IL-1β, and/or IL-36β concentration of about $EC_{50}$ the antibody has an $IC_{50}$ of 10 nM or less, 5 nM or less, or 1 nM or less. In some embodiments the anti-IL1RAP antibody inhibits IL-1β stimulated release of IL6 from primary human monocytes; optionally, wherein at an IL-1β concentration of about $EC_{50}$ the antibody has an $IC_{50}$ of 10 nM or less, 5 nM or less, or 1 nM or less. In some embodiments the anti-IL1RAP antibody inhibits IL-33 stimulated release of INF-γ from human natural killer (NK) cells; optionally, wherein at an IL-33 concentration of about $EC_{50}$ the antibody has an $IC_{50}$ of 10 nM or less, 5 nM or less, or 1 nM or less. In some embodiments, the antibody inhibits IL-36β stimulated release of IL8 from human epidermal keratinocytes (HEKn); optionally, wherein at an IL-36β concentration of about EC60 the antibody has an $IC_{50}$ of 10 nM or less, 5 nM or less, or 2 nM or less. In some embodiments, the antibody inhibits IL-33 stimulated phosphorylation in basophils; optionally, wherein at an IL-33 concentration of about $EC_{56}$ the antibody has an $IC_{50}$ of 75 nM or less, 50 nM or less, or 45 nM or less. In some embodiments, the antibody inhibits IL-33 stimulated release of INF-γ from CD4+ T cells; optionally, wherein at an IL-33 concentration of about $EC_{34}$ the antibody has an $IC_{50}$ of 75 nM or less, 50 nM or less, or 45 nM or less.

2. Antibody Fragments

In some embodiments, the anti-IL1RAP antibody of the present disclosure can be an antibody fragment. Antibody fragments useful with the binding determinants the present disclosure include, but are not limited to, Fab, Fab', Fab'-SH, F(ab')$_2$, Fv, monovalent, one-armed (or single-armed) antibodies, scFv fragments, and other fragments described herein and known in the art. For a review of various antibody fragments, see e.g., Hudson et al., *Nat. Med.*, 9: 129-134 (2003). For a review of scFv fragments, see, e.g., Pluckthun, in The Pharmacology of Monoclonal Antibodies, vol. 113, Rosenburg and Moore eds., (Springer-Verlag, New York), pp. 269-315 (1994); see also WO93/16185; and U.S. Pat. Nos. 5,571,894 and 5,587,458. For a description of Fab and F(ab')$_2$ fragments comprising salvage receptor binding epitope residues and having increased in vivo half-life, see U.S. Pat. No. 5,869,046. Other monovalent antibody forms are described in, e.g., WO2007/048037, WO2008/145137, WO2008/145138, and WO2007/059782. Monovalent, single-armed antibodies are described, e.g., in WO2005/063816. Diabodies are antibody fragments with two antigen-binding sites that may be bivalent or bispecific (see e.g., EP0404097; WO93/01161; Hudson et al., *Nat. Med.*, 9: 129-134 (2003); and Holliger et al., *Proc. Natl. Acad. Sci. USA*, 90: 6444-6448 (1993)).

In some embodiments, the antibody fragments are single-domain antibodies which comprise all or a portion of the heavy chain variable domain or all or a portion of the light chain variable domain of an antibody. In some embodiments, a single-domain antibody is a human single-domain antibody (Domantis, Inc., Waltham, MA; see, e.g., U.S. Pat. No. 6,248,516).

Antibody fragments can be made by various techniques, including but not limited to proteolytic digestion of an intact antibody as well as production by recombinant host cells (e.g., *E. coli* or phage), as described herein.

It is contemplated that any of the anti-IL1RAP antibodies of the present disclosure can be prepared as antibody fragments using the methods and techniques known in the art and/or described herein. For example, the preparation and analysis of Fab versions of various anti-IL1RAP antibodies of the present disclosure are described in Example 8.

3. Chimeric and Humanized Antibodies

In some embodiments, the anti-IL1RAP antibody of the present disclosure can be a chimeric antibody. (See e.g., chimeric antibodies as described in U.S. Pat. No. 4,816,567; and Morrison et al., *Proc. Natl. Acad. Sci. USA*, 81:6851-6855 (1984)). In one embodiment, a chimeric antibody comprises a non-human variable region (e.g., a variable region derived from a mouse, rat, hamster, rabbit, or non-human primate, such as a monkey) and a human constant region. In some embodiments, a chimeric antibody is a "class switched" antibody in which the class or subclass has been changed from that of the parent antibody. It is contemplated that chimeric antibodies can include antigen-binding fragments thereof.

In some embodiments, the anti-IL1RAP antibody of the present disclosure is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the CDR residues are derived) to restore or improve antibody specificity or affinity.

Humanized antibodies and methods of making them are reviewed, e.g., in Almagro and Fransson, *Front. Biosci.*, 13: 1619-1633 (2008), and are further described, e.g., in Riechmann et al., *Nature*, 332:323-327 (1988); Queen et al., *Proc. Nat'l Acad. Sci. USA*, 86: 10029-10033 (1989); U.S. Pat. Nos. 5,821,337, 7,527,791, 6,982,321, and 7,087,409; Kashmiri et al., *Methods*, 36:25-34 (2005) (describing SDR (a-HVR) grafting); Padlan, *Mol. Immunol.*, 28:489-498 (1991) (describing "resurfacing"); Dall'Acqua et al., *Methods*, 36:43-60 (2005) (describing "FR shuffling"); and Osbourn et al., *Methods*, 36:61-68 (2005) and Klimka et al., *Br. J. Cancer*, 83:252-260 (2000) (describing the "guided selection" approach to FR shuffling).

Human framework regions that useful for humanization include but are not limited to: framework regions selected using the "best-fit" method (see, e.g., Sims et al., *J. Immunol.*, 151:2296 (1993)); framework regions derived from the consensus sequence of human antibodies of a particular subgroup of light or heavy chain variable regions (see, e.g., Carter et al., *Proc. Natl. Acad. Sci. USA*, 89:4285 (1992); and Presta et al., J. Immunol, 151:2623 (1993)); human mature (somatically mutated) framework regions or human germline framework regions (see, e.g., Almagro and Fransson, *Front. Biosci.* 13: 1619-1633 (2008)); and framework regions derived from screening FR libraries (see, e.g., Baca et al., J. Biol. Chem. 272: 10678-10684 (1997) and Rosok et al., *J. Biol. Chem.*, 271:22611-22618 (1996)).

It is contemplated that any of the anti-IL1RAP antibodies of the present disclosure can be prepared as humanized antibodies using the methods and techniques known in the art and/or described herein. For example, the preparation and analysis of humanized versions of an anti-IL1RAP antibody of the present disclosure are described in Examples 5-7.

4. Human Antibodies

In some embodiments, the anti-IL1RAP antibody of the present disclosure can be a human antibody. Human antibodies can be produced using various techniques known in the art. Human antibodies are described generally in van Dijk and van de Winkel, *Curr. Opin. Chem. Biol.*, 5: 368-74 (2001) and Lonberg, *Curr. Opin. Immunol.*, 20:450-459 (2008). Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23:1117-1125 (2005). See also, e.g., XENOMOUSE™ technology in U.S. Pat. Nos. 6,075,181 and 6,150,584; HUMAB® technology in U.S. Pat. No. 5,770,429; K-M MOUSE® technology in U.S. Pat. No. 7,041,870; and VELOCIMOUSE® technology in U.S. Pat. Appl. Pub. No. US 2007/0061900). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. See, e.g., Kozbor, *J. Immunol*, 133: 3001 (1984); Brodeur et al., Monoclonal Antibody Production Techniques and Applications, pp. 51-63 (Marcel Dekker, Inc., New York, 1987); and Boerner et al., *J. Immunol.*, 147: 86 (1991). Human antibodies generated via human B-cell hybridoma technology are also described in Li et al., *Proc. Natl. Acad. Sci. USA*, 103:3557-3562 (2006). Additional methods describing production of monoclonal human IgM antibodies from hybridoma cell lines include those described in e.g., U.S. Pat. No. 7,189,826. Human hybridoma technology (i.e., the trioma technique) is described in e.g., Vollmers et al., *Histology and Histopathology*, 20(3):927-937 (2005) and Vollmers et al., *Methods and Findings in Experimental and Clinical Pharmacology*, 27(3): 185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

It is contemplated that any of the anti-IL1RAP antibodies of the present disclosure can be prepared as human antibodies using the methods and techniques known in the art and/or described herein.

5. Library-Derived Antibodies

In some embodiments, the anti-IL1RAP antibody of the present disclosure may be isolated by screening combinatorial libraries for antibodies with the desired activity or activities. For example, a variety of methods are known in the art for generating phage display libraries and screening such libraries for antibodies possessing the desired binding characteristics. The use of phage display for preparation of affinity matured variants of the humanized version of the anti-IL1RAP antibody of the present disclosure are described in the Examples disclosed herein. Other methods for producing such library-derived antibodies can be found in e.g., Hoogenboom et al., *Methods in Molecular Biology*, 178: 1-37 (O'Brien et al., ed., *Antibody Phage Display*, Humana Press, Totowa, NJ, 2001); McCafferty et al., *Nature*, 348:552-554; Clackson et al., *Nature*, 352: 624-628

(1991); Marks et al., *J. Mol. Biol.*, 222: 581-597 (1992); Marks and Bradbury, *Methods in Molecular Biology*, 248: 161-175 (Lo, ed., *Antibody Engineering*, Humana Press, Totowa, NJ, 2003); Sidhu et al., *J. Mol. Biol.*, 338(2): 299-310 (2004); Lee et al., *J. Mol. Biol.*, 340(5): 1073-1093 (2004); Fellouse, *Proc. Natl. Acad. Sci. USA*, 101(34): 12467-12472 (2004); and Lee et al., *J. Immunol. Methods*, 284(1-2): 119-132(2004).

It is contemplated that combinatorial library screening can be used to generate variants of the anti-IL1RAP antibodies of the present disclosure using the methods and techniques known in the art and/or described herein. For example, the use of phage display library generation and screening to prepare a wide-range of affinity matured variants of a humanized anti-IL1RAP antibody of the present disclosure is described in Example 8.

6. Multispecific Antibodies

In some embodiments, the anti-IL1RAP antibody of the present disclosure is a multispecific antibody, e.g., a bispecific antibody. In some embodiments, the multispecific antibody is a monoclonal antibody having at least two different binding sites, each with a binding specificity for a different antigen, at least one of which specifically binds IL1RAP. In some embodiments, at least one of binding sites specifically binds a cytotoxic agent. In exemplary embodiments, an anti-IL1RAP antibody of the present disclosure is a bispecific antibody and can be used to localize a cytotoxic agent to cells which express IL1RAP.

Techniques for making multispecific antibodies include, but are not limited to, recombinant co-expression of two immunoglobulin heavy chain-light chain pairs having different specificities (see e.g., Milstein and Cuello, *Nature*, 305: 537 (1983), WO 93/08829, and Traunecker et al., *EMBO J.*, 10: 3655 (1991)). "Knob-in-hole" engineering can also be used (see, e.g., U.S. Pat. No. 5,731,168).

Multispecific antibodies can also be made by engineering "electrostatic steering" effects that favor formation of Fc-heterodimeric antibody molecules rather than homodimers (WO 2009/089004A1); cross-linking two or more antibodies or fragments (see, e.g., U.S. Pat. No. 4,676,980, and Brennan et al., *Science*, 229: 81 (1985)); using leucine zippers to produce bispecific antibodies (see, e.g., Kostelny et al., *J. Immunol*, 148(5): 1547-1553 (1992)); using "diabody" technology for making bispecific antibody fragments (see, e.g., Holliger et al., *Proc. Natl. Acad. Sci. USA*, 90:6444-6448 (1993)); using single-chain Fv (scFv) dimers (see, e.g. Gruber et al., *J. Immunol*, 152:5368 (1994)); or tri-specific antibodies (see e.g., Tutt et al., *J. Immunol.*, 147: 60 (1991).

It is contemplated that any of the anti-IL1RAP antibodies of the present disclosure can be prepared as multispecific antibodies using the methods and techniques known in the art and/or described herein.

7. Antibody Variants

In some embodiments, variants of the anti-IL1RAP antibody of the present disclosure are also contemplated. For example, antibodies with improved binding affinity and/or other biological properties of the antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristic of IL1RAP antigen binding. It is contemplated that a wide-range of variants of the anti-IL1RAP antibodies of the present disclosure can be prepared using the methods and techniques known in the art and/or described herein, including but not limited to: (i) amino acid substitution, insertion and/or deletion variants; (ii) glycosylation variants; (iii) Fc region variants; (iv) cysteine engineered variants; and (v) derivatized variants. Examples 5-9, Table 2, and the Sequence Listing of the present disclosure provide a large number of exemplary variants of the hybridoma-derived 11C5(Hy) anti-IL1RAP antibody as well as its humanized version h11C5. The exemplified variants comprise one or more of the following: an amino acid substitution in CDR-H2 to eliminate a cysteine liability (e.g., C59Y); an Fc region variant that confers in effectorless function (e.g., N297G); and a range of single, double, triple amino acid substitutions in the CDRs and variable domain regions that increase antigen affinity and/or cell-based blocking activity (e.g., SEQ ID NOs: 12-35, 38-61, 64-76, 79-120, 123-139, 142-201, 204-225, 228-239, 259-278, and 280-310).

A. Substitution, Insertion, and Deletion Variants

In some embodiments, anti-IL1RAP antibody variants having one or more amino acid substitutions in addition to those described herein are provided. Sites for mutagenesis can include the HVRs and FRs. Typical "conservative" amino acid substitutions and/or substitutions based on common side-chain class or properties are well-known in the art and can be used in the embodiments of the present disclosure. The present disclosure also contemplates variants based on non-conservative amino acid substitutions in which a member of one of amino acid side chain class is exchanged for an amino acid from another class.

Amino acid side chains are typically grouped according to the following classes or common properties: (1) hydrophobic: Met, Ala, Val, Leu, Ile, Norleucine; (2) neutral hydrophilic: Cys, Ser, Thr, Asn, Gln; (3) acidic: Asp, Glu; (4) basic: His, Lys, Arg; (5) chain orientation influencing: Gly, Pro; and (6) aromatic: Trp, Tyr, Phe.

Techniques are well-known in the art for amino acid substitution into an antibody and subsequent screening for desired function, e.g., retained/improved antigen binding, decreased immunogenicity, or improved ADCC or CDC.

Amino acid substitution variants can include substituting one or more hypervariable region residues of a parent antibody (e.g., a humanized or human antibody). Generally, the resulting variant(s) selected for further study will have modifications in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described in the Examples herein. Briefly, one or more HVR residues are mutated and the variant antibodies displayed on phage and screened for a particular biological activity (e.g., binding affinity).

A useful method for identifying residues or regions of an antibody that may be targeted for mutagenesis is "alanine scanning mutagenesis" (see e.g., Cunningham and Wells (1989) *Science*, 244: 1081-1085). In this method, a residue or group of target residues (e.g., charged residues such as Arg, Asp, His, Lys, and Glu) are identified and replaced by a neutral or negatively charged amino acid (e.g., Ala or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen can be determined. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intra-sequence insertions of single or multiple amino acid residues. Examples of terminal insertions include an antibody with an N-terminal methionyl residue. Other insertional variants of the antibody molecule include the fusion to the N- or C-terminus of the antibody to an enzyme or a polypeptide which increases the serum half-life of the antibody.

Substitutions can be made in HVRs to improve antibody affinity. Such alterations may be made in "hotspots," i.e., residues encoded by codons that undergo mutation at high frequency during the somatic maturation process (see, e.g., Chowdhury, *Methods Mol.*, Biol. 207: 179-196 (2008)) with the resulting variant $V_H$ or $V_L$ being tested for binding affinity. In one embodiment, affinity maturation can be carried out by constructing and reselecting from secondary libraries (see e.g., in Hoogenboom et al., *Methods in Molecular Biology*, 178: 1-37 (O'Brien et al., ed., *Antibody Phage Display*, Humana Press, Totowa, NJ, (2001).) Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In some embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots." In some embodiments of the variant $V_H$ and $V_L$ sequences provided above, each HVR either is unaltered, or contains no more than one, two or three amino acid substitutions.

B. Glycosylation Variants

In some embodiments, the anti-IL1RAP antibody of the present disclosure is altered to increase or decrease the extent to which the antibody is glycosylated. Addition or deletion of glycosylation sites to an antibody can be carried out by altering the amino acid sequence such that one or more glycosylation sites is created or removed.

In embodiments where the antibody comprises an Fc region, the carbohydrate attached to the Fc region can be altered. Typically, native antibodies produced by mammalian cells comprise a branched, biantennary oligosaccharide attached by an N-linkage to Asn297 of the CH2 domain of the Fc region (see, e.g., Wright et al., *TIBTECH*, 15:26-32 (1997)). The oligosaccharide may include various carbohydrates, such as mannose, N-acetyl glucosamine (GlcNAc), galactose, and sialic acid, as well as, a fucose attached to a GlcNAc in the "stem" of the bi-antennary oligosaccharide structure. In some embodiments, the modifications of the oligosaccharide of an Fc region of an antibody can create a variant with certain improved properties.

In some embodiments, the anti-IL1RAP antibody of the present disclosure can be a variant of a parent antibody, wherein the variant comprises a carbohydrate structure that lacks fucose attached (directly or indirectly) to an Fc region. For example, the amount of fucose in such antibody may be from about 1% to about 80%, from about 1% to about 65%, from about 5% to about 65%, or from about 20% to about 40%. The amount of fucose can be determined by calculating the average amount of fucose within the sugar chain at Asn297, relative to the sum of all glyco-structures attached to Asn 297 (e.g., complex, hybrid and high mannose structures) as measured by MALDI-TOF mass spectrometry (see e.g., WO 2008/077546). Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies.

In some embodiments, the fucosylation variants can have improved ADCC function. See, e.g., US Patent Publication Nos. US 2003/0157108, or US 2004/0093621. Examples of "defucosylated" or "fucose-deficient" antibodies and associated methods for preparing them are disclosed in e.g., US2003/0157108; US2003/0115614; US2002/0164328; US2004/0093621; US2004/0132140; US2004/0110704; US2004/0110282; US2004/0109865; WO2000/61739; WO2001/29246; WO2003/085119; WO2003/084570; WO2005/035586; WO2005/035778; WO2005/053742; WO2002/031140; Okazaki et al., *J. Mol. Biol.*, 336: 1239-1249 (2004); Yamane-Ohnuki et al., *Biotech. Bioeng.* 87: 614 (2004).

Cell lines useful for producing defucosylated antibodies include Led 3 CHO cells deficient in protein fucosylation (see e.g., Ripka et al., *Arch. Biochem. Biophys.*, 249:533-545 (1986); US2003/0157108, and WO2004/056312), and knockout cell lines, such as alpha-1,6-fucosyltransferase gene, FUT8, knockout CHO cells (see, e.g., Yamane-Ohnuki et al., *Biotech. Bioeng.* 87: 614 (2004); Kanda, Y. et al., *Biotechnol. Bioeng.*, 94(4):680-688 (2006); and WO2003/085107).

C. Fc Region Variants

In some embodiments, an anti-IL1RAP antibody of the present disclosure can comprise one or more amino acid modifications in the Fc region (i.e., an Fc region variant). The Fc region variant may comprise a human Fc region sequence (e.g., a human IgG1, IgG2, IgG3, or IgG4 Fc region) comprising an amino acid substitution at one or more amino acid residue positions. A wide range of Fc region variants known in the art that are useful with the anti-IL1RAP antibodies of the present disclosure are described below.

In some embodiments, the anti-IL1RAP antibody is an Fc region variant which has altered effector function. In some embodiments, the antibody with altered effector function possesses some (but not all of) the effector functions, decreased effector function, or none of the effector functions (e.g., effectorless) of the parent antibody. Effectorless Fc region variants are more desirable for certain applications where effector function (such as ADCC) is unnecessary or deleterious, and/or in vivo half-life of the antibody is important.

Fc region variant antibodies with reduced effector function, or which are effectorless, can include an amino acid substitution at one or more of the following Fc region positions: 238, 265, 269, 270, 297, 327 and 329. (see, e.g., U.S. Pat. No. 6,737,056). Such Fc region variants can include amino acid substitutions at two or more of positions 265, 269, 270, 297 and 327. Such Fc region variants can also include substitutions of both residues 265 and 297 to alanine (see e.g., U.S. Pat. No. 7,332,581). As disclosed in the Examples and elsewhere herein, in some embodiments, the anti-IL1RAP antibodies of the present disclosure are effectorless Fc region variants. In some embodiments, the effectorless Fc region variants of the anti-IL1RAP antibodies comprise the amino acid substitution N297G.

Fc region variants having improved or diminished binding to FcRs are disclosed in e.g., U.S. Pat. No. 6,737,056; WO 2004/056312; and Shields et al., *J. Biol. Chem.*, 276(9): 6591-6604 (2001). Fc region variants having improved ADCC can comprise one or more amino acid substitutions at e.g., positions 298, 333, and/or 334 of the Fc region (based on EU numbering). Fc region variants having altered (i.e., either improved or diminished) C1q binding and/or Complement Dependent Cytotoxicity (CDC), as described in e.g., U.S. Pat. No. 6,194,551, WO99/51642, and Idusogie et al., *J. Immunol.*, 164: 4178-4184 (2000). Fc region variants with increased half-lives and improved binding to the neonatal Fc receptor (FcRn) are disclosed in e.g., US2005/0014934A1 (Hinton et al.). Such Fc region variants comprise amino acid substitutions at one or more of positions: 238, 256, 265, 272, 286, 303, 305, 307, 311, 312, 317, 340, 356, 360, 362, 376, 378, 380, 382, 413, 424, and 434. Other Fc region variants with increased half-lives include the set of YTE mutations at positions 252, 254, and 256 (i.e., M252Y/S254T/T256E) described in e.g., U.S. Pat. No. 7,658,921B2 (Dall'Acqua et al.). As disclosed in the Examples and elsewhere herein, in some embodiments, the anti-IL1RAP antibodies of the present disclosure are Fc region variants that include the set of YTE mutations. Other examples of Fc region variants can be found in e.g., U.S. Pat. Nos. 5,648,260 and 5,624,821; and WO94/29351.

As noted elsewhere herein, the Fc region of a naturally occurring antibody typically includes a C-terminal lysine at position 447 (Lys447). This C-terminal lysine, however, is often cleaved from the Fc region during the production of recombinant antibodies in cell culture due to enzymatic cleavage (e.g., production in CHO cells). Accordingly, it is intended that any of the anti-IL1RAP antibodies described herein as comprising an Fc region with a C-terminal lysine, also include the identical anti-IL1RAP antibody comprising an Fc region except without a C-terminal lysine. Similarly, it is intended that any of the anti-IL1RAP antibodies described herein as comprising an Fc region without a C-terminal lysine, also include the identical anti-IL1RAP antibody comprising a Fc region except with a C-terminal lysine.

Generally, in vitro and/or in vivo cytotoxicity assays can be carried out to confirm the reduction/depletion of CDC and/or ADCC activities in an Fc region variant. For example, Fc receptor (FcR) binding assays can be conducted to ensure that the antibody lacks FcγR binding (hence likely lacking ADCC activity) but retains FcRn binding ability. The primary cells for mediating ADCC, NK cells express FcγRIII only, whereas monocytes express FcγRI, FcγRII, and FcγRIII. Non-limiting examples of in vitro assays to assess ADCC activity of a molecule of interest is described in U.S. Pat. No. 5,500,362 (see, e.g. Hellstrom, et al., *Proc. Nat'l Acad. Sci. USA,* 83:7059-7063 (1986)) and Hellstrom, et al., *Proc. Nat'l Acad. Sci. USA,* 82: 1499-1502 (1985); U.S. Pat. No. 5,821,337 (see Bruggemann, M. et al., *J. Exp. Med.,* 166: 1351-1361 (1987)). Alternatively, non-radioactive assay methods may be employed (see, for example, ACTI™ nonradioactive cytotoxicity assay for flow cytometry (CellTechnology, Inc. Mountain View, CA; and CytoTox96® non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al., *Proc. Nat'l Acad. Sci. USA,* 95:652-656 (1998). C1q binding assays may also be carried out to confirm that the antibody is unable to bind C1q and hence lacks CDC activity. See, e.g., C1q and C3c binding ELISA in WO2006/029879 and WO2005/100402. To assess complement activation, a CDC assay may be performed (see, e.g., Gazzano-Santoro et al., *J. Immunol. Methods,* 202: 163 (1997), Cragg, M. S. et al., *Blood* 101, 1045-1052 (2003); and Cragg, M. S. and M. J. Glennie, *Blood,* 103:2738-2743 (2004)). FcRn binding and in vivo clearance/half-life determinations can be performed using methods known in the art (see, e.g., Petkova, et al., *Intl. Immunol.,* 18(12): 1759-1769 (2006)).

It is contemplated that a wide-range of Fc region variants of the anti-IL1RAP antibodies of the present disclosure can be prepared using the methods and techniques known in the art and/or described herein. For example, the Fc region variant prepared with the N297G amino acid substitution confers effectorless function on anti-IL1RAP antibodies with retention of cell-based blocking activity as described in Example 9.

D. Cysteine Engineered Variants

In some embodiments, it is contemplated that the anti-IL1RAP antibody described herein can be substituted at specific non-CDR positions with cysteine residues so as to create reactive thiol groups. Such engineered "thioMAbs" can be used to conjugate the antibody to e.g., drug moieties or linker-drug moieties and thereby create immunoconjugates, as described elsewhere herein. Cysteine engineered antibodies can be generated as described in e.g., U.S. Pat. No. 7,521,541. In some embodiments, any one or more of the following antibody residues can be substituted with cysteine: V205 (Kabat numbering) of the light chain; A118 (EU numbering) of the heavy chain; and S400 (EU numbering) of the heavy chain Fc region.

E. Derivatized Variants

In some embodiments, the anti-IL1RAP antibody of the present disclosure may be further modified (i.e., derivatized) with non-proteinaceous moieties. Non-proteinaceous moieties suitable for derivatization of the antibody include, but are not limited to, water soluble polymers, such as: polyethylene glycol (PEG), copolymers of ethylene glycol and propylene glycol, carboxy-methylcellulose, dextran, polyvinyl alcohol, polyvinyl pyrrolidone, poly-1,3-dioxolane, poly-1,3,6-trioxane, ethylene/maleic anhydride copolymer, poly-amino acid homo-polymers or random co-polymers, and dextran or poly(n-vinyl pyrrolidone)polyethylene glycol, propropylene glycol homo-polymers, polypropylene oxide/ethylene oxide co-polymers, polyoxy-ethylated polyols (e.g., glycerol), polyvinyl alcohol, and mixtures thereof. In some embodiments, modification of the antibody can be carried out using methoxy-polyethylene glycol propionaldehyde. The polymers may be of any molecular weight and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody, e.g., whether the antibody derivative will be used in a therapy under defined conditions.

8. Immunoconjugates

In some embodiments, the anti-IL1RAP antibody of the present disclosure can also be an immunoconjugate, wherein the immunoconjugate comprises an anti-IL1RAP antibody conjugated to one or more cytotoxic agents. Suitable cytotoxic agents contemplated by the present disclosure include chemotherapeutic agents, drugs, growth inhibitory agents, toxins (e.g., protein toxins, enzymatically active toxins of bacterial, fungal, plant, or animal origin, or fragments thereof), or radioactive isotopes.

In some embodiments, the immunoconjugate is an antibody-drug conjugate (ADC) in which an anti-IL1RAP antibody, as described herein, is conjugated to one or more drugs.

In some embodiments, an immunoconjugate of the present disclosure comprises an anti-IL1RAP antibody as described herein conjugated to a drug or therapeutic agent for the treatment of an IL-1, IL-33, IL-36, and/or IL1RAP-mediated disease or condition.

In some embodiments, an anti-IL1RAP antibody as described herein can be conjugated to an enzymatically active toxin or a fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins, *Momordica charantia* inhibitor, curcin, crotin, *Sapaonaria officinalis* inhibitor, gelonin, mitogellin, restrictocin, phenomycin, enomycin, and the tricothecenes.

In some embodiments, an immunoconjugate of the present disclosure comprises an anti-IL1RAP antibody as described herein conjugated to a radioactive isotope (i.e., a radioconjugate). A variety of radioactive isotopes are available for the production of such radioconjugates. Examples include $^{211}$At, $^{131}$I, $^{125}$I, $^{90}$Y, $^{186}$Re, $^{188}$Re, $^{153}$Sm, $^{212}$Bi, $^{32}$P, $^{212}$Pb, and radioactive isotopes of Lu. In some embodiments, the immunoconjugate may comprise a radioisotope for scintigraphic detection, or a spin label for NMR detection or MRI. Suitable radioisotopes or spin labels can include, as $^{123}$I, $^{131}$I, $^{111}$In, $^{13}$C, $^{19}$F, $^{15}$N, $^{17}$O, various isotopes of Gd, Mn, and Fe.

Immunoconjugates of an anti-IL1RAP antibody and a cytotoxic agent, can be made using a variety of well-known bifunctional reagents and chemistries suitable for conjugating to proteins. Such reagents include but are not limited to: N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (e.g., dimethyl adipimidate HQ), active esters (e.g., disuccinimidyl suberate), aldehydes (e.g., glutaraldehyde), bis-azido compounds (e.g., bis-(p-azidobenzoyl)-hexanediamine), bis-diazonium derivatives (e.g., bis-(p-diazoniumbenzoyl)-ethylenediamine), diisocyanates (e.g., toluene-2,6-diisocyanate), and bis-active fluorine compounds (e.g., 1,5-difluoro-2,4-dinitrobenzene).

Reagents for preparing immunoconjugates of the present disclosure can also include commercially available "cross-linking" reagents such as: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) (see e.g., Pierce Biotechnology, Inc., Rockford, IL, U.S.A).

9. Synthetic Antibodies

In some embodiments, the anti-IL1RAP antibody of the present disclosure can be a synthetic antibody comprising a set of CDRs from an anti-IL1RAP immunoglobulin (e.g., CDR-L1, etc.) grafted onto a scaffold or framework other than an immunoglobulin scaffold or framework, such as an alternative protein scaffold, or an artificial polymer scaffold.

Exemplary alternative protein scaffolds contemplated for preparation of synthetic antibodies of the present disclosure can include, but are not limited to: fibronectin, neocarzinostatin CBM4-2, lipocalins, T-cell receptor, protein-A domain (protein Z), Im9, TPR proteins, zinc finger domains, pVIII, avian pancreatic polypeptide, GCN4, WW domain Src homology domain 3, PDZ domains, TEM-1 beta-lactamase, thioredoxin, staphylococcal nuclease, PHD-fmger domains, CL-2, BPTI, APPI, HPSTI, ecotin, LACI-D1, LDTI, MTI-II, scorpion toxins, insect defensin-A peptide, EETI-II, Min-23, CBD, PBP, cytochrome b-562, Ldl receptor domains, gamma-crystallin, ubiquitin, transferrin, and/or C-type lectin-like domains.

Exemplary artificial polymer (non-protein) scaffolds useful for synthetic antibodies are described in e.g., Fiedler et al., (2014) "Non-Antibody Scaffolds as Alternative Therapeutic Agents," in Handbook of Therapeutic Antibodies (eds. S. Dübel and J. M. Reichert), Wiley-VCH Verlag GmbH & Co.; Gebauer et al., *Curr. Opin. Chem. Biol.*, 13:245-255 (2009); Binz et al., *Nat. Biotech.*, 23(10): 1257-1268 (2005).

IV. Recombinant Methods and Compositions

The anti-IL1RAP antibody of the present disclosure can be produced using recombinant methods and materials well-known in the art of antibody production. In some embodiments, the present disclosure provides an isolated nucleic acid encoding an anti-IL1RAP antibody. The nucleic acid can encode an amino acid sequence comprising the $V_L$ and/or an amino acid sequence comprising the $V_H$ of the antibody (e.g., the light and/or heavy chains of the antibody). In some embodiments, one or more vectors (e.g., expression vectors) comprising nucleic acid sequences encoding an anti-IL1RAP antibody of the present disclosure are provided. In some embodiments, a host cell comprising nucleic acid sequences encoding an anti-IL1RAP antibody of the present disclosure are provided. In one embodiment, the host cell has been transformed with a vector comprising a nucleic acid that encodes an amino acid sequence comprising the $V_L$ of the antibody and an amino acid sequence comprising the $V_H$ of the antibody. In another embodiment, the host cell has been transformed with a first vector comprising a nucleic acid that encodes an amino acid sequence comprising the $V_L$ of the antibody and a second vector comprising a nucleic acid that encodes an amino acid sequence comprising the $V_H$ of the antibody.

In some embodiments of the recombinant methods, the host cell used is a eukaryotic cell, such as a Chinese Hamster Ovary (CHO) cell, or a lymphoid cell (e.g., Y0, NS0, Sp20). In one embodiment, a method of making an anti-IL1RAP antibody is provided, wherein the method comprises culturing a host cell comprising a nucleic acid encoding the antibody, as provided above, under conditions suitable for expression of the antibody, and optionally recovering the antibody from the host cell (or host cell culture medium).

Briefly, recombinant production of an anti-IL1RAP antibody is carried out by isolating a nucleic acid encoding an antibody (e.g., as described herein) and inserting this nucleic acid into one or more vectors for further cloning and/or expression in a host cell. Such nucleic acids are readily isolated and sequenced using conventional procedures well-known in the art (e.g., by using oligonucleotide probes that are capable of binding specifically to genes encoding the heavy and light chains of the desired antibody). Suitable host cells and culturing methods for cloning or expressing the antibody-encoding vectors are well-known in the art and include prokaryotic or eukaryotic cells. Typically, after expression, the antibody may be isolated from cell paste in a soluble fraction and further purified. In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern (see e.g., Gerngross, *Nat. Biotech.*, 22: 1409-1414 (2004), and Li et al., *Nat. Biotech.*, 24:210-215 (2006)).

Suitable host cells for the expression of glycosylated anti-IL1RAP antibodies of the present disclosure can also be derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts (see, e.g., U.S. Pat. Nos. 5,959,177, 6,040,498, 6,420,548, and 7,125,978.

Examples of mammalian host cell lines useful for the production of the anti-IL1RAP antibodies of the present disclosure include Chinese hamster ovary (CHO) cells, including DHFR-CHO cells (see e.g., Urlaub et al., *Proc. Natl. Acad. Sci. USA*, 77:4216 (1980)); myeloma cell lines such as Y0, NS0 and Sp2/0; monkey kidney CVI line transformed by SV40 (COS-7); human embryonic kidney line (293 or 293 cells as described, e.g., in Graham et al., *J. Gen Virol.*, 36:59 (1977)); baby hamster kidney cells (BHK); mouse Sertoli cells (TM4 cells as described, e.g., in Mather, *Biol. Reprod.*, 23:243-251 (1980)); monkey kidney cells (CVI); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells (see e.g., in Mather et al., *Annals N.Y. Acad. Sci.*, 383:44-68 (1982)); MRC 5 cells; and FS4 cells. For a general review of useful mammalian host cell lines suitable for antibody production, see, e.g., Yazaki and Wu, Methods in Molecular Biology, Vol. 248 (B. K. C. Lo, ed., *Antibody Engineering*, Humana Press, Totowa, NJ), pp. 255-268 (2003).

V. Pharmaceutical Compositions and Formulations of Anti-IL1RAP Antibodies

The present disclosure also provides pharmaceutical compositions and pharmaceutical formulations comprising an anti-IL1RAP antibody. In some embodiments, the present disclosure provides a pharmaceutical formulation comprising an anti-IL1RAP antibody as described herein and a pharmaceutically acceptable carrier. Such pharmaceutical formulations can be prepared by mixing an anti-IL1RAP antibody, having the desired degree of purity, with one or more pharmaceutically acceptable carriers. Typically, such antibody formulations can be prepared as an aqueous solution (see e.g., U.S. Pat. No. 6,171,586, and WO2006/044908) or as a lyophilized formulation (see e.g., U.S. Pat. No. 6,267,958).

It is also contemplated that the compositions and formulations comprising an anti-IL1RAP antibody as disclosed herein may further contain other active ingredients (i.e., therapeutic agents) in addition to the anti-IL1RAP, useful for the particular indication being treated in the subject to whom the formulation is administered. Preferably, any additional therapeutic agent has activity complementary to that of the anti-IL1RAP antibody activity and the activities do not adversely affect each other. Accordingly, in some embodiments, the disclosure provides a pharmaceutical composition comprising an anti-IL1RAP antibody as disclosed herein, and a pharmaceutically acceptable carrier, and further comprises a therapeutic agent useful for treatment of an IL-1, IL-33, IL-36, and/or IL1RAP-mediated disease or condition. In some embodiments, for example wherein the disease indication is cancer the therapeutic agent is a chemotherapeutic agent appropriate for the particular cancer. In some embodiments, the further therapeutic agent in the composition is an antagonist of a IL-1, IL-33, IL-36 signaling pathway.

Pharmaceutically acceptable carriers are generally non-toxic to recipients at the dosages and concentrations employed. A wide range of such pharmaceutically acceptable carriers are well-known in the art (see e.g., Remington's Pharmaceutical Sciences 16th edition, Osol, A. Ed. (1980)). Exemplary pharmaceutically acceptable carriers useful in the formulations of the present disclosure can include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polyethylene glycol (PEG).

Pharmaceutically acceptable carriers useful in the formulations of the present disclosure can also include interstitial drug dispersion agents, such as soluble neutral-active hyaluronidase glycoproteins (sHASEGP) (see e.g., US Pat. Publ. Nos. 2005/0260186 and 2006/0104968), such as human soluble PH-20 hyaluronidase glycoproteins (e.g., rHuPH20 or HYLENEX®, Baxter International, Inc.).

additional therapeutic agents and active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

In some embodiments, the formulation can be a sustained-release preparation of the antibody and/or other active ingredients. Suitable examples of sustained-release preparations include semipermeable matrices of solid hydrophobic polymers containing the antibody, which matrices are in the form of shaped articles, e.g. films, or microcapsules.

Typically, the formulations of the present disclosure to be administered to a subject are sterile. Sterile formulations may be readily prepared using well-known techniques, e.g., by filtration through sterile filtration membranes.

IV. Uses and Methods of Treatment

It is contemplated that any of the compositions or formulations comprising an anti-IL1RAP antibody of the present disclosure can be used for any methods or uses, such as in therapeutic methods, that utilize their ability to specifically bind to IL1RAP and/or block the activity of IL1RAP, particularly blocking the ability of IL1RAP to mediate intracellular signaling by the IL-1 family cytokines, IL-1α, IL-1β, IL-33, IL-36α, IL-36β, and/or IL-36γ. The intracellular signaling pathways mediated by IL1RAP include the IL-1, IL-33, and IL-36 pathways, and more specifically, include at least the signaling pathways stimulated by the cytokine agonists IL-1α, IL-1β, IL-33, IL-36α, IL-36β, and/or IL-36γ. Inhibition of the IL1RAP-mediated signaling pathways can be assayed in vitro using known cell-based blocking assays including the HEK-BLUE™ reporter cell assays and primary cell-based blocking assays described in the Examples of the present disclosure.

An IL1RAP mediated disease can include any disease or condition associated with elevated levels in bodily fluids or tissue of the IL-1 family of cytokines for which IL1RAP acts as a co-receptor in mediating signaling: IL-1α, IL-1β, IL-33, IL-36α, IL-36β, and/or IL-36γ. Elevated levels of IL-1α, IL-1β, IL-33, IL-36α, IL-36β, and/or IL-36γ can include, for example, levels that exceed those normally found in a particular cell or tissue, or can be any detectable level in a cell or tissue that normally does not express these cytokines. Typically, IL1RAP mediated conditions or diseases exhibit the following characteristics: (1) pathologies associated with the condition or disease can be experimentally induced in animals by administration of IL-1α, IL-1β, IL-33, IL-36α, IL-36β, and/or IL-36γ, and/or by up-regulation of expression of IL-1α, IL-1β, IL-33, IL-36α, IL-36β, and/or IL-36γ; and (2) pathologies associated with the condition or disease generated in experimental animal models can be inhibited by agents that are known inhibit the action of IL-1α, IL-1β, IL-33, IL-36α, IL-36β, and/or IL-36γ.

IL-1α, IL-1β, IL-33, IL-36α, IL-36β, and/or IL-36γ are known to be pro-inflammatory cytokines, however, the aberrant function of the IL-1, IL-33, and/or IL-36 signaling pathways stimulated by these cytokines as mediated by IL1RAP as co-receptor, are known to be associated with a wide range of diseases and conditions generally including but not limited to inflammatory diseases, autoimmune diseases, respiratory diseases, metabolic disorders, infections, and cancers.

For example, a wide range conditions and diseases associated with aberrant function of IL-33 signaling, and consequently, also mediated by the co-receptor activity of IL1RAP include but are not limited to: mediated disorder may be an inflammatory condition (e.g., asthma, airway hyperresponsiveness, airway inflammation, sepsis, septic shock, atopic dermatitis, allergic rhinitis, rheumatoid arthritis, or chronic obstructive pulmonary disease (COPD)); an immune disorder (e.g., asthma, rheumatoid arthritis, allergy, atopic allergy, anaphylaxis, anaphylactic shock, allergic rhinitis, psoriasis, inflammatory bowel disease (IBD), Crohn's disease, diabetes, or liver disease); a fibrotic disorder (e.g., idiopathic pulmonary fibrosis (IPF)); an eosinophilic disorder (e.g., eosinophil-associated gastrointestinal disorder, such as eosinophilic esophagitis); an infection (e.g., helminth, protozoan, such as Leishmania major, or viral infection, such as RSV or influenza); pain (e.g., inflammatory pain); a central nervous system disorder (e.g., Alzheimer's disease); a solid tumor (e.g., breast tumor, colon tumor, prostate tumor, lung tumor, kidney tumor, liver tumor, pancreas tumor, stomach tumor, intestinal tumor, brain tumor, bone tumor, or skin tumor); or an ophthalmologic disorder. Specific ophthalmologic disorders mediated by IL-33 include but are not limited to: age-related macular degeneration (AMD), including wet AMD, dry AMD, intermediate AMD, advanced AMD, and geographic atrophy (GA)), retinopathy (e.g., diabetic retinopathy (DR), retinopathy of prematurity (ROP), and high-altitude DR), polypoidal choroidal vasculopathy (PCV), diabetic macular edema, dry eye disease, Behcet's disease, retinal detachment, glaucoma, uveitis (e.g., infectious and non-infectious uveitis), retinitis pigmentosa, Leber's congenital amaurosis, Stargardt's disease, traumatic eye injury, and conjunctivitis (e.g., infectious conjunctivitis, non-infectious conjunctivitis, and allergic conjunctivitis).

Similarly, a wide range of conditions and diseases associated with aberrant function of IL-1, and consequently, also mediated by the co-receptor activity of IL1RAP include but are not limited to: acute pancreatitis; amyotrophic lateral sclerosis (ALS); Alzheimer's disease; cachexia/anorexia, including AIDS-induced cachexia; asthma and other pulmonary diseases; atherosclerosis; autoimmune vasculitis; chronic fatigue syndrome; *Clostridium* associated illnesses, including *Clostridium*-associated diarrhea; coronary conditions and indications, including congestive heart failure, coronary restenosis, myocardial infarction, myocardial dysfunction (e.g., related to sepsis), and coronary artery bypass graft; cancer, such as multiple myeloma and myelogenous (e.g., AML or CML) and other leukemias, as well as tumor metastasis; diabetes (e.g., insulin-dependent diabetes); endometriosis; fever, fibromyalgia; glomerulonephritis; graft versus host disease/transplant rejection; hemorrhagic shock; hyperalgesia; inflammatory bowel disease; inflammatory conditions of a joint, including osteoarthritis, psoriatic arthritis and rheumatoid arthritis; inflammatory eye disease, as may be associated with, e.g., corneal transplant; ischemia, including cerebral ischemia (e.g., brain injury as a result of trauma, epilepsy, hemorrhage or stroke, each of which may lead to neurodegeneration); Kawasaki's disease; learning impairment; lung diseases (e.g., ARDS); multiple sclerosis; myopathies (e.g., muscle protein metabolism, especially in sepsis); neurotoxicity (e.g., as induced by HIV); osteoporosis; pain, including cancer-related pain; Parkinson's disease; periodontal disease; pre-term labor; psoriasis; reperfusion injury; septic shock; side effects from radiation therapy; temporal mandibular joint disease; sleep disturbance; uveitis; or an inflammatory condition resulting from strain, sprain, cartilage damage, trauma, orthopedic surgery, infection or other disease processes.

Agents that act as antagonists or inhibitors of the IL-1, IL-33, and/or IL-36 signaling pathways are in clinical development for the treatment of a range of diseases and conditions, including but not limited to the following: acne, acute severe ulcerative colitis, adult-onset Still's disease, allergic rhinitis, arthritis (including gouty, juvenile, osteo, and rheumatoid), arthritis pain, asthma, atherosclerosis, atopic eczema, Behcet's disease, cachexia, cancer (including breast, colorectal, non-small cell lung, and pancreatic), chronic obstructive pulmonary disease, dry eye syndrome, familial cold autoinflammatory syndrome, familial Mediterranean fever, food allergy, generalized pustular psoriasis, hidradenitis suppurativa, hyper-IgD syndrome, hyperuricemia, Muckle-Wells syndrome, neonatal onset multisystem inflammatory disease, musculoskeletal pain, palmoplantar pustulosis, peripheral vascular disease, polymyalgia rheumatica, nasal polyp, psoriasis, pyoderma gangrenosum, restenosis, sickle-cell anemia, sinusitis, TNF receptor associated periodic syndrome, type-2 diabetes, and ulcerative colitis.

It is contemplated that any of the compositions or formulations comprising an anti-IL1RAP antibody of the present disclosure can be used in a method or use for the treatment of any of the above-listed diseases or conditions associated with aberrant function of the IL-1, IL-33, and/or IL-36 signaling pathway and therefore mediated by the co-receptor activity of IL1RAP. Generally, these conditions and diseases include but are not limited to inflammatory diseases, autoimmune diseases, respiratory diseases, metabolic disorders, infections, and cancers.

Accordingly in some embodiments, the compositions or formulations comprising an anti-IL1RAP antibody of the present disclosure can be used in a method, therapy, medicament, diagnostic, or use for use in the treatment of a condition or disease selected from acne, acute pancreatitis, acute severe ulcerative colitis, adult-onset Still's disease, age-related macular degeneration (AMD), airway hyperresponsiveness, airway inflammation, allergic conjunctivitis, allergic rhinitis, allergy, Alzheimer's disease, amyotrophic lateral sclerosis (ALS), anaphylaxis, arthritis pain, asthma, atherosclerosis, atopic dermatitis, atopic eczema, autoimmune vasculitis, Behcet's disease, bone cancer, brain cancer, breast cancer, cachexia/anorexia, cartilage damage, cerebral ischemia, chronic fatigue syndrome, chronic obstructive pulmonary disease, *Clostridium* associated illnesses, colon cancer, congestive heart failure, conjunctivitis, coronary artery bypass graft, coronary restenosis, Crohn's disease, diabetes, diabetic macular edema, diabetic retinopathy, dry eye disease, endometriosis, eosinophil-associated gastrointestinal disorder, eosinophilic esophagitis, familial cold autoinflammatory syndrome, familial Mediterranean fever, fever, fibromyalgia, fibrotic disorder, food allergy, generalized pustular psoriasis, glaucoma, glomerulonephritis, gouty arthritis, graft versus host disease, helminth infection, hemorrhagic shock, hidradenitis suppurativa, hyperalgesia, hyper-IgD syndrome, hyperuricemia, idiopathic pulmonary fibrosis (IPF), cancer-related pain, infection, inflammatory bowel disease (IBD), inflammatory conditions resulting from strain, inflammatory eye disease associated with corneal transplant, inflammatory pain, influenza, intestinal cancer, ischemia, juvenile arthritis, Kawasaki's disease, kidney cancer, Leber's congenital amaurosis, liver cancer, liver disease, lung cancer, Muckle-Wells syndrome, multiple myeloma, multiple sclerosis, musculoskeletal pain, myelogenous and other leukemias, myocardial dysfunction, myopathies, nasal polyp, neonatal onset multisystem inflammatory disease, neurotoxicity, non-infectious conjunctivitis, non-small cell lung cancer, orthopedic surgery, osteoarthritis, osteoporosis, pain, palmoplantar pustulosis, pancreas cancer, Parkinson's disease, periodontal disease, peripheral vascular disease, polymyalgia rheumatica, polypoidal choroidal vasculopathy (PCV), pre-term labor, prostate cancer, protozoan infection, psoriasis, psoriatic arthritis, pyoderma gangrenosum, reperfusion injury, respiratory syncytial virus (RSV), restenosis, retinal detachment, retinitis pigmentosa, retinopathy of prematurity (ROP), rheumatoid arthritis, septic shock, sickle-cell anemia, side effects from radiation therapy, sinusitis, skin cancer, sleep disturbance, sprain, Stargardt's disease, stomach cancer, temporal mandibular joint disease, TNF receptor associated periodic syndrome, transplant rejection, trauma, traumatic eye injury, type-2 diabetes, ulcerative colitis, and uveitis.

As disclosed herein, including in the Examples below, the anti-IL1RAP antibodies of the present disclosure have the ability to decrease, inhibit, and/or block intracellular signaling mediated by IL1RAP, including the IL-1, IL-33, and IL-36 signaling pathways. Accordingly, in some embodiments, the present disclosure provides a method of treating a IL1RAP-mediated disease or condition in a subject, the method comprising administering to the subject a therapeutically effective amount of an anti-IL1RAP antibody of the present disclosure or administering to a subject in need thereof a therapeutically effective amount of a pharmaceutical composition comprising an anti-IL1RAP antibody of the present disclosure and a pharmaceutically acceptable carrier.

As disclosed elsewhere herein, the anti-IL1RAP antibodies of the present disclosure have the ability to decrease, inhibit, and/or block the IL-1, IL-33, and IL-36 signaling pathways. Accordingly, the present disclosure also provides methods of treating diseases and conditions responsive to a decrease, inhibition, and/or blocking of the IL-1, IL-33, and/or IL-36 signaling pathways.

Additionally, the anti-IL1RAP antibodies of the present disclosure have the ability to decrease, inhibit, and/or block intracellular signaling stimulated by the agonists IL-1α, IL-1β, IL-33, IL-36α, IL-36β, and/or IL-36γ. Accordingly, the present disclosure also provides methods of treating diseases and conditions responsive to a decrease, inhibition, and/or blocking of intracellular signaling stimulated by the agonists IL-1α, IL-1β, IL-33, IL-36α, IL-36β, and/or IL-36γ.

The IL-1 signaling pathways, which are also IL1RAP-mediated pathways, have been associated with many forms of cancer. Accordingly, in some embodiments, the present disclosure provides a method of treating cancer in a subject, the method comprising administering to the subject in need thereof a therapeutically effective amount of an anti-IL1RAP antibody of the present disclosure or administering to a subject a therapeutically effective amount of a pharmaceutical composition comprising an anti-IL1RAP antibody of the present disclosure and a pharmaceutically acceptable carrier.

All three of the IL-1, IL-33, and/or IL-36 signaling pathways, which are also IL1RAP-mediated pathways, have been associated with asthma. Accordingly, in some embodiments, the present disclosure provides a method of treating asthma in a subject, the method comprising administering to the subject in need thereof a therapeutically effective amount of an anti-IL1RAP antibody of the present disclosure or administering to a subject a therapeutically effective amount of a pharmaceutical composition comprising an anti-IL1RAP antibody of the present disclosure and a pharmaceutically acceptable carrier.

In some embodiments, the present disclosure provides a method of treating and/or preventing a IL1RAP-mediated disease, a IL-1, IL-33, and IL-36 signaling pathway mediated disease, and/or a disease mediated by intracellular signaling stimulated by the agonists IL-1α, IL-1β, IL-33, IL-36α, IL-36β, and/or IL-36γ. In such method of treatment embodiments, the method comprises administering to a subject in need thereof, a therapeutically effective amount of an anti-IL1RAP antibody, or a composition or pharmaceutical formulation comprising an anti-IL1RAP antibody as described herein.

Administration of the antibody, composition, or pharmaceutical formulation in accordance with the method of treatment provides an antibody-induced therapeutic effect that protects the subject from and/or treats the progression of a IL1RAP-mediated disease in a subject. In some embodiments, the method of treatment can further comprise administration of one or more additional therapeutic agents or treatments known to those of skill in the art to prevent and/or treat the IL1RAP-mediated disease or condition. Such methods comprising administration of one or more additional agents can encompass combined administration (where two or more therapeutic agents are included in the same or separate formulations), and separate administration, in which case, administration of the antibody composition or formulation can occur prior to, simultaneously, and/or following, administration of the additional therapeutic agent.

In some embodiments of the methods of treatment of the present disclosure, the anti-IL1RAP antibody or pharmaceutical formulation comprising an anti-IL1RAP antibody is administered to a subject by any mode of administration that delivers the agent systemically, or to a desired target tissue. Systemic administration generally refers to any mode of administration of the antibody into a subject at a site other than directly into the desired target site, tissue, or organ, such that the antibody or formulation thereof enters the subject's circulatory system and, thus, is subject to metabolism and other like processes.

Accordingly, modes of administration useful in the methods of treatment of the present disclosure can include, but are not limited to, injection, infusion, instillation, and inhalation. Administration by injection can include intravenous, intramuscular, intraarterial, intrathecal, intraventricular, intracapsular, intraorbital, intracardiac, intradermal, intraperitoneal, transtracheal, subcutaneous, subcuticular, intraarticular, subcapsular, subarachnoid, intraspinal, intracerebrospinal, and intrasternal injection and infusion.

In some embodiments, a pharmaceutical formulation of the anti-IL1RAP antibody is formulated such that the antibody is protected from inactivation in the gut. Accordingly, the method of treatments can comprise oral administration of the formulation.

In some embodiments, use of the compositions or formulations comprising an anti-IL1RAP antibody of the present disclosure as a medicament are also provided. Additionally, in some embodiments, the present disclosure also provides for the use of a composition or a formulation comprising an anti-IL1RAP antibody in the manufacture or preparation of a medicament, particularly a medicament for treating, preventing or inhibiting an IL1RAP-mediated disease. In a further embodiment, the medicament is for use in a method for treating, preventing or inhibiting an IL1RAP-mediated disease comprising administering to an individual having an IL1RAP-mediated disease an effective amount of the medicament. In certain embodiments, the medicament further comprises an effective amount of at least one additional therapeutic agent, or treatment.

In a further embodiment, the medicament is for use in treating, inhibiting or preventing an IL1RAP-mediated disease in a subject comprising administering to the subject an amount effective of the medicament to treat, inhibit or prevent the IL1RAP-mediated disease.

For the prevention or treatment of a IL1RAP-mediated disease or condition, the appropriate dosage of the anti-IL1RAP antibody contained in the compositions and formulations of the present disclosure (when used alone or in combination with one or more other additional therapeutic agents) will depend on the specific disease or condition being treated, the severity and course of the disease, whether the antibody is administered for preventive or therapeutic purposes, the previous therapy administered to the patient, the patient's clinical history and response to the antibody, and the discretion of the attending physician. The anti-IL1RAP antibody included in the compositions and formulations described herein, can be suitably administered to the patient at one time, or over a series of treatments. Various dosing schedules including but not limited to single or multiple administrations over various time-points, bolus administration, and pulse infusion are contemplated herein.

Depending on the type and severity of the disease, about 1 µg/kg to 15 mg/kg of anti-IL1RAP antibody in a formulation of the present disclosure is an initial candidate dosage for administration to a human subject, whether, for example, by one or more separate administrations, or by continuous infusion. Generally, the administered dosage of the antibody would be in the range from about 0.05 mg/kg to about 10 mg/kg. In some embodiments, one or more doses of about 0.5 mg/kg, 2.0 mg/kg, 4.0 mg/kg or 10 mg/kg (or any combination thereof) may be administered to a patient.

Dosage administration can be maintained over several days or longer, depending on the condition of the subject, for example, administration can continue until the IL1RAP-mediated disease is sufficiently treated, as determined by methods known in the art. In some embodiments, an initial higher loading dose may be administered, followed by one or more lower doses. However, other dosage regimens may be useful. The progress of the therapeutic effect of dosage administration can be monitored by conventional techniques and assays.

Accordingly, in some embodiments of the methods of the present disclosure, the administration of the anti-IL1RAP antibody comprises a daily dosage from about 1 mg/kg to about 100 mg/kg. In some embodiments, the dosage of anti-IL1RAP antibody comprises a daily dosage of at least about 1 mg/kg, at least about 5 mg/kg, at least about 10 mg/kg, at least about 20 mg/kg, or at least about 30 mg/kg.

Additionally, the anti-IL1RAP antibodies of the present disclosure may be used in assay methods for the detection of IL1RAP. Due to their ability to bind human IL1RAP with high affinity, the anti-IL1RAP antibodies disclosed herein are appropriate for a wide range of assay methods and formats. It is contemplated that the anti-IL1RAP antibodies can be employed in any known assay method, such as competitive binding assays, direct and indirect sandwich assays, immunoprecipitation assays and enzyme-linked immunosorbent assays (ELISA) (See, Sola, 1987, Monoclonal Antibodies: A Manual of Techniques, pp. 147-158, CRC Press, Inc.) for the detection and quantitation of IL1RAP. Accordingly, in some embodiments, the present disclosure provides a method for detecting the level of IL1RAP in a biological sample, the method comprising the step of contacting the sample with an anti-IL1RAP antibody as disclosed herein. Further, in some embodiments, it is contemplated that the method of detecting the level of IL1RAP in a biological sample can be used for detecting and/or diagnosing an IL1RAP-mediated condition or disease in a biological sample, e.g., from a human subject.

EXAMPLES

Various features and embodiments of the disclosure are illustrated in the following representative examples, which are intended to be illustrative, and not limiting. Those skilled in the art will readily appreciate that the specific examples are only illustrative of the invention as described more fully in the claims which follow thereafter. Every embodiment and feature described in the application should be understood to be interchangeable and combinable with every embodiment contained within.

Example 1

Generation of IL1RAP Polypeptides

This example illustrates the preparation of the various IL1RAP polypeptide constructs used as antigens in eliciting and screening the anti-IL1RAP antibodies of the present disclosure.

The extracellular domain of hu-IL1RAP was purified recombinantly as full-length and individual domains (i.e., D1, D2, D3) based upon structural information in Wang et al., *Nat. Immunol.*, 11:905-912 (2010). The amino acid sequence boundaries of the expression constructs are provided above in Table 1 and the accompanying Sequence Listing. All of the recombinant IL1RAP polypeptide constructs had the following "GGGS-V5-6XHis" C-terminal tag for purification and detection purposes: GGGSGKPIPN-PLLGLDSTHHHHHH (SEQ ID NO: 319). The constructs of the individual domains (e.g., D1, D1D2, D3) had the following "GGGS-V5-Avi-6XHis" C-terminal tag (which also includes an "Avi" tag) for purification and detection purposes: GGGSGKPIPNPLLGLDSTGLNDIFEAQK-IEWHEHHHHHH (SEQ ID NO: 320).

The IL1RAP construct proteins were expressed in Expi293F cells (Thermo Fisher Scientific, Waltham, MA, USA) according to the manufacturer's protocol. Cells were harvested after 5 days and the clarified supernatant was supplemented with 20 mM imidazole pH 7.5 and applied to HisTrap FF crude columns (GE Healthcare, Chicago, IL, USA) equilibrated in 20 mM Tris-HCl, 150 mM NaCl (TBS), 20 mM imidazole pH 7.5. Proteins were eluted with a 20 CV gradient to 100% TBS, 500 mM imidazole pH 7.5. Elution fractions containing protein were pooled and loaded onto Superdex 75 or Superdex 200 increase columns (GE Healthcare, Chicago, IL, USA) depending on the molecular weight of the protein. Peak fractions containing monomeric protein were pooled and stored in 1×PBS, pH 7.5 or 25 mM HEPES, 150 mM NaCl (HBS), pH 8.0.

Example 2

Generation of Anti-Human IL1RAP Antibodies Using Hybridoma Methods, Screening and Selection for Further Characterization This example illustrates the methods using mouse hybridoma technology to generate anti-hu-IL1RAP antibodies, and methods to screen and select antibodies for further characterization.

Immunizations and fusions: Balb/c, Swiss Webster and SJ/L mice were immunized with the hu-M-IL1RAP polypeptide construct of SEQ ID NO: 3 (see Table 1) comprising the extracellular domain of the membrane form of hu-IL1RAP using 50 µg/mouse. Following the initial immunization, subsequent boost immunizations of the following 3 different IL1RAP immunogens were administered on a schedule and for the duration necessary to induce a suitable titer of anti-IL1RAP antibody in the mice: 25 µg/mouse of the polypeptide of SEQ ID NO: 3 (hu-M-IL1RAP), 25 µg/mouse of the polypeptide of SEQ ID NO: 9 (mo-M-IL1RAP), or 25 µg/mouse of the polypeptide of SEQ ID NO: 6 (hu-M-IL1RAP-D3). The adjuvant Magic Mouse (Creative Diagnostics, Shirley, NY) was used for all immunizations. Titers were determined by ELISA as described below. Mice selected based on their titers were given a final pre-fusion boost without adjuvant. One day later, spleens were harvested and processed according to standard protocols. Splenocytes were fused with myeloma P3X63Ag8.653 cells (American Type Culture Collection CRL 1580) using PEG and following standard protocols and plated into 96-well plates at approximately 50,000 myeloma cells/well using standard techniques to maximize clonality of the resulting colonies. Parental hybridomas were selected using selection medium supplemented with AH (Azaserine+Hypoxanthine).

ELISA assays: After 12-14 days of culture, hybridoma supernatants were collected and subjected to primary screening by ELISA with 96 well plates coated with the hu-M-IL1RAP extracellular domain of SEQ ID NO: 3. ELISA assays were performed generally as described in Baker et al., *Trends Biotechnol.*, 20:149-156 (2002). Briefly, 96-well MAXISORP® flat bottom plates (Thermo Fisher Scientific, Waltham, MA; catalogue number 439454) were coated overnight at 4° C. with 50 µL/well of protein at a concentration of 1 µg/mL in coating buffer (0.05 M carbonate buffer, pH 9.6 or phosphate buffered saline, PBS). After removing the coating solution, unspecific binding was blocked by adding 200 µL of assay/blocking solution containing 1% bovine serum albumin (BSA) in phosphate buffered saline (PBS) pH 7.4 (ELISA diluent) and incubation at room temperature for one hour with agitation or overnight at 4° C. without agitation. Plates were then washed three times with 300 µL of PBS, 0.05% TWEEN®-20 (wash buffer). 100 µL of culture supernatant from individual hybridoma clones (or purified antibodies at the indicated concentration) was added to individual wells followed by incubation at room temperature for one hour with agitation. Plates were washed three times with wash buffer, then 50 µL/well of goat anti-mouse IgG Fc conjugated to horseradish peroxidase (Bethyl Laboratories, Montgomery, TX, USA; catalogue number A90-131P) at 1:3,000 dilution or goat anti-mouse IgG (H+L) conjugated to horseradish peroxidase (Jackson ImmunoResearch, Inc., West Grove, PA, USA; catalogue number 109-035-088) at 1:10,000 dilution in ELISA diluent was added. The plate was incubated at room temperature for one hour with agitation, washed six times with wash buffer and developed for 3-10 minutes by adding 50 pL/well of tetramethylbenzidine (TMB) microwell peroxidase substrate (Scytek Laboratories, Inc., Logan, UT, USA; catalogue number TM1999). Enzymatic color development was stopped by acidification with 50 µL/well of 2 N $H_2SO_4$ (Sigma-Aldrich Corporation, St. Louis, MO, USA; catalogue number 258105). Plates were analyzed with a SpectraMax i3X plate reader (Molecular Devices LLC, San Jose, CA, USA) at a wavelength of 450 nm.

This primary ELISA assay screen identified a total of 470 anti-human IL1RAP binders from the hybridomas generated by three Swiss Webster mice immunized with the hu-M-IL1RAP polypeptide of SEQ ID NO: 3 and the hu-M-IL1RAP-D3 polypeptide of SEQ ID NO: 6. These 470 parental hybridomas were expanded to 24-well plates and a confirmatory ELISA screening was carried out as described above resulting in 315 confirmed hu-IL1RAP binders.

HEK-Blue Cell-Based Blocking Assays of Hybridomas, Screening for Sub-Cloning and Purification The 315 hybridomas confirmed positive for hu-M-IL1RAP binding were further characterized for their ability to inhibit the IL-1 mediated IL1R1/IL1RAP and the IL-33 mediated ST2/IL1RAP signaling pathways using the HEK-Blue cell-based blocking assay described below.

HEK Blue cell lines: The HEK-Blue cell lines, described in this and the following examples, use the HEK-293 cell line (human embryonic kidney epithelial cells) as the original parental lineage. The HEK-Blue IL-1/IL-33 sensor cells, which are responsive to stimulation by IL-1α, IL-1β, and IL-33, were obtained from InvivoGen (InvivoGen, San Diego, CA, USA; catalog number hkb-il33). These IL-1/IL-33 sensor cells were generated by stable transfection of HEK-Blue IL-1β sensor cells (InvivoGen; catalog number hkb-il1b) with the human ST2 gene expressing the IL-33 receptor ST2. HEK-Blue IL-1β cells express an NF-κB/AP-1 SEAP (secreted embryonic alkaline phosphatase)

reporter gene and contain an inactivated TNF-α response to ensure SEAP production is representative of IL-1 or IL-33 pathway activation. The HEK-Blue IL-1/IL-33 responsive cells were maintained according to manufacturer's guidelines. Briefly, the cells were maintained in a standard growth medium consisting of DMEM (Corning, Inc., Corning, NY, USA), supplemented with 10% fetal bovine serum (FBS) (Atlanta Biologicals, Inc., Flowery Branch, GA, USA), 100 IU/mL penicillin and 100 μg/mL streptomycin. The growth medium was further supplemented with 100 μg/mL zeocin to maintain the plasmid coding for SEAP, 200 μg/mL hygromycin B to maintain IL-1 specificity and 100 μg/mL blasticidin to maintain the plasmid encoding ST2.

HEK-Blue SEAP assays: The HEK-Blue IL-1/IL-33 responsive sensor cells were used for all HEK-Blue SEAP assays where IL-1α, IL-1β, or IL-33 stimulation occurred. An agonist dose-response curve, consisting of an eight-point serial dilution series, was generated in advance of all assays, to provide an estimate of the half maximal effective concentration ($EC_{50}$) of agonist to be used in the assay. 24 hours prior to experimental use, the cells were plated on 96-well, flat-bottom plates at a concentration resulting in a minimum of 80% confluency at the time of use. The desired agonist was added to the cells to a final volume 200 μL and the cells incubated for 24 hours at 37° C. with 5% $CO_2$. SEAP production was quantified using a SEAP detection assay. The SEAP detection medium QUANTI-Blue (InvivoGen) was used to determine the level of SEAP with the various conditions indicated and per general manufacturer's guidelines. Specifically, 20 μL of cell culture supernatant (collected 24 hours post-agonist addition) was added to 130 μL of QUANTI-Blue detection medium. The reaction was allowed to proceed for one hour at 37° C., at which point a SpectraMax (Molecular Devices) spectrophotometer was used to measure the absorbance at a wavelength of 650 nm in conjunction with SoftMax Pro software (Molecular Devices). The raw assay data was analyzed using GraphPad Prism 7 software to perform a non-linear regression determination of the agonist $EC_{50}$ value in the assay.

HEK-Blue SEAP assays of non-purified anti-hu-IL1RAP antibodies in hybridoma cell culture supernatant (SN) were performed as described above but with the following modifications. Non-purified, hybridoma cell culture SN containing the anti-hu-IL1RAP antibody was added to HEK-Blue IL-1/IL-33 cells at 4× the final volume in 50 μL. The cells and antibody-containing hybridoma cell culture SN were incubated for one-hour at 37° C. with 5% $CO_2$. Following the one-hour antibody incubation, the agonist was added to the wells containing the cells and antibodies at 4× the desired concentration, and in a manner resulting in 1× the final desired concentration within a total volume of 200 μL. The percent inhibition was calculated by deducting the absorbance value obtained from the negative control from the value obtained from the sample (in this case anti-hu-IL1RAP antibody-containing hybridoma cell culture SN). The negative control-adjusted sample was then used to determine the ratio in relation to the positive control (cells exposed to the agonist only in the absence of antibody-containing hybridoma cell culture SN).

HEK-Blue SEAP assays performed using purified hybridoma-derived anti-hu-IL1RAP antibodies were performed similarly to the above assay with hybridoma cell culture SN. Briefly, the antibody was incubated with cells, in the absence of agonist within the standard growth medium, for one hour at 37° C. with 5% $CO_2$. Following the one-hour incubation, the desired agonist, at the estimated $EC_{50}$ concentration, was added to a final volume 200 μL and the experiment was allowed to proceed for an additional 24 hours. The negative control (NC), represents cells exposed to growth medium only, while the positive control (PC) represents cells exposed to the agonist only (in the absence of antagonistic or control antibodies).

To determine the half maximal inhibitory concentration ($IC_{50}$) of the antibodies (including Fabs as described in following Examples), a seven-point serial dilution series was used (starting at the concentration indicated). As with the agonist dose response curves mentioned previously, non-linear regression analysis was performed using GraphPad Prism 7 software to determine the $IC_{50}$ value from the assay results.

The following commercially available human cytokines were used as agonists in HEK-Blue assays: IL-1α (Gibco/Thermo Fisher Scientific), IL-1β (InvivoGen, San Diego, CA, USA) and IL-33 (InvivoGen; or PeproTech US, Rocky Hill, NJ, USA).

The ELISA screening and HEK-Blue cell-based blocking assay results were used to select a panel of 15 parental hybridoma lines for sub-cloning and purification. The selected hybridomas and the results of the HEK-Blue cell-based blocking assays are shown below in Table 3.

TABLE 3

ELISA and HEK-Blue cell-based blocking assay results for selected parental hybridomas

| Hybridoma | ELISA Screening ($A_{450}$) | HEK-Blue assays (% inhibition) | |
|---|---|---|---|
| | | IL-1β | IL-33 |
| 9D5 | 1.050 | 40 | 18 |
| 13D8 | 1.006 | 48 | 33 |
| 10A11 | 0.990 | 53 | 51 |
| 8H1 | 0.987 | 45 | 26 |
| 5A8 | 1.127 | 88 | 69 |
| 2E11 | 0.825 | 66 | 42 |
| 6G2 | 0.577 | 73 | 41 |
| 3H2 | 0.813 | 43 | 54 |
| 3A2 | 1.780 | 35 | 33 |
| 3C2 | 1.648 | 34 | 38 |
| 10B8 | 1.591 | 47 | 31 |
| 15E2 | 2.129 | 35 | 25 |
| 4C6 | 1.965 | 64 | 35 |
| 10D7 | 1.746 | 50 | 42 |
| 11C5 | 1.441 | 84 | 65 |

Hybridoma sub-cloning and purification: sub-cloning was performed by standard limiting dilution with subclones confirmed by ELISA screening (as described above). The subclones were scaled-up to 30 mL cultures in serum free medium. Antibodies were purified as follows. Supernatant media was clarified by centrifugation at 300 g for 10 min to remove cells and by filtration with a 0.22 μm pore size filter. Clarified supernatant media was mixed with POROS Mab-Capture A resin (Thermo Fisher Scientific, Waltham, MA, USA) equilibrated with PBS buffer, and incubated with gentle rotation for 1.5 hours at room temperature. After incubation, the slurry was loaded into a column and the resin was washed with 20 column volumes (CV) of PBS buffer containing 0.5 M NaCl. IgG molecules were eluted with 3 CV of 0.1 M acetic acid, 0.15 M NaCl. The eluent was quickly neutralized to pH 5.2 with 1 M MOPS, pH 7.0 and buffer exchanged into PBS buffer using a PD-10 desalting column (GE Healthcare).

Characterization of Purified Hybridoma Antibodies

ELISA assays: ELISA assays (as described above) were used to confirm the ability of the purified antibodies obtained from the 15 parental hybridomas to bind to hu-M-IL1RAP polypeptide, as well as the soluble hu-S-IL1RAP polypeptide (SEQ ID NO: 7), and determine the extent of cross-reactivity to mouse mo-M-IL1RAP polypeptide (SEQ ID NO: 9), and cynomolgus monkey cyno-M-IL1RAP polypeptide (SEQ ID NO: 8). Serial dilutions of the 15 antibodies purified from the hybridomas were tested starting at 20 nM and $EC_{50}$ for each was calculated as shown below in Table 4.

TABLE 4

ELISA assay results for 15 purified antibodies derived from hybridomas

| Hybridoma Source of Purified mAb | ELISA $EC_{50}$ for Antigen Binding (nM) | | | |
|---|---|---|---|---|
| | hu-M-IL1RAP (SEQ ID NO: 3) | hu-S-IL1RAP (SEQ ID NO: 7) | cy-M-IL1RAP (SEQ ID NO: 8) | mo-M-IL1RAP (SEQ ID NO: 9) |
| 9D5 | 0.039 | 0.036 | 0.043 | no binding |
| 13D8 | 0.039 | 0.035 | 0.032 | no binding |
| 10A11 | 0.039 | 0.035 | 0.032 | no binding |
| 8H1 | 0.262 | 0.186 | 0.257 | no binding |
| 5A8 | 0.011 | no binding | 0.009 | 0.013 |
| 2E11 | 0.016 | no binding | 0.014 | 0.012 |
| 6G2 | weak binding | weak binding | weak binding | weak binding |
| 3H2 | ~0.813 | 0.724 | 0.347 | 0.208 |
| 3A2 | 0.019 | 0.018 | 0.017 | no binding |
| 3C2 | 0.019 | 0.022 | 0.017 | no binding |
| 10B8 | 0.031 | 0.029 | 0.032 | no binding |
| 15E2 | 0.007 | N/A | 0.005 | no binding |
| 4C6 | 0.194 | 0.179 | 0.190 | no binding |
| 10D7 | 0.017 | 0.017 | 0.017 | no binding |
| 11C5 | 0.026 | 0.029 | 0.024 | no binding |

Binding domain mapping: Binding domain mapping of the 15 purified antibodies was carried out using the above-described ELISA assay with the following IL1RAP polypeptide constructs coated at 1 µg/ml on the assay plates: hu-M-IL1RAP, hu-M-IL1RAP-D1, hu-M-IL1RAP-D1D2, and hu-M-IL1RAP-D3. The 15 mAbs were tested at a concentration of 10 nM and the ELISA assay results are shown below in Table 5.

TABLE 5

Domain mapping by ELISA assay for purified hybridoma-derived antibodies

| Hybridoma Source of Purified mAb | ELISA IL1RAP Domain Mapping ($A_{450}$) | | | | |
|---|---|---|---|---|---|
| | hu-M-IL1RAP (SEQ ID NO: 3) | hu-M-IL1RAP-D1 Construct (SEQ ID NO: 4) | hu-M-IL1RAP-D1D2 Construct (SEQ ID NO: 5) | hu-M-IL1RAP-D3 Construct (SEQ ID NO: 6) | IL1RAP Domain Bound |
| 9D5 | 1.137 | 0.047 | 0.957 | 0.045 | D2 |
| 13D8 | 1.118 | 0.046 | 0.044 | 1.455 | D3 |
| 10A11 | 1.178 | 0.046 | 0.046 | 1.395 | D3 |
| 8H1 | 1.087 | 0.045 | 0.602 | 0.045 | D2 |
| 5A8 | 1.249 | 0.045 | 0.058 | 1.542 | D3 |
| 2E11 | 1.250 | 0.046 | 0.049 | 1.486 | D3 |
| 6G2 | 0.358 | 0.046 | 0.049 | 0.419 | D3 |
| 3H2 | 1.198 | 0.073 | 0.049 | 0.586 | D3 |
| 3A2 | 1.285 | 0.045 | 0.047 | 1.507 | D3 |
| 3C2 | 1.214 | 0.045 | 0.048 | 1.496 | D3 |
| 10B8 | 1.245 | 0.045 | 0.047 | 1.518 | D3 |
| 15E2 | 1.437 | 0.054 | 0.055 | 1.720 | D3 |
| 4C6 | 1.286 | 0.053 | 0.046 | 1.572 | D3 |
| 10D7 | 1.215 | 0.046 | 0.044 | 1.468 | D3 |
| 11C5 | 1.232 | 0.048 | 0.048 | 1.442 | D3 |

HEK-Blue assay: The purified anti-hu-IL1RAP antibodies derived from the 15 parental hybridomas were tested to determine their ability to block IL-1β and IL-33 mediated activation of the IL1R1/IL1RAP and ST2/IL1RAP pathways using the HEK-Blue assay as described above. Dose responses were carried out for all of the mAbs and a determination of the extent of inhibition of IL-1β and IL-33 mediated activation at an antibody concentration of 100 nM was calculated as percentage of maximum signal obtained from cells exposed to agonist only. Results of these HEK-Blue assays are shown below in Table 6.

TABLE 6

HEK Blue assay of hybridoma-derived purified anti-hu-IL1RAP antibodies

| Hybridoma Source of Purified mAb | HEK blue assay (% inhibition at 100 nM) | |
|---|---|---|
| | IL-1β | IL-33 |
| 9D5 | 86 | 46 |
| 13D8 | 89 | 69 |
| 10A11 | 72 | 56 |
| 8H1 | 64 | 27 |
| 5A8 | 16 | 16 |
| 2E11 | 10 | 10 |
| 6G2 | 19 | 13 |
| 3H2 | 14 | 10 |
| 3A2 | 28 | 48 |
| 3C2 | 20 | 45 |
| 10B8 | 34 | 13 |
| 15E2 | 46 | 29 |
| 4C6 | 49 | 29 |
| 10D7 | 29 | 26 |
| 11C5 | 99 | 93 |

As shown by the HEK-Blue assay results of Table 6, of all antibodies tested only the mAb from hybridoma 11C5 demonstrated full or near full blocking activity of both the IL-1β and IL-33 activated pathways at a concentration of 100 nM (99% and 93%, respectively).

OCTET binding affinity: Binding affinities of the purified mAb from the 11C5 hybridoma (hereinafter "11C5(Hy)") to the hu-M-IL1RAP and cyno-M-IL1RAP polypeptide constructs were measured using OCTET® Bio-Layer Interferometry (BLI) binding analysis (Pall ForteBio USA, Fremont, CA, USA). The BLI experimental format immobilizes the antibody on a biolayer surface with the IL1RAP antigen in solution. The hu-M-IL1RAP polypeptide of SEQ ID NO: 3, the cyno-M-IL1RAP polypeptide of SEQ ID NO: 8, or the purified mAb from hybridoma 11C5 were diluted, each in a final volume of 200 μL, in the experimental buffer (PBS buffer with 0.01% Tween-20). All samples were placed in black 96-well plates and the experiment was performed at 25° C. The purified mAb from hybridoma 11C5 was diluted to a final concentration of 35 nM and immobilized on the Anti-Mouse IgG Fc Capture (AMC) biosensors (Pall ForteBio). The analytes were serially diluted in the experimental buffer in a range from 0.9-25 nM. The biosensors were equilibrated in experimental buffer at 25° C. for ten minutes prior to starting the experiment.

The kinetics experiment was performed with the following steps, where the step name, solution and time are listed: Baseline (buffer—60 seconds), Loading (antibody—200 seconds), Baseline 2 (buffer—minimum 120 seconds), Association (analyte—200-300 seconds) and Dissociation (buffer—1000 seconds). The BLI signal resulting from analyte association and dissociation of the antigens from the immobilized antibody was analyzed using the OCTET® Data Analysis software (Pall ForteBio). First, a reference subtraction was performed on all recorded traces using the reference well (biosensor that underwent the same steps as experimental wells but no analyte for the Association step), then all the traces were aligned to the beginning of the Association step. The entirety of the Association and Dissociation steps were used in a Global fit (minimum of four analyte concentration traces) in a 1:1 binding model to calculate the $K_D$ for mAb 11C5(Hy) with each analyte. Results of this OCTET BLI analysis are shown below in Table 7.

TABLE 7

BLI measured binding affinities of purified 11C5(Hy)
with hu-M-IL1RAP and cyno-M-IL1RAP

| Antibody | Antigen | $k_{on}$ (1/Ms) | $k_{dis}$ (1/s) | $K_D$ (M) |
|---|---|---|---|---|
| 11C5(Hy) | hu-M-IL1RAP | 4.69E+05 | 1.03E−04 | 2.19E−10 |
| 11C5(Hy) | cyno-M-IL1RAP | 4.13E+05 | 5.74E−05 | 1.42E−10 |

Summary: The purified anti-M-IL1RAP antibody derived from hybridoma 11C5, 11C5(Hy), was selected for further characterization and affinity maturation based on its superior properties in the assays described above. Namely, the 11C5 (Hy) mAb binds to domain 3 (D3) of IL1RAP, binds equally well to the hu-M-IL1RAP, hu-S-IL1RAP, and the cyno-M-IL1RAP polypeptides as determined by ELISA, and exhibits full or near full blocking activity on both the IL-1β and IL-33 activated pathways as determined by HEK-Blue assay. The 11C5(Hy) mAb, however, does not cross-react with the mouse-M-IL1RAP polypeptide of SEQ ID NO: 9.

Example 3

Sequencing of Selected Anti-Human IL1RAP Antibodies

This example illustrates the determination of the sequences of the hybridoma-derived anti-hu-IL1RAP antibodies.

The following protocols were used to identify, clone and sequence the genes encoding the antibody heavy and light chain fragments from the selected hybridomas.

The hybridoma of interest was grown to a density of $1-3 \times 10^5$ in standard hybridoma medium (DMEM/F12, 10% FBS, 1% Glutamax, 1% pen/strep) for 7-10 days in a T75 flask with >80% viability. 1-3 million cells from cultures were pelleted in a 15 mL falcon tube at 300 g for 5 minutes. Pelleted cells were washed by resuspending them in 5 mL ice cold PBS. After centrifugation at 300 g for 5 minutes, the PBS was removed and the cells resuspended and lysed in 1 mL of TRIZOL reagent (Life Technologies, Carlsbad, CA, USA). The lysate was passed through a 1 mL syringe with a 20G1 gauge needle (BD 305175) 20 times to ensure complete lysis of the cells. The TRIZOL/cell suspension was immediately frozen on dry ice and stored at −80° C. until processing.

Total RNA was isolated from the lysate using Direct-zol RNA Miniprep Plus kit (Zymo Research, Irvine, CA, USA) and 5 μg of total RNA was used to generate 5'-RACE-ready hybridoma cDNA using the SMARTer RACE 5' kit (Takara Bio, Japan). The following mouse $V_H$ family specific variable region primers were used to amplify the heavy chain and light chain specific gene fragments from the cDNA: TCTTGTCCACCTTGGTGCTGCTGGCCGG (SEQ ID NO: 321), and TTTGTC-CACCGTGGTGCTGCTGGCTGGT (SEQ ID NO: 322). The following mouse Vkappa family specific variable region primer, GATCAGTCCAACTGTTCAGGACGCC (SEQ ID NO: 323), or the mouse Vlambda family specific variable region primers, ACACTCAGCACGGGACAAACTCTTCTCCACAGT (SEQ ID NO: 324), ACACTCTGCAGGAGACA-GACTCTTTTCCACAGT (SEQ ID NO: 325), and ACACTCAGCACGGGACAAACTCTTCTCCACATG (SEQ ID NO: 326) were used in conjunction with the universal primer provided in the kit in 5'-RACE PCR reactions.

The PCR products were purified and cloned into pRACE using the In-Fusion cloning kit (Takara Bio, Japan). Both strands were sequenced using a Sanger sequencer with M13 forward and M13 reverse primers.

The light and heavy variable domain amino acid sequences, $V_L$ and $V_H$, determined for the mAb derived from hybridoma 11C5 are listed in Table 2 above and provided in the accompanying Sequence Listing as SEQ ID NO: 257 and 279, respectively.

Additionally, the $V_L$ and $V_H$ sequences determined for the mAbs derived from hybridomas 10A11, 9D5, 8H1, and 13D8 are listed in Table 2 and provided in the accompanying Sequence Listing as SEQ ID NOs: 311, 312, 313, 314, 315, 316, 317, and 318, respectively.

Example 4

Inhibition of IL-1, IL-33, and IL-36 Stimulated Intracellular Signaling By 11C5 Hybridoma-Derived Anti-Hu-IL1RAP mAb This example illustrates that the purified anti-hu-IL1RAP mAb derived from 11C5, 11C5(Hy), is capable of blocking IL-1α, IL-1β, IL-33, and IL-36α, IL-36β and IL-36γ stimulated intracellular signaling as determined in a HEK-Blue cell-based blocking assay. Briefly, HEK-Blue IL-1/IL-33 sensor cells, or HEK-Blue IL-33 sensor cells transiently transfected with the IL-36 receptor IL1RL2, were used to determine whether 11C5(Hy) blocks the IL-1, IL-33, and IL-36 dependent signaling pathways. Both of these HEK-Blue cell lines express an NF-κB/AP-1 SEAP reporter gene that allows for IL-1, IL-33, or IL-36 activation to be monitored via a simple SEAP detection assay.

Materials and Methods

HEK-Blue cells: The HEK-Blue IL-1/IL-33 sensor cells used in this example have been described above in Example 2. The HEK-Blue IL-33 sensor cells (InvivoGen; catalog number hkb-hil33) are similar to the HEK-Blue IL-1/IL-33 cells but have both IL-1 and TNF-α responses blocked. The HEK-Blue IL-33 cells were maintained per manufacturer guidelines, using the standard growth medium previously described and supplemented with 1×HEK-Blue Selection antibiotics (InvivoGen; catalog number hb-sel) to maintain the plasmids encoding for SEAP, ST2, and IL-33 specificity.

Transient transfection of HEK-Blue IL-33 cells with IL-36 receptor: The plasmid containing the human IL1RL2 gene, encoding the IL-36 receptor, was generated by Avant-Gen (custom order). HEK-Blue IL-33 sensor cells were transiently transfected using LyoVec (InvivoGen) according to manufacturer's guidelines. Briefly, LyoVec-DNA complexes were added directly to cells suspended in standard growth medium, at a concentration that would produce a minimum of 80% confluency 24 hours post-transfection, and immediately plated on 96-well, flat-bottom plates. 24 hours post-transfection, the cells were used in a standard HEK-Blue SEAP assay.

HEK-Blue SEAP assay: HEK-Blue IL-1/IL-33 cells were used for all HEK-Blue SEAP assays where IL-1 or IL-33 stimulation occurred and have been described above in Example 2. For assays with IL-36 stimulation, HEK-Blue IL-33 cells transiently expressing the IL-36 receptor, IL1RL2 were employed. These transiently transfected HEK-Blue IL-33 sensor cells are responsive to stimulation by IL-36α, IL-36β, and IL-36-γ. The human IL-36α, IL-36β, and IL-36γ cytokines were cleaved off the N-terminal sequence to produce fully mature cytokines. Values for agonist $EC_{50}$ and antagonist antibody $IC_{50}$ were obtained as previously described. The negative control (NC) represents cells exposed to growth medium only, while the positive control (PC) represents cells exposed to the agonist only (in the absence of antagonistic or control antibodies).

Results

Figure 1A:
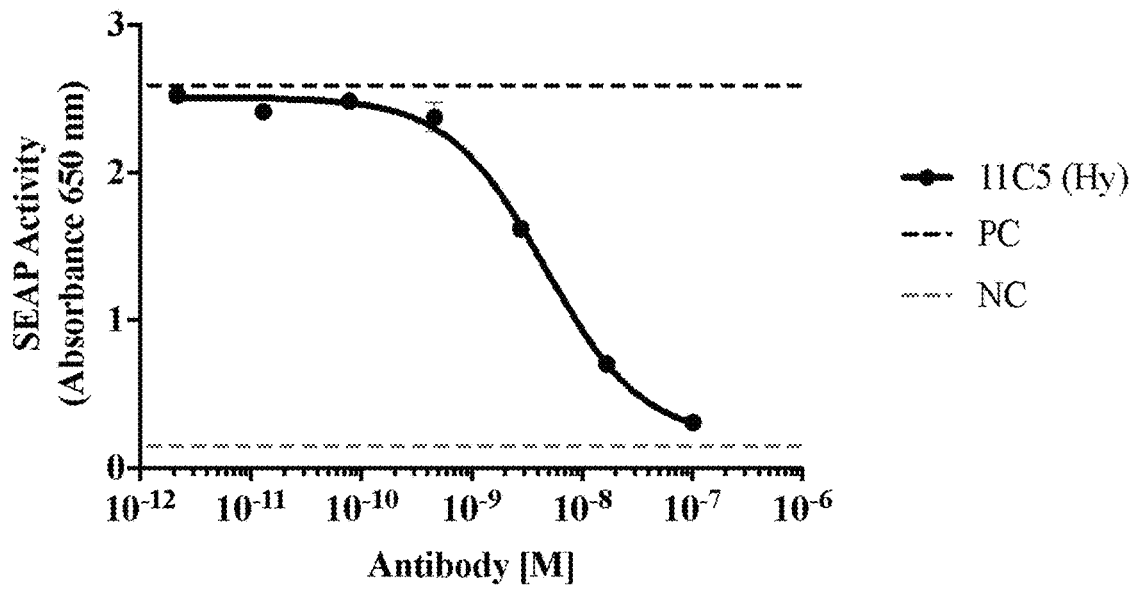
FIGS. 1A, 1B, 1C, 1D, 1E, and 1F depict plots of results for the mouse hybridoma-derived anti-hu-IL1RAP antibody, 11C5(Hy) in inhibition assays of IL-1, IL-33, and IL-36 stimulated intracellular signaling assessed in HEK-BLUE™ IL-1/IL-33 responsive sensor cells, or HEK-BLUE™ IL-36 responsive sensor cells (i.e., IL-33 cells transiently expressing the IL-36 receptor) and stimulated with the various shown agonists.
Figure 1B:
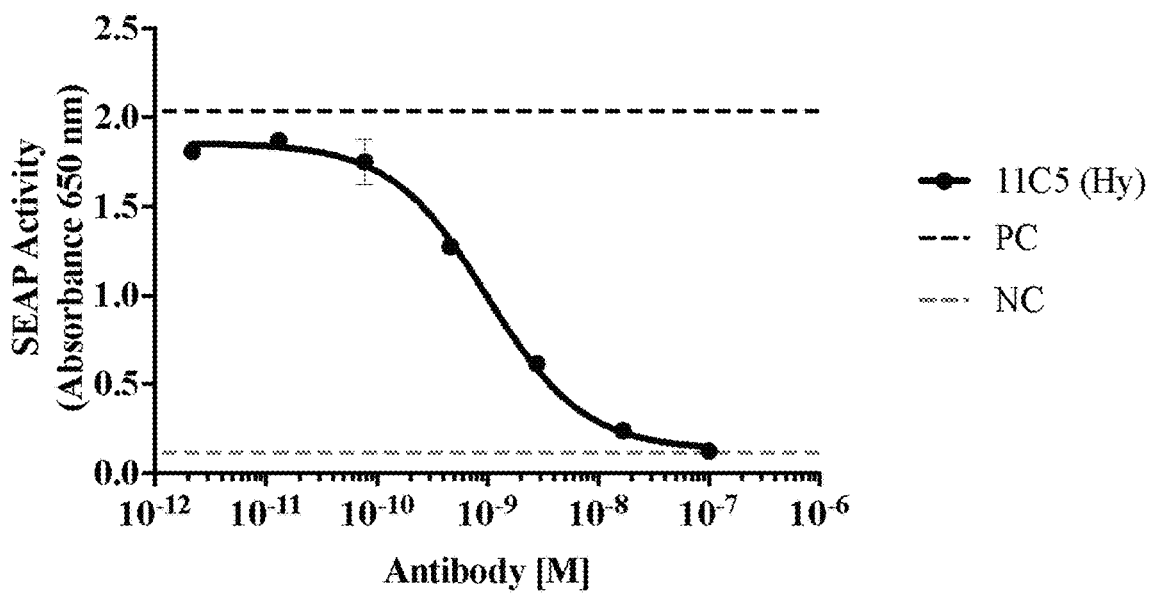

The 11C5(Hy) mAb was incubated with HEK-Blue IL-1/IL-33 cells for one hour, prior to the addition of IL-1α (FIG. 1A) or IL-1β (FIG. 1B) at a concentration previously determined to be roughly equivalent to an $EC_{55-60}$. The 11C5(Hy) mAb exhibited strong blocking activity with an $IC_{50}$ equal to 4.7E–09 M and 1.0E–09 M for IL-1α and IL-1β, respectively. At an antibody concentration of 100 nM, near complete inhibition (94% and 99% for IL-1α and IL-1β, respectively) was observed when compared to the respective positive (PC) and negative (NC) controls.

Figure 1C:
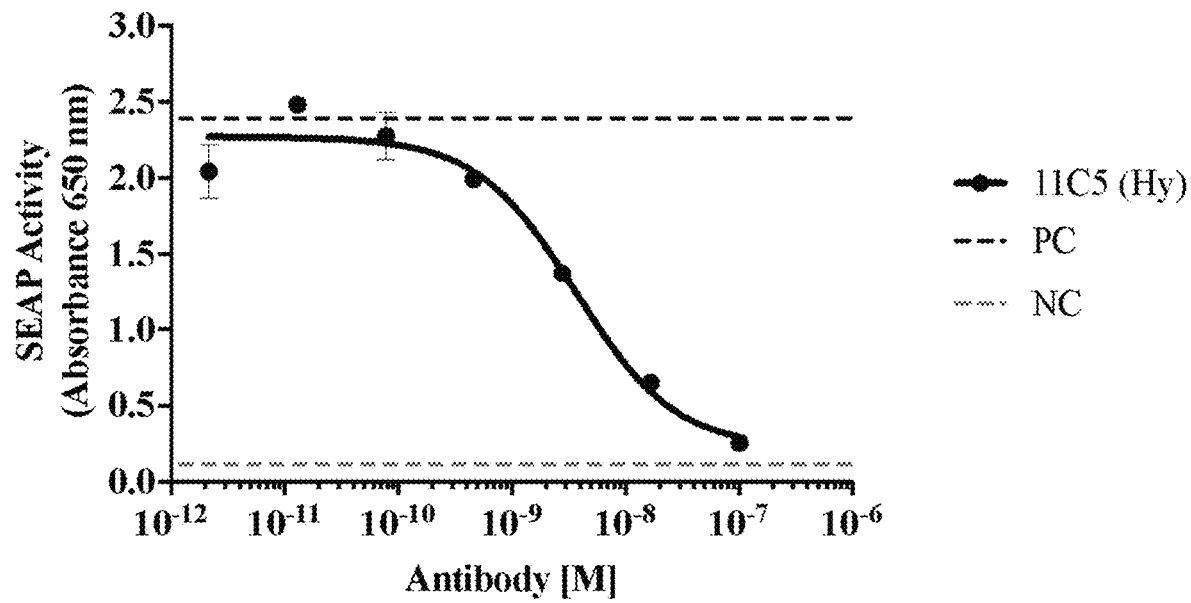

A similar assay was performed to determine the blocking potency and efficacy in IL-33 stimulated HEK-Blue IL-1/IL-33 cells (FIG. 1C). As was observed for the IL-1 blocking assays, 11C5(Hy) exhibited strong blocking activity upon IL-33 stimulation ($IC_{50}$=3.71 E–09 M), with near complete blocking (93%) observed at the maximum concentration of antibody tested (100 nM).

Figure 1D:
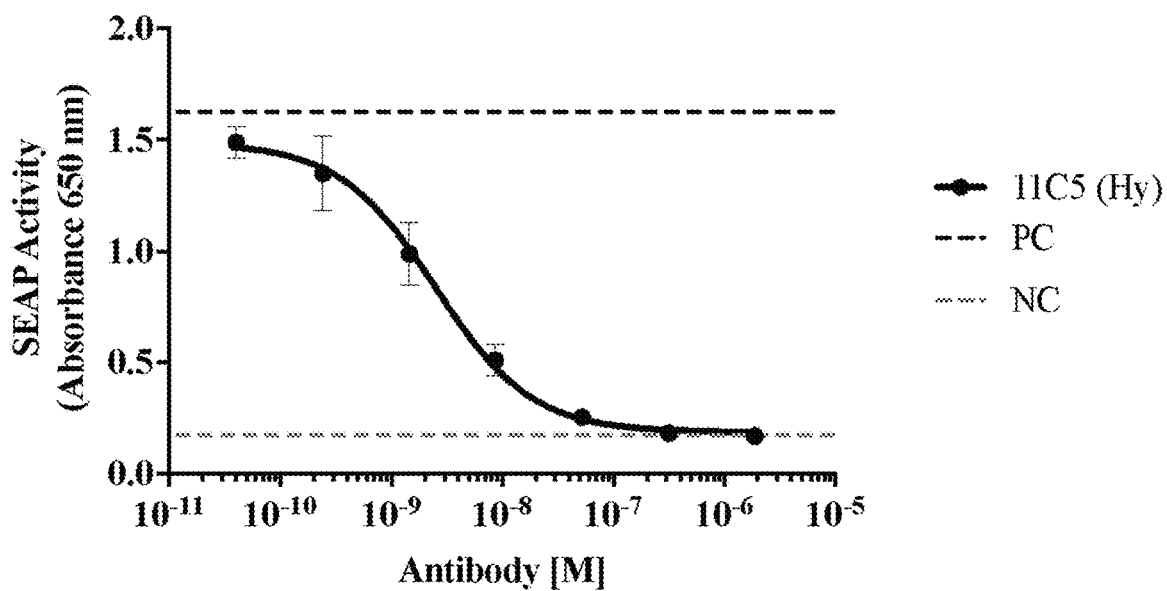
Figure 1E:
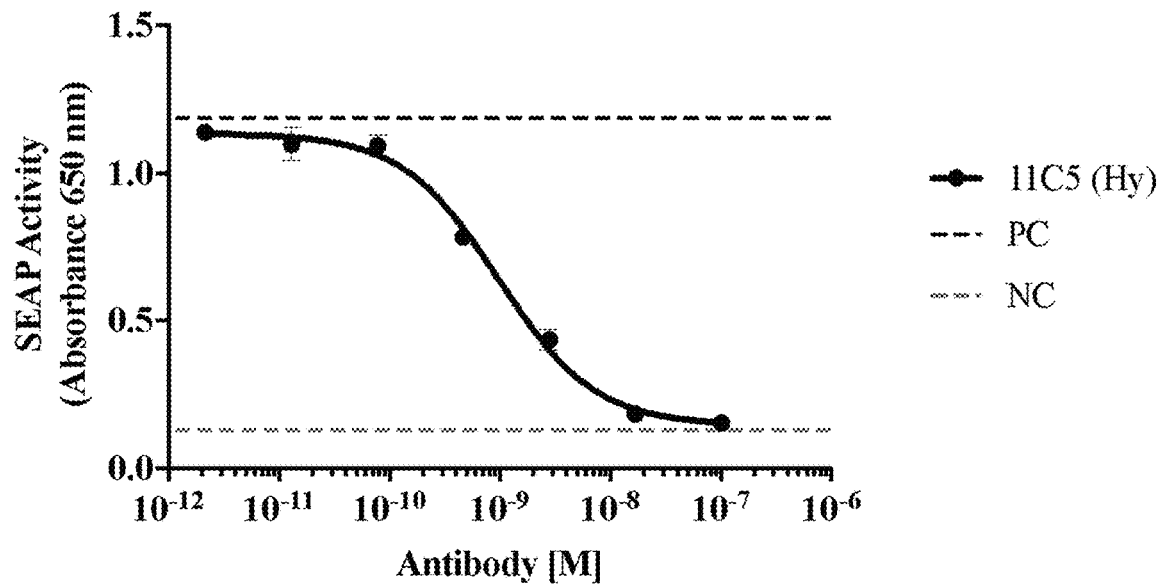
Figure 1F:
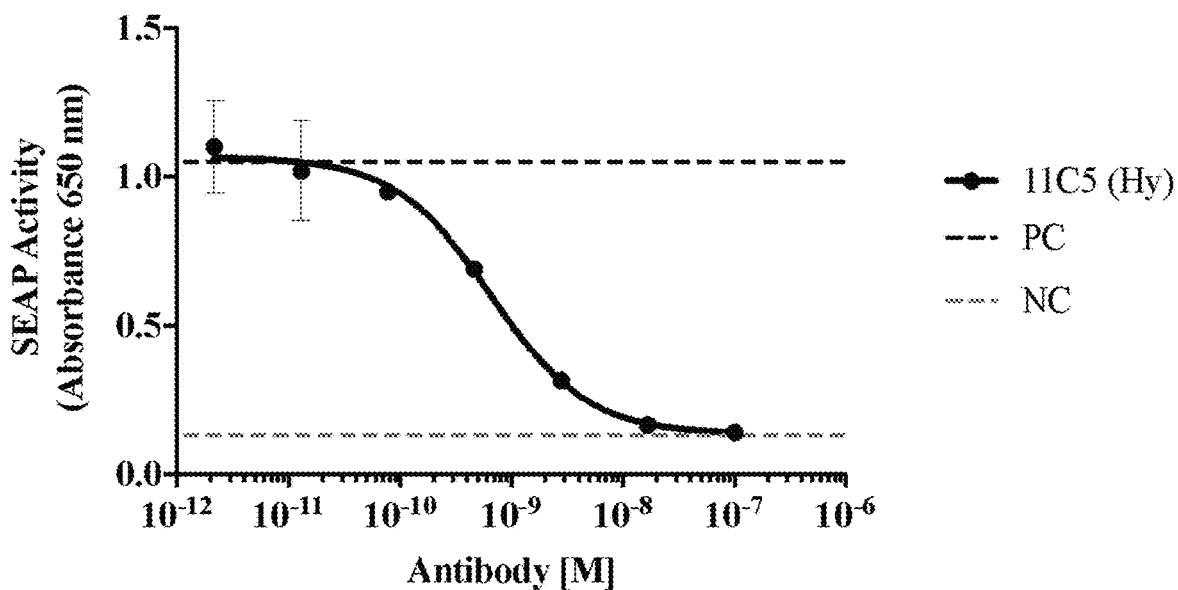

HEK-Blue IL-36 responsive cells (i.e., the IL-33 cells transiently expressing the IL-36 receptor IL1RL2) were incubated with 11C5(Hy) for one hour, followed by stimulation with IL-36α (FIG. 1D), IL-36β (FIG. 1E) or IL-36γ (FIG. 1F). At an 11C5(Hy) antibody concentration of 100 nM, near complete inhibition of IL-36 dependent signaling was observed, specifically, 98%, 98% and 99% inhibition of IL-36α, IL-36β and IL-36γ, respectively. $IC_{50}$ values were 2.52E–09 M, 9.81E–10 M and 6.65E–10 M for IL-36α, IL-36β and IL-36γ, respectively.

The $IC_{50}$ values and % inhibition of mAb 11C5(Hy) in the HEK-Blue assays are summarized below in Table 8.

TABLE 8

11C5(Hy) mAb blocking activity in HEK Blue assay, $IC_{50}$ and inhibition at 100 nM of antibody

| Agonist | $IC_{50}$ (M) | Inhibition (%) |
| --- | --- | --- |
| IL-1α | 4.70E–09 | 94 |
| IL-1β | 1.00E–09 | 99 |
| IL-33 | 3.71E–09 | 93 |
| IL-36α | 2.52E–09 | 98 |
| IL-36β | 9.81E–10 | 98 |
| IL-36γ | 6.65E–10 | 99 |

As shown by the results in Table 8 above, the purified hybridoma-derived antibody 11C5(Hy) is capable of potently blocking all three pathways of interest (IL-1, IL-33 and IL-36) upon stimulation of all six cytokines (IL-1α, IL-1β, IL-33, IL-36α, IL-36β and IL-36γ) in the HEK Blue cell-based blocking assays.

Example 5

Preparation of Humanized, Chimeric, and C59 Mutant Versions of Anti-IL1RAP mAb 11C5(Hy)

This example illustrates the preparation of humanized and chimeric versions of the murine anti-IL1RAP mAb 11C5 (Hy) derived from the hybridoma 11C5. Additionally, the example illustrates the preparation of the murine, humanized and chimeric variants of 11C5(Hy) mAb with substitution of a heavy chain cysteine residue at position 59 with a series of alternative amino acids: C59A, C59S, C59T, C59V, and C59Y.

Humanization of Murine Anti-IL1RAP 11C5 Variable Region Sequences

The murine 11C5(Hy) antibody light chain variable region ($V_L$) sequence of SEQ ID NO: 257 and the heavy chain variable region ($V_H$) sequence of SEQ ID NO: 279 were aligned against human germline antibody sequences. The human germline kappa light chain (Gene ID—V gene: IGKV1-NL1*01, J gene: IGKJ4*02) and the human germline heavy chain (Gene ID—V gene: IGHV3-7*03, J gene: IGHJ4*03) were identified as the closest human frameworks. The amino acid sequence alignments of the $V_L$ and $V_H$ domains of the murine 11C5(Hy), the closest human germline sequence, and the humanized, h11C5 are shown in FIG. 2.

The complementarity-determining regions (CDRs) of the murine 11C5(Hy) light and heavy chains were grafted into the identified closest light and heavy chain human frameworks, respectively, to generate a humanized antibody clone (hereinafter referred to as "h11C5"). Positions 24-34 in CDR-L1, 50-56 in CDR-L2 and 89-97 in CDR-L3 of the murine 11C5(Hy) $V_L$ sequence (SEQ ID NO: 257) were grafted into the human kappa light chain framework acceptor. Positions 31-35 in CDR-H1, 50-65 in CDR-H2, and 95-102 in CDR-H3 of the murine 11C5(Hy) $V_H$ sequence (SEQ ID NO: 279) were grafted into the human heavy chain framework acceptor. Position 48 in framework region 2 of the murine 11C5(Hy) light chain was also grafted into the human kappa light chain framework acceptor as this position was found to be part of the $V_H$-$V_L$ interacting interface or the framework residues acting as "Vernier" zone, which may adjust the CDR structure and fine-tune it to fit to the antigen (see e.g., Foote et al., *J. Mol. Biol.*, 224: 4887-499 (1992)).

Humanized variable domain sequences were synthesized as DNA fragments with AgeI as the 5' flanking restriction enzyme site and KpnI as the 3' flanking restriction enzyme site for $V_L$, and with AgeI as the 5' flanking restriction enzyme site and BstEII as the 3' flanking restriction enzyme site for $V_H$. A light chain expression plasmid for h11C5 was derived by replacing the AgeI-KpnI fragment with the synthesized h11C5 $V_L$ DNA fragment in the pRK plasmid containing the complete human kappa light chain constant domain. A heavy chain expression plasmid for h11C5 was derived by replacing the AgeI-BstEII fragment with the synthesized h11C5 $V_H$ DNA fragment in the pRK plasmid containing the complete human IgG1 heavy constant domain.

For comparison with the humanized h11C5 antibody, DNA fragments of the murine 11C5(Hy) $V_L$ and $V_H$ sequences were synthesized as described above. Plasmids expressing the light chain and heavy chain of the murine 11C5(Hy) or a chimeric version of 11C5 (containing murine $V_L$ and $V_H$ domains, and human CL and CH1-CH3 domains) were constructed by cloning synthesized DNA fragments into pRK plasmids carrying murine IgG2a or human IgG1 constant domains, respectively.

Generation of Heavy Chain Cys59 Variants of Anti-IL1RAP 11C5

The CDR-H2 sequence of $V_H$ of murine 11C5(Hy) contains an unpaired cysteine residue at position 59 (Cys59) which can be a major liability in the further therapeutic development of the antibody. To remove this liability, a series of variants of the $V_H$ domain sequence with amino substitutions of the cysteine (C) at position 59 with either alanine (A), serine (S), threonine (T), valine (V), or tyrosine (Y) were synthesized. The substitutions were selected based on the amino acid side-chain similarity to cysteine (alanine, serine, threonine, and valine) or based on the closest germline sequence at position 59 (tyrosine). The series of Cys59 mAb variants, generated in the context of the $V_H$ sequences of each of murine 11C5 ("11C5(Hy)"), chimeric 11C5 ("c11C5"), and humanized 11C5 ("h11C5"), were synthesized as DNA fragments with AgeI as the 5' flanking restriction enzyme site and BstEII as the 3' flanking restriction enzyme site. The heavy chain expressing plasmids for the Cys59 variants were generated as described above.

Generation of the Recombinant Versions of the 11C5 (Hy)-Derived Murine, Chimeric and Humanized Anti-IL1RAP mAbs and Their Cys59 Variants The expression of recombinant IgG molecules was performed using the Expi293F expression system (Life Technologies, Carlsbad, CA, USA) in accordance with the instructions provided by the manufacturer. The ratio of the plasmids for the heavy chain and the light chain was kept at 1 to 1 for the transfection reaction and the transfected cells were cultured for 6 days before harvest.

Recombinant IgG molecules were purified with the following protocol. Supernatant media were clarified by centrifugation at 300 g for 10 min to remove cells and by filtration with a 0.22 µm pore size filter. Clarified supernatant media were mixed with POROS MabCapture A resin (Thermo Scientific) equilibrated with PBS buffer and incubated with gentle rotation for 1.5 hours at room temperature. After incubation, the slurry was loaded into a column and the resin was washed with 20 column volumes of PBS buffer containing 0.5 M NaCl. Recombinant IgG molecules were then eluted with 3 column volumes of 0.1 M acetic acid, 0.15 M NaCl. The eluent was quickly neutralized to pH 5.2 with 1 M MOPS, pH 7.0 and buffer exchanged to PBS buffer with a PD-10 column (GE).

Binding Affinity of the Recombinant Versions of the 11C5(Hy)-Derived Murine, Chimeric and Humanized Anti-IL1RAP mAbs and Their Cys59 Variants The binding affinity of recombinant versions of the murine ("m11C5"), chimeric ("c11C5"), and humanized ("h11C5") mAbs derived from 11C5(Hy) for the hu-M-IL1RAP polypeptide of SEQ ID NO: 3 was measured by OCTET Bio-Layer Interferometry (BLI) binding analysis (Pall ForteBio).

The experimental format has the antibody immobilized on the biolayer surface and the antigen IL1RAP was in solution. Recombinant hu-M-IL1RAP and all 11C5 variants were diluted (each in a final volume of 200 µL) in the experimental buffer (PBS buffer with 0.01% Tween-20). All samples were placed in black 96-well plates and the experiment was performed at 25° C. The murine and chimeric 11C5 variants (35 nM) were immobilized on the Anti-Mouse IgG Fc Capture (AMC) biosensors (Pall ForteBio). The Anti-Human IgG Fc Capture (AHC) biosensors (Pall ForteBio) were used for the humanized 11C5 variants (35 nM). The hu-M-IL1RAP analyte solution was serially diluted in the experimental buffer in a range from 1-81 nM. The biosensors were equilibrated in experimental buffer at 25° C. for ten minutes prior to starting the experiment.

The kinetics experiment was performed with the following steps, where the step name, solution and time are listed: Baseline (buffer—60 seconds), Loading (antibody—200 seconds), Baseline 2 (buffer—minimum 120 seconds), Association (analyte—200-300 seconds) and Dissociation (buffer—1000 seconds).

The resulting BLI signal from analyte association and dissociation from the immobilized antibody was analyzed using the Octet Data Analysis software (Pall ForteBio). First, a reference subtraction was performed on all recorded traces using the reference well (biosensor that underwent the same steps as experimental wells but no analyte for the Association step), then all the traces were aligned to the beginning of the Association step. The entirety of the Association and Dissociation steps were used in a Global fit (minimum of four analyte concentration traces) in a 1:1 binding model to calculate the $K_D$ for each 11C5 variant with hu-M-IL1RAP. The calculated $K_D$ values are listed below in Table 9.

TABLE 9

OCTET BLI results for hu-M-IL1RAP binding to recombinant murine, chimeric and humanized 11C5 mAb and their Cys59 variants

| Recombinant mAb based on 11C5(Hy) | OCTET $K_D$ (M) |
| --- | --- |
| m11C5 | 3.70E−10 |
| m11C5_C59A | 5.13E−10 |
| m11C5_C59S | 5.98E−10 |
| m11C5_C59T | 1.38E−09 |
| m11C5_C59V | 6.04E−10 |
| m11C5_C59Y | 5.24E−10 |
| h11C5 | 1.06E−09 |
| h11C5_C59A | 2.06E−09 |
| h11C5_C59S | 1.08E−09 |

TABLE 9-continued

OCTET BLI results for hu-M-IL1RAP binding to recombinant murine, chimeric and humanized 11C5 mAb and their Cys59 variants

| Recombinant mAb based on 11C5(Hy) | OCTET $K_D$ (M) |
|---|---|
| h11C5_C59T | 3.26E−09 |
| h11C5_C59Y | 1.34E−09 |
| c11C5 | 6.99E−10 |
| c11C5_C59A | 7.56E−10 |
| c11C5_C59Y | 4.46E−10 |

Example 6

Non-Specific Binding Assessment of Humanized 11C5

This example illustrates a baculovirus (BV) particles ELISA assay showing that humanized 11C5 (h11C5) exhibits no non-specific binding.

The following protocols were used to assess non-specific binding of h11C5 to baculovirus (BV) particles in accordance with the protocols described in Hotzel et al., mAbs, 4(6): 753-760 (2012). Briefly, BV particles were coated on 96-well ELISA plates as a 2.5% suspension at 4° C. overnight. The plates were then blocked with 1% BSA, 0.05% Tween-20 in PBS at room temperature for an hour. Serially diluted h11C5 anti-hu-IL1RAP antibody was added to the plates for an hour and bound antibodies were detected with goat anti-human IgG conjugated to horseradish peroxidase (Jackson ImmunoResearch), followed by the addition of 3,3',5,5'-tetramethylbenzidine substrate (Thermo Fisher Scientific) and 2 N sulfuric acid. The absorbance at 450 nm was measured and compared to reference antibodies.

Figure 3:
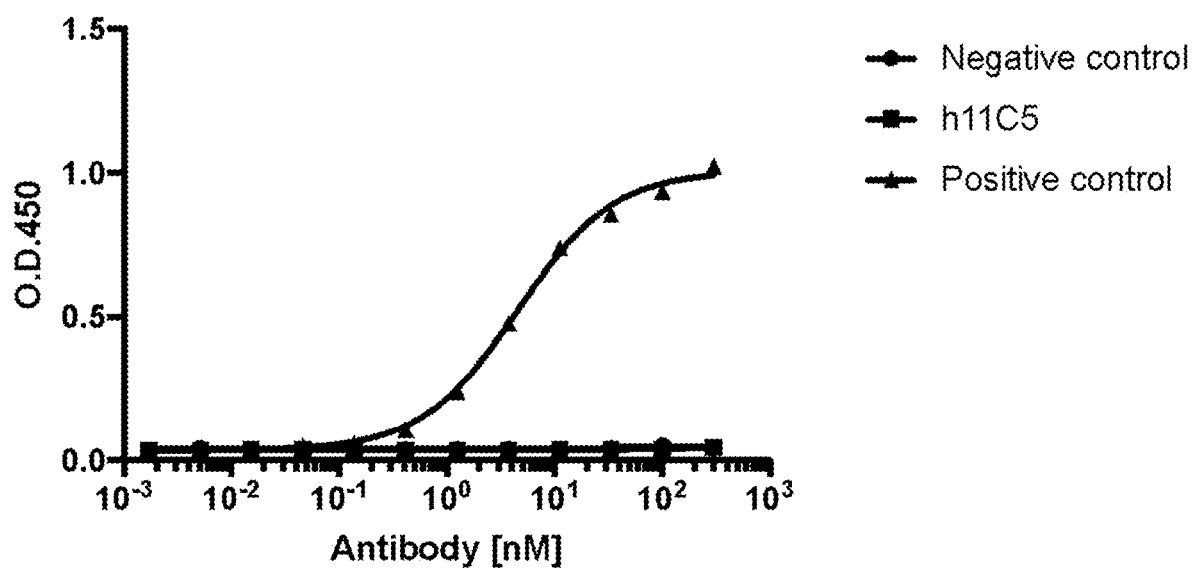
FIG. 3 depicts a plot of the concentrations of the humanized anti-hu-IL1RAP antibody, h11C5 and positive and negative control reference antibodies versus baculovirus (BV) particles ELISA signal at 450 nm, indicating the absence of non-specific binding by h11C5 to BV particles.

Results: As shown by the plot of FIG. 3, the h11C5 antibody showed no detectable BV ELISA signal at 450 nm, indicating the absence of any non-specific binding to BV particles.

Example 7

Functional Assays of Murine, Chimeric, and Humanized Anti-IL1RAP Antibodies Based on 11C5

This example illustrates cell-based blocking assays of the recombinant murine, chimeric, and humanized anti-IL1RAP antibodies described in Examples 4 and 5 to determine their respective abilities to inhibit IL-1, IL-33, and IL-36 stimulated intracellular signaling.

Materials & Methods

Cell Lines and HEK-Blue Assays: Cell lines and HEK-Blue assays used in this Example 7 are described above in Examples 2 and 4.

Primary Human Lung Fibroblasts and Associated Assays: Primary human lung fibroblasts (PHLFs) are commercially available and were obtained from Lonza (catalog number CC-2512). Cells were isolated from normal (disease free) donated human tissue and cryopreserved by the manufacturer. The cells were thawed and maintained using the general guidelines recommended by the manufacturer. PHLFs were maintained in a growth medium consisting of FibroLife Basal Medium (LifeLine), supplemented with 2% human AB serum (Corning) that was heat-inactivated prior to use (56° C. for 30 minutes), 7.5 mM Glutamax (Gibco), 100 IU/mL penicillin and 100 µg/mL streptomycin. The day prior to experimental use, PHLFs were seeded on flat-bottom, 96-well plates at a concentration that would result in ~80-85% confluency the day of use.

Prior to use in antibody blocking assays, the agonist $EC_{50}$ was determined by performing an agonist dose-response curve in a similar manner as described in Example 2 for the HEK-Blue cells with the following modifications. After addition of the agonist to PHLFs in wells containing PHLF growth medium only (final volume 200 µL), the cells were returned to the tissue culture incubator (37° C. with 5% $CO_2$) for four hours. Tissue culture supernatant was then collected and stored at 4° C. for 1-3 days. The IL-8 (human) AlphaLISA Detection Kit (Perkin Elmer) was used to quantify the level of IL-8 present in the supernatant collected. The assay was performed as instructed within the manufacturer guidelines. Raw data obtained using an EnVision-Alpha Reader (Perkin Elmer) was analyzed using Graph Pad Prism software, with interpolations performed using non-linear regression analysis (curve fit), Sigmoidal, 4PL, X is log(concentration) and weighting defined by "Weight by $1/Y^2$". Interpolated data was then analyzed using standard non-linear regression analysis.

The cell-based blocking assays were performed as in Example 4 but in a manner conducive to obtaining $IC_{50}$ values, with modifications to specifically account for PHLF usage. Briefly, c11C5_C59Y, or an appropriate antibody control (e.g., Hu IgG1 Ctrl), was incubated with PHLFs for 1 hour at 37° C., followed by the addition of agonist (IL-1α or IL-36β). The experiment was allowed to proceed for an additional four hours (37° C. with 5% $CO_2$), with cell culture supernatants collected and quantification of IL-8 performed as described above.

Primary Human Monocytes and Associated Assays. Primary human monocytes (PHMOs) isolated by negative immunomagnetic selection, also known as "untouched," are commercially available and were obtained from STEMCELL Technologies. Monocytes were thawed according to general manufacturer guidelines and maintained in the standard growth medium as described in Example 4. For antibody blocking assays, PHMOs were plated the day before the assay at 80,000/well on a flat-bottom, 96-well plate. The antibody, c11C5_C59Y, or appropriate antibody isotype control (Hu IgG Ctrl), was incubated with PHMOs for 1 hour at 37° C. with 5% $CO_2$, followed by the addition of the agonist of interest (e.g., IL-1β). The final volume for all wells was 200 µL, where the positive control (PC) indicates growth medium and agonist only, and negative control (NC) indicates PHMOs and growth medium only.

Tissue culture supernatant was collected twenty-four hours after agonist addition and stored at −80° C. until an ELISA assay could be performed to determine the level of IL-6 present. A human IL-6 ELISA kit (Thermo Fisher Scientific) was used to quantify the level of IL-6 in the supernatant. Raw data analysis and interpolations were performed using Graph Pad Prism software and non-linear regression analysis. Prior to antibody blocking assays, an agonist dose-response curve was generated to determine $EC_{50}$ values as generally described in Example 2, with modifications to specifically account for usage of PHMOs and as described above. Antibody $IC_{50}$ values were determined in the same manner.

Primary Human NK Cells and Associated Assays. Primary human NK cells isolated by negative immunomagnetic selection were obtained commercially from STEMCELL Technologies (Vancouver, Canada). On the day of experimental use, NK cells were thawed according to general manufacturer guidelines with the following modifications. Cells were thawed in a thawing media consisting of RPMI (Corning) supplemented with 0.05 mg/mL DNAse I (STEMCELL Technologies). Post-thaw the cells were given a minimum of a 1 hour recovery time (37° C. with 5% $CO_2$) prior to experimental use and were maintained in an NK growth medium consisting of RPMI (Corning) supplemented with 10% human AB serum (Corning), that was heat-inactivated prior to use (56° C. for 30 minutes), 1 mM Sodium Pyruvate (Corning Cellgro), 2 mM Glutamax (Gibco) and 1×MEM Non-Essential Amino Acids (Gibco).

Prior to experimental use in antibody blocking assays, the agonist $EC_{50}$ was determined by performing an agonist dose-response curve in a similar manner as described for the HEK-Blue cells in Example 2, with the following modifications. NK cells were seeded at 50,000/well in a round-bottom, 96-well plate. Following addition of the agonist to the NK cells suspended in NK growth medium only (final volume 200 µL), the cells were returned to the tissue culture incubator (37° C. with 5% $CO_2$) for 24 hours. In addition to the standard negative control (NC) containing NK growth medium only, the positive control (PC) consisted of NK growth medium containing both IL-33 (at the specified concentration) and 0.1 ng/mL of IL-12. An additional "IL-12 only" control was also included.

Tissue culture supernatant was collected 24 hours after agonist addition and stored at 4° C. for 1-3 days. The level of IFN-γ present in the supernatants was determined using a human IFN-γ ELISA kit (Invitrogen/Thermo Fisher Scientific) according to manufacturer guidelines. Non-linear regression analysis was performed using Graph Pad Prism 7 software to obtain final $EC_{50}$ values.

Antibody blocking assays were performed similarly, but in a manner conducive to obtaining $IC_{50}$ values as generally described in Example 2 and modified to specifically account for NK cell usage, as detailed above. In brief, c11C5_C59Y, or an appropriate antibody isotype control (Hu IgG Ctrl), was incubated with NK cells for 1 hour at 37° C., followed by the addition of agonist (IL-33+IL-12, or IL-12 only). The experiment proceeded an additional 24 hours (37° C. with 5% $CO_2$), with cell culture supernatants collected and quantification of IFNγ performed as described above.

Results

To determine the blocking potency and efficacy of the recombinant, humanized 11C5 ("h11C5"), we performed a HEK-Blue IL-1/IL-33 blocking assay. The original murine hybridoma derived antibody ("11C5(Hy)") and a recombinant, murine effectorless version ("m11C5") were also assayed to assess any potential loss in blocking activity as a result of humanization, as well as an effectorless human IgG isotype control ("Hu IgG1 Ctrl").

Figure 4A:
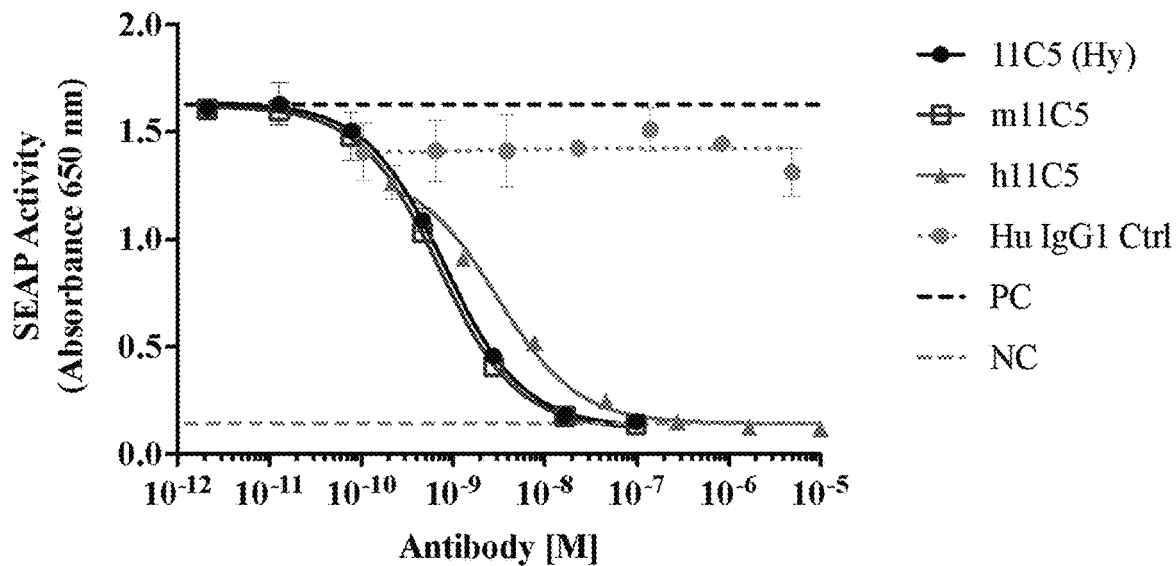
FIGS. 4A, 4B, 4C, 4D, 4E, 4F, 4G, and 4H depict plots of intracellular signaling inhibition assay results for the following recombinantly prepared antibodies based on the hybridoma-derived anti-hu-IL1RAP antibody, 11C5(Hy): murine 11C5 ("m11C5"), chimeric 11C5 ("c11C5"), humanized 11C5 mAb ("h11C5"), C59Y variant of c11C5 ("c11C5_C59Y"), and C59Y variant of h11C5 ("h11C5_C59Y"). For comparison, plots of the assay results for 11C5(Hy) and human isotype control antibody ("Hu IgG1 Ctrl") were also included.
Figure 4B:
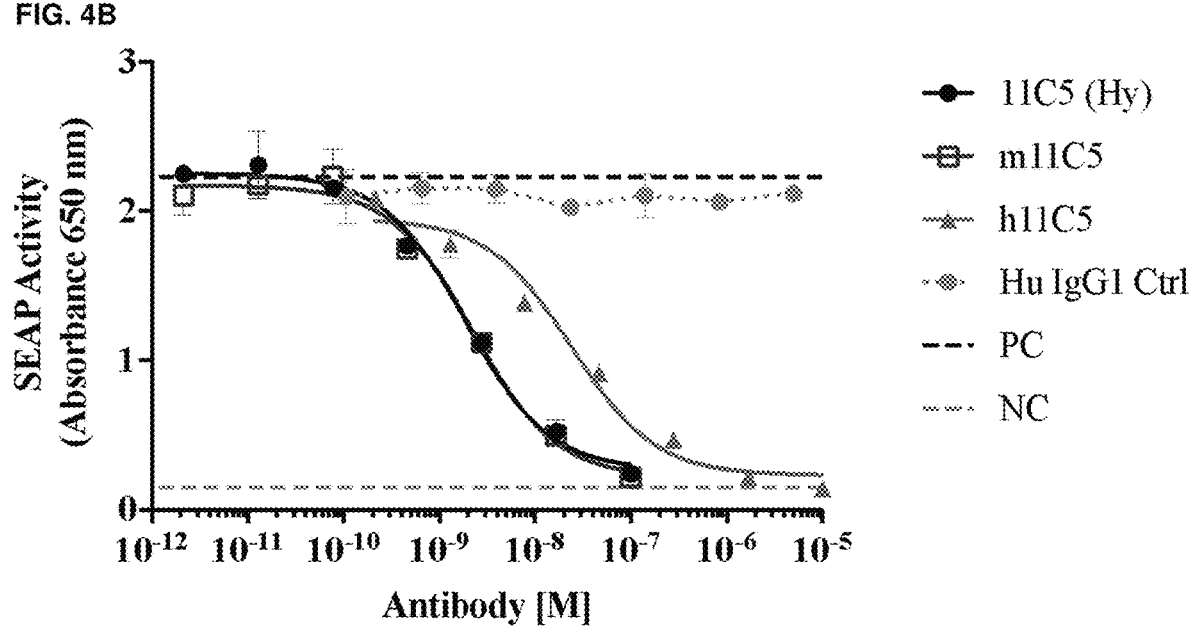
Figure 4C:
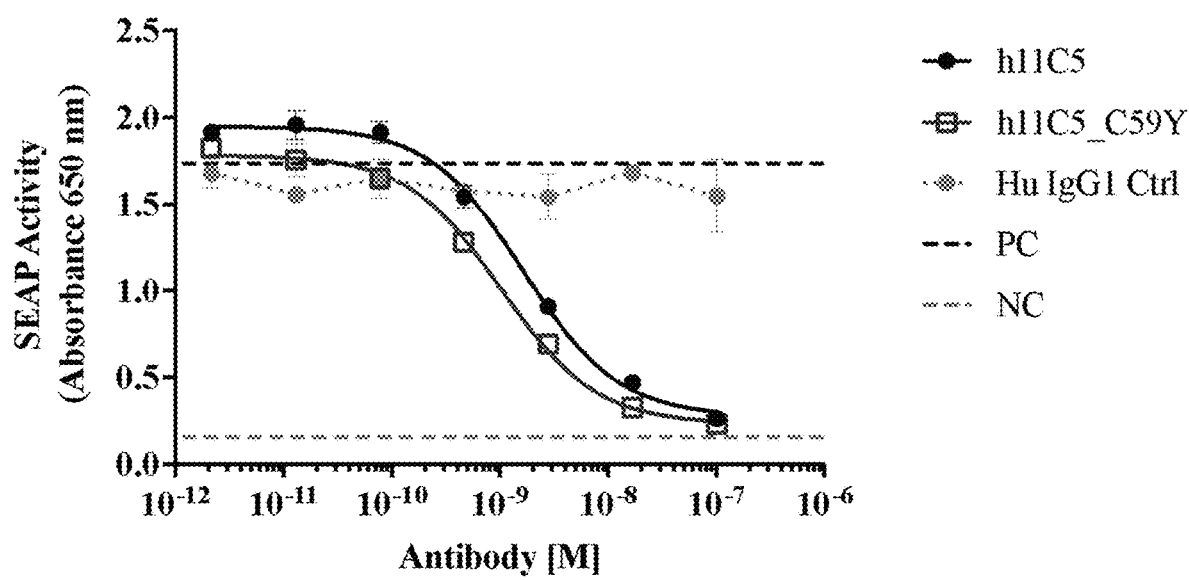
Figure 4D:
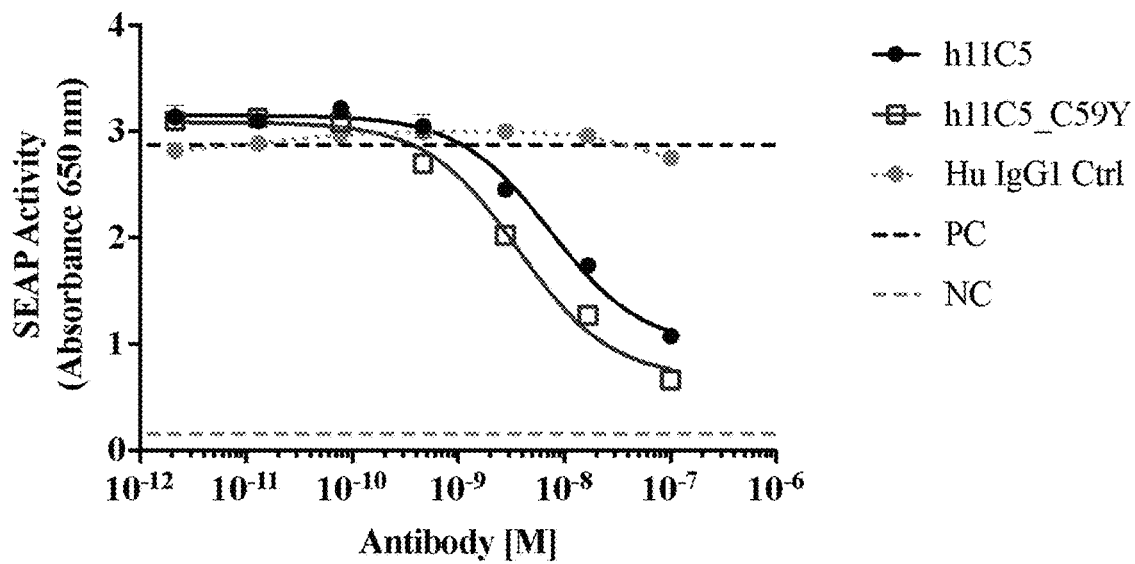

Humanization resulted in a slight loss in blocking activity in both IL-1β (FIG. 4A) and IL-33 (FIG. 4B) stimulated cells. The humanized antibody h11C5 demonstrated 98% inhibition ($IC_{50}$=3.12 nM) with IL-1β stimulated cells, compared to m11C5, the recombinant version of the hybridoma-derived 11C5(Hy), which exhibited complete inhibition at 100 nM ($IC_{50}$=0.705 nM). Likewise, for IL-33 stimulated cells, h11C5 at 100 nM exhibited 80% inhibition ($IC_{50}$=24.0 nM) compared to the 96% inhibition observed with m11C5 ($IC_{50}$=2.25 nM). As shown in FIGS. 4C and 4D, the IL-1β and IL-33 blocking activity of h11C5 was partially restored by the 11C5_C59Y variant, which removes the C59 liability.

For h11C5_C59Y, the $IC_{50}$ for IL-1β blocking activity improved to 1.03 nM, and $IC_{50}$ for IL-33 blocking activity improved to 3.75 nM.

In summary, the hybridoma-derived anti-Hu IL1RAP antibody, 11C5(Hy) was successfully humanized with only a slight reduction in its ability to block the IL-1 and IL-33 dependent pathways, which was partially restored by the C59Y substitution in the $V_H$ region.

Although the HEK-Blue cell lines utilized thus far provided a quick and simple way to assess IL-1, IL-33, or IL-36 pathway activation, cell lines such as these may not be representative of what may occur in vivo. Therefore, we sought to evaluate the blocking activity of 11C5 utilizing primary human cells. Human lung fibroblasts are known to express the IL-1 receptor (IL1R1) and its associated coreceptor, IL1RAP. Further, they are believed to contribute to both the innate and inflammatory immune responses (Suwara, Green et al., 2014). To determine the extent to which the 11C5 antibody inhibits IL-1 signaling in primary human lung fibroblasts (PHLFs), the general experimental approach utilized for HEK-Blue cell line assays was modified to account for the specific and technical requirements of PHLFs. Additionally, a recombinant chimeric version of the 11C5 antibody featuring the effectorless N297G mutation ("c11C5_C59Y") was used in the assay.

Figure 4E:
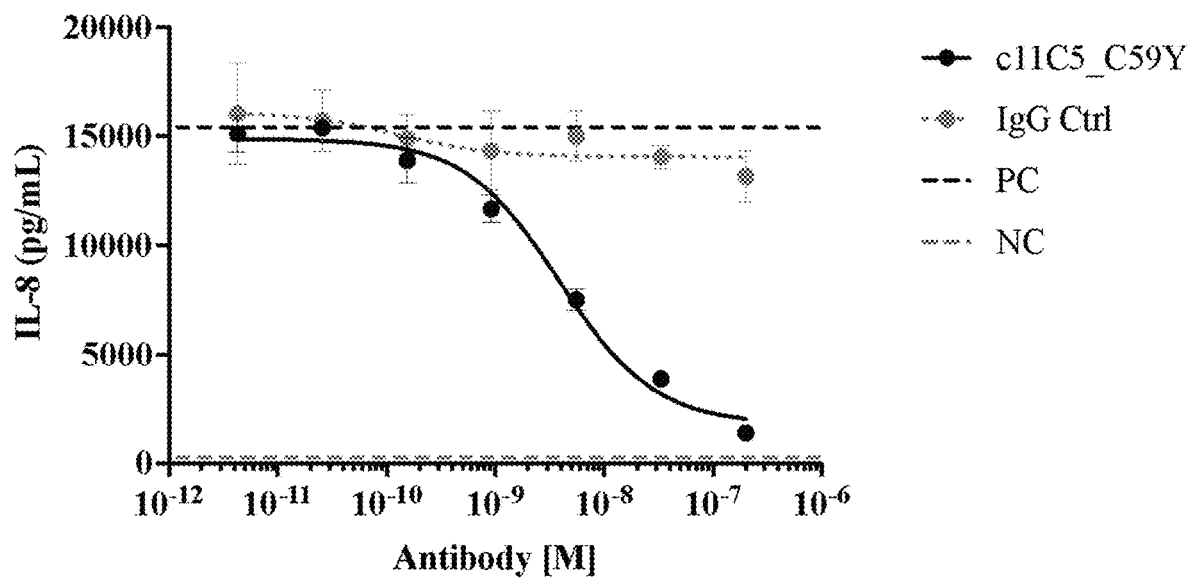

As shown in FIG. 4E, c11C5_C59Y demonstrated remarkably similar blocking activity of IL-1α mediated IL-8 production in PHLFs as was observed for IL-1α stimulated activity in the HEK-Blue assay (see FIG. 1A), with an $IC_{50}$ of approximately 4 nM observed in both cases ($IC_{50}$ 3.96 nM and 87% inhibition at 100 nM of c11C5_C59Y in PHLFs).

Figure 4F:
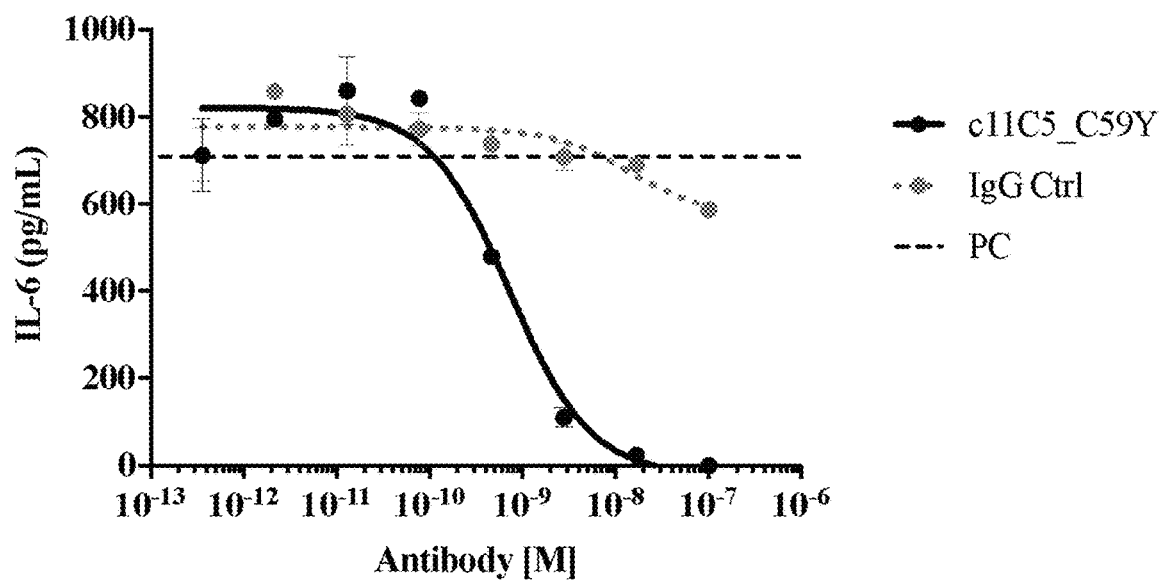

The IL-1 pathway is believed to contribute to airway inflammation and human monocytes are known to respond to IL-1 (Sims and Smith 2010). As shown in FIG. 4F, when primary human monocytes (PHMOs) were stimulated with IL-1β in the presence of c11C5_C59Y, 100% inhibition of IL-6 production was observed and an $IC_{50}$ of 0.733 nM. This demonstrates that c11C5_C59Y is capable of completely blocking IL-1β mediated signaling in PHMOs.

The role and contribution of the IL-33 pathway to the symptoms of asthma is well documented (see e.g., Sims and Smith, Nat. Rev. Immunol., 10(2): 89-102 (2010), Garlanda et al., Immunity, 39(6):1003-1018 (2013), Saluja et al., Clin. Transl. Allergy, 5:33 (2015)). To ascertain whether c11C5_C59Y was capable of blocking the IL-33 pathway in primary human cells, an assay was carried out using human NK cells. IL-12 is known to stimulate the expression of ST2 (the IL-33 receptor) by NK cells, and is regarded as a general NK stimulation factor, increasing the production of IFN-γ and proliferation, as well as enhancing cytotoxicity (see e.g., Liew et al., Nat. Rev. Immunol., 16(11); 676-689 (2016), Granzin et al., Front. Immunol., 8:458 (2017)). Primary human NK cells stimulated with IL-33 in the presence of IL-12 produce IFN-γ, whereas NK cells exposed only to IL-12 fail to produce detectable IFN-γ.

Figure 4G:
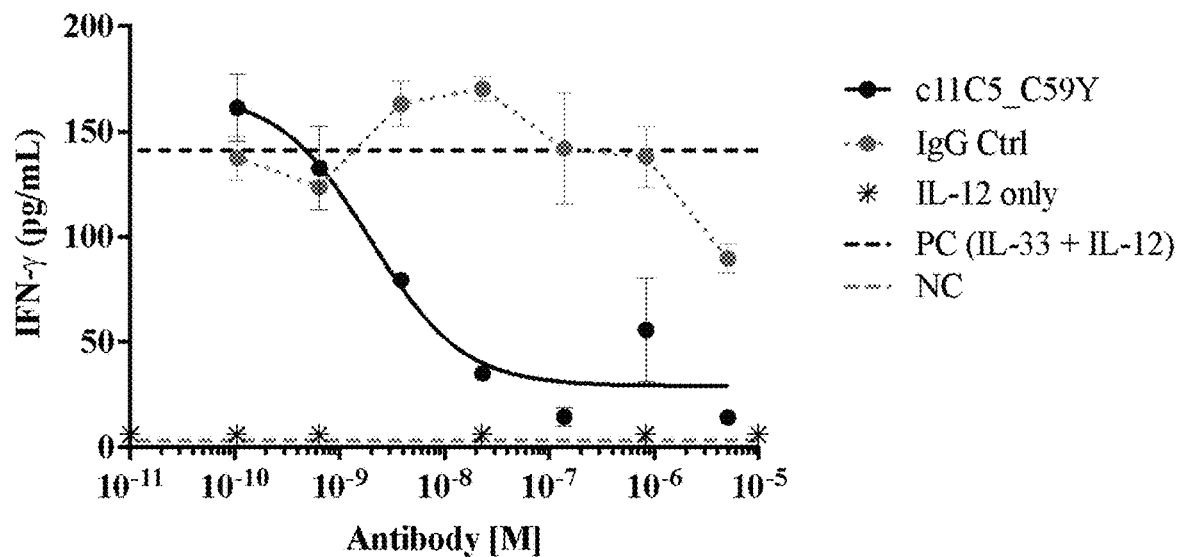

To determine the extent to which c11C5_C59Y blocks IL-33/IL-12 signaling in human NK cells, c11C5_C59Y, or an effectorless isotype control antibody ("IgG Ctrl"), was incubated with human NK cells for one hour, followed by IL-33/IL-12 stimulation for 24 hours. As shown in FIG. 4G, IFN-γ production was detectable in the human NK cells incubated with the control antibody but was reduced to levels near that of the NC in the NK cells incubated with c11C5_C59Y with an $IC_{50}$ of 2.90 nM and 87% inhibition at 100 nM.

Figure 4H:
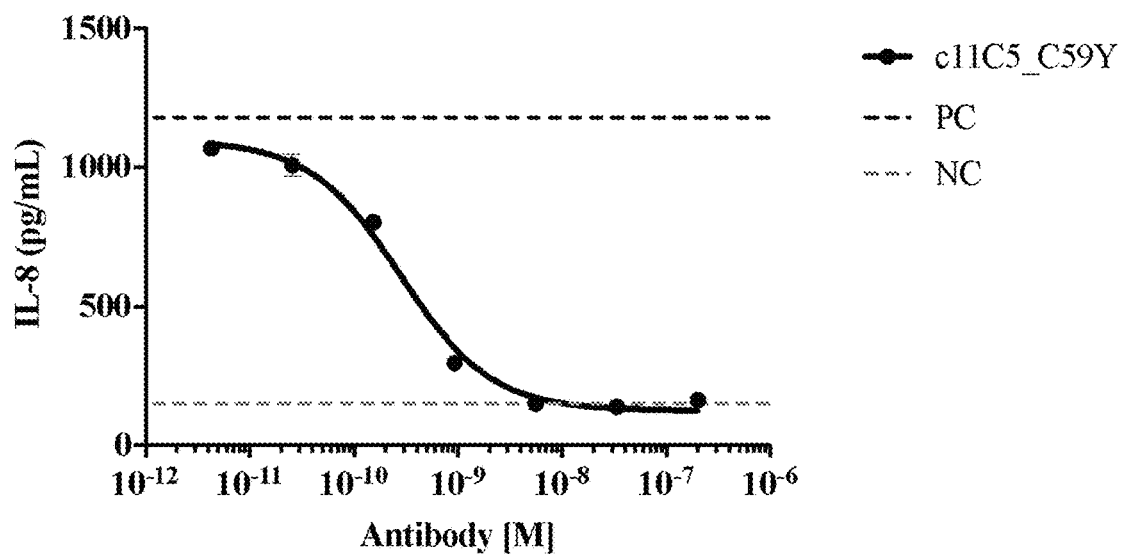

The airway epithelium, epithelial and immune cell crosstalk, and the interactions between epithelial cells and fibroblasts are gaining increasing attention for their role in immune inflammation and asthma (see e.g., Lambrecht and Hammad (2012); Nowarski et al., *Cell,* 168(3):362-375 (2017)). Bronchial epithelial cells are known to contribute to the production of inflammatory cytokines, such as IL-1 and IL-36, following injury or stress, such as viral or bacterial infection and exposure to cigarette smoke. Further, lung fibroblasts are known to respond to IL-1 and IL-36 to induce inflammatory responses (see e.g., Suwara et al., *Mucosal Immunol.,* 7(3): 684-693 (2014); Bassoy et al., *Immunol. Rev.,* 281(1):169-178 (2018)). As shown in FIG. 4H, c11C5_C59Y was shown to block IL-36β stimulation of PHLFs and found to reduce IL-8 production to a level comparable to PHLFs in the NC group (100% inhibition), with an $IC_{50}$ of 0.28 nM.

As shown by the results of this Example 7, including the results for c11C5_C59Y summarized below in Table 10, recombinant antibodies based on the hybridoma-derived anti-hu-IL1RAP antibody, 11C5(Hy), are capable of blocking IL-1, IL-33 and IL-36 signaling in both HEK-Blue cell lines and primary human cells. Moreover, the primary human cell assays further validate the use of the HEK-Blue cell line assays.

TABLE 10

Results for primary human cell signaling inhibition by c11C5_C59Y.

| Primary Human Cell Type | IL-1α | | IL-β | | IL-33 | | IL-36β | |
|---|---|---|---|---|---|---|---|---|
| | $IC_{50}$ (nM) | % Inhib. | $IC_{50}$ (nM) | % Inhib. | $IC_{50}$ (nM) | % Inhib. | $IC_{50}$ (nM) | % Inhib. |
| Lung fibroblasts | 3.96 | 87 | ND | ND | ND | ND | 0.284 | 100 |
| Monocytes | ND | ND | 0.733 | 100 | ND | ND | ND | ND |
| NK cells | ND | ND | ND | ND | 2.90 | 87 | ND | ND |

Percent inhibition "% Inhib." is inhibition observed with c11C5_C59Y at 100 nM
For Human NK cells, IL-33 values represent IL-33 + IL-12.
ND = Not determined Example 8

Affinity Maturation of Humanized Anti-IL1RAP Antibodies Using Phage Library Panning This example illustrates phage library construction and panning techniques used for affinity maturation of the humanized anti-IL1RAP antibody h11C5 to improve binding to human IL1RAP.

Humanized 11C5 C59Y/A43S Affinity Maturation NNK Library Construction

An affinity maturation process was carried out to further improve the binding affinity of the h11C5_C59Y antibody to hu-IL1RAP. Before beginning construction of the libraries, an alanine (A) to serine (S) substitution (A43S) was introduced into framework region 2 of the h11C5_C59Y light chain. The A43S substitution was introduced to minimize the potential effect of altering the $V_H$-$V_L$ interacting interface due to the humanization process (Foote et al., *J. Mol. Biol.,* 224:487-499 (1992)). Accordingly, the phage libraries were constructed based on using the h11C5_C59Y/A43S variant as the parent sequence. The phage libraries were constructed in Fab-amber format for monovalent Fab phage display with residue randomization of either light chain or heavy chain CDR residues using the NNK degenerate codon that encodes for all 20 amino acids (Brenner et al., *Proc. Natl, Acad. Sci. USA,* 89(12):5381-5383 (1992)). Mutagenesis oligonucleotides were designed to apply one NNK mutation to a CDR residue in each of the three light chain or heavy chain CDRs. Thus, each member of the libraries carries three NNK degenerate codons, one for each CDR of light chain or heavy chain. Synthesized mutagenesis oligonucleotides were then used to construct the light chain or heavy chain libraries using Kunkel mutagenesis (Kunkel et al., *Methods Enzymol.,* 154:367-382 (1987)). The resultant library DNA was electroporated into *E. coli* XL1 cells, yielding approximately $1.3 \times 10^9$ transformants.

The hu-M-IL1RAP polypeptide construct of SEQ ID NO: 3 (2 μg/mL) was coated on Maxisorp plates overnight at 4° C. For the first panning round, plates and phage libraries were blocked in PBS buffer containing 0.05% TWEEN® 20 and 1% BSA for either 1 hour (plates) or 30 minutes (phage libraries). Plates were washed in Wash Buffer (PBS buffer containing 0.05% TWEEN® 20) and incubated with blocked phage libraries for 2 hours with shaking. Non-specifically bound phage was removed by washing vigorously with Wash Buffer. Specifically bound phage was eluted with 0.1 N HCl and neutralized using ¹⁄₁₀th v/v 1.3 M Tris base. Non-specific interactions were inhibited by adding ¹⁄₁₀th v/v 1% BSA.

The second panning round was identical to the first except for the use of SUPERBLOCK™ PBS buffer (Pierce) and 0.05% TWEEN® 20 for the blocking step.

For panning rounds three through five, phage libraries were incubated with blocking buffer (PBS buffer with 1% BSA in round 3 and SUPERBLOCK™ PBS buffer (Pierce) and 0.05% TWEEN® 20 in rounds 4 and 5) for 30 minutes and then incubated with decreasing concentrations of biotinylated hu-M-IL1RAP for 1 hour. Hu-M-IL1RAP-bound phage were captured on blocked neutravidin-coated plates, washed extensively with Wash Buffer, and eluted and neutralized in the same manner as in rounds 1 and 2. In the final selection round, 1000× non-biotinylated hu-M-IL1RAP was added as a competitor to increase the selection stringency.

To extract sequences from affinity maturation libraries using NGS, phagemid double stranded DNA was isolated from *E. coli* XL-1 cells carrying phagemids from the initial phage library (unsorted libraries) and from the second and third rounds of solution selection (sorted libraries). Purified DNA was used as the template to generate amplicons of $V_L$ and $V_H$ regions using Illumina 16s library preparation protocol (Illumina, Inc., San Diego, CA, USA). Sequencing adapters and dual-index barcodes were added using Illumina Nextera XT Index Kit (Illumina, Inc.). In preparation for sequencing on Illumina MiSeq, adapter-ligated amplicons were subjected to standard Illumina library denaturing and sample loading protocol using MiSeq Reagent Kit v3 (600 cycles) (Illumina, Inc.). Paired-end sequencing was performed to cover the entire length of the amplicon with insert size of 200 bp to 300 bp.

NGS Data Analysis of h11C5_C59Y/A43S Affinity Maturation Libraries

Paired-end sequencing data were first assembled using paired-end assembler PANDAseq (see e.g., Masella et al., *BMC Bioinformatics,* 13:31 (2012)) to obtain complete amplicons. Quality control (QC) was then performed on identified amplicons, where each amplicon was checked for no insertion or deletion of sequences and no stop codons, each CDR sequence was allowed to carry only up to one NNK mutation and no non-NNK mutation. Position weight matrices were generated by calculating the frequency of all mutations of every randomized position. Enrichment ratios for each mutation were calculated by dividing the frequency of a given mutation at a given position in the sorted sample with the frequency of the very same mutation in the unsorted sample, as described previously (Koenig et al., *J. Biol. Chem.*, 290(36):21773-27896 (2015)). Analysis of the NGS data identified a wide range of amino acid substitutions in each of the six CDRs that result in an anti-IL1RAP antibody that retains high-affinity for hu-M-IL1RAP, and which are listed below in Table 11.

TABLE 11

| CDR amino acid substitutions that retain high-affinity IL1RAP binding |
|---|
| CDR-L1: Y30W, Y30F, S31H, S31R, S31K, S31Q, S31M, S31Y, S31L, S31N, L33G, L33I, L33T, L33V, L33M, L33N, L33Q, L33S, L33A, L33Y, A34N, A34S, A34T, A34G |
| CDR-L2: A51D, A51E, A51F, A51G, A51H, A51I, A51K, A51L, A51M, A51N, A51Q, A51R, A51S, A51T, A51V, A51W, A51Y, K52G, K52N, L54W, L54Y, L54H, L54F |
| CDR-L3: Q89S, H90S, W92I, W92K, W92F, W92Y, W92A, W92H, W92G, W92M, W92V, T94I, T94V |
| CDR-H1: F29A, F29D, F29E, F29G, F29H, F29I, F29K, F29L, F29M, F29N, F29P, F29Q, F29R, F29S, F29T, F29V, F29W, F29Y, S30K, S30P, S30Q, S30E, S30G, S30T, S30R, N31E, N31D, N31K, N31Q, N31R, N31G, Y32E, Y32D, Y32H, Y32S, Y32V, Y32A, A33N, A33S, M34W, M34V, S35G |
| CDR-H2: V51S, V51N, V51A, T52S, E52aD, E52aN, E52aT, G53P, G53V, G53T, G53I, G54D, G54E, G54F, G54H, G54I, G54K, G54L, G54M, G54N, G54P, G54Q, G54R, G54T, G54V, G54W, G54Y, D55P, D55G, D55A, D55Q, D55E, D55H, D55K, D55N, D55R, D55S, Y56W, N57G, N57A, N57P, N57R, C59Y, C59A, C59D, C59R, C59F, D61S, D61W |
| CDR-H3: A93S, A93T, A93G, R94M, R94L, R94N, R94I, R94Q, R94V, R94H, R96A, R96D, R96Q, R96S, R96E, R96M, R96N, R96I, F100aM, F100aL, F100aW |

Further analysis of the NGS data from the affinity maturation libraries resulted in calculated enrichment ratios and predicted affinity improvements for a selected subset of variant h11C5 antibodies with amino acid substitutions predicted to exhibit the highest affinity improvements shown below in Table 12.

TABLE 12

| h11C5 variant identifier | Mutation | Enrichment ratio (at the highest selection stringency) | Fold Improvement in $K_D$ @ 25° C. | Fold Improvement in $K_D$ @ 37° C. |
|---|---|---|---|---|
| | | $V_L$ Region Variants | | |
| K1 | Y30W | 3.5232 | 9.06 | N/A |
| K2 | L33G | 1.7116 | 9.74 | N/A |
| K3 | W92K | 3.3093 | 6.44 | N/A |
| K4 | W92L | 0.4157 | 2.29 | N/A |
| K7 | A51R | 2.8920 | 28.32 | N/A |
| K8 | A51L | 2.9008 | 25.73 | N/A |
| K9 | A51D | 2.8372 | 16.05 | N/A |
| K10 | A51Y | 2.9532 | 39.42 | 8.99 |
| K12 | W92I | 3.3636 | 8.20 | N/A |
| K14 | T94I | 1.7397 | 3.69 | N/A |
| K15 | T94V | 0.9867 | 2.81 | N/A |
| | | $V_H$ Region Variants | | |
| H1 | R96A | 4.5496 | 2.70 | N/A |
| H2 | R96D | 4.0599 | 7.99 | 2.39 |
| H3 | V51S | 3.4198 | 8.51 | 2.14 |

TABLE 12-continued

| h11C5 variant identifier | Mutation | Enrichment ratio (at the highest selection stringency) | Fold Improvement in $K_D$ @ 25° C. | Fold Improvement in $K_D$ @ 37° C. |
|---|---|---|---|---|
| H4 | F29Q | 3.0243 | 8.00 | N/A |
| H6 | R96Q | 3.8026 | 7.20 | 1.43 |

Biacore Analysis of Fab Variants with Affinity Matured $V_L$ or $V_H$ Regions

Mutations identified from the affinity matured $V_L$ or $V_H$ libraries with a high enrichment ratio were selected for cloning as single, double, or triple mutations into a mammalian Fab expression construct containing an 8×His tag to generate Fab proteins. Plasmids encoding the affinity matured $V_L$ or $V_H$ regions were transfected into Expi293F cells (Thermo Fisher Scientific) for 20-30 mL expression using a 1:1 ratio of HC:LC. The Fab proteins were purified with a HisPur Ni-NTA column by diluting the supernatant 1.5× with 1× phosphate-buffered saline pH 7.2 (PBS), adding 10 mM imidazole, and binding to resin in batch mode for 2 hours. After incubation, the slurry was loaded into a column and the resin was washed with 20 column volumes (CV) of PBS+20 mM imidazole. Recombinant Fab molecules were eluted with 5 CV PBS+250 mM imidazole. Purified Fabs were buffer exchanged into PBS using a PD10 desalting column (GE Healthcare).

Surface plasmon resonance (SPR) analysis was used to determine binding affinity for hu-M-IL1RAP of the purified Fabs containing the selected single, double, and triple mutations in either the $V_L$ or $V_H$ regions using a BIACORE™ 8K instrument. Briefly, a 1:4 dilution of Biotin CAPture Reagent (GE Healthcare) into HBS-EP buffer (0.01 M HEPES pH 7.4, 0.15 M NaCl, 3 mM EDTA, 0.005% Surfactant P20) was applied to the chip at 2 μL/min flow rate. For kinetics measurements, 5 nM biotinylated hu-M-IL1RAP was captured at 10 μL/min to achieve ~50 response units in the second flow cell (FC2). FC1 was kept as a reference. Next, 2-fold serial dilutions of the Fab protein in HBS-P buffer (0.01 M HEPES pH 7.4, 0.15 M NaCl, 0.005% surfactant P20) from low (0.31 nM) to high (20 nM) were injected (flow rate: 10 μL/min) at either 25° C. or 37° C. The sensorgrams were recorded and subjected to reference and buffer subtraction before data analysis with the BIACORE® 8K Evaluation Software (version 1.1.1.7442). Association rates ($k_{on}$) and dissociation rates ($k_{off}$) were calculated using a simple one-to-one Langmuir binding model. The equilibrium dissociation constant ($K_D$) was calculated as the ratio of $k_{off}/k_{on}$.

Results

The Biacore affinity results for the affinity matured Fab variants are summarized below in Table 13. Many of the variants showed improved binding affinity. Variant K13, which introduced the A51Y and W92I mutations into the parent sequence improved the affinity 9-fold over the input parental Fab of h11C5_C59Y/A43S.

TABLE 13

Affinity of h11C5 Fab variants with mutations in either $V_L$ or $V_H$ region

| Variant | Mutations (relative to parent Fab) | $k_{on}$ @ 25° C. (1/Ms) | $k_{off}$ @ 25° C. (1/s) | $K_D$ @ 25° C. (M) | $k_{on}$ @ 37° C. (1/Ms) | $k_{off}$ @ 37° C. (1/s) | $K_D$ @ 37° C. (M) |
|---|---|---|---|---|---|---|---|
| Parent Fab | n/a | 1.39E+06 | 4.68E-04 | 3.37E-10 | 6.08E+06 | 1.63E-03 | 2.68E-10 |
| $V_L$ Region Variants | | | | | | | |
| K1 | Y30W | 4.82E+06 | 1.80E-04 | 3.72E-11 | | | |
| K2 | L33G | 4.57E+06 | 1.58E-04 | 3.46E-11 | | | |
| K3 | W92K | 3.78E+06 | 1.98E-04 | 5.23E-11 | | | |
| K4 | W92L | 5.12E+06 | 7.51E-04 | 1.47E-10 | | | |
| K5 | Y30W/W92L | 5.11E+06 | 2.68E-04 | 5.24E-11 | | | |
| K6 | Y30W/W92F | 4.25E+06 | 6.25E-05 | 1.47E-11 | | | |
| K7 | A51R | 5.25E+06 | 6.26E-05 | 1.19E-11 | | | |
| K8 | A51L | 5.15E+06 | 6.76E-05 | 1.31E-11 | | | |
| K9 | A51D | 4.93E+06 | 1.03E-04 | 2.10E-11 | | | |
| K10 | A51Y | 5.92E+06 | 5.06E-05 | 8.55E-12 | 5.12E+06 | 1.53E-04 | 2.98E-11 |
| K11 | A51R/K52G | 4.83E+06 | 1.02E-04 | 2.12E-11 | | | |
| K12 | W92I | 5.58E+06 | 2.30E-04 | 4.11E-11 | | | |
| K13 | A51Y/W92I | 6.15E+06 | 4.36E-05 | 7.09E-12 | 4.01E+06 | 1.17E-04 | 2.93E-11 |
| K14 | T94I | 5.95E+06 | 5.43E-04 | 9.13E-11 | | | |
| K15 | T94V | 5.67E+06 | 6.80E-04 | 1.20E-10 | | | |
| K17 | A51Y/W92K | 5.63E+06 | 3.58E-05 | 6.37E-12 | 3.60E+06 | 1.59E-04 | 4.41E-11 |
| K18 | A51Y/L33G | 6.52E+06 | 1.23E-04 | 1.89E-11 | | | |
| $V_H$ Region Variants | | | | | | | |
| H1 | R96A | 1.75E+06 | 2.18E-04 | 1.25E-10 | | | |
| H2 | R96D | 5.19E+06 | 2.19E-04 | 4.22E-11 | 6.50E+06 | 7.29E-04 | 1.12E-10 |
| H3 | V51S | 5.26E+06 | 2.08E-04 | 3.96E-11 | 4.82E+06 | 6.02E-04 | 1.25E-10 |
| H4 | F29O | 5.49E+06 | 2.31E-04 | 4.21E-11 | | | |
| H5 | V51S/G54H | 4.71E+06 | 2.35E-04 | 5.00E-11 | | | |
| H6 | R96O | 5.34E+06 | 2.50E-04 | 4.68E-11 | 3.76E+06 | 7.08E-04 | 1.88E-10 |
| H7 | F29E/N57G/R96A | | | | 5.13E+06 | 5.11E-04 | 9.98E-11 |
| H8 | F29S/E52aV/R96A | | | | 5.27E+06 | 8.99E-04 | 1.70E-10 |
| H9 | G54V/R96A | | | | 4.94E+06 | 4.01E-04 | 8.11E-11 |
| H10 | F29S/D55G/R96S | | | | 5.34E+06 | 7.02E-04 | 1.31E-10 |
| H11 | W97F | | | | 9.58E+06 | 4.41E-03 | 4.60E-10 |
| H12 | M34V | | | | 5.70E+06 | 1.74E-03 | 3.05E-10 |

Fab Proteins of Combined $V_L$ and $V_H$ Region Variants with Improved Affinity

The Fab variants exhibiting the most improved $K_D$ values were selected from the $V_L$ region (K10, K13, and K17) and the $V_H$ region (H2 and H3) variants to generate variants comprising both $V_L$ and $V_H$ region variants. BIACORE™ SPR analysis of the resulting combination variants was performed as described above, and the results are summarized below in Table 14. The combination Fab variants K10/H2, K13/H2, and K13/H3 exhibited ~12-13-fold improved affinity over the input parental Fab of h11C5_C59Y/A43S.

TABLE 14

Affinity of h11C5 Fab variants with combined variant $V_L$ and $V_H$ regions

| Variant | Mutations (relative to parent Fab) | $k_{on}$ @ 25° C. (1/Ms) | $k_{off}$ @ 25° C. (1/s) | $K_D$ @ 25° C. (M) | $k_{on}$ @ 37° C. (1/Ms) | $k_{off}$ @ 37° C. (1/s) | $K_D$ @ 37° C. (M) |
|---|---|---|---|---|---|---|---|
| Parent Fab | — | 1.39E+06 | 4.68E-04 | 3.37E-10 | 6.08E+06 | 1.63E-03 | 2.68E-10 |
| K10/H2 | $V_L$-A51Y $V_H$-R96D | | | | 5.54E+06 | 1.11E-04 | 2.01E-11 |
| K10/H3 | $V_L$-A51Y $V_H$-V51S | | | | 5.06E+06 | 1.23E-04 | 2.42E-11 |
| K13/H2 | $V_L$-A51Y/W92I $V_H$-R96D | | | | 5.08E+06 | 1.15E-04 | 2.27E-11 |
| K13/H3 | $V_L$-A51Y/W92I $V_H$-V51S | | | | 5.17E+06 | 1.09E-04 | 2.11E-11 |
| K17/H2 | $V_L$-A51Y/W92K $V_H$-R96D | | | | 4.15E+06 | 1.21E-04 | 2.93E-11 |
| K17/H3 | $V_L$-A51Y/W92K $V_H$-V51S | | | | 3.81E+06 | 1.20E-04 | 3.15E-11 |
| K13/H12 | $V_L$-A51Y/W92I $V_H$-M34V | | | | 4.90E+06 | 1.78E-04 | 3.63E-11 |

Example 9

Assays of Affinity Matured Anti-IL1RAP Antibodies

This example illustrates cell-based blocking assays used to characterize the functional activity of the affinity matured humanized anti-IL1RAP antibody variants described in Example 8, both in Fab and full-length IgG forms.

Materials and Methods

Cell Lines and HEK-Blue Assays. The cell lines and HEK-Blue related assays of this Example 9 were carried out described in Example 2.

Production of Full-length h11C5 IgG Variants. Plasmids encoding the heavy or light chain were transfected into Expi293F cells (Thermo Fisher Scientific) for 30 mL expression using a 1:1 ratio of HC:LC. IgGs were purified with a HiTrap MabSelect SuRe column (GE Healthcare) by flowing the supernatant over the column, washing with 20 column volumes (CV) of PBS+500 mM NaCl, and equilibrating with 20 CV of PBS. IgGs were eluted with 5 CV 0.1 M acetic acid+150 mM NaCl, pH 3.0, and were immediately neutralized with 0.2 CV 1.0 M MOPS, pH 7. IgGs were purified further via gel filtration using an S200 preparatory-grade sizing column (GE Healthcare) in 2×PBS, pH 6.5.

Results

Figure 5A:
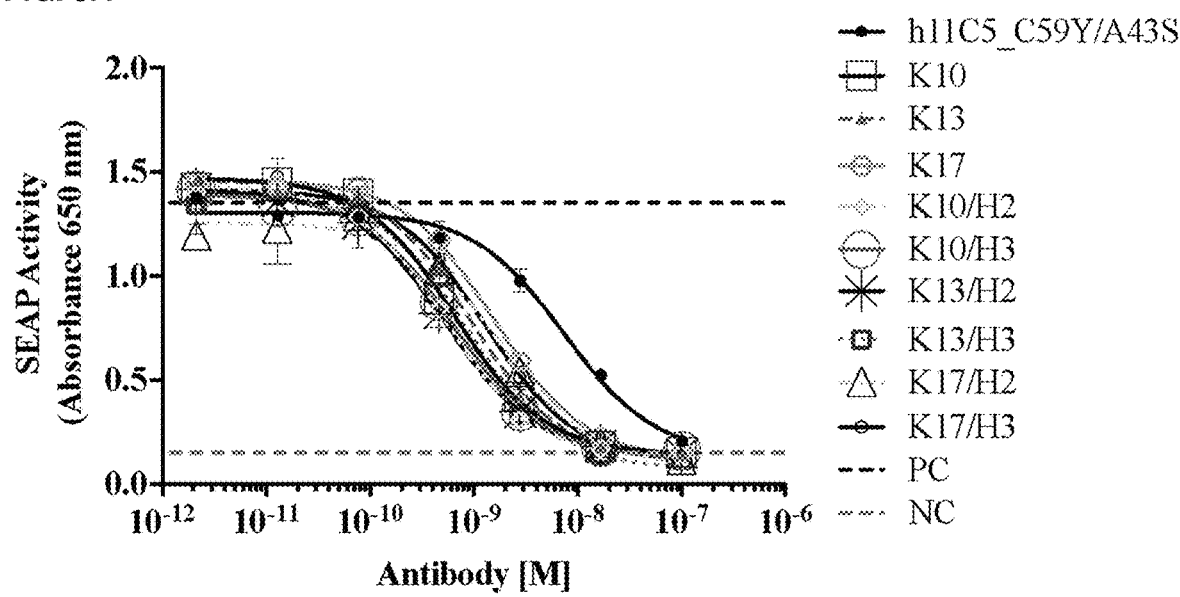
FIGS. 5A, 5B, 5C, 5D, 5E, and 5F depict plots of HEK-Blue intracellular signaling inhibition assay results for affinity matured variants of h11C5_C59Y/A43S, either Fab or IgG proteins, containing single, double, or triple mutations in either or both the $V_L$ or $V_H$ regions as described in Examples 9 and 10.
Figure 5B:
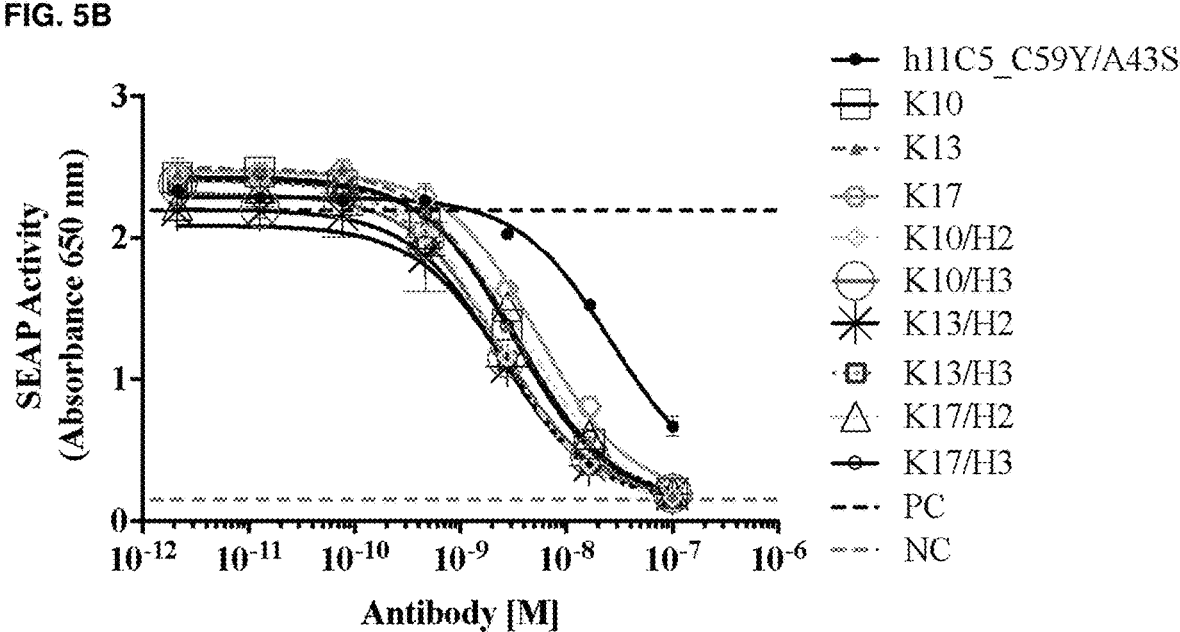
Figure 5C:
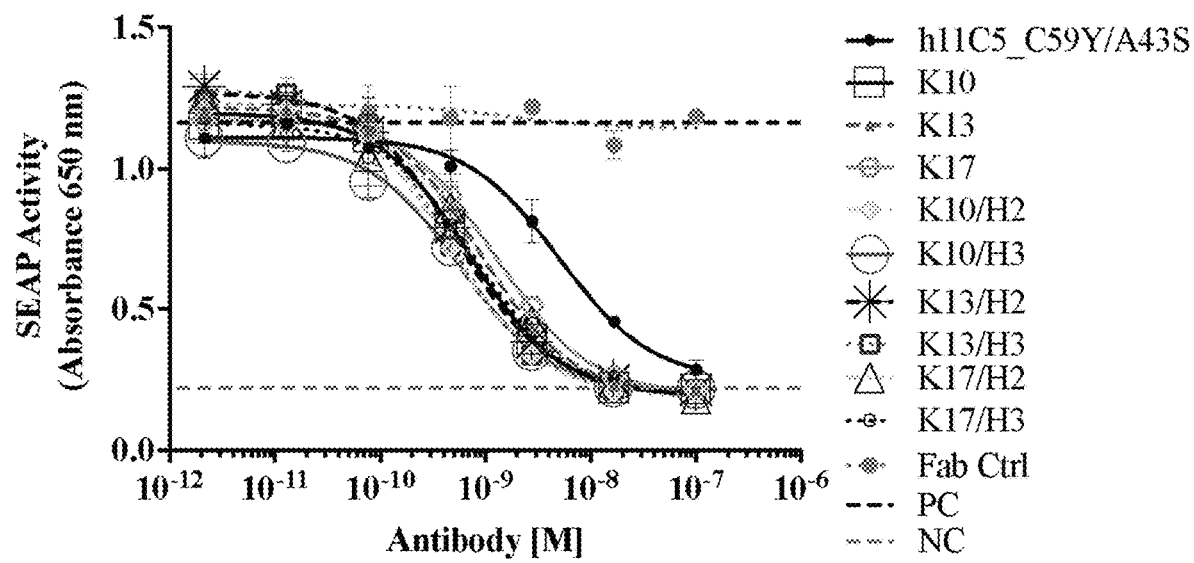

HEK-Blue assays (as used in Examples 4 and 7) with the affinity matured Fab variants of Example 8, as well as full-length IgG versions of the variant antibodies, were carried out to determine whether the observed improvements in binding affinity for hu-M-IL1RAP correlated with improvements in blocking IL-1, IL-33, and IL-36 signaling activity. As shown in FIGS. 5A, 5B, and 5C, the nine Fab variants showing greatest affinity improvement in Example 8 (i.e., K10, K13, K17, K10/H2, K10/H3, K13/H2, K13/H3, K17/H2, K17/H3) also exhibited increased inhibition of IL-1, IL-33 and IL-36 signaling activity relative to the parent Fab of h11C5_C59Y/A43S in the HEK-Blue assays. The potency ($IC_{50}$) and % inhibition at 100 nM for the nine affinity matured Fab variants are summarized below in Table 15.

TABLE 15

Inhibitory potency of affinity matured h11C5 Fab variants

| Variant | Mutations (relative to parent Fab) | IL-1β $IC_{50}$ (M) | % Inhib. | IL-33 $IC_{50}$ (M) | % Inhib. | IL-36α $IC_{50}$ (M) | % Inhib. |
|---|---|---|---|---|---|---|---|
| Parent Fab | n/a | 7.45E−09 | 96 | 2.64E−08 | 77 | 5.09E−09 | 96 |
| K10 | $V_L$-A51Y | 6.60E−10 | 100 | 3.26E−09 | 98 | 7.06E−10 | 100 |
| K13 | $V_L$-A51Y/W92I | 9.40E−10 | 100 | 3.17E−09 | 98 | 8.84E−10 | 100 |
| K17 | $V_L$-A51Y/W92K | 1.59E−09 | 100 | 5.38E−09 | 96 | 1.27E−09 | 100 |
| K10/H2 | $V_L$-A51Y $V_H$-R96D | 5.52E−10 | 100 | 2.17E−09 | 99 | 4.81E−10 | 100 |
| K10/H3 | $V_L$-A51Y $V_H$-V51S | 6.42E−10 | 99 | 2.43E−09 | 98 | 5.82E−10 | 100 |
| K13/H2 | $V_L$-A51Y/W92I $V_H$-R96D | 5.39E−10 | 100 | 2.39E−09 | 98 | 5.48E−10 | 99 |
| K13/H3 | $V_L$-A51Y/W92I $V_H$-51S | 8.98E−10 | 100 | 2.07E−09 | 99 | 4.62E−10 | 98 |
| K17/H2 | $V_L$-A51Y/W92K $V_H$-R96D | 1.86E−09 | 100 | 4.71E−09 | 97 | 9.30E−10 | 100 |
| K17/H3 | $V_L$-A51Y/W92K $V_H$-V51S | 1.32E−09 | 100 | 3.53E−09 | 98 | 8.00E−10 | 100 |

Figure 5D:
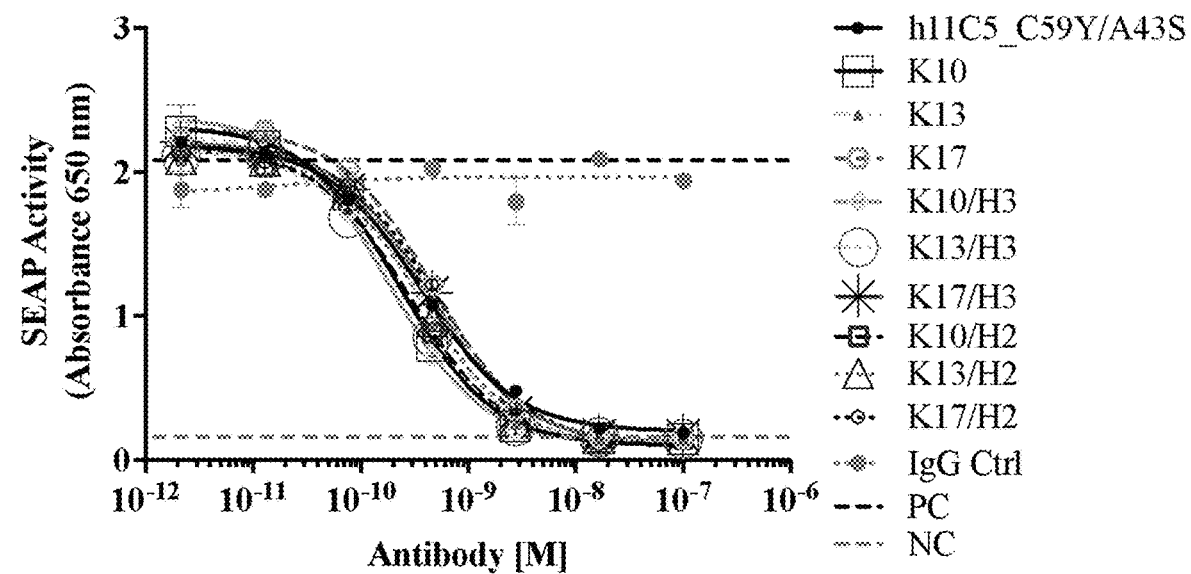
Figure 5E:
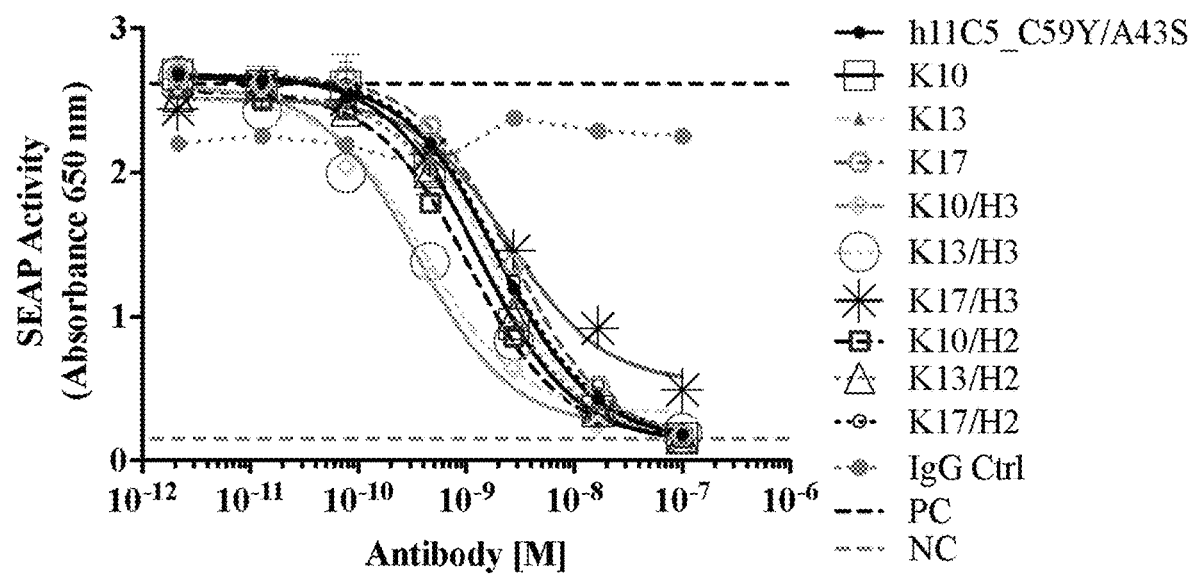
Figure 5F:
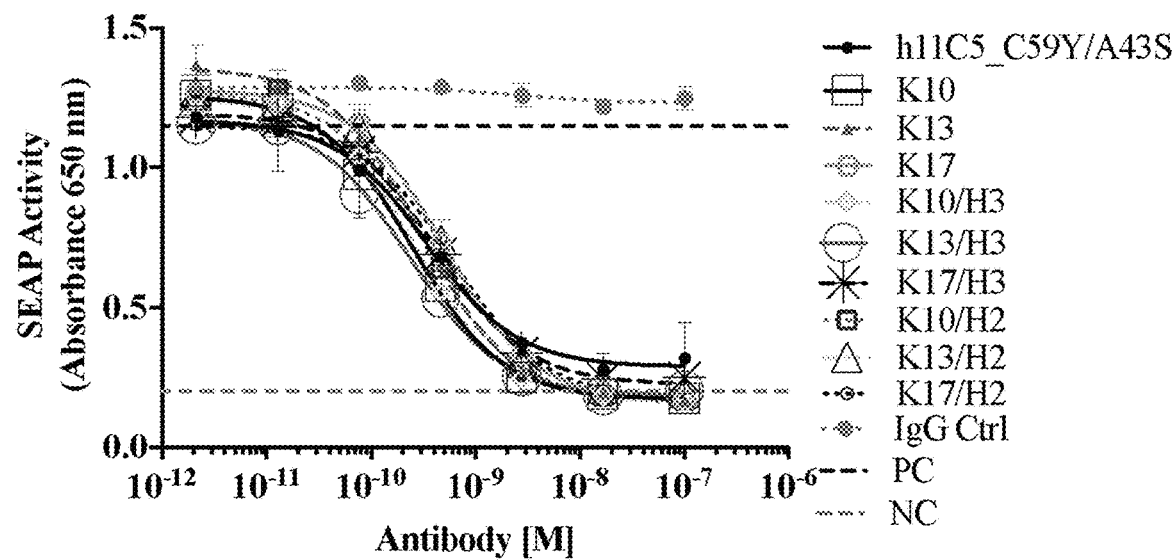

The same affinity matured variants were also assayed as full-length IgG antibodies with the effectorless N297G mutation. As shown in FIGS. 5D and 5F, similar results were observed in the assays utilizing IL-1β or IL-36α-stimulated HEK-Blue IL-1/IL-33 cell or IL-33 cells (transiently expressing the IL-36 receptor IL1RL2), respectively. As shown in FIG. 5E, however, most, but not all of the variants exhibited increased blocking activity for IL-33 stimulated HEK-Blue IL-1/IL-33 cells. The potency ($IC_{50}$) and % inhibition at 100 nM for the full-length IgG affinity matured variants are summarized below in Table 16.

TABLE 16

Inhibitory potency of affinity matured h11C5 IgG variants.

| Variant[1] | Mutations (relative to parent IgG Ab) | IL-1 $IC_{50}$ (M) | IL-1 % Inhib. | IL-33 $IC_{50}$ (M) | IL-33 % Inhib. | IL-36α $IC_{50}$ (M) | IL-36α % Inhib. |
|---|---|---|---|---|---|---|---|
| Parent IgG Ab | n/a | 3.63E−10 | 99 | 2.04E−09 | 99 | 3.40E−10 | 89 |
| K10 | $V_L$-A51Y | 2.30E−10 | 100 | 1.37E−09 | 100 | 2.47E−10 | 100 |
| K13 | $V_L$-A51Y/W92I | 3.32E−10 | 100 | 1.77E−09 | 100 | 3.03E−10 | 100 |
| K17 | $V_L$-A51Y/W92K | 4.68E−10 | 100 | 2.74E−09 | 99 | 4.95E−10 | 100 |
| K10/H2 | $V_L$-A51Y $V_H$-R96D | 2.85E−10 | 100 | 1.06E−09 | 100 | 3.40E−10 | 100 |
| K10/H3 | $V_L$-A51Y $V_H$-V51S | 1.77E−10 | 100 | 3.54E−10 | 99 | 2.80E−10 | 100 |
| K13/H2 | $V_L$-A51Y/W92I $V_H$-R96D | 3.61E−10 | 100 | 1.52E−09 | 99 | 4.77E−10 | 100 |
| K13/H3 | $V_L$-A51Y/W92I $V_H$-V51S | 2.51E−10 | 100 | 4.25E−10 | 98 | 2.32E−10 | 100 |
| K17/H2 | $V_L$-A51Y/W92K $V_H$-R96D | 5.13E−10 | 100 | 2.08E−09 | 100 | 6.22E−10 | 100 |
| K17/H3 | $V_L$-A51Y/W92K $V_H$-V51S | 4.29E−10 | 100 | 2.50E−09 | 87 | 4.18E−10 | 96 |

[1]All of the IgG variants shown also contain the N297G mutation that confers effectorless function.

Example 10 pH-Dependent Binding of h11C5 Variants

This example illustrates the kinetics of some of the affinity matured h11C5 variants of Example 9 in binding hu-IL1RAP and cyno-IL1RAP at pH 6 and pH 7.4. In order to prolong the half-life of 11C5 variants in vivo, we sought to increase the affinity of h11C5 for FcRn, the neonatal Fc receptor, at pH 6 (while keeping the affinity at neutral pH unchanged). Upon administration, IgGs are initially internalized into the cell and subsequently processed in the endosome (see e.g., Kuo et al., *MAbs,* 3(5), 422-430 (2011). Acidification of the endosome facilitates binding of the IgG Fc fragment to FcRn, a high-affinity interaction at low pH (see e.g., Roopenian et al., *Nature Reviews Immunology,* 7(9), 715-725 (2007). After transport to the cell surface as a complex, the IgG is released back into circulation due to the lower affinity of FcRn for Fc at neutral pH. This process of recycling protects IgGs from degradation, thereby contributing to their long half-life in vivo.

Mutations that increase the affinity of IgG for FcRn at low pH could result in greater half-life of the therapeutic antibody in vivo by allowing the antibody to be recycled to the cell surface and back into circulation. However, target-mediated drug disposition (TMDD) of the therapeutic molecule by IL1RAP could prevent recycling by FcRn. An h11C5 variant with a relatively fast off-rate ("koff") to IL1RAP at acidic pH could limit the interference from TMDD and may benefit the most from mutations that enhance FcRn binding.

To determine which h11C5 variant of Example 9 has the best chance of escaping TMDD at low pH, we measured the kinetics of h11C5 variants binding IL1RAP at pH 7.4 and pH 6. The h11C5 variant from Example 9, K17/H2 (or "YKD") has the fastest $k_{off}$ at pH 6 of the four tested 11C5 variants. This suggests that YKD has the best chance of escaping target-mediated drug disposition (TMDD) and therefore could benefit the most from FcRn-binding mutations.

Materials and Methods

BIACORE SPR analysis of h11C5 IgG Variants at pH 7.4 and pH 6: BIACORE™ SPR analysis of four h11C5 IgG variants binding hu-M-IL1RAP (SEQ ID NO: 3) and cyno-M-IL1RAP (SEQ ID NO: 8) at pH 7.4 was performed as described in Example 8, with either 0.6 nM biotinylated hu-M-IL1RAP or 1.8 nM cyno-M-IL1RAP captured on the chip and 3-fold serial dilutions of 11C5 IgG from low (0.103 nM) to high (10 nM) injected as analyte at 37° C. For binding of 11C5 variants to hu-M-IL1RAP and cyno-M-IL1RAP at pH 6, methods are identical to binding at pH 7.4, except for the use of pH 6 running buffer (10 mM MES pH 6, 150 mM NaCl, 0.005% (w/v) P20), which was also used to dilute the Biotin CAPture reagent (GE Healthcare) 1:4.

Results

Results for the BIACORE SPR analysis at pH 7.4 and pH 6 are summarized in Table 17, where $K_D$ is the apparent affinity measured (given that IgG is the analyte in this format), and $k_{off}$ is the off-rate.

TABLE 17

BIACORE SPR kinetics of h11C5 variants binding
hu-M-IL1RAP and cyno-M-IL1RAP at pH 7.4 and pH 6.

| Variant | Antigen (on Chip) | pH 7.4 | | | pH 6 | | | $K_D$ (7.4) ratio to YIS [1] | $K_D$ (6)/$K_D$ (7.4) [2] | $k_{off}$ (6) ratio to YIS [3] |
|---|---|---|---|---|---|---|---|---|---|---|
| | | $k_{on}$ (1/Ms) | $k_{off}$ (1/s) | $K_D$ (M) | $k_{on}$ (1/Ms) | $k_{off}$ (1/s) | $K_D$ (M) | | | |
| K13/H3 "YIS" | cyno-M-IL1RAP | 2.14E+06 | 3.00E−05 | 1.40E−11 | 2.01E+06 | 6.94E−05 | 3.45E−11 | 1 | 2.5 | 1 |
| K17/H3 "YKS" | cyno-M-IL1RAP | 2.04E+06 | 4.51E−05 | 2.21E−11 | 1.20E+06 | 1.21E−04 | 1.01E−10 | 1.6 | 4.6 | 1.7 |
| K13/H2 "YID" | cyno-M-IL1RAP | 1.89E+06 | 4.62E−05 | 2.44E−11 | 2.16E+06 | 2.15E−04 | 9.93E−11 | 1.7 | 4.1 | 3.0 |
| K17/H2 "YKD" | cyno-M-IL1RAP | 2.00E+06 | 6.80E−05 | 3.39E−11 | 1.98E+06 | 3.24E−04 | 1.64E−10 | 2.4 | 4.8 | 4.7 |
| K13/H3 "YIS" | hu-M-IL1RAP | 1.85E+06 | 3.94E−05 | 2.13E−11 | 2.12E+06 | 1.50E−04 | 7.05E−11 | 1 | 3.3 | 1 |
| K17/H3 "YKS" | hu-M-IL1RAP | 1.71E+06 | 3.87E−05 | 2.26E−11 | 1.90E+06 | 1.82E−04 | 9.62E−11 | 1.1 | 4.3 | 1.2 |
| K13/H2 "YID" | hu-M-IL1RAP | 1.93E+06 | 2.69E−05 | 1.40E−11 | 2.94E+06 | 4.14E−04 | 1.41E−10 | 0.66 | 10.0 | 2.8 |
| K17/H2 "YKD" | hu-M-IL1RAP | 1.90E+06 | 3.51E−05 | 1.85E−11 | 2.98E+06 | 5.60E−04 | 1.88E−10 | 0.86 | 10.0 | 3.8 |

[1] "$K_D$ (7.4) ratio to YIS": ranks affinity at pH 7.4 relative to 11C5-YIS; compares binding of the four 11C5 variants to IL1RAP and the chance to get internalized into the cells for disposition. 11C5-YKD has the weakest affinity to cyno-M-IL1RAP at pH 7.4 relative to h11C5-YIS (which shows the strongest affinity).
[2] "$K_D$ (6)/$K_D$ (7.4)": compares the affinity of each variant at pH 6 versus at pH 7.4 for either hu-M-IL1RAP or cyno-M-IL1RAP. All four variants show weaker affinity at pH 6 than at pH 7.4 (for both antigens), with 11C5-YKD showing the greatest change in affinity at pH 6.
[3] "koff (6) ratio to YIS": ranks the off-rates of the four 11C5 variants at pH 6 relative to 11C5-YIS. 11C5-YKD has the fastest off-rate ("koff") at pH 6, while 11C5-YIS has the slowest off-rate at pH 6 (for both hu-M-IL1RAP and cyno-M-IL1RAP). The faster off-rate of 11C5-YKD at pH 6 (i.e., the largest value for "koff (6) ratio to YIS").

The faster off-rate of the h11C5 variant YKD at pH 6 (i.e., the largest value for "$k_{off}$(6) ratio to YIS") suggests that this variant likely will have the best chance of escaping target-mediated drug disposition (TMDD). If the h11C5-IL1RAP complex is internalized and processed in the endosome, the YKD variant would dissociate from IL1RAP the fastest relative to the other h11C5 variants. FcRn could then bind free h11C5 and deliver it to the cell surface, allowing the drug to be released back into circulation. Therefore, h11C5 variant YKD may benefit the most from additional mutations in the Fc region that increase the affinity for FcRn at acidic pH but not at neutral pH.

Example 11

Generation of h11C5 Variants with YTE Mutation

This example illustrates the methods to generate h11C5 variants that facilitate binding of the IgG Fc fragment to FcRn with higher affinity at low pH and the methods to further characterize the variants.

Materials and Methods

Generation of Antibodies with YTE Mutations: The YTE triple mutation M252Y/S254T/T256E (numbered by Eu index, YTE) that is known to increase the affinity of the Fc fragment to FcRn (see e.g., Dall'Acqua et al., *J Immunol* 169(9): 5171-5180 (2002)) was introduced by gene synthesis into the Fc portion of h11C5 variants described in Examples 9 and 10, YKD and YIS, to generate YKD/YTE and YIS/YTE. The recombinant antibodies YKD/YTE and YIS/YTE were generated as described in Example 5.

BIACORE SPR Analysis of 11C5 IgG Variants with YTE Substitutions: BIACORE™ SPR binding analysis of variant h11C5 antibodies, YIS, YIS/YTE, YKD, and YKD/YTE to hu-M-IL1RAP and cyno-M-IL1RAP at pH 7.4 and 37° C. was performed as described in Example 10.

Assay of FcRn binding at pH 6.0 and 7.4: To determine the binding affinity of YKD and YKD/YTE to human FcRn and cyno FcRn, SPR measurement with a BIACORE™ 8K instrument was performed. Briefly, a Series S sensor chip CAP was used to capture biotinylated human FcRn or cyno FcRn for binding measurement. 1:4 dilution of Biotin CAPture Reagent (GE Healthcare, catalogue number 28-9202-34) into HBS-EP buffer (0.01 M HEPES pH 7.4, 0.15 M NaCl, 3 mM EDTA, 0.005% Surfactant P20) was applied to the chip at 2 μL/min flow rate. 10 nM biotinylated human FcRn (Acro biosystems, catalogue number FCN-H52W7) or cyno FcRn (Acro biosystems, catalogue number FCM-05284) was captured at 10 μL/min to achieve approximately 50 response units in the second flow cell (FC2). The first flow cell (FC1) was kept as a reference. Next, 3-fold serial dilutions of YKD or YKD/YTE IgG in MES buffer (10 mM MES pH 6.0, 150 mM NaCl, 0.005% surfactant P20) or HBS-P buffer (0.01 M HEPES pH 7.4, 0.15 M NaCl, 0.005% surfactant P20) from low (1.37 nM) to high (1000 nM) concentration were injected at a flow rate of 30 μL/min at 25° C. The sensorgrams were recorded and subject to reference and buffer subtraction before evaluating by BIACORE® 8K Evaluation Software (version 1.1.1.7442).

Baculovirus (BV) ELISA to Determine Non-Specific Binding of h11C5 Variants with YTE mutations: Non-specific binding of YIS/YTE and YKD/YTE was assessed by BV ELISA as described in Example 6, except with plates blocked with 1% BSA in PBS (no 0.05% Tween-20).

Results

Generation of antibodies with YTE mutations: The Fc fragment with YTE substitutions was generated and its amino acid sequence is listed in Table 2 and provided in the accompanying Sequence Listing as SEQ ID NO: 327.

BIACORE SPR analysis of h11C5 variants with YTE mutations: The binding results, comparing YKD/YTE and YIS/YTE to their parental molecules YKD and YIS, respectively, are summarized in Table 18.

TABLE 18

BIACORE SPR kinetics of h11C5 YTE variants binding hu-M-IL1RAP and cyno-M-IL1RAP.

| h11C5 Variant (Analyte) | Antigen (on chip) | pH 7.4, 37° C. | | | $K_D$ YTE/ $K_D$ Parental |
|---|---|---|---|---|---|
| | | $k_{on}$ (1/Ms) | $k_{off}$ (1/s) | $K_D$ (M) | |
| YKD | hu-M-IL1RAP | 2.03E+06 | 6.15E−05 | 3.04E−11 | — |
| YKD/YTE | hu-M-IL1RAP | 2.02E+06 | 5.12E−05 | 2.54E−11 | 0.84 |
| YIS | hu-M-IL1RAP | 2.55E+06 | 3.33E−05 | 1.30E−11 | — |
| YIS/YTE | hu-M-IL1RAP | 3.42E+06 | 4.43E−05 | 1.30E−11 | 0.99 |
| YKD | cyno-M-IL1RAP | 2.41E+06 | 5.39E−05 | 2.23E−11 | — |
| YKD/YTE | cyno-M-IL1RAP | 2.24E+06 | 4.90E−05 | 2.19E−11 | 0.98 |
| YIS | cyno-M-IL1RAP | 2.87E+06 | 3.34E−05 | 1.16E−11 | — |
| YIS/YTE | cyno-M-IL1RAP | 3.85E+06 | 3.07E−05 | 7.98E−12 | 0.69 |

$K_D$ is the apparent affinity measured (given that IgG is the analyte in this experimental format), and $k_{off}$ is the off-rate. The affinities of YKD/YTE and YIS/YTE for either hu-M-IL1RAP or cyno-M-IL1RAP are not significantly different than the affinities of their respective parental molecules as shown by the ratio of their $K_D$ values ("$K_D$ YTE/$K_D$ Parental") which are within 2-fold. Therefore, it is concluded that the addition of the YTE substitutions does not affect binding to IL1RAP.

Assay of FcRn Binding at pH 6.0 and 7.4: SPR measurement was used to determine the binding affinity of YKD and YKD/YTE to hu-FcRn and cyno-FcRn at pH values of 6.0 and 7.4. The equilibrium dissociation constant ($K_D$) value was calculated using steady state analysis to compare human FcRn and cyno FcRn binding between YKD and YKD/YTE at pH 6.0 and pH 7.4. As shown in Table 19, the results indicate that YKD/YTE clearly improves human FcRn and cyno FcRn binding at pH 6.0 but not at pH 7.4.

TABLE 19

Measured $K_D$ values for binding to human and cyno FcRn at pH 6.0 and 7.4

| h11C5 Variant | Binding at pH 6.0 | | Binding at pH7.4 | |
|---|---|---|---|---|
| | human FcRn $K_D$ (nM) | cyno FcRn $K_D$ (nM) | human FcRn $K_D$ (nM) | cyno FcRn $K_D$ (nM) |
| YKD | 558 | 45.6 | >1000 | >1000 |
| YKD/YTE | 130 | 21.4 | >1000 | >1000 |

Baculovirus (BV) ELISA to determine non-specific binding of h11C5 YTE variants: As shown in Table 20, neither YIS/YTE nor YKD/YTE antibodies showed detectable BV ELISA absorbance signal at 450 nm above the medium-control antibody sample. Therefore, the introduction of YTE mutations has not introduced non-specific binding to BV particles.

TABLE 20

BV ELISA assay of non-specific binding

| Antibody Concentration (nM) | Absorbance @ 450 nm | | | |
|---|---|---|---|---|
| | 11C5-YKD/YTE | 11C5-YIS/YTE | 11C5-YKD | Medium Control |
| 300 | 0.123 | 0.194 | 0.110 | 0.561 |
| 100 | 0.095 | 0.112 | 0.102 | 0.269 |
| 33 | 0.088 | 0.091 | 0.088 | 0.168 |
| 0 | 0.084 | 0.086 | 0.116 | 0.097 |

Example 12

Cell-Based Assays of Blocking Activity of Anti-Human IL1RAP Antibodies with YTE Mutations This example illustrates functional inhibition of the IL-1, IL-33 and IL-36 pathways in HEK-Blue reporter and primary cell-based assays using variant anti-human IL1RAP antibodies containing the YTE mutations described in Example 11.

Materials and Methods

Cell Lines and HEK-Blue Reporter Cell Assay: Cell lines and HEK-Blue reporter assays were carried out as described in Examples 2 and 4.

Primary Human NK Cells and Associated Assays: Primary human NK cells and associated assays, including agonist dose response and antibody blocking assays, have been previously described and discussed in Example 7. Antibody blocking assays in this example were performed in the same manner, with the exception of the blocking antibodies used, namely YKD/YTE and YKD (described in Example 11). Negative and positive controls have been described in Example 7. The percent inhibition was calculated by deducting the value obtained with the negative control from the value obtained using the indicated antibody concentration. The negative control-adjusted value was then used to determine the ratio in relation to the positive control. If the negative control value could not be interpolated (e.g., below the threshold of detection), the percent inhibition is reflective of the ratio of the value obtained using the indicated antibody concentration, in relation to the positive control only. The human cytokines IL-33 and IL-12 were obtained commercially (Peprotech).

Primary Human Lung Fibroblasts and Associated Assays: the primary human lung fibroblasts (PHLFs) used and associated assays were as described in Example 7. The positive control represents PHLFs in the presence of agonist only (IL-1α or IL-36β). Antibody blocking assays were performed at an agonist concentration near or greater than $EC_{55}$. The negative control represents PHLFs that have not been exposed to an agonist or antibody. The percent inhibition was calculated as described above for the primary human NK cell assays. Human IL-36β, processed to produce a fully mature cytokine, was generated in-house. Human IL-1α was obtained commercially (Gibco).

Primary Human Monocytes and Associated Assays: Monocyte assays were carried out as described in Example 7 with the following exceptions: monocytes were seeded in 96-well plates and given a 3 hour recovery time (37° C. with 5% $CO_2$) prior to experimental use.

Human Epidermal Keratinocytes and Associated Assays: Human Epidermal Keratinocytes (HEKn pooled), isolated from multiple neonatal foreskins were obtained from Thermo Fisher Scientific (catalog number 13401). HEKn cells were thawed and subcultured according to general manufacturer guidelines and maintained in EpiLife® Medium (catalog number M-EPI-500-CA) supplemented with 1% human keratinocyte growth supplement (HKGS) (catalog number S-001-5) and 1× Penicillin-Streptomycin Solution (Corning, catalog number 30-002-CI). For antibody blocking assays, HEKn cells were thawed and cultured until they reached 80% confluency. The cells were then plated at 10,000/well on a flat-bottom, 96-well plates and incubated overnight (roughly 18 hours) at 37° C., with 5% $CO_2$. Following overnight incubation, the HEKn cells were exposed to a solution of 11C5-YKD, 11C5-YKD/YTE, or an appropriate antibody isotype control (IgG Ctrl), and incubated for 1 hour at 37° C. with 5% $CO_2$, followed by the addition of agonist (IL-36β at $EC_{60}$). The positive control condition (PC) included cells, growth medium, and the agonist (IL-36β). The negative control condition (NC) included cells and growth medium only. Tissue culture supernatant was collected twenty-four hours after agonist addition and stored at −80° C. until ELISAs were performed to determine the level of IL-8. A human IL-8 ELISA kit (Invitrogen/Thermo Fisher Scientific) was used to quantify the level of IL-8 in the supernatant, per manufacturer's recommendations. Prior to antibody blocking assays, an agonist and antagonist dose-response curve was generated to determine the $EC_{50}$ and $IC_{50}$ (respectively) as described in Example 5.

Basophil cell assay: The following protocol is modified from the assay method described in PCT Publ. No. WO2016077381A1, which is hereby incorporated by reference herein. PBMCs were isolated from peripheral whole blood collected in sodium heparin (Stemcell Tech). Blood was diluted 1:1 with PBS. 30 mL diluted blood was layered over 15 mL Ficoll Paque Premium (GE Healthcare 17-5442-03), and samples were spun at 400 g for 20 min at 20° C. with no brake. The PBMC-containing layer was transferred to a 50 mL tube and washed twice with 50 mL PBS. The washed PBMCs were resuspended in PBS, diluted to 20 million cells/mL, and plated at 1 million cells (50 µL) per well of a v-bottom 96 well plate. 25 µL of serially diluted antibody solution at 4× final concentration in PBS was added to the wells, and the plate was incubated at 37° C. with 5% $CO_2$. After 60 minutes, 25 µL of IL-33 (Peprotech 200-33) at 4× final concentration in PBS was added to the wells (100 µL final volume). Cells were incubated for 20 minutes at 37° C. with 5% $CO_2$, followed by the addition of 100 µL pre-warmed Phosflow Fix Buffer I (BD 557870). The plate was incubated at 37° C. with 5% $CO_2$ for 10 minutes then centrifuged at 500 g for 5 minutes. The supernatant was discarded and the cells were resuspended in FACS buffer (PBS+0.5% BSA+0.05% sodium azide). The plate was centrifuged at 500 g for 5 minutes and the supernatant was discarded. The cell pellets were resuspended in the residual volume by briefly vortexing the plate, and 100 µL of ice-cold Phosflow Perm Buffer II (BD 558052) was slowly added to each well. The plate was stored in Perm Buffer II overnight at −20° C. The following day, the plate was spun at 500 g for 5 minutes and the cells were washed twice with FACS buffer. The cells were stained with the following antibodies in 50 µL FACS buffer for 1 h at room temperature: anti-CD123 FITC (Ebiosciences 11-1239-42, diluted 1:10), anti-phospho-p38 PE (Cell Signaling Technology 6908S, diluted 1:50), anti-HLA-DR BV421 (Biolegend 307636, diluted 1:20), and anti-CD203c APC (Biolegend 324610 1:200). In some wells an isotype control (Cell Signaling Technology 4752S) was substituted for the anti-phospho-p38 PE antibody to facilitate the gating of the phospho-p38 positively stained population. The cells were washed twice with FACS buffer, resuspended in FACS buffer and read on a CytoFLEX flow cytometer (Beckman Coulter). Compensation controls were prepared using Ultracomp beads (ThermoFisher 01-2222-41) and run alongside the cells. Phospho-p38 staining was analyzed in CD123+ HLADR− basophils using Flowjo software (BD). CD203c staining was used to validate the identity of basophils gated based on CD123+ HLADR−. The % phospho-p38-positive data from CD123+ HLADR− basophils was analyzed using GraphPad Prism 7 software to determine the antibody $IC_{50}$ value in the assay. Agonist dose responses were run alongside antibody dose responses. Cells incubated with the antibody dose responses were stimulated with agonist at the estimated $EC_{50}$ based on prior experiments. Positive controls were treated with the agonist at the estimated $EC_{50}$ and were treated with PBS in place of antibody solution. Negative controls were treated with PBS in place of both antibody and agonist solution. Data are plotted as mean±SD, 2 replicates per concentration.

CD4 T cell assay: The following protocol is based on the method described in Komai-Koma et al., *Immunobiology*, 221(3):412-417 (2016). Flat-bottom 96 well plates were coated overnight at 4° C. with 100 µL of 3 µg/mL anti-CD3 antibody (Invitrogen 16-0037-85). PBMCs were isolated from peripheral whole blood collected in sodium heparin (Stemcell Tech) as described above. CD4+ T cells were isolated from PBMCs using negative selection (Miltenyi Biotec 130-096-533), according to the manufacturer's instructions. Following isolation, the cells were resuspended in T cell medium (RPM1-1640, 5% heat-inactivated human A/B serum, 100 U/mL penicillin, 100 µg/mL streptomycin, 1×MEM non-essential amino acids, 1 mM sodium pyruvate) at 500,000 cells/mL. The anti-CD3 coated plates were washed once with PBS, and 50,000 CD4+ cells (100 µL) were added per well. Antibodies were serially diluted at 4× final concentration in T cell medium, and 50 µL antibody solution was added to each well. The plates were incubated at 37° C. with 5% $CO_2$. After one hour, 50 µL T cell medium containing IL-33 (Peprotech 200-33) and IL-12 (Peprotech 200-12) at 4× final concentration were added to each well (200 µL total, 10 ng/mL final concentration IL-12), and the plates were returned to the incubator. After 72 hours, IFN-γ levels in the T cell supernatant were measured using a conventional IFN-γ ELISA kit (Invitrogen 88-7316-88). The data were interpolated and analyzed using GraphPad Prism 7 software to determine the antibody $IC_{50}$ value in the assay. Agonist dose responses were run alongside antibody dose responses. Cells incubated with the antibody dose responses were stimulated with agonist at the estimated $EC_{50}$ based on prior experiments. Positive controls were treated with the agonist at the estimated $EC_{50}$ and T cell medium in place of antibody solution. Negative controls were treated with T cell medium in place of antibody and IL-33, while the IL-12 final concentration remained 10 ng/mL. Percent inhibition was calculated as the reduction in response at peak antibody concentration divided by the total response magnitude: % inhibition=100%*(positive control−antibody treated)/(positive control−negative control). Data are plotted as mean±SEM, three replicates per antibody concentration.

Results

Figure 6A:
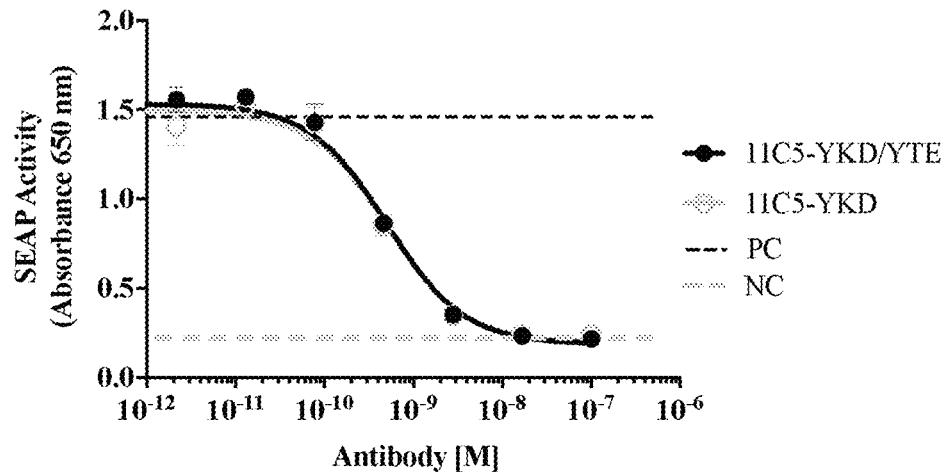
FIGS. 6A, 6B, and 6C depict plots of HEK-Blue intracellular signaling inhibition assay results for the h11C5 variant, YKD/YTE (or "11C5-YKD/YTE") in comparison to h11C5 variant YKD (or "11C5-YKD") as described in Example 12.
Figure 6B:
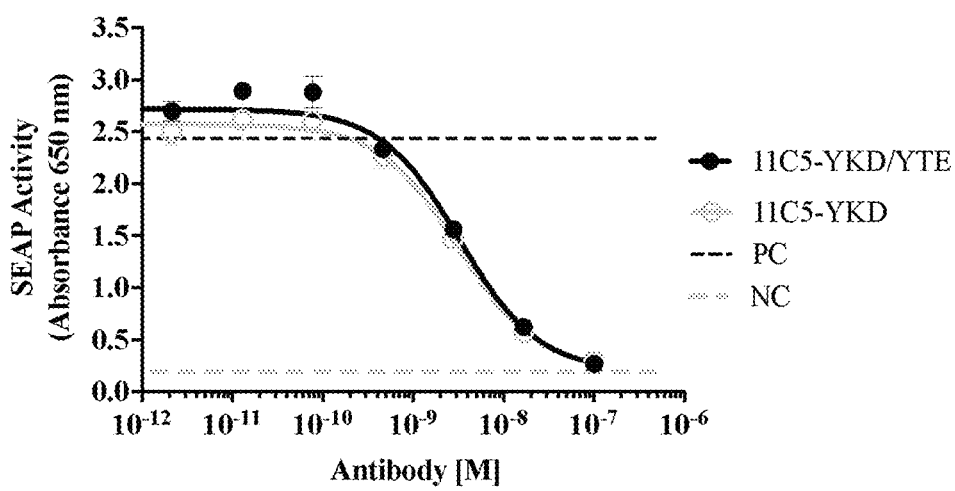
Figure 6C:
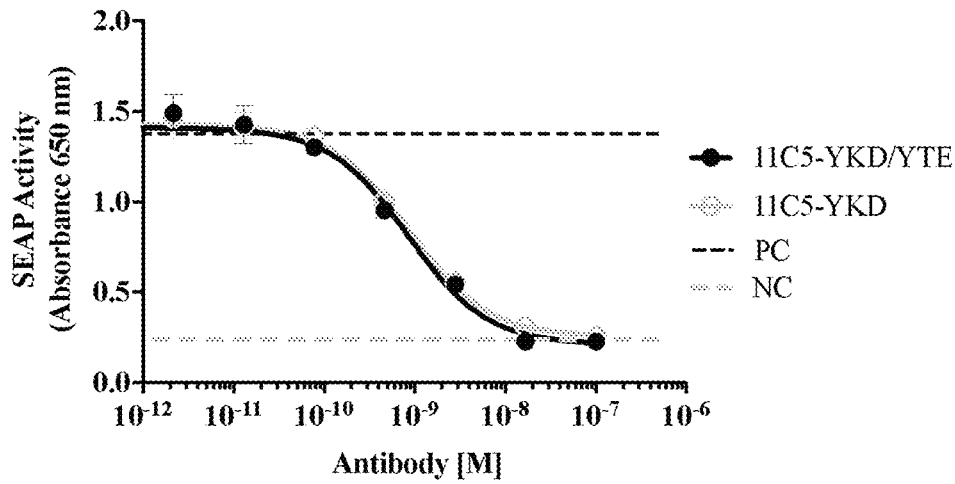

Functional Inhibition of IL-1, IL-33 and IL-36 pathways in the HEK-Blue Assay: To confirm that the blocking potency and efficacy of the h11C5 variant YKD was unaltered by the addition of the YTE mutations, a comparison of functional inhibition by YKD and YKD/YTE in the HEK-Blue IL-1/IL-33/IL-36 blocking assays was carried out as described in Examples 2 and 4. As shown in FIGS. 6A, 6B, and 6C, YKD ("11C5-YKD") and YKD/YTE ("11C5-YKD/YTE") showed similar blocking activity in IL-1β, IL-33, and IL-36β stimulated cells. With IL1β stimulated cells, YKD and YKD/YTE have identical potency ($IC_{50}$=0.51 nM) and near complete inhibition at 100 nM, 97% and 98%, respectively. For IL-33 stimulated HEK-Blue cells, both YKD and YKD/YTE exhibited a potency around 3 nM (11C5-YKD $IC_{50}$=3.15 nM; 11C5-YKD/YTE $IC_{50}$=3.3 nM), with near complete inhibition at 100 nM (95% and 97% inhibition for YKD and YKD/YTE, respectively.) Finally, when HEK-Blue cells were stimulated with IL-36β, both molecules inhibited at a potency of 0.9 nM ($IC_{50}$) with 98% or greater inhibition at 100 nM. In summary, the humanized variant anti-hu-IL1RAP antibodies YKD and YKD/YTE exhibited comparable potency and near complete blocking of SEAP production in HEK-Blue IL-1, IL-33 and IL-36 assays.

YKD/YTE and YKD Inhibit IL-1, IL-33 and IL-36 Activation in Primary Cells: As discussed in Example 7, the HEK-Blue reporter cell lines can provide a fast assay to determine blocking activity of 11C5 variants following activation of the IL-1, IL-33 and IL-36 pathways. Further characterization of the blocking activity of h11C5 variants was carried out in assays with more physiological relevance using primary human cell based experiments. In addition to the primary cell assays described in Example 7, the present example includes functional inhibition assays utilizing human epidermal keratinocytes (HEKn), basophils and CD4 T-cells.

Figure 7:
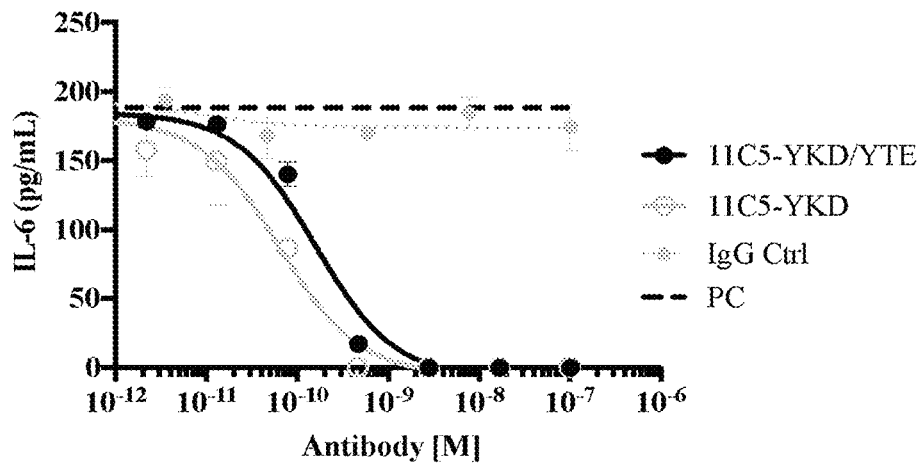
FIG. 7 depicts plots of assays of the blocking efficacy of the h11C5 variant antibody, YKD/YTE (or "11C5-YKD/YTE") in comparison to YKD (or "11C5-YKD"), or an isotype control (IgG Ctrl) in monocytes stimulated with IL-1β, at an agonist concentration greater than $EC_{55}$ (as described in Example 12). The error bars shown are representative of the standard deviation from duplicate samples. The positive control (PC) is represented by a black, dashed line, while the negative control (NC) is represented by a grey, dashed line.
Figure 8:
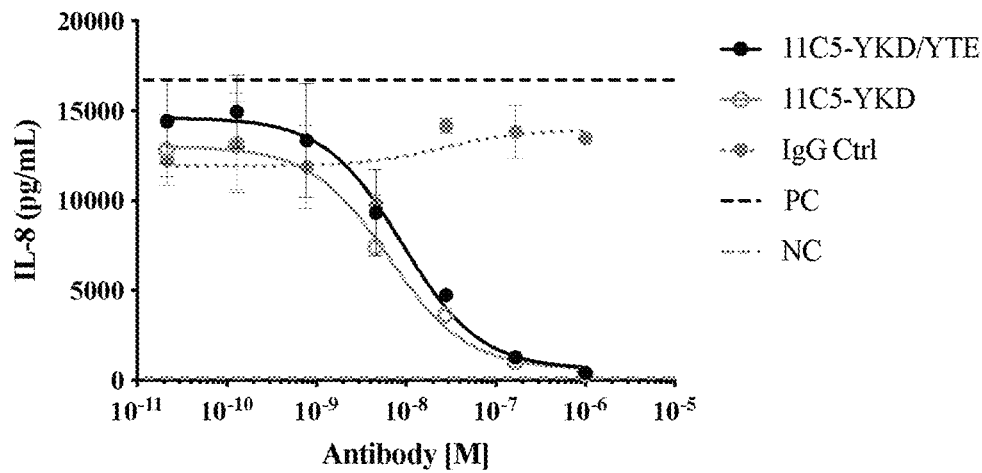
FIG. 8 depicts plots of assays of the blocking efficacy of h11C5 variant YKD/YTE (or "11C5-YKD/YTE") in comparison to variant YKD (or "11C5-YKD"), or an isotype control (IgG Ctrl) in PHLF cells stimulated with IL-1α at an agonist concentration near or greater than $EC_{55}$ (as described in Example 12). The error bars shown are representative of the standard deviation from duplicate samples. The positive control (PC) is represented by a black, dashed line, while the negative control (NC) is represented by a grey, dashed line.

Assays in human monocytes (PHMOs) and PHLFs were utilized to confirm that YKD and YKD/YTE have comparable potency and efficacy in blocking the IL-1 pathway in primary human cells. As shown in FIG. 7, when primary human monocytes (PHMOs) were stimulated with IL-1β in the presence of YKD or YKD/YTE, complete inhibition of IL-6 production was observed. Both antibodies demonstrated similar potency ($IC_{50}$=63 pM and 158 pM, for YKD and YKD/YTE, respectively). PHLFs were stimulated with IL-1α ($EC_{55}$), in the presence of YKD/YTE, YKD, or an isotype control. As shown by the plots in FIG. 8, the presence of either h11C5 antibody variant resulted in near complete inhibition of IL-8 production (98% and 99% for YKD/YTE and YKD, respectively) in IL-1α stimulated PHLFs, with similar $IC_{50}$ values observed for the two antibodies ($IC_{50}$=6.47 nM and 9.10 nM for YKD/YTE and YKD, respectively.) In summary, the assay results demonstrate that YKD/YTE and YKD exhibit comparable efficacy and potency, including complete inhibition of IL-6 production in IL-1β stimulated PHMOs and complete blockade of IL-8 production in IL-1α stimulated PHLFs.

Figure 9:
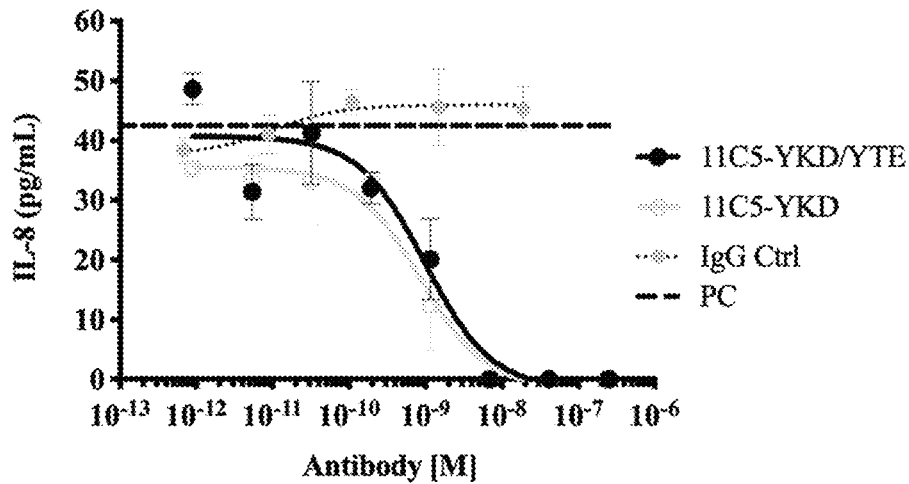
FIG. 9 depicts plots of assays of the blocking efficacy of the h11C5 variant antibody, YKD/YTE (or "11C5-YKD/YTE") in comparison to YKD (or "11C5-YKD"), or an isotype control (IgG Ctrl) in HEKn cells stimulated with IL-36β at an agonist concentration greater than $EC_{55}$ (as described in Example 12). The error bars shown are representative of the standard deviation from duplicate samples. The positive control (PC) is represented by a black, dashed line.
Figure 10:
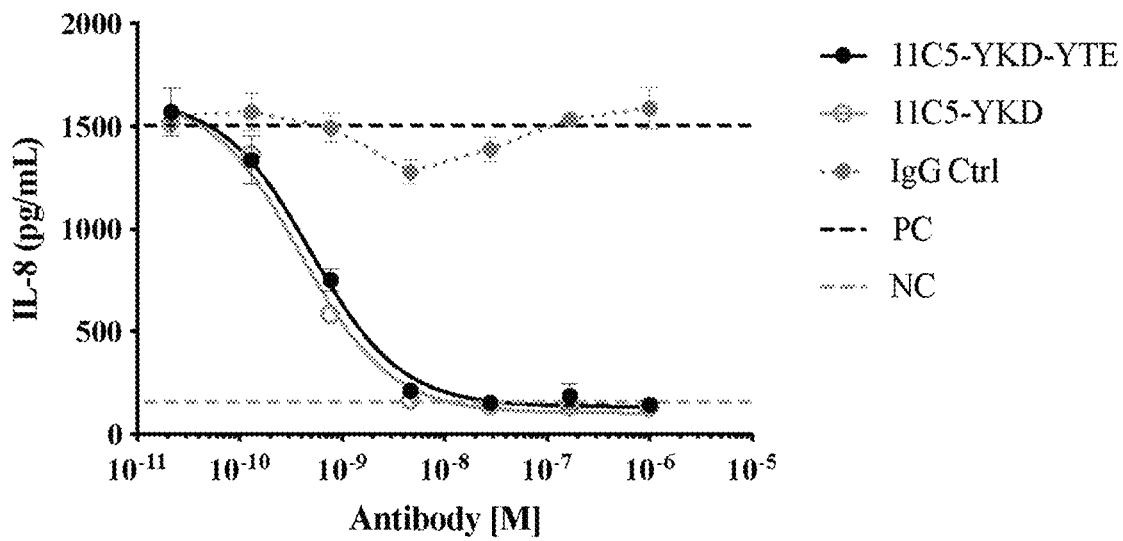
FIG. 10 depicts plots of assays of the blocking efficacy of the h11C5 variant antibody, YKD/YTE (or "11C5-YKD/YTE") in comparison to YKD (or "11C5-YKD"), or an isotype control (IgG Ctrl) in PHLF cells stimulated with IL-36β at an agonist concentration near or greater than $EC_{55}$ (as described in Example 12). The error bars shown are representative of the standard deviation from duplicate samples. The positive control (PC) is represented by a black, dashed line, while the negative control (NC) is represented by a grey, dashed line.

Assays in HEKn cells and PHLFs were used to verify that YKD/YTE and YKD exhibited comparable potency and efficacy in blocking the IL-36 pathway. The IL-36 receptor, and its receptor accessory protein (IL1RAP), are known to be expressed on human keratinocytes (see e.g., Ding et al., Oncotarget, 9(2) 2895-2901 (2017)). HEKn cells stimulated with IL-36β produce IL-8, which can be detected in the supernatant via a standard ELISA. To determine whether YKD/YTE and YKD can block IL-8 production in IL-36β stimulated HEKn cells, HEKn cells were incubated with serial dilutions of either YKD/YTE, YKD, or an isotype control (IgG ctrl). As shown in FIG. 9, both YKD and YKD/YTE demonstrated complete inhibition (100%) of IL-8 production. Both variants exhibited similar potency, with $IC_{50}$ values of 1.39 nM and 1.16 nM for YKD and YKD/YTE, respectively. As shown in FIG. 10, when YKD/YTE and YKD were tested for their ability to block IL-8 production in IL-36β stimulated PHLFs, both exhibited complete inhibition of IL-8 production. Moreover, both antibody variants had similar inhibitory potency ($IC_{50}$=0.50 nM and 0.39 nM for YKD/YTE and YKD, respectively). In summary, YKD/YTE and YKD have comparable efficacy and potency in blocking IL-8 production in IL-36β stimulated HEKn cells and IL-36β stimulated PHLFs.

Figure 11:
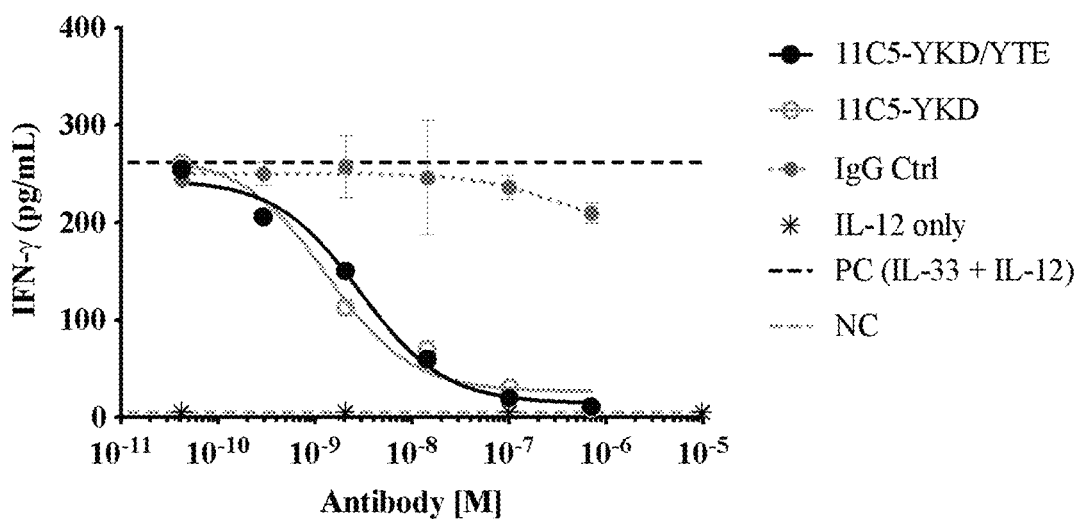
FIG. 11 depicts plots of assays of the blocking efficacy of the h11C5 variant antibody, YKD/YTE (or "11C5-YKD/YTE") in comparison to YKD (or "11C5-YKD"), or an isotype control (IgG Ctrl), in primary human NK cells stimulated with IL-33 in the presence of IL-12 (as described in Example 12). The IL-33 is at an effective concentration equivalent to $EC_{50}$. The error bars shown are representative of the standard deviation from duplicate samples. The positive control (PC) is represented by a black, dashed line, while the negative control (NC) is represented by a grey, dashed line.
Figure 12:
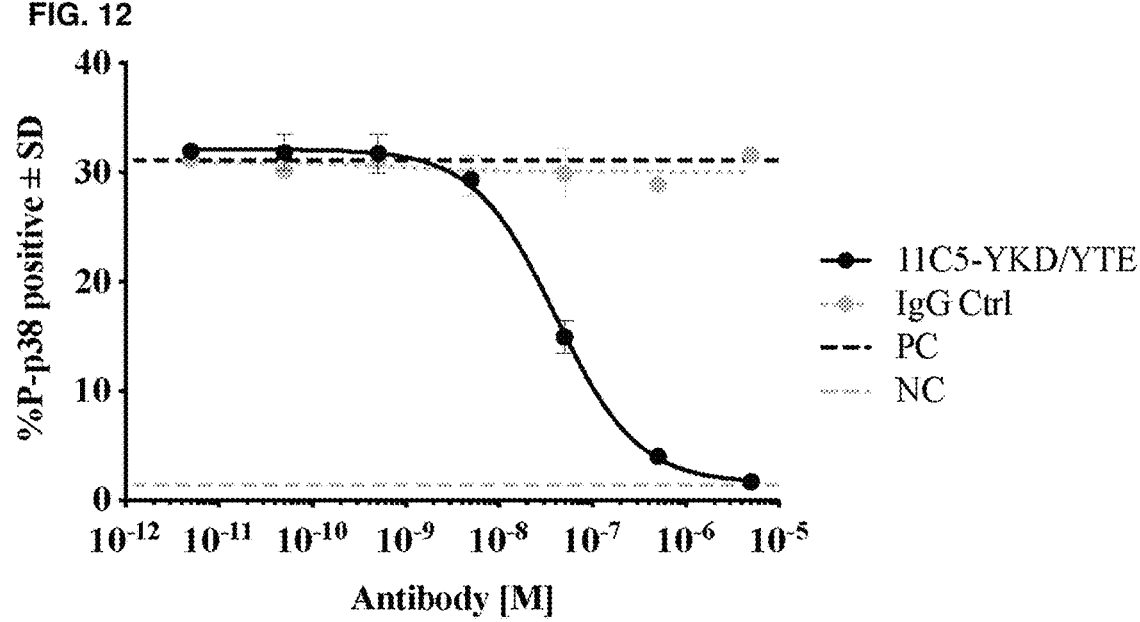
FIG. 12 depicts plots of assays of the blocking efficacy of the h11C5 variant antibody, YKD/YTE (or "11C5-YKD/YTE") or an isotype control (IgG Ctrl) in basophils stimulated with IL-33 at an agonist concentration of $EC_{56}$ (as described in Example 12). The error bars shown are representative of the standard deviation from duplicate samples. The positive control (PC) is represented by a black, dashed line, while the negative control (NC) is represented by a grey, dashed line.
Figure 13:
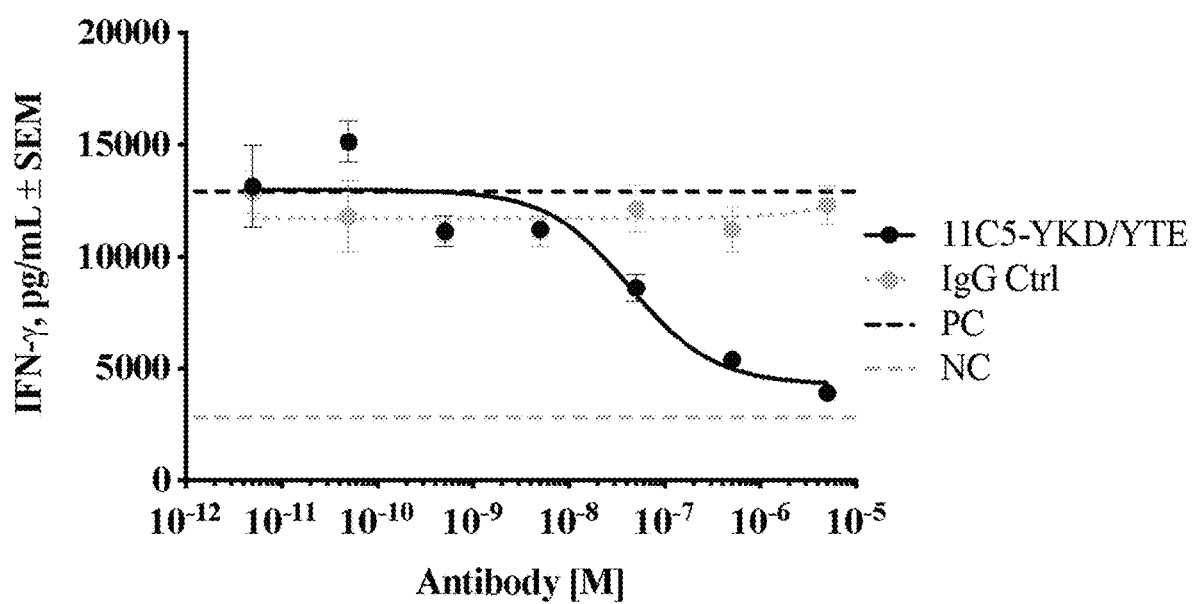
FIG. 13 depicts plots of assays of the blocking efficacy of the h11C5 variant antibody, YKD/YTE (or "11C5-YKD/YTE") or an isotype control (IgG Ctrl) in CD4+ T cells stimulated with IL-33 at an agonist concentration of $EC_{34}$ (as described in Example 12). The error bars shown are representative of the standard error of the mean from triplicate samples. The positive control (PC) is represented by a black, dashed line, while the negative control (NC) is represented by a grey, dashed line.

Assays also confirmed that YKD/YTE could block the IL-33 pathway in primary human NK cells, basophils and CD4+ T cells. As described in Example 7, primary human NK cells stimulated with IL-33 in the presence of IL-12 produce IFN-γ, unlike NK cells exposed to IL-12 only, which fail to produce detectable IFN-γ. As shown in FIG. 11, IFN-γ was detectable in the supernatant of NK cells incubated with the isotype control antibody, but treatment of human NK cells with YKD/YTE or YKD blocked nearly all IFN-γ production (96% and 97% inhibition for YKD/YTE and YKD, respectively). The $IC_{50}$ values observed for the two antibodies were 1.32 nM for YKD/YTE and 2.93 nM for YKD. Basophils have been observed in increased numbers in the lungs of asthmatic patients (see e.g., Schwartz et al., *European Journal of Pharmacology*, 778: 90-95 (2016)). YKD/YTE was tested for its ability to block IL-33 stimulation of basophils. IL-33 stimulation of PBMCs led to the phosphorylation of p38 MAPK in basophils. PBMCs were incubated with YKD/YTE for one hour, followed by 20 minutes of stimulation with IL-33 at the estimated $EC_{50}$. As shown by the results in FIG. 12, YKD/YTE essentially completely blocked p38 phosphorylation in basophils (99% inhibition) with an $IC_{50}$ of 41 nM at agonist $EC_{56}$. To examine YKD/YTE efficacy and potency in CD4+ T cells, CD4+ T cells were co-stimulated with IL-33 and IL-12 and IFN-γ production was assayed. The CD4+ T cells were incubated with YKD/YTE for one hour, followed by stimulation with IL-12 at 10 ng/mL and IL-33 at an estimated $EC_{50}$. As shown in FIG. 13, YKD/YTE nearly completely blocked IFN-γ production (89% inhibition) with an $IC_{50}$ of 44 nM at agonist $EC_{34}$. In summary, YKD/YTE and YKD demonstrated similar blocking potency and efficacy in IL-33 stimulated primary human NK cells. Moreover, YKD/YTE completely blocked IL-33 induced phosphorylation of p38 MAPK in basophils and nearly completely blocked IFN-γ production in IL-33 stimulated CD4+ T cells.

Accordingly, the results of this Example 12 demonstrate that YKD/YTE and YKD blocked IL-1, IL-33 and IL-36 activation in cell lines (HEK-Blue reporter cell lines) and all primary human cell assays described. The results include near or complete blockade of IL-1 activation in PHLFs and PHMOs, IL-33 activation in NK cells, basophils and CD4 T cells, and IL-36 activation in PHLFs and HEKns. Furthermore, YKD/YTE and YKD exhibited comparable efficacy and potency in all functional assays performed.

Example 13

Lack of Cytotoxicity of Anti-Human IL1RAP Antibody Variants

This example illustrates assays of antibody-dependent cellular cytotoxicity (ADCC), complement-dependent cytotoxicity (CDC), and antibody-dependent cellular phagocytosis (ADCP) that demonstrate the lack of cytotoxicity of the anti-human IL1RAP antibodies YKD/YTE, 11C5-N297G, and YKD.

Materials and Methods

Reagents: The antibodies used in the assays were: YKD/YTE (as described in Example 11); YKD (as described in Example 8); 11C5-N297G (the parental 11C5 molecule containing the N297G mutation, as described in Examples 5 and 7); 11C5 wt (the parental 11C5 molecule lacking the N297G mutation and the YKD mutations that increase affinity); an isotype control hIgG1(N297G); and the anti-CD20 antibody, Rituximab (Genentech, South San Francisco, CA) as a positive control antibody known to have cytotoxic activity. The following cell lines were utilized: Jurkat, Daudi and THP-1 (ATCC, Manassas, Virginia). PBMCs, primary human neutrophils, and primary human monocytes were obtained from Stemcell Technologies. The Jurkat cell line was used as control due to its significant IL1RAP expression. The Daudi cell line, which expresses CD20, was used as an additional positive control and functioned as a target cell line for the anti-CD20 antibody, Rituximab.

ADCC Assay: To determine whether YKD/YTE and related molecules displayed ADCC activity, NK cells were used as effector cells for the target cells consisting of monocytes, neutrophils or Jurkat cells. An effector:target (E:T) ratio of 8:1 was applied for the assay. The target cells were labeled with CellTrace Violet staining (Invitrogen). After labeling, the target cells ($1\times10^4$ cells per well in 96-well plates) were mixed with the indicated antibodies at four different concentrations and then further mixed with NK cells ($8\times10^4$ cells per well in 96-well plates) in RPMI complete medium. The reaction proceeded for 5 hours at 37° C. After incubation, cells were washed once with PBS and then stained with Propidium Iodide (PI) (Life Technologies) for 15 minutes. Cells were then analyzed using a CytoFLEX flow cytometer (Beckman Coulter) and Flowjo software (BD). Cell death was calculated based on the percentage of PI stained cells within the CellTrace Violet stained live target cell population.

CDC Assay: To determine whether YKD/YTE and related molecules displayed CDC activity, normal human serum from Quidel (catalogue number A113, San Diego, Calif.) was used as cytotoxicity effector, and 20% of the serum was applied to the assay medium. The target cells (human monocytes, neutrophils and Jurkat cells) were labeled with CellTrace Violet staining. After labeling, the target cells ($5\times10^4$ cells per well, 96-well plates) were mixed with the indicated antibodies at four different concentrations and then further mixed with normal human serum (final concentration of 20%) in AIM-V Medium CTS™ (catalogue number 0870112-DK, Life Technologies). The reactions were incubated at 37° C. for 1 hour. After incubation, cells were washed once with PBS and then stained with PI for 15 minutes. As previously described for the ADCC assay, the cell samples were analyzed using flow cytometry and the percent of cell death (cytotoxicity) was determined.

ADCP Assay: To ascertain whether ADCP activity was present for YKD/YTE and related molecules, human THP-1 derived macrophage cells were used as effector cells, with target cells consisting of human monocytes, neutrophils, Jurkat or Daudi cells. THP-1 cells were treated with phorbol myristate acetate (PMA) (Sigma Aldrich) for two days and then further stimulated with IFN-γ (50 ng/ml) and lipopolysaccharide (LPS) (Sigma Aldrich). The E:T ratio for the ADCP reaction was 2:1. The target cells (human monocytes, neutrophils, Jurkat or Daudi cells) were labeled with CellTrace Violet staining and THP-1 cells were labeled with PKH26 labeling kit (catalogue number PKH26PCL-1 KT, Sigma). After labeling, the target cells ($5\times10^4$ cells per well in 96-well plates) were combined with the indicated antibodies at four different concentrations and then further mixed with THP-1 derived macrophage cells ($1\times10^5$ cells per well in 96-well plates) in RPMI complete medium. The reactions were incubated at 37° C. for 5 hours. After incubation, cells were analyzed by flow cytometry for fluorescence of CellTrace Violet (PB450 channel to identify the target cells) and PKH26 fluorescence (PE channel to identify the THP-1 derived macrophage effector cells). Cell phagocytosis is indicated by the cells that are dually fluorescent, i.e., fluorescence observed in both the PB450 and PE channels. The phagocytosis rate is calculated as the number of cells with dual fluorescence over the labeled target cells.

Results

IL1RAP is expressed in human blood cells such as neutrophils and monocytes, therefore determining the extent to which an anti-IL1RAP antibody, such as YKD/YTE, exhibits ADCC, CDC, or ADCP activity, each of which can cause cytotoxicity in vivo, is important for further clinical development. Assays to determine the extent of ADCC, CDC, or ADCP activity for YKD/YTE were performed as described above. As summarized in Table 21 (below), the anti-IL1RAP antibodies, 11C5-N297G, YKD, YKD/YTE showed no cytotoxic activities in the assays. ("+" indicates positive cytotoxicity and "–" indicates no cytotoxicity).

TABLE 21

| | ADCC, CDC, or ADCP cytotoxicity activity results | | | | | | | | | | | |
|---|---|---|---|---|---|---|---|---|---|---|---|---|
| | Target Cells and Antibodies Tested | | | | | | | | | | | |
| | Jurkat | | | | Neutrophil | | | | Monocyte | | | |
| Assay | 11C5 wt | 11C5-N297G | YKD | YKD/YTE | 11C5 wt | 11C5-N297G | YKD | YKD/YTE | 11C5 wt | 11C5-N297G | YKD | YKD/YTE |
| CDC | – | – | – | – | – | – | – | – | – | – | – | – |
| ADCC | + | – | – | – | – | – | – | – | – | – | – | – |
| ADCP | – | – | – | – | – | – | – | – | – | – | – | – |

As shown by the results in Table 21, YKD/YTE, 11C5-N297G, and YKD did not exhibit cytotoxic effects on human monocytes and neutrophils, or Jurkat cells. The parental molecule 11C5 wt, which lacks the N297G mutation that abolishes effector function, did not exhibit cytotoxicity as measured by the CDC or ADCP assay, but did exhibit some weak activity in the ADCC assay. In the three assays, the positive control antibody Rituximab displayed the expected level of cytotoxic activity (data not shown). In summary, the anti-IL1RAP antibodies YKD/YTE, 11C5-N297G, and YKD did not exhibit cytotoxic activity as determined by assays evaluating ADCC, CDC and ADCP activity.

Example 14

Pharmacokinetics of Variant Anti-Human IL1RAP Antibodies

This example illustrates studies performed in cynomolgus monkeys to characterize the pharmacokinetics (PK) of YKD and YKD/YTE, a variant of YKD with alterations in the Fc region which improve binding affinity to FcRn. Studies 1 and 2 examined the PK of YKD at single intravenous (IV) doses ranging from 1-40 mg/kg in order to characterize the PK of the antibody over a broad dose range and quantify potential target mediated clearance mechanisms. Study 3 examined the PK of the variant YKD/YTE at single intravenous IV doses ranging from 3-40 mg/kg in cynomolgus monkeys in order to determine the impact of the YTE mutations on YKD pharmacokinetics.

Materials and Methods

Study Design and Pharmacokinetic Sampling Schedule: Two studies (1 and 2) were conducted to examine the PK of YKD in cynomolgus monkeys. An additional study 3 was conducted to examine the PK of YKD/YTE. All studies utilized IV dosing. Test articles were formulated in 200 mM arginine succinate at pH 5.5. Blood was collected via the cephalic vein of each animal at the following timepoints: pre-dose, 10 min, 2 h, 8 h, and on day 1, 2, 4, 7, 10, 14, 17, 21, 24, 28. PK samples were processed to serum. A summary of the study designs is shown in Table 22 (below).

TABLE 22

Summary of experimental design of PK studies 1, 2 and 3.

| Study | Number of Animals[1] | Anti-IL1RAP Antibody | Dose Route | Dose Level (mg/kg) | Dose Concentration (mg/mL) | Dose Volume (mL/kg) |
|---|---|---|---|---|---|---|
| 1 | 1M/1F | YKD | IV | 20 | 10 | 2 |
| 2 | 1M/1F | YKD | IV | 1 | 10 | 0.3 |
|   | 1M/1F |     | IV | 3 | 10 | 0.75 |
|   | 1M/1F |     | IV | 10 | 10 | 2 |
|   | 1F    |     | IV | 40 | 10 | 8 |
| 3 | 2M/2F | YKD/YTE | IV | 40 | 20 | 2 |
|   | 2M/2F |     | IV | 10 | 20 | 0.5 |
|   | 2M/2F |     | IV | 3 | 20 | 0.15 |

[1]Males and females are indicated by M and F, respectively.

Bioanalytical Assays for Measuring Drug Concentrations: The concentration of IL1RAP specific antibodies in monkey serum was measured using an ELISA assay calibrated using a standard curve generated from 7 standards with a working range from 50 to 0.78 ng/mL, plus a zero standard in a 0.2% monkey serum matrix. QC samples were prepared in 0.2% monkey serum at a concentration of 40 ng/mL, 8 ng/mL, and 2 ng/mL. The extracellular domain of human IL1RAP protein (SEQ ID NO: 3) was coated onto microtiter plates and then used to capture anti-IL1RAP antibodies from dosed samples, calibration standards and quality control samples. The captured anti-IL1RAP antibodies were detected by a goat anti-human IgG polyclonal antibody conjugated with horseradish peroxidase (HRP). A chromogenic substrate tetramethylbenzidine (TMB) was added to react with HRP. The reaction was then stopped by an acid solution to achieve an absorbance signal that is proportional to the amount of anti-IL1RAP captured in each well. The signal intensities of the calibration standards and their respective nominal concentrations were fitted using a weighted 4 Parameter Logistic (4PL) model to generate a calibration equation. Using the equation, the concentration of anti-IL1RAP in each sample was calculated from the average of the duplicate determination.

Methods of Pharmacokinetic Analysis: Data from studies 1 and 2 were combined to estimate the PK parameters of YKD. Data from study 3 was used to estimate the PK parameters of YKD-YTE. Compartmental modeling and parameter estimation were conducted using PK/PD modeling software ADAPT V (D'Argenio, D. Z. et al., ADAPT 5 User's Guide: Pharmacokinetic/Pharmacodynamic Systems Analysis Software, Biomedical Simulations Resource, Los Angeles, CA (2009)). For each dose group, group mean concentration-time profiles were first generated; the group mean concentration-time profiles from multiple dose groups were then simultaneously fit to various candidate model structures. Data from both genders were combined to calculate group mean concentration-time profiles, based on the lack of significant gender difference upon visual inspection. All analytically reportable PK data was included in the compartmental data analyses.

Figure 14A:
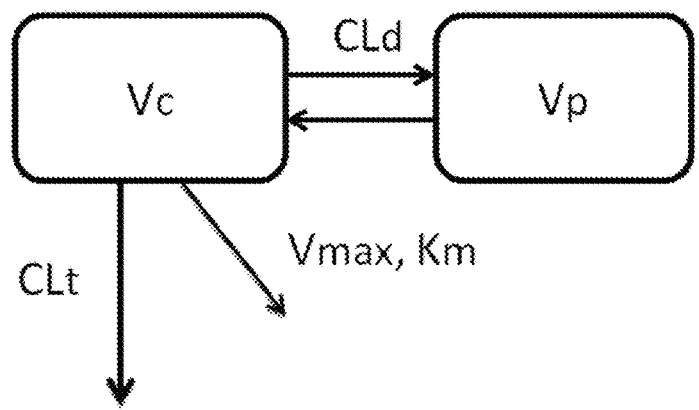
FIG. 14A depicts the non-linear two compartment model that best described the data obtained from pharmacokinetic studies 1, 2 and 3 performed in cynomolgus monkeys as described in Example 14. Model parameters, variables and initial conditions were defined as following: "Vc" is the volume of the central compartment, per body weight in mL/kg units; "Vp" is the volume of the peripheral compartment, per body weight, in mL/kg units; "CLt" is the linear clearance assumed to occur via FcRn-mediated IgG catabolism and recycling, per body weight in units of mL/day/kg; "CLd" is the distributional clearance between the central and the peripheral compartments, per body weight in units of mL/day/kg; "A(1)(t)" is the amount of drug in the central compartment at time t, per body weight, and thus, the model prediction of plasma concentration time profile was "A(1)(t)/Vc" in units of µg/kg, with A(1)(0)=0; and "A(2)(t)" is the amount of drug in the peripheral compartment at time t, per body weight in units of µg/kg with A(2)(0)=0.

Model selection was guided using the Akiake Information criterion (AIC). Parameters were estimated using the Maximum Likelihood Estimation method (D'Argenio, D. Z., et al., ADAPT 5 User's Guide: Pharmacokinetic/Pharmacodynamic Systems Analysis Software, Biomedical Simulations Resource, Los Angeles, CA (2009)). The nonlinear two-compartment model depicted in FIG. 14A was found to describe the group mean data the best.

Results

Figure 14B:
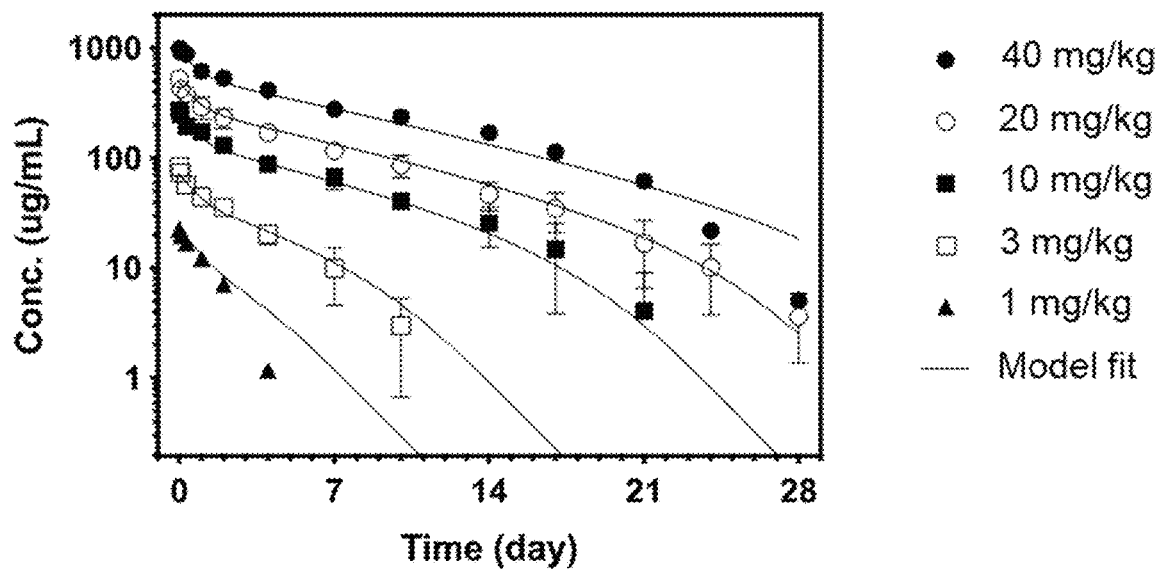
FIGS. 14B and 14C depict the pharmacokinetics of YKD (FIG. 14B) and YKD/YTE (FIG. 14C) following administration of single IV doses of antibody in cynomolgus monkeys as described in Example 14.
Figure 14C:
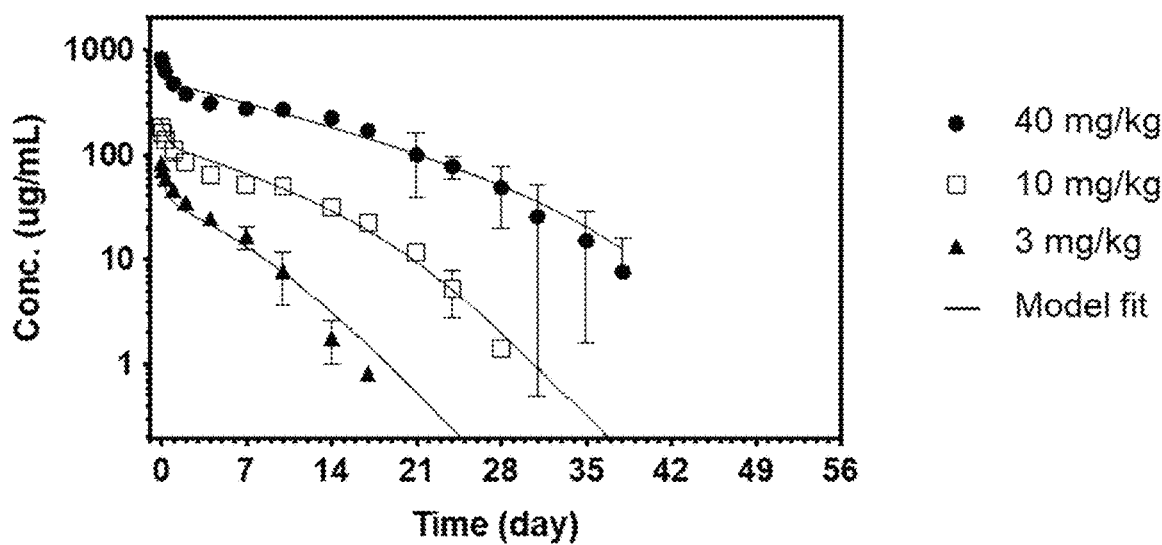

Time profiles of the group mean serum concentrations of YKD and YKD/YTE are shown in FIG. 14B and FIG. 14C, respectively. For both antibodies, concentrations declined more rapidly at low versus high doses, suggesting nonlinear PK over the dose range of 1-40 mg/kg, likely due to binding to target IL1RAP. Group mean data were fit to a nonlinear two compartment model as described above and depicted in FIG. 14A. The resulting PK parameter estimates for anti-human IL1RAP antibodies YKD and YKD-YTE are summarized in Table 23 (below).

TABLE 23

PK parameter estimates of 11C5-YKD and 11C5-YKD/YTE.

|  | $CL_t$ (mL/day/kg) | $V_c$ (mL/kg) | $CL_d$ (mL/day/kg) | $V_p$ (mL/kg) | $V_{max}$ (µg/day/kg) | $k_m$ (µg/mL) | $t_{1/2}$[1] (day) |
|---|---|---|---|---|---|---|---|
| YKD | 6.3 | 40.6 | 20.0 | 23.5 | 165 | 4.55 | 7.4 |
| YKD/YTE | 4.9 | 46.0 | 48.7 | 30.6 | 238 | 13.6 | 11.0 |

[1] $t_{1/2}$ is a calculated parameter and estimates the half-life of the antibody when concentrations are high and target-mediated clearance is negligible.

The linear clearance (CL$_t$) and t$_{1/2}$ for the variant anti-hu-IL1RAP antibody YKD were 6.3 mL/day/kg and 7.4 days, respectively. These values were within the range expected for an IgG1 in cynomolgus monkeys. The anti-hu-IL1RAP antibody variant YKD/YTE exhibited decreased CL$_t$ (4.9 mL/day/kg) and increased t$_{1/2}$ (11.9 days) compared to YKD, demonstrating that the YKD/YTE variant has improved PK properties relative to YKD in cynomolgus monkeys.

Example 15

Epitope Residue Mapping of Anti-Human IL1RAP Antibodies

This example illustrates the methods using phage display technology, coupled with Next Generation Sequencing (NGS), to identify human IL1RAP residues that are important for binding of the h11C5 variants, K13/H3 (or "YIS") and K17/H3 (or "YKS"). Libraries of human IL1RAP variants were displayed on the phage and the libraries were subjected to phage panning against YIS, YKS or reference antibodies. Phage carrying human IL1RAP variants that retained the binding to the antibodies were purified and the human IL1RAP sequences were obtained by NGS. Mutations on human IL1RAP that were deleterious to YIS or YKS binding but not to the reference antibodies binding were identified and defined as the epitope residues.

Materials and Methods

The amino acid sequence of human IL1RAP (SEQ ID NO: 1) from Ser21 to Lys350 was selected to be displayed on the phage. As described in Table 5 of Example 2 (above) 11C5 binds domain three of human IL1RAP. Therefore, the phage libraries displaying variants of human IL1RAP were constructed by residue randomization using the NNK degenerate codon that encodes for all 20 amino acids only in domain three of IL1RAP (Lys238 to Lys350 of SEQ ID NO: 1). Mutagenesis was carried out as described in Example 8 except that the mutagenesis oligonucleotides were designed to allow only one NNK mutation to occur in the human IL1RAP domain three residue in each member of the libraries. The resulting library DNA was electroporated into *E. coli* XL1 cells, yielding approximately 4.6×10$^9$ transformants.

The first round of phage panning was performed as described in Example 8 except 1 μg/mL of the variant antibodies YIS, YKS, or a reference antibody that binds to human IL1RAP domain one (SEQ ID NO: 4) was coated on Maxisorp plates. The reference antibody that binds to human IL1RAP domain one serves as a control in the process to identify mutations that are deleterious to the general folding of the human IL1RAP but not necessarily deleterious to the binding of 11C5 antibodies to human IL1RAP domain three.

The second to fourth rounds of phage panning were performed as described in Example 8 except that the blocked phage libraries were incubated with decreasing concentrations of biotinylated YIS, YKS, or the reference antibody for 1 hour. The antibody-bound phage were captured on blocked neutravidin-coated plates, washed extensively with Wash Buffer, and eluted and neutralized in the same manner as in round 1.

The sequences of the initial phage libraries (unsorted samples) and rounds 2 to 4 of pannings (sorted samples) were extracted using NGS as described in Example 8 except that the human IL1RAP domain three amplicons were generated for NGS.

After NGS, paired-end sequencing data assembly and quality control of the sequencing reads were carried out as described in Example 8. Reads from rounds 2 to 4 of phage pannings were pooled together for data analysis. Position weight matrices were generated by calculating the frequency of all mutations for every randomized position. Enrichment ratios for each mutation were calculated by dividing the frequency of a given mutation at a given position in the sorted sample with the frequency of the very same mutation in the unsorted sample, as described in Example 8.

Results

NGS data was used to analyze the impact of substitutions at each amino acid position of human IL1RAP domain three with respect to binding of YIS or YKS. Enrichment ratios that were less than zero indicated amino acid substitutions deleterious to the binding of YIS, YKS or the reference antibody. The NGS data was further used to flag substitutions of human IL1RAP domain three residues that were not detrimental to the reference antibody binding but were deleterious to YIS or YKS binding. Human IL1RAP domain three residue positions where a high number of flagged substitutions were observed were likely to be part of the YIS or YKS binding epitope as the residue randomization was applied to the domain three and should not affect the reference antibody that binds to human IL1RAP domain one.

As shown in FIG. 15, when the identified IL1RAP epitope residues are mapped on a crystal structure of the human IL-1β, IL-1R1 and IL1RAP ternary complex (PDB:3O4O), their distribution is clustered and located at the binding interface between IL1RAP and the binary complex of IL-1β and IL-1R1. The epitope data of the present example thus provides a structural explanation for how the binding of anti-hu-IL1RAP antibodies of the present disclosure, such as YIS or YKS, can block formation of the ternary complex and thereby inhibit downstream intracellular signaling events. Furthermore, in view of the overall similarity of the structural interaction between IL1RAP and IL-33/ST2 (Günther et al., *Immunity*, 47:510-523 (2017)) or IL-36/IL1RL2 (Yi et al., *The Journal of Biological Chemistry*, 291(32): 16597-16609 (2016)), the epitope data of the present example also supports a likely structural explanation for the ability of the anti-IL1RAP antibodies of the present disclosure, such as YIS and YKS, to also block these two pathways.

Table 24 shows the relative number of flagged substitutions observed at the human IL1RAP domain three positions (+++: equal or more than 9 flagged substitutions; ++: 6~8 flagged substitutions; +: 3~5 flagged substitutions; −: less than 3 flagged substitutions). Residues with high numbers of flagged substitutions were deemed more likely to be part of the epitope.

TABLE 24

Flagged substitutions for IL1RAP domain three binding

| D3 Position | YKS | YIS | D3 Position | YKS | YIS | D3 Position | YKS | YIS |
|---|---|---|---|---|---|---|---|---|
| K238 | − | − | S276 | − | − | Q314 | − | − |
| N239 | − | − | R277 | − | + | I315 | − | − |
| A240 | − | − | N278 | − | − | L316 | − | |
| V241 | − | − | E279 | − | − | S317 | + | + |

TABLE 24-continued

Flagged substitutions for IL1RAP domain three binding

| D3 Position | YKS | YIS | D3 Position | YKS | YIS | D3 Position | YKS | YIS |
|---|---|---|---|---|---|---|---|---|
| P242 | − | − | V280 | + | + | I318 | + | + |
| P243 | ++ | ++ | W281 | − | − | K319 | − | − |
| V244 | ++ | ++ | W282 | + | + | K320 | − | − |
| I245 | +++ | +++ | T283 | + | + | V321 | + | + |
| H246 | ++ | + | I284 | + | + | T322 | + | + |
| S247 | ++ | ++ | D285 | + | + | S323 | − | − |
| P248 | +++ | +++ | G286 | + | + | E324 | − | − |
| N249 | ++ | ++ | K287 | + | + | D325 | + | + |
| D250 | ++ | ++ | K288 | − | − | L326 | − | − |
| H251 | ++ | + | P289 | + | + | K327 | − | − |
| V252 | − | − | D290 | − | − | R328 | − | − |
| V253 | + | + | D291 | − | − | S329 | + | + |
| Y254 | ++ | ++ | I292 | − | − | Y330 | + | + |
| E255 | − | + | T293 | − | − | V331 | + | + |
| K256 | − | − | I294 | − | − | C332 | + | + |
| E257 | + | ++ | D295 | + | + | H333 | + | + |
| P258 | ++ | ++ | V296 | − | − | A334 | ++ | ++ |
| G259 | ++ | ++ | T297 | − | − | R335 | ++ | ++ |
| E260 | + | + | I298 | − | − | S336 | + | + |
| E261 | +++ | +++ | N299 | − | − | A337 | − | − |
| L262 | +++ | +++ | E300 | + | − | K338 | − | − |
| L263 | + | + | S301 | − | − | G339 | − | − |
| I264 | ++ | ++ | I302 | − | − | E340 | − | − |
| P265 | + | + | S303 | − | − | V341 | − | − |
| C266 | +++ | +++ | H304 | − | − | A342 | − | − |
| T267 | +++ | +++ | S305 | − | − | K343 | − | − |
| V268 | + | + | R306 | − | − | A344 | − | − |
| Y269 | − | − | T307 | − | − | A345 | + | + |
| F270 | + | + | E308 | − | − | K346 | − | − |
| S271 | − | + | D309 | − | + | V347 | ++ | ++ |
| F272 | − | − | E310 | + | + | K348 | − | − |
| L273 | − | − | T311 | + | − | Q349 | − | − |
| M274 | + | + | R312 | − | − | K350 | − | − |
| D275 | − | − | T313 | − | − | | | |

As demonstrated by the results listed in Table 24, the epitope for high affinity antibody 11C5 binding to human IL1RAP residues mainly within the D3 domain at positions 243-255, positions 257-268 and positions 333-336. Most of these sites cluster together on the surface of domain 3 of IL1RAP (see FIG. 15). These discontinuous residues are mapped to a main patch which is concluded to be the epitope of the antibody, 11C5, and its variants as disclosed herein.

Example 16

Generation of Surrogate Anti-Mouse IL1RAP Antibodies

This example illustrates the use of mouse hybridoma technology to generate anti-mu-IL1RAP antibodies, characterization of the anti-mu-IL1RAP antibody 14F4, and methods for use of this surrogate antibody for in vivo mouse studies.

Materials and Methods

Immunizations and fusions: IL1RAP knock-out mice (The Jackson Laboratory, Stock No. 003284) were immunized three times with 25 µg/immunization/mouse of mu-M-IL1RAP-D3 (mu-IL1RAP domain 3 with residue boundaries K239-T368) (SEQ ID NO: 337). Each mouse was given five subsequent immunizations of 25 µg total/immunization/mouse with a 1:1 mixture of mu-M-IL1RAP (the extracellular portion fused with a C-terminal 6×Histidine tag) (SEQ ID NO: 9) and mu-M-IL1RAP-D3 (SEQ ID NO: 337). The Sigma Adjuvant System (Sigma-Aldrich) was used for all immunizations. Mice were then given a final boost of 25 µg/mouse of a 1:1 mixture of mu-M-IL1RAP and mu-M-IL1RAP-D3 without adjuvant. Three days later, spleens were harvested and processed according to standard protocols. Splenocytes were fused with myeloma Sp2/0 cells (ATCC) using PEG following standard protocols and were plated into 96-well plates. Parental hybridomas were selected using selection medium supplemented with hypoxanthine-aminopterin-thymidine.

ELISA assays: After 12-14 days of culture, hybridoma supernatants were collected and subjected to primary screening by ELISA with 96-well plates coated with 1 µg/mL mu-M-IL1RAP in PBS. Hybridoma supernatants (65 µL/well) were incubated on coated plates for at least 1 hour at room temperature, and the plates were washed three times with wash buffer (PBS with 0.05% Tween-20). Goat-anti-mouse-Fc-HRP secondary (Jackson Immunoresearch, diluted 1:5000 in PBS) was added (65 µL/well) and incubated at room temperature for one hour. After washing three times with wash buffer, 1-Step Ultra TMB ELISA Substrate developing solution (Thermo Pierce Scientific, 65 µL/well) was added and incubated at room temperature for 20 min. The absorbance at 650 nm was read without quenching the developer.

Parental hybridomas that were positive in the primary ELISA screen were expanded to 24-well plates in media containing hypoxanthine-thymidine, and a confirmatory ELISA screen was carried out as described in Example 2 using mu-M-IL1RAP coated at 1 µg/mL. Hybridoma clones of interest were subcloned using limited dilution at a density of 0.5 cells/well, and cell pellets were used for determining heavy-chain and light-chain sequences of each antibody clone (described below).

Sequencing and recombinant production of 14F4: The determination of the sequences of the hybridoma-derived anti-mu-IL1RAP antibodies was performed as described in Example 3. The recombinant anti-mu-IL1RAP antibody 14F4 was generated as described in Example 5.

BIACORE SPR analysis of recombinant 14F4 binding mu-IL1RAP: Surface plasmon resonance (SPR) analysis was used to determine the binding affinity of 14F4 for mu-IL1RAP using a BIACORE™ 8K instrument. For kinetics measurements, recombinant 14F4 was diluted to 10 µg/mL in HBS-P buffer (0.01 M HEPES pH 7.4, 0.15 M NaCl, 0.005% surfactant P20) and captured on an anti-mouse chip (GE Healthcare) at 10 µL/min in the second flow cell (FC2). FC1 was kept as a reference. Next, 3-fold serial dilutions of mu-M-IL1RAP in HBS-P from low (0.14 nM) to high (100 nM) were injected (flow rate: 30 µL/min) at 37° C. The chip was regenerated two times before each analyte injection using 60 mM hydrochloric acid (flow rate: 90 µL/min). The sensorgrams were recorded and subject to reference and buffer subtraction before data analysis with the BIACORE® 8K Evaluation Software (version 1.1.1.7442). Association rates ($k_{on}$) and dissociation rates ($k_{off}$) were calculated using a simple one-to-one Langmuir binding model. The equilibrium dissociation constant ($K_D$) was calculated as the ratio of $k_{off}/k_{on}$.

BV ELISA for determination of non-specific binding of recombinant 14F4: BV ELISA was performed as detailed in Example 11 using 14F4 to determine the degree of non-specific binding.

Assays of specific binding activity for IL1RAP: In order to determine the specificity of 14F4 for different domains of hu-IL1RAP and mu-IL1RAP, ELISA was used as described previously in Example 2, with the following proteins individually coated at 1 µg/mL: mu-M-IL1RAP (SEQ ID NO: 337), mu-M-IL1RAP-D1D2 (domain 1-2, S21-P237) (SEQ ID NO: 338), hu-M-IL1RAP (SEQ ID NO: 3), hu-M-IL1RAP-D1 (domain 1, S21-Q133) (SEQ ID NO: 4), and hu-M-IL1RAP-D3 (domain 3, K238-T367) (SEQ ID NO: 6). Recombinant 14F4 was assayed at a concentration of 10 nM.

115

Results

Generation of anti-mu-IL1RAP Antibodies: Following immunization of IL1RAP knock-out mice and subsequent harvest of splenocytes, parental hybridomas (generated via PEG fusion) were screened by ELISA for binding to mu-M-IL1RAP (SEQ ID NO: 9). The primary ELISA assay screen identified a total of 17 anti-mouse IL1RAP binders from hybridomas, which were further confirmed to bind mu-M-IL1RAP by ELISA after expansion into 24-well plates. Following screening of all 17 supernatants in the HEK-Blue SEAP assay as described in Example 2 (data not shown), 14F4 was selected based on its ability to block all three pathways (IL-1, IL-33, and IL-36). The clone 14F4 was selected for sequencing of its $V_L$ and $V_H$ regions from hybridoma cells, recombinant expression and purification.

Kinetics of recombinant 14F4 binding to mu-IL1RAP: As shown in Table 25, recombinant 14F4 binds mu-M-IL1RAP (SEQ ID NO: 9) with $K_D$=0.219 nM.

TABLE 25

BIACORE SPR result for recombinant 14F4 binding to mu-IL1RAP

| Analyte in Solution | Ligand (on chip) | pH 7.4, 37° C. | | |
|---|---|---|---|---|
| | | $k_{on}$ (1/MS) | $k_{off}$ (1/s) | $K_D$ (M) |
| mu-IL1RAP-ECD-His | Recombinant 14F4 | 1.03E+06 | 2.25E−04 | 2.19E−10 |

BV ELISA results for non-specific binding: As shown in Table 26, recombinant 14F4 does not show BV ELISA signal greater than the medium control, suggesting that 14F4 has no non-specific binding to BV particles.

TABLE 26

Recombinant 14F4 shows no non-specific binding by baculovirus (BV) ELISA.

| Antibody Concentration (nM) | Absorbance @ 450 nm | | |
|---|---|---|---|
| | Recombinant 14F4 | Medium Control | Negative Control |
| 300 | 0.071 | 0.307 | 0.129 |
| 100 | 0.057 | 0.138 | 0.045 |
| 33 | 0.046 | 0.081 | 0.046 |
| 0 | 0.074 | 0.045 | 0.045 |

Assays of specific binding activity for IL1RAP: As shown in Table 27, recombinant anti-mu-IL1RAP antibody, 14F4 shows no binding to human IL1RAP but shows comparable binding between mu-M-IL1RAP (SEQ ID NO: 9) and mu-M-IL1RAP-D1D2 (SEQ ID NO: 338), suggesting that 14F4 specifically binds either murine IL1RAP domain 1 or domain 2.

TABLE 27

ELISA assay of 14F4 binding to mu-IL1RAP and hu-IL1RAP domains

| | Absorbance @ 450 nm | | | | | | |
|---|---|---|---|---|---|---|---|
| Analyte | mu-M-IL1RAP | mu-M-IL1RAP-D1D2 | hu-M-IL1RAP | hu-M-IL1RAP-D1 | hu-M-IL1RAP-D3 | Apparent Binding Domains |
| Recombinant 14F4 | 1.3 | 1.329 | no binding | no binding | no binding | Mouse Domain 1 or Domain 2 |

Example 17

Cell-Based Assays of IL1RAP Blocking Activity of Surrogate Anti-Mouse IL1RAP Antibody 14F4

This example illustrates the ability of the anti-mu-IL1RAP surrogate antibody 14F4 to block all three pathways (IL-1 mediated, IL-33 mediated, and IL-36 mediated) in mouse cell lines or primary mouse cells.

Materials and Methods

NIH-3T3 Cells and Associated Assays: The mouse fibroblast cell line, NIH-3T3, was obtained commercially (ATCC CRL-1658). NIH-3T3 cells were maintained in culture according to manufacturer's guidelines, utilizing a standard growth medium consisting of DMEM (Corning 10-013-CV), supplemented with 10% fetal bovine serum (FBS; Atlanta Biologicals), 100 IU/mL penicillin, 100 µg/mL streptomycin, 1× Non-essential amino acids (Gibco 11140-050, 100× solution) and 1X Glutamax (Gibco 35050-61, 100× solution). Mouse IL-1β (Peprotech) and IL-36α (BioLegend) were obtained commercially.

Antibody blocking assays and agonist dose response curves were performed in a similar manner as described in Example 7, with some modifications to account for the conditions of the present example. In brief, the day prior to experimental use, NIH-3T3 cells were seeded on flat-bottom, 96-well plates at a concentration that would result in ~80-85% confluency the day of use. On the day of the assay, the surrogate antibody 14F4, or an isotype control, was incubated with NIH-3T3 cells for 1 hour (37° C. with 5% $CO_2$), followed by the addition of agonist (IL-1β or IL-36α). The experiment was allowed to proceed for an additional twenty-four hours (37° C. with 5% $CO_2$). Cell culture supernatants were collected and the levels of IL-6 production were determined by ELISA (Thermo Fisher Scientific) according to manufacturer's guidelines. For all antibody blocking assays described, NIH-3T3 cells were stimulated at an agonist concentration of $EC_{85}$ or greater. The positive control consisted of NIH-3T3 cells with growth medium and agonist only (no antibody present), while the negative control samples consisted of NIH-3T3 cells with growth medium only (in the absence of agonist stimulation and antibodies).

J774-Dual Cells and Associated Assays: J774-Dual cells were derived from the mouse J774.1 macrophage-like cell line. These cells have been engineered to express an NF-κB reporter gene, the secreted embryonic alkaline phosphatase (SEAP). J774-Dual cells are commercially available and were obtained from InvivoGen (catalog number j774d-nfis). J774-Dual cells were thawed according to general manufacturer's guidelines and maintained in cell culture medium including: DMEM (2 mM L-glutamine, 3.7 g/L sodium bicarbonate, 4.5 g/L glucose and 1.0 mM sodium pyruvate) with 10% heat-inactivated fetal bovine serum (30 min at 56° C.), 100 µg/ml Normocin (InvivoGen catalog number ant-nr-1), 1× Penicillin-Streptomycin Solution and supplemented with selection antibiotics Blasticidin (InvivoGen catalog number ant-bl-1) and Zeocin (InvivoGen catalog number ant-zn-1). For antibody blocking assays, J774-Dual cells were cultured in cell culture medium without selection antibiotics (Blasticidin and Zeocin) until cells reached 80% confluency. Then cells were plated at 50,000/well on flat-bottom, 96-well plates and incubated at 37° C. with 5% $CO_2$ overnight (about 18 hours). 14F4 was incubated with J774-Dual cells for 1 hour prior to the addition of agonist (mouse IL-33 at $EC_{55}$, PeproTech, catalog number 1209434). The cells were further incubated for twenty-four hours at 37° C. with 5% $CO_2$. SEAP production in the supernatant was quantified using the SEAP detection assay described in Example 2. The positive control condition (PC) included cells, growth medium and agonist (IL-33) and the negative control condition (NC) included cells and growth medium only. Data was analyzed using GraphPad Prism 7 software, with non-linear regression analysis performed to determine agonist $EC_{50}$ values. Prior to antibody blocking assays, an agonist and antagonist dose-response curve was generated to determine the $EC_{50}$ and $IC_{50}$ (respectively) as described in Example 5.

Primary Mouse Embryonic Fibroblasts and Associated Assays: Primary mouse embryonic fibroblasts (Primary MEFs) were obtained from Lonza (catalog number M-FB-481). These primary cells are dissociated from Day 14 and 15 post-coitus CD-1 mouse embryos, expanded in culture, and then cryopreserved by the manufacturer. The cells were thawed and maintained in culture using DMEM with 4.5 g/L glucose, L-glutamine, and sodium pyruvate (Corning, catalog number 10-013-CV) supplemented with 10% heat inactivated fetal bovine serum (Atlanta Biologicals, catalog number S11150H), 10 IU penicillin, and 10 µg/mL streptomycin (Corning, catalog number 30-002-CI), following the guidelines provided by the manufacturer. Mouse IL-36β was obtained from Biolegend (catalog #554506).

Agonist dose response curve and antibody blocking assay was performed as described in Example 7, with modifications as mentioned below. Briefly, primary MEFs were seeded on a flat-bottomed, 96 well plate at a density of 15,000 cells/well in the aforementioned growth media. The cells were incubated overnight at 37° C. with 5% $CO_2$. After overnight incubation, 14F4 or the isotype control was incubated with primary MEFs for 1 h at 37° C. with 5% $CO_2$. This was followed by the addition of a predetermined concentration of agonist (mouse IL-1β or IL-36β). The final volume in each well was 200 µL and the antibody blocking assay was performed at agonist $EC_{70}$ or higher.

After agonist stimulation, cells were incubated at 37° C., 5% $CO_2$ for 21 hours. Subsequently, the plates were spun down and the supernatant was collected to determine the levels of mouse IL-6 secreted using a commercially available mouse IL-6 ELISA kit (Invitrogen/Thermo Fisher Scientific catalog number 88-7064-88), following manufacturer's guidelines. The positive control wells consisted of cells containing agonist in growth media and negative control wells consisted of cells with only growth media. Data analysis was performed using Graphpad Prism 7 software, with nonlinear regression (curve fit) to determine agonist $EC_{50}$ and antagonist $IC_{50}$ values.

Results

The surrogate anti-mouse IL1RAP antibody, 14F4 (prepared as described in Example 16) was selected to demonstrate in vivo efficacy in mouse models. Prior to in vivo studies, 14F4 was assayed in vitro for efficacy in blocking all three IL1RAP-mediated pathways (IL-1, IL-36 and IL-33) using mouse cell lines and primary cell assays.

The NIH-3T3 cell line was used to determine whether 14F4 was able to block the mouse IL-1 and IL-36 pathways in vitro. NIH-3T3 cells are known to be responsive to IL-1 stimulation, and therefore express IL1RAP (see e.g., Smeets et al., *Arthritis and Rheumatism*, 52(7):2202-2211 (2005)). NIH-3T3 cells were stimulated with IL-1β, as described above and exposed to either 14F4, to block IL1-β stimulation, or an isotype control antibody. IL-6 production was measured in the supernatant of cells exposed to the isotype control antibody, as well as the positive control cells. As shown in Table 28 (below), the NIH-3T3 cells receiving the anti-mouse IL1RAP antibody 14F4, exhibited near complete reduction in the level of IL-6 detected (98% inhibition) compared to the positive control. 14F4 inhibited IL-1β induced IL-6 production with an $IC_{50}=1.36$ nM, which is near the potency observed with YKD/YTE ($IC_{50}=0.51$ nM) in the HEK-Blue assays described in Example 12.

The NIH-3T3 cells were also found to be responsive to IL-36, secreting IL-6 in a dose dependent manner upon stimulation with IL-36α (data not shown). Maximum IL-6 production observed was similar whether NIH-3T3 cells were stimulated with IL-1β or IL-36α. As shown in Table 28, the 14F4 blocking assay carried out using NIH-3T3 cells stimulated with IL-36α resulted in 100% inhibition of IL-6 production. Furthermore, 14F4 was able to inhibit IL-36α induced IL-6 production with greater potency than observed following IL-1β stimulation ($IC_{50}=0.18$ nM), with complete inhibition by 14F4 observed at 16.7 nM. As described in Example 12, this sub-nanomolar inhibitory potency of 14F4 is comparable to that observed for the anti-human IL1RAP antibody YKD/YTE in the IL-36 HEK-Blue assay. In summary, the surrogate anti-mu-IL1RAP mouse antibody 14F4 effectively inhibited IL-1 and IL-36 induced IL-6 production in the mouse cell line NIH-3T3 and demonstrated comparable potency in vitro as was observed for the anti-hu-IL1RAP antibody, YKD/YTE.

The macrophage-like J774-Dual cell line was used to determine whether 14F4 can block the mouse IL-33 stimulated pathway in vitro. IL-33 and its receptor IL1R1 are broadly expressed in many immune cells, including macrophages. Activated ST2 signaling by IL-33 results in NF-κB activation in macrophages (see e.g., Kakkar et al., *Nature Reviews. Drug Discovery*, 7(10), 827-840 (2008)). As shown in Table 28, 14F4 displayed blocking activity in IL-33 stimulated J774 cells with 97% inhibition ($IC_{50}=6.6$ nM) at 2 µM. This inhibitory potency with IL-33 stimulation is similar to that observed for the anti-human IL1RAP antibody YKD/YTE as described in the HEK-Blue assay ($IC_{50}=3.30$ nM) of Example 12.

The ability of the surrogate antibody, 14F4 to block IL-1 and IL-36 stimulated pathways was determined in primary MEFs. Primary MEFs have the ability to produce IL-6 in response to IL-1 stimulation, suggesting the expression of IL1RAP (see e.g., Nold-Petry et al., *Journal of Biological Chemistry*, 284(38): 25900-25911 (2009)). Since these primary mouse fibroblasts express IL1RAP and the mouse embryonic fibroblast cell line NIH-3T3 respond to IL-36 stimulation, it was reasoned that primary MEFs should also be responsive to IL-36 stimulation. Indeed, upon stimulation with IL-36β, the primary MEFs secreted IL-6 in a dose dependent manner (data not shown). As shown in Table 28, 14F4 shows essentially complete inhibition of IL-1β stimulated IL-6 production with respect to the positive control with an $IC_{50}$ of 6.1 nM. Similarly, IL-36β stimulated IL-6 production was completely inhibited with an $IC_{50}$ value of 0.094 nM. In conclusion, 14F4 has the ability to completely block both the IL-1 and IL-36 pathway in primary MEFs, albeit with much greater potency for IL-36 as compared to the IL-1 pathway.

TABLE 28

Cell-based assay results for surrogate anti-mu-IL1RAP antibody, 14F4. Functional Characterization of the Surrogate Antibody 14F4

| Pathway | Cell Type | $IC_{50}$ (M)[1] | % Inhib.[2] | Conc. (M) |
|---|---|---|---|---|
| IL-1 | NIH-3T3 | 1.36 E−09 | 98 | 1.00 E−07 |
| | Primary MEFs | 6.10 E−09 | 99 | 1.00 E−06 |
| IL-33 | J774-Dual | 6.60 E−09 | 97 | 2.00 E−06 |
| IL-36 | NIH-313 | 1.84 E−10 | 100 | 1.67 E−08 |
| | Primary MEFs | 9.40 E−11 | 100 | 1.00 E−06 |

[1]$IC_{50}$ determined as described in Example 17.
[2]% Inhib. reflects the maximal inhibition observed at the concentration referenced (Conc. M).

In summary, the above results with 14F4 support its use as a surrogate antibody for mouse in vivo studies to determine efficacy and the effects of blocking the IL-1, IL-33 and IL-36 pathways simultaneously through IL1RAP inhibition.

Example 18

In Vivo Efficacy of Surrogate Anti-Mouse IL1RAP Antibodies

This example illustrates that the mouse surrogate antibody 14F4 is a functional in vivo blocker of at least two IL-1 family pathways, and also a functional blocker of more complex phenotypes induced in mouse models of asthma.

Materials and Methods

The protocols for the studies in the in vivo mouse model studies are summarized in Table 29.

TABLE 29

TABLE 29 In vivo study protocols

| Model | Challenge | Dosing | End-point | Key readout |
|---|---|---|---|---|
| Single IL-1β challenge | i.p. 50 ng IL-1β (Day 0) | 30 mg/kg (Day −1) | 2 h | serum IL-6 |
| Single IL-36α challenge | i.n. 10 ng IL-36α (Day 0) | 30 mg/kg (Day −1) | Day 1 | cells in BAL |
| Multiple IL-1β challenge | i.n. 30 ng IL-1β (Days 0, 1, and 2) | 30 mg/kg (Days −1 and 2) | Day 3 | cells in BAL, lung chemokines and cytokines |
| Acute HDM asthma model | i.n. 25 μg HDM (Days 0-3, 6-10, 13, 14) | 30 mg/kg (Days −1, 2, 6, 9, and 13) | Day 15 | serum HDM-specific IgE and IgG1 |

Animals and husbandry: Female BALB/cAnNHsd mice were purchased from Envigo and used between the ages of 6-13 weeks. Mice were fed irradiated Harlan Teklad global 18% protein rodent diet and ad libitum water. Animals were housed in Innovive disposable ventilated caging with corn cob bedding at 60 complete air changes per hour. The environment was controlled to a temperature range of 70°±2° F. and a humidity range of 30-70%. All animal work was performed according to Animal Care Use Protocol approved by Explora's Institutional Animal Care and Use Committee (San Diego, CA).

In vivo treatments: For intranasal (i.n.) treatments, mice were anesthetized with 3-4% isoflurane (VetOne, Boise, Idaho) and allowed to inhale via nostrils 35 μl of solution administered by a micropipette. Mice were euthanized by administering an anesthetizing dose of 2.5% 2,2,2-tribromo-ethyl alcohol solution (Sigma Aldrich, St.Louis, Mo), followed by bilateral thoracotomy or cervical dislocation (for single IL-1β challenge only).

Data analysis: For all in vivo studies, GraphPad Prism 8 software was used for data and statistical analyses. Mann-Whitney test was performed between the IgG control-dosed, unchallenged mice and the IgG control-dosed, challenged mice to determine whether cytokine or HDM challenge caused a statistically significant increase in the biological response. After determining significance, a Mann-Whitney test was performed between the IgG control-dosed, challenged mice and the 14F4-dosed, challenged mice.

A. Single cytokine challenge models and associated assays: The single IL-1β challenge study protocol was modified based on Gabrielsson et al., *European Journal of Pharmaceutical Sciences: Official Journal of the European Federation for Pharmaceutical Sciences*, 67:144-159 (2015). On Day −1, mice were dosed intraperitoneally (i.p.) with 30 mg per kg average group body weight IgG control or 14F4, in a total volume of 100-200 μl. On Day 0, mice were challenged i.p. with D-PBS or 50 ng IL-1β in a total volume of 100 μl. Two hours after challenge, mice were euthanized, blood was collected via cardiac puncture, and placed in a BD Microtainer serum separation tube (BD Biosciences). After at least 30 minutes, the tubes were centrifuged for 9,300×g for 5 min, and serum was collected and archived at −80° C. Mouse serum IL-6 concentrations were measured by commercial IL-6 ELISA kit (Invitrogen/ThermoFisher Scientific catalogue number 88-7064-88) as per the manufacturer's instructions. Serum samples were diluted 1:5 for the assay.

The single IL-36α challenge study protocol was modified based on Ramadas et al., *PloS One,* 7(9):e45784 (2012). On Day −1, mice were dosed i.p. with antibodies similarly to the single IL-1β challenge study. On Day 0, mice were challenged i.n. with D-PBS or 10 ng IL-36α in a total volume of 35 μl. On Day 1, mice were euthanized. Bronchoalveolar lavage (BAL) was performed by making an incision in the trachea, inserting a 20G blunt end needle or 18G catheter sheath, and injecting and retrieving 0.8 mL HBSS/2 mM EDTA buffer using a 1 mL syringe. This procedure was performed 3 times. To determine the number of cell types in the BAL fluid, the BAL fluid was centrifuged for 10 min at 365×g. After removing the supernatant, 2 mL of 1× Lysing Buffer (BD Biosciences, catalogue number 555899) was added to the cells to lyse any red blood cells. After 2 min, 5 mL of D-PBS/2% FBS buffer was added to stop the reaction. The cells were centrifuged for 5 min at 365×g. After removing the supernatant, the cells were resuspended in HBSS/2 mM EDTA, transferred to a 96-well round-bottom plate, centrifuged for 2 min at 570×g, and the supernatant was removed. All staining steps were performed on ice and in the dark. To stain dead cells, 25 μl of LIVE/DEAD Fixable Far Red Dead Cell Stain Kit (1:1000 dilution, ThermoFisher) was added. After 15-20 min, 25 μl of anti-CD16/32 (2.4G2, BD Biosciences) in FACS staining buffer was added to the cells to block Fc receptor binding. After 15 min, the cells were then stained by adding antibodies in 50 µl of Brilliant Stain Buffer (BD Biosciences) to the wells. The antibodies were all used at 1:200 dilution. The following antibodies were purchased from Tonbo Biosciences (San Diego, CA): Ly6G-FITC (1A8) and CD11b-APC (M1/70). The following antibodies were purchased from BD Biosciences: SiglecF-PE (E50-2440) and CD11c-BV785 (N418). Ly6C-PerCp-Cyanine5.5 (HK1.4) was purchased from ThermoFisher. After 30 min, the cells were washed 2-3 times in FACS buffer. After washing, the cells were resuspended in FACS buffer and then analyzed on a CytoFlex flow cytometer. Data was analyzed using the FlowJo 10 software. After gating on cells and excluding dead cells and alveolar macrophages (SiglecF$^+$CD11c$^+$), the cell types were defined based on expression of markers: eosinophils (SiglecF$^+$CD11c$^-$Ly6G$^-$), neutrophils (Ly6G$^+$Ly6C$^+$CD11b$^+$SiglecF$^-$CD11c$^-$), and monocytes (Ly6C$^+$Ly6G$^-$CD11b$^+$SiglecF$^-$CD11c$^-$). To calculate the number of cell types in the BAL fluid, the percentages of each cell type out of total acquired cells were multiplied by the whole cell counts. Whole cell counts were obtained using the Guava easyCyte 5HT System flow cytometer (EMD Millipore, Billerica, MA) using the ViaCount Assay, per manufacturer's instructions.

B. Multiple IL-1β cytokine challenge model and associated assays: The multiple IL-1β challenge study protocol was based on Kim et al., *American Journal of Respiratory and Critical Care Medicine*, 196(3):283-297 (2017). On Day −1 and Day 2, mice were i.p. dosed with antibodies similarly to the single IL-1β challenge study. On Day 0, 1, and 2 mice were i.n. challenged with D-PBS or 30 ng IL-1β in a total volume of 35 µl in D-PBS. On Day 3, mice were euthanized. BAL was performed as previously described. The left, middle, inferior, and post-caval lung lobes were collected in 2.0 mL tubes, flash frozen, and archived at −80° C. for subsequent protein chemokine/cytokine analysis. Cell analysis of the BAL was performed as previously described, except cells were stained with LIVE/DEAD Fixable Aqua Dead Cell Stain Kit (1:250 dilution, ThermoFisher), and the following antibodies, all at 1:200 dilution: Ly6G-FITC (Tonbo Biosciences, 1A8); SiglecF-PE (BD Biosciences, E50-2440); Ly6C-PerCp-Cyanine5.5 (Thermo Fisher, HK1.4); CD11b-APC-Cy7 (BD Biosciences, M1/70); CD11c-BV785 (Biolegend, N418); CD3-PE-Cy7 (Biolegend, 17A2); CD4-BV605 (BD Biosciences, RM4-5); CD19-BV650 (BD Biosciences, 1 D3); T1/ST2-BV421 (BD Biosciences, U29-93); and MHC class II-APC (ThermoFisher, M5/114.15.2). Data was analyzed using the FlowJo 10 software. After gating on cells, and excluding dead cells and alveolar macrophages (CD11c$^+$SiglecF$^+$), the following cell types in the BAL were defined based on the expression of the following markers: neutrophils (Ly6G$^+$Ly6C$^+$CD11b$^+$), eosinophils (SiglecF$^+$CD11c$^-$Ly6G$^-$), dendritic cells (CD11c$^+$MHCII$^+$Ly6G$^-$SiglecF$^-$), monocytes (Ly6C$^+$Ly6G$^-$CD11b$^+$SiglecF$^-$), CD4 T cells (CD3$^+$CD4$^+$CD19$^-$CD11b$^-$Ly6G$^-$SiglecF$^-$), T1-ST2+ CD4 T cells (CD3$^+$CD4$^+$T1/ST2$^+$CD19$^-$ CD11b$^-$Ly6G$^-$SiglecF$^-$), CD8 T cells (CD3$^+$CD4$^-$CD19$^-$CD11b$^-$Ly6G$^-$SiglecF$^-$), and B cells (CD19$^+$MHCII$^+$CD3$^-$CD11b$^-$Ly6G$^-$SiglecF$^-$). Cell counts in the BAL were calculated as described above. For lung chemokine/cytokine protein analysis, lung samples were homogenized in Tissue Extraction Reagent I (ThermoFisher Scientific, catalogue number FNN0071), containing Protease and Phosphatase Inhibitor Cocktail (Thermo Fisher Scientific, catalogue number 78443) using Tissuelyser II (QIAGEN), with 25 Hz for 2 minutes for 3 cycles. The homogenates were centrifuged at 9,300×g at 4° C. for 10 minutes. Protein amount in the tissue lysate (supernatant) was quantified with Pierce bicinchoninic acid (BCA) protein assay (ThermoFisher Scientific, catalogue number 23227). The lysates were stored at −80° C. for cytokine assay. Supernatant was used for cytokine measurement. The levels of murine cytokines and chemokines (CXCL1, CXCL2, IFNγ, IL-10, IL-12, IL-1α, IL-1β, IL-2, IL-25, IL-4, IL-5, IL-6, IL-13, IL-17A, IL-33, TNFα, and TSLP) in 200 µg of total protein lung lysates were measured using the mouse custom ProcartaPlex 17-plex kit (Invitrogen/Thermo Fisher Scientific, catalogue number PPX-17-MXCE4AT) as per the manufacturer's instructions.

C. Acute house dust mite (HDM) asthma model and associated assays: The acute house dust mite (HDM) asthma model was based on Piyadasa et al., *Biology Open*, 5(2): 112-121 (2016). On Days −1, 2, 6, 9, and 13, mice were dosed i.p. with IgG control or 14F4 at 30 mg/kg. On Days 0-3, 6-10, 13, and 14, mice were challenged i.n. with saline or 25 µg HDM (Stallergenes Greer, Lenoir, NC, catalogue number XPB82D3A.5). On Day 15, the mice were euthanized, and serum from blood was collected as described previously. Serum concentrations of mouse antibodies were measured using HDM-specific IgE (Chondrex, Redmond, WA, catalogue number 3037) and HDM-specific IgG1 (Chondrex, catalogue number 3034) kits per manufacturer's instructions. Serum samples were diluted 1:4 for HDM specific IgE and 1:12 for HDM-specific IgG1 measurements.

Results

As shown by the results of Example 17, the mouse surrogate antibody 14F4 is able to block all three IL-1 family pathways in in vitro cell based assays. To determine whether 14F4 is able to block these pathways in vivo, the present Example 18 tested the ability of 14F4 to block individual pathways in short pharmacodynamic (PD) assays. Previous studies demonstrated that IL-1 family cytokines have acute effects when administered in vivo (see e.g., Gabrielsson et al., *European Journal of Pharmaceutical Sciences: Official Journal of the European Federation for Pharmaceutical Sciences*, 67: 144-159 (2015); Ramadas et al., *PloS One*, 7(9): e45784 (2012)). Similarly, as shown by the results depicted in FIGS. 16A and 16B, mice challenged systemically with IL-1β responded with a rapid increase in serum IL-6 levels compared to mice challenged with PBS (FIG. 16A). Mice challenged i.n. with IL36α responded with a rapid influx of neutrophils in the lung airspace compared to mice challenged with PBS (FIG. 16B). Treatment with 14F4 affected both of these observed immune responses. As shown in FIG. 16A, mice dosed with 14F4 prior to challenge exhibited a strong inhibition in the IL-1β-induced increase in serum IL-6 level (88% inhibition). Additionally, as shown in FIG. 16B, mice dosed with 14F4 prior to challenge exhibited decreased IL-36α-induced neutrophil influx (100% inhibition) in the lung airspace. These results strongly suggest that 14F4 has the ability to block the IL-1 and IL-36 signaling pathways in vivo.

The studies of the present example were also used to determine whether 14F4 has the ability to block complex phenotypes seen in human asthma. Previous studies have shown that mice challenged with IL-1β once a day over the course of 4 days have increased numbers of neutrophils, macrophages, and lymphocytes in the lung airspace (see e.g., Kim et al., *American Journal of Respiratory and Critical Care Medicine*, 196(3): 283-297 (2017)). The IL-1β-induced neutrophil influx has been shown to be steroid-resistant, similar to what is seen in human patients with severe, uncontrolled asthma. As shown by the results depicted in the plots of FIGS. 17A-17E, the mice challenged with IL-1β over the course of 3 dayshad significantly increased neutrophils (FIG. 17A), CD4 T cells (FIG. 17B), T1-ST2$^+$ CD4 T cells (FIG. 17C), monocytes (FIG. 17D), and dendritic cells (FIG. 17E) in the lung airspace. As shown by the plots depicted in FIGS. 18A-18C, the multiple IL-1β challenge also led to increased levels of the inflammatory cytokines IL-1β (FIG. 18A) and IL-17A (FIG. 18B), and the neutrophil-attracting chemokine CXCL1 (FIG. 18C), in the lung tissue. Levels of CXCL2, IFN-γ, IL-10, IL-12, IL-1α, IL-2, IL-25, IL-4, IL-5, IL-6, IL-13, IL-33, TNF-α, and TSLP were either below limit of detection or not upregulated after multiple IL-1β challenges (data not shown). Treatment with 14F4 decreased these observed effects in IL-1β challenged mice. As shown in FIGS. 17A-17E, the mice challenged with IL-1β over the course of 3 days and treated with 14F4 had decreased numbers of neutrophils (74% inhibition) (FIG. 17A), CD4 T cells (75% inhibition) (FIG. 17B), T1-ST2$^+$ CD4 T cells (76% inhibition) (FIG. 17C), monocytes (58% inhibition) (FIG. 17D), and dendritic cells (64% inhibition) (FIG. 17E) in the lung airspace. As shown in FIGS. 18A-18C, 14F4 treatment resulted in significant decreases in the levels of IL-1β (88% inhibition) (FIG. 18A), IL-17A (89% inhibition) (FIG. 18B), and CXCL1 (68% inhibition) (FIG. 18C) in the lung tissue. These results strongly suggest that 14F4 has the ability to block more complex immune responses that develop over several days.

After determining that 14F4 has the ability to block complex, immune phenotypes in a reductionist, cytokine challenge model, the ability of 14F4 to block asthma-like phenotypes induced by a relevant and complex human allergen, house dust mite (HDM), was further tested (see e.g., Nials et al., *Disease Models & Mechanisms*, 1(4-5): 213-220 (2008)). As shown in FIGS. 19A and 19B, similar to previous studies (see e.g., Piyadasa et al., *Biology Open*, 5(2): 112-121 (2016)), mice challenged with HDM had significantly elevated levels of HDM-specific IgE (FIG. 19A) and IgG1 (FIG. 19B) compared to mice challenged with saline. The mice challenged with HDM and treated with 14F4, however, showed significant decrease in HDM-specific IgE (64% inhibition) (FIG. 19A) and HDM-specific IgG1 (70% inhibition) (FIG. 19B) compared to mice treated with IgG ctrl. These results indicate that blocking IL-1 family signaling may be able to partially block the development of asthma-like phenotypes.

While the foregoing disclosure of the present invention has been described in some detail by way of example and illustration for purposes of clarity and understanding, this disclosure including the examples, descriptions, and embodiments described herein are for illustrative purposes, are intended to be exemplary, and should not be construed as limiting the present disclosure. It will be clear to one skilled in the art that various modifications or changes to the examples, descriptions, and embodiments described herein can be made and are to be included within the spirit and purview of this disclosure and the appended claims. Further, one of skill in the art will recognize a number of equivalent methods and procedures to those described herein. All such equivalents are to be understood to be within the scope of the present disclosure and are covered by the appended claims.

Additional embodiments of the invention are set forth in the following claims.

The disclosures of all publications, patent applications, patents, or other documents mentioned herein are expressly incorporated by reference in their entirety for all purposes to the same extent as if each such individual publication, patent, patent application or other document were individually specifically indicated to be incorporated by reference herein in its entirety for all purposes and were set forth in its entirety herein. In case of conflict, the present specification, including specified terms, will control.

BIBLIOGRAPHY

1. Almagro, J. C. and J. Fransson, "Humanization of antibodies." *Front Biosci*, 2008. 13: 1619-33 (2008).
2. Baca, M., et al., "Antibody humanization using monovalent phage display." *J Biol Chem*, 272(16): 10678-84 (1997).
3. Baker et al., "Rapid monitoring of recombinant protein products: a comparison of current technologies." *Trends Biotechnol.*, 20:149-156 (2002).
4. Bassoy, et al., "Regulation and function of interleukin-36 cytokines." *Immunol. Rev.* 281(1): 169-178 (2018).
5. Binz et al., "Engineering novel binding proteins from nonimmunoglobulin domains." *Nat. Biotech.*, 23(10): 1257-1268 (2005).
6. Boerner, P., et al., "Production of antigen-specific human monoclonal antibodies from in vitro-primed human splenocytes."*J Immunol*, 1991. 147(1): 86-95 (1991).
7. Brennan, M., P. F. Davison, and H. Paulus, "Preparation of bispecific antibodies by chemical recombination of monoclonal immunoglobulin G1 fragments." *Science*, 229(4708): p. 81-3 (1985).
8. Brenner et al., "*Encoded combinatorial chemistry.*" *Proc. Natl. Acad. Sci. USA*, 89(12): 5381-5383 (1992).
9. Bruggemann, M. et al., "Comparison of the effector functions of human immunoglobulins using a matched set of chimeric antibodies." *J. Exp. Med.*, 166: 1351-1361 (1987).
10. Capel, P. J. et al., "Heterogeneity of human IgG Fc receptors." *Immunomethods* 4, 25-34 (1994).
11. Carter, P., et al., "Humanization of an anti-p185HER2 antibody for human cancer therapy." *Proc Natl Acad Sci USA*, 89(10): p. 4285-9 (1992).
12. Clackson, T., et al., "Making antibody fragments using phage display libraries." *Nature*, 352(6336): 624-8 (1991).
13. Clynes et al., "Fc receptors are required in passive and active immunity to melanoma." *Proc. Nat'l Acad. Sci. USA*, 95:652-656 (1998).
14. Cragg, M. S. and Glennie M. J., "Antibody specificity controls in vivo effector mechanisms of anti-CD20 reagents," *Blood*, 103(7): 2738-43 (2004).
15. Cragg, M. S. et al., "Complement-mediated lysis by anti-CD20 mAb correlates with segregation into lipid rafts," *Blood*, 101(3): 1045-53 (2003).
16. Cunningham, B. C. and J. A. Wells, "High-resolution epitope mapping of hGH-receptor interactions by alanine-scanning mutagenesis." *Science*, 1989. 244(4908): 1081-5 (1989).
17. D'Argenio et al., *ADAPT 5 User's Guide: Pharmacokinetic/Pharmacodynamic Systems Analysis Software*. Biomedical Simulations Resource, Los Angeles, CA (2009).
18. Daeron, M. "Fc receptor biology." *Annu Rev Immunol* 15, 203-234 (1997).
19. Dall' Acqua et al., "Increasing the Affinity of a Human IgG1 for the Neonatal Fc Receptor: Biological Consequences," *J Immunol*, 169(9), 5171-5180 (2002). https://doi.org/10.4049/jimmunol.169.9.5171
20. Dall'Acqua, W. F., et al., "Antibody humanization by framework shuffling." *Methods*, 36(1): p. 43-60 (2005).

21. de Haas, M. et al., "Fc gamma receptors of phagocytes." *J Lab Clin Med* 126, 330-341 (1995).
22. Ding et al., "IL-36 cytokines in autoimmunity and inflammatory disease." *Oncotarget*, 9(2), 2895-2901 (2017). https://doi.org/10.18632/oncotarget.22814
23. Fellouse, F. A., C. Wiesmann, and S. S. Sidhu, "Synthetic antibodies from a four-amino-acid code: a dominant role for tyrosine in antigen recognition." *Proc Natl Acad Sci USA*, 101(34): p. 12467-72 (2004).
24. Fiedler et al., "Non-Antibody Scaffolds as Alternative Therapeutic Agents," in Handbook of Therapeutic Antibodies (eds. S. Dübel and J. M. Reichert), Wiley-VCH Verlag GmbH & Co (2014).
25. Flatman, S. et al., "Process analytics for purification of monoclonal antibodies." *Journal of chromatography. B, Analytical technologies in the biomedical and life sciences* 848, 79-87 (2007).
26. Foote et al., "Antibody framework residues affecting the conformation of the hypervariable loops." *J. Mol. Biol.,* 224: 487-499 (1992).
27. Gabrielsson et al., "Modeling and design of challenge tests: Inflammatory and metabolic biomarker study examples," *European Journal of Pharmaceutical Sciences: Official Journal of the European Federation for Pharmaceutical Sciences*, 67, 144-159 (2015). https://doi.org/10.1016/j.ejps.2014.11.006
28. Garlanda et al., "The interleukin-1 family: back to the future." *Immunity* 39(6): 1003-1018 (2013).
29. Gazzano-Santoro et al., "A non-reactive complement-dependent cytotoxicity assay for anti-CD20 monoclonal antibody." *J. Immunol. Methods*, 202(2): 163-171 (1997).
30. Gebauer et al., "Engineered protein scaffolds as next-geneartion antibody therapeutics." *Curr. Opin. Chem. Biol.*, 13:245-255 (2009)
31. Gerngross, "*Advances in the production of human therapeutic proteins in yeasts and filamentous fungi.*" *Nat. Biotech.*, 22: 1409-1414 (2004).
32. Graham et al., "Characteristics of a human cell line transformed by DNA from human adenovirus type 5." *J. Gen Virol.*, 36:59 (1977).
33. Granzin et al., "Shaping of Natural Killer Cell Antitumor Activity by Ex Vivo Cultivation." *Front. Immunol.* 8: 458 (2017).
34. Gruber, M., et al., "Efficient tumor cell lysis mediated by a bispecific single chain antibody expressed in *Escherichia coli.*" *J Immunol*, 152(11): p. 5368-74 (1994).
35. Günther et al., "IL-1 family cytokines use distinct molecular mechanisms to signal through their shared co-receptor," *Immunity*, 47(3), 510-523. e4 (2017). https://doi.org/10.1016/j.immuni.2017.08.004
36. Gunther, S., and E. J. Sundberg, "Molecular determinants of agonist and antagonist signaling through the IL-36 receptor." *J Immunol* 193, 921-930 (2014).
37. Guyer, R. L. et al., "Immunoglobulin binding by mouse intestinal epithelial cell receptors." *J Immunol* 117, 587-593 (1976).
38. Hass et al., (2016). PCT publication no. WO2016077381A1.
39. Hellstrom, et al., "Strong antitumor activities of IgG3 antibodies to a human melanoma-associated ganglioside." *Proc. Nat'l Acad. Sci. USA*, 82: 1499-1502 (1985).
40. Hellstrom, et al., "Antitumor effects of L6, an IgG2a antibody that reacts with most human carcinomas." *Proc. Nat'l Acad. Sci. USA*, 83:7059-7063 (1986).
41. Holliger, P., T. Prospero, and G. Winter, "'Diabodies': small bivalent and bispecific antibody fragments." *Proc Natl Acad Sci USA*, 90(14): p. 6444-8 (1993).
42. Hoogenboom et al., *Methods in Molecular Biology*, 178: 1-37 (O'Brien et al., ed., *Antibody Phage Display*, Humana Press, Totowa, NJ, (2001).
43. Hotzel et al., "A strategy for risk mitigation of antibodies with fast clearance." *mAbs*, 4(6): 753-760 (2012).
44. Hudson, P. J. and C. Souriau, "Engineered antibodies." *Nat Med*, 9(1): p. 129-34 (2003).
45. Idusogie et al., "Mapping of the C1q binding site on rituxan, a chimeric antibody with a human IgG1 Fc." *J. Immunol.*, 164: 4178-4184 (2000).
46. Kabat, E. A. (Bethesda, Md. (Bethesda, 20892): U.S. Dept. of Health and Human Services, Public Health Service, National Institutes of Health, 1991., 2019).
47. Kakkar et al., "The IL-33/ST2 pathway: therapeutic target and novel biomarker," *Nature Reviews. Drug Discovery*, 7(10), 827-840 (2008). https://doi.org/10.1038/nrd2660.
48. Kanda, Y. et al., "Comparison of cell clines for stable production of fucose-negative antibodies with enhanced ADCC." *Biotechnol. Bioeng.*, 94(4):680-688 (2006).
49. Kashmiri, S. V., et al., "SDR grafting—a new approach to antibody humanization." *Methods*, 36(1): p. 25-34 (2005).
50. Kim et al.,"Role for NLRP3 Inflammasome-mediated, IL-1β-Dependent Responses in Severe, Steroid-Resistant Asthma," *American Journal of Respiratory and Critical Care Medicine*, 196(3), 283-297 (2017). https://doi.org/10.1164/rccm.201609-1830OC
51. Kim et al., "Localization of the site of murine IgG1 molecule that is involved in binding to the murine intestinal Fc receptor," *Eur. J. Immunol.*, 24:2429-2434 (1994)
52. Klimka, A., et al., "Human anti-CD30 recombinant antibodies by guided phage antibody selection using cell panning." *Br J Cancer*, 83(2): p. 252-60 (2000).
53. Koenig et al., *J. Biol. Chem.* 290(36): 21773-21786 (2015).
54. Komai-Koma et al., "Interleukin-33 promoting Th1 lymphocyte differentiation dependents on IL-12," *Immunobiology*, 221(3), 412-417 (2016). https://doi.org/10.1016/j.imbio.2015.11.013
55. Kostelny, S. A., M. S. Cole, and J. Y. Tso, "Formation of a bispecific antibody by the use of leucine zippers." *J Immunol*, 148(5): p. 1547-53 (1992).
56. Kozbor, D., et al., "A human hybrid myeloma for production of human monoclonal antibodies." *J Immunol*, 133(6): p. 3001-5 (1984).
57. Kuby Immunology.—NLM Catalog—NCBI, (available at https://www.ncbi.nlm.nih.gov/nlmcatalog/101275636).
58. Kunkel et al., "Rapid and efficient site-specific mutagenesis without phenotypic selection." *Methods Enzymol.*, 154: 367-382 (1987).
59. Kuo et al., "Neonatal Fc receptor and IgG-based therapeutics," *MAbs*, 3(5), 422-430 (2011). https://doi.org/10.4161/mabs.3.5.16983
60. Lambrecht et al., "The airway epithelium in asthma." *Nat. Med.* 18(5): 684-692 (2012).
61. Lee, C. V., et al., "High-affinity human antibodies from phage-displayed synthetic Fab libraries with a single framework scaffold." *J Mol Biol*, 340(5): p. 1073-93 (2004).
62. Lee, C. V., S. S. Sidhu, and G. Fuh, "Bivalent antibody phage display mimics natural immunoglobulin." *J Immunol Methods*, 284(1-2): p. 119-32 (2004).
63. Li et al., "Optimization of humanized IgGs in glycoengineered *Pichia pastoris.*" *Nat. Biotech.*, 24(2):210-215 (2006).

64. Li, J., et al., "Human antibodies for immunotherapy development generated via a human B cell hybridoma technology." *Proc Natl Acad Sci USA*, 103(10): p. 3557-62 (2006).
65. Liew et al., (2016). "Interleukin-33 in health and disease." *Nat. Rev. Immunol.* 16(11): 676-689 (2016).
66. Lonberg, N., "Fully human antibodies from transgenic mouse and phage display platforms." *Curr Opin Immunol*, 20(4): p. 450-9 (2008).
67. Lonberg, N., "Human antibodies from transgenic animals." *Nat Biotechnol*, 23(9): p. 1117-25 (2005).
68. Mather, "Establishment and characterization of two distinct mouse testicular epithelial cell lines." *Biol. Reprod.*, 23:243-252 (1980).
69. Mather et al., "Culture of testicular cells in hormone-supplemented serum-free medium." *Annals N.Y. Acad. Sci.*, 383:44-68 (1982).
70. Marks and Bradbury, *Methods in Molecular Biology*, 248: 161-175 (Lo, ed., *Antibody Engineering*, Humana Press, Totowa, NJ, 2003).
71. Masella et al., "PANDAseq: paired-end assembler for illumina sequences." *BMC Bioinformatics*, 13:31 (2012).
72. McCafferty, J., et al., "Phage antibodies: filamentous phage displaying antibody variable domains."*Nature*, 348 (6301): p. 552-4 (1990).
73. Nials et al., "Mouse models of allergic asthma: Acute and chronic allergen challenge." *Disease Models & Mechanisms*, 1(4-5), 213-220 (2008). https://doi.org/10.1242/dmm.000323
74. Nold-Petry et al., "Increased Cytokine Production in Interleukin-18 Receptor α-deficient Cells Is Associated with Dysregulation of Suppressors of Cytokine Signaling," *Journal of Biological Chemistry*, 284(38), 25900-25911 (2009). https://doi.org/10.1074/jbc.M109.004184
75. Nowarski et al., "The Stromal Intervention: Regulation of Immunity and Inflammation at the Epithelial-Mesenchymal Barrier." *Cell* 168(3): 362-375 (2017).
76. Okazaki et al., "Fucose depletion from human IgG1 oligosaccharide enhances binding enthalpy and association rate between IgG1 and Fc-γ-RIIIa." *J. Mol. Biol.*, 336: 1239-1249 (2004).
77. Osbourn, J., M. Groves, and T. Vaughan, "From rodent reagents to human therapeutics using antibody guided selection." *Methods*, 36(1): p. 61-8 (2005).
78. Padlan, E. A., "A possible procedure for reducing the immunogenicity of antibody variable domains while preserving their ligand-binding properties." *Mol Immunol*, 1991. 28(4-5): p. 489-98 (1991).
79. Petkova, et al., "Enhanced half-life of genetically engineered human IgG1 antibodies in a humanized FcRn mouse model: potential application in humorally mediated autoimmune disease." *Intl. Immunol.*, 18(12): 1759-1769 (2006).
80. Piyadasa et al., (2016). "Biosignature for airway inflammation in a house dust mite-challenged murine model of allergic asthma," *Biology Open*, 5(2), 112-121 (2016). https://doi.org/10.1242/bio.014464
81. Portolano, S., et al., "Lack of promiscuity in autoantigen-specific H and L chain combinations as revealed by human H and L chain 'roulette'." *J Immunol*, 150(3): p. 880-7 (1993).
82. Presta, L. G., et al., "Humanization of an antibody directed against IgE." *J Immunol*, 151(5): p. 2623-32 (1993).
83. Queen, C., et al., "A humanized antibody that binds to the interleukin 2 receptor." *Proc Natl Acad Sci USA*, 86(24): p. 10029-33 (1989).
84. Ramadas, et al., "IL-36α exerts pro-inflammatory effects in the lungs of mice." *PloS One*, 7(9), e45784 (2012). https://doi.org/10.1371/journal.pone.0045784
85. Ravetch, J. V. and J. P. Kinet, "Fc receptors." *Annu Rev Immunol* 9, 457-492 (1991).
86. Riechmann, L., et al., "Reshaping human antibodies for therapy." *Nature*, 332(6162): p. 323-7 (1988).
87. Ripka et al., "Two Chinese hamster ovary glycosylation mutants affected in the conversion of GDP-mannose to GDP-fucose." *Arch. Biochem. Biophys.*, 249:533-545 (1986).
88. Roopenian et al., "FcRn: the neonatal Fc receptor comes of age," *Nature Reviews Immunology*, 7(9), 715-725 (2007). https://doi.org/10.1038/nri2155
89. Rosok, M. J., et al., "A combinatorial library strategy for the rapid humanization of anticarcinoma BR96 Fab." *J Biol Chem*, 271(37): p. 22611-8 (1996).
90. Saluja et al., "The role of IL-33 and mast cells in allergy and inflammation." *Clin. Transl. Allergy* 5: 33 (2015).
91. Schwartz et al., "Basophils in inflammation," *European Journal of Pharmacology*, 778, 90-95 (2016). https://doi.org/10.1016/j.ejphar.2015.04.049
92. Shields et al., "High resolution mapping of the binding site on human IgG1 for Fc gamma RI, Fc Gamma RII, Fc gamma RIII, and FcRn and design of IgG1 variants with improved binding to the Fc gamma R." *J. Biol. Chem.*, 276(9): 6591-6604 (2001).
93. Sidhu, S. S., et al., "Phage-displayed antibody libraries of synthetic heavy chain complementarity determining regions." *J Mol Biol*, 338(2): p. 299-310 (2004).
94. Sims et al., "The IL-1 family: regulators of immunity." *Nat. Rev. Immunol.* 10(2): 89-102 (2010).
95. Sims, M. J., et al., "A humanized CD18 antibody can block function without cell destruction." *J Immunol*, 151(4): p. 2296-308 (1993).
96. Smeets et al., "Soluble interleukin-1 receptor accessory protein ameliorates collagen-induced arthritis by a different mode of action from that of interleukin-1 receptor antagonist," *Arthritis and Rheumatism*, 52(7), 2202-2211 (2005). https://doi.org/10.1002/art.21108
97. Sola, (1987). *Monoclonal Antibodies: A Manual of Techniques*, pp. 147-158, CRC Press, Inc.
98. Suwara et al., "IL-1alpha released from damaged epithelial cells is sufficient and essential to trigger inflammatory responses in human lung fibroblasts." *Mucosal Immunol.* 7(3): 684-693 (2014).
99. Towne, J. E., et al., "Interleukin (IL)-1F6, IL-1F8, and IL-1F9 signal through IL-1Rrp2 and IL-1RAcP to activate the pathway leading to NF-kappaB and MAPKs." *J Biol Chem*, 279(14): p. 13677-88 (2004).
100. Traunecker et al., "Bispecific single chain molecules (Janusins) target cytotoxic lymphocytes on HIV infected cells," *EMBO J.*, 10(12):3655-9 (1991).
101. Tutt, A., G. T. Stevenson, and M. J. Glennie, "Trispecific F(ab')3 derivatives that use cooperative signaling via the TCR/CD3 complex and CD2 to activate and redirect resting cytotoxic T cells." *J Immunol*, 147(1): p. 60-9 (1991).
102. Urlaub et al., "Isolation of Chinese hamster cell mutants deficient in dihydrofolate reductase activity." *Proc. Natl. Acad. Sci. USA*, 77:4216 (1980).
103. van Dijk, M. A. and J. G. van de Winkel, "Human antibodies as next generation therapeutics." *Curr Opin Chem Biol*, 5(4): p. 368-74 (2001).
104. Vollmers, H. P. and S. Brandlein, "Death by stress: natural IgM-induced apoptosis." *Methods Find Exp Clin Pharmacol*, 27(3): p. 185-91 (2005).

105. Vollmers, H. P. and S. Brandlein, "The 'early birds:' natural IgM antibodies and immune surveillance." *Histol Histopathol*, 20(3): p. 927-37 (2005).
106. Wang et al., "Structural insights into the assembly and activation of IL-1β with its receptors." *Nat. Immunol.*, 11:905-912 (2010).
107. Wright et al., "Effect of glycosylation on antibody function: implications for genetic engineering." *TIBTECH*, 15:26-32 (1997).
108. Yamane-Ohnuki et al., "Establishment of FUT8 knockout Chinese hamster ovary cells: an ideal host cell line for producing completely defucosylated antibodies with enhanced antibody-dependent cellular cytotoxicity." *Biotech. Bioeng.* 87: 614 (2004).
109. Yazaki and Wu, *Methods in Molecular Biology*, Vol. 248 (B. K. C. Lo, ed., *Antibody Engineering*, Humana Press, Totowa, NJ), pp. 255-268 (2003).
110. Yi et al., "Structural and Functional Attributes of the Interleukin-36 Receptor." *The Journal of Biological Chemistry*, 291(32), 16597-16609 (2016). https://doi.org/10.1074/jbc. M116.723064
111. Zapata, G. et al., "Engineering linear F(ab')2 fragments for efficient production in Escherichia coli and enhanced antiproliferative activity." *Protein Eng* 8, 1057-1062 (1995).

What is claimed is:

1. A method of treating an IL1RAP mediated disease in a subject, wherein the IL1RAP mediated disease is asthma, comprising administering to the subject a therapeutically effective amount of an antibody, wherein the antibody comprises: (i) a first light chain hypervariable region (HVR-L1), a second light chain hypervariable region (HVR-L2), and a third light chain hypervariable region (HVR-L3), and (ii) a first heavy chain hypervariable region (HVR-H1), a second heavy chain hypervariable region (HVR-H2), and a third heavy chain hypervariable region (HVR-H3); wherein:
   (a) HVR-L1 comprises an amino acid sequence of SEQ ID NO: 11;
   (b) HVR-L2 comprises an amino acid sequence selected from SEQ ID NO: 37, and 54;
   (c) HVR-L3 comprises an amino acid sequence selected from SEQ ID NO: 63, 69, and 70;
   (d) HVR-H1 comprises an amino acid sequence of SEQ ID NO: 78;
   (e) HVR-H2 comprises an amino acid sequence selected from SEQ ID NO: 191, and 195;
   (f) HVR-H3 comprises an amino acid sequence selected from SEQ ID NO: 203 and 215.

2. The method of claim 1, wherein the antibody comprises:
   a first light chain framework region (FR-L1) comprising an amino acid sequence of SEQ ID NO: 244;
   a second light chain framework region (FR-L2) comprising an amino acid sequence of SEQ ID NO: 246;
   a third light chain framework region (FR-L3) comprising an amino acid sequence of SEQ ID NO: 247; and
   a fourth light chain framework region (FR-L4) comprising an amino acid sequence of SEQ ID NO: 248; or
   a first heavy chain framework region (FR-H1) comprising an amino acid sequence of SEQ ID NO: 253;
   a second heavy chain framework region (FR-H2) comprising an amino acid sequence of SEQ ID NO: 254;
   a third heavy chain framework region (FR-H3) comprising an amino acid sequence of SEQ ID NO: 255; and
   a fourth heavy chain framework region (FR-H4) comprising an amino acid of SEQ ID NO: 256.

3. The method of claim 1, wherein the antibody comprises a light chain variable domain ($V_L$) amino acid sequence having at least 90% identity to SEQ ID NO: 259; and/or a heavy chain variable domain ($V_H$) amino acid sequence having at least 90% identity to SEQ ID NO: 290.

4. The method of claim 3, wherein the antibody comprises:
   the light chain variable domain ($V_L$) amino acid sequence of SEQ ID NO: 259, and the heavy chain variable domain ($V_H$) amino acid sequence of SEQ ID NO: 290;
   the light chain variable domain ($V_L$) amino acid sequence of SEQ ID NO: 268, and the heavy chain variable domain ($V_H$) amino acid sequence of SEQ ID NO: 307;
   the light chain variable domain ($V_L$) amino acid sequence of SEQ ID NO: 268, and the heavy chain variable domain ($V_H$) amino acid sequence of SEQ ID NO: 298;
   the light chain variable domain ($V_L$) amino acid sequence of SEQ ID NO: 269, and the heavy chain variable domain ($V_H$) amino acid sequence of SEQ ID NO: 307;
   the light chain variable domain ($V_L$) amino acid sequence of SEQ ID NO: 269, and the heavy chain variable domain ($V_H$) amino acid sequence of SEQ ID NO: 298;
   the light chain variable domain ($V_L$) amino acid sequence of SEQ ID NO: 269, and the heavy chain variable domain ($V_H$) amino acid sequence of SEQ ID NO: 297;
   the light chain variable domain ($V_L$) amino acid sequence of SEQ ID NO: 270, and the heavy chain variable domain ($V_H$) amino acid sequence of SEQ ID NO: 307; or
   the light chain variable domain ($V_L$) amino acid sequence of SEQ ID NO: 270, and the heavy chain variable domain ($V_H$) amino acid sequence of SEQ ID NO: 298.

5. The method of claim 1, wherein the antibody comprises a light chain (LC) amino acid sequence having at least 90% identity to SEQ ID NO: 328; and/or a heavy chain (HC) amino acid sequence having at least 90% identity to SEQ ID NO: 332.

6. The method of claim 5, wherein the antibody comprises:
   the light chain (LC) amino acid sequence of SEQ ID NO: 328, and the heavy chain (HC) amino acid sequence of SEQ ID NO: 332;
   the light chain (LC) amino acid sequence of SEQ ID NO: 329, and the heavy chain (HC) amino acid sequence of SEQ ID NO: 335;
   the light chain (LC) amino acid sequence of SEQ ID NO: 329, and the heavy chain (HC) amino acid sequence of SEQ ID NO: 336;
   the light chain (LC) amino acid sequence of SEQ ID NO: 329, and the heavy chain (HC) amino acid sequence of SEQ ID NO: 333;
   the light chain (LC) amino acid sequence of SEQ ID NO: 329, and the heavy chain (HC) amino acid sequence of SEQ ID NO: 334;

the light chain (LC) amino acid sequence of SEQ ID NO: 330, and the heavy chain (HC) amino acid sequence of SEQ ID NO: 335;

the light chain (LC) amino acid sequence of SEQ ID NO: 330, and the heavy chain (HC) amino acid sequence of SEQ ID NO: 336;

the light chain (LC) amino acid sequence of SEQ ID NO: 330, and the heavy chain (HC) amino acid sequence of SEQ ID NO: 333;

the light chain (LC) amino acid sequence of SEQ ID NO: 330, and the heavy chain (HC) amino acid sequence of SEQ ID NO: 334;

the light chain (LC) amino acid sequence of SEQ ID NO: 331, and the heavy chain (HC) amino acid sequence of SEQ ID NO: 335;

the light chain (LC) amino acid sequence of SEQ ID NO: 331, and the heavy chain (HC) amino acid sequence of SEQ ID NO: 336;

the light chain (LC) amino acid sequence of SEQ ID NO: 331, and the heavy chain (HC) amino acid sequence of SEQ ID NO: 333; or the light chain (LC) amino acid sequence of SEQ ID NO: 331, and the heavy chain (HC) amino acid sequence of SEQ ID NO: 334.

7. The method of claim 1, wherein an IL-1 stimulated signal, an IL-33 stimulated signal, or an IL-36 stimulated signal in the subject is decreased by at least 90%.

8. The method of claim 1, wherein an intracellular signal initiated by one or more of IL-1α, IL-1β, IL-33, IL-36α, IL-36β, and IL-36γ agonist binding to its cognate receptor in the subject is decreased by at least 90%.

9. The method of claim 1, wherein the antibody specifically binds to one or more amino acid residues within domain 3 of human IL1RAP, wherein domain 3 comprises positions 238-367 of the amino acid sequence of SEQ ID NO: 1 or 3.

10. The method of claim 1, wherein the antibody does not bind to amino acid residues within domain 1 or domain 2 of human IL1RAP; optionally, wherein domain 1 and domain 2 comprise positions 21-237 of the amino acid sequence of SEQ ID NO: 1 or 3.

11. The method of claim 1, The antibody of claim 1, wherein the antibody cross-reacts with a cynomolgus monkey IL1RAP polypeptide of SEQ ID NO: 8.

12. The method of claim 1, wherein the antibody is a full-length antibody of class IgG; optionally, wherein the class IgG antibody has an isotype selected from IgG1, IgG2, IgG3, and IgG4.

13. The method of claim 1, wherein the antibody is an Fc region variant; optionally wherein the Fc region variant alters effector function or alters half-life.

14. The method of claim 13, wherein the Fc region variant comprises a set of YTE mutations.

15. The method of claim 13, wherein the Fc region variant decreases effector function.

16. The method of claim 1, wherein the antibody is formulated in a pharmaceutical composition comprising the antibody and a pharmaceutically acceptable carrier.

17. The method of claim 1, wherein the antibody is administered systemically.

18. The method of claim 1, wherein the antibody is administered at a dose of from about 1 pg/kg to about 15 mg/kg.

19. The method of claim 1, wherein the method further comprises administering to the subject a dose of up to about 100 mg/kg.

\* \* \* \* \*

SEQUENCE LISTING

```
<160> NUMBER OF SEQ ID NOS: 338

<210> SEQ ID NO 1
<211> LENGTH: 570
<212> TYPE: PRT
<213> ORGANISM: homo sapiens

<400> SEQUENCE: 1

Met Thr Leu Leu Trp Cys Val Val Ser Leu Tyr Phe Tyr Gly Ile Leu
1               5                   10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
```

| | | 275 | | | 280 | | | 285 | | | |
|---|---|---|---|---|---|---|---|---|---|---|---|

Pro Asp Asp Ile Thr Ile Asp Val Thr Ile Asn Glu Ser Ile Ser His
       290                       295                       300

Ser Arg Thr Glu Asp Glu Thr Arg Thr Gln Ile Leu Ser Ile Lys Lys
305                       310                     315                  320

Val Thr Ser Glu Asp Leu Lys Arg Ser Tyr Val Cys His Ala Arg Ser
                 325                     330                   335

Ala Lys Gly Glu Val Ala Lys Ala Ala Lys Val Lys Gln Lys Val Pro
            340                     345                   350

Ala Pro Arg Tyr Thr Val Glu Leu Ala Cys Gly Phe Gly Ala Thr Val
                 355                     360                   365

Leu Leu Val Val Ile Leu Ile Val Val Tyr His Val Tyr Trp Leu Glu
       370                     375                   380

Met Val Leu Phe Tyr Arg Ala His Phe Gly Thr Asp Glu Thr Ile Leu
385                       390                     395                  400

Asp Gly Lys Glu Tyr Asp Ile Tyr Val Ser Tyr Ala Arg Asn Ala Glu
                 405                     410                   415

Glu Glu Glu Phe Val Leu Leu Thr Leu Arg Gly Val Leu Glu Asn Glu
            420                     425                   430

Phe Gly Tyr Lys Leu Cys Ile Phe Asp Arg Asp Ser Leu Pro Gly Gly
                 435                     440                   445

Ile Val Thr Asp Glu Thr Leu Ser Phe Ile Gln Lys Ser Arg Arg Leu
       450                     455                   460

Leu Val Val Leu Ser Pro Asn Tyr Val Leu Gln Gly Thr Gln Ala Leu
465                       470                     475                  480

Leu Glu Leu Lys Ala Gly Leu Glu Asn Met Ala Ser Arg Gly Asn Ile
                 485                     490                   495

Asn Val Ile Leu Val Gln Tyr Lys Ala Val Lys Glu Thr Lys Val Lys
            500                     505                   510

Glu Leu Lys Arg Ala Lys Thr Val Leu Thr Val Ile Lys Trp Lys Gly
                 515                     520                   525

Glu Lys Ser Lys Tyr Pro Gln Gly Arg Phe Trp Lys Gln Leu Gln Val
       530                     535                   540

Ala Met Pro Val Lys Lys Ser Pro Arg Arg Ser Ser Ser Asp Glu Gln
545                       550                     555                  560

Gly Leu Ser Tyr Ser Ser Leu Lys Asn Val
                 565                     570

```
<210> SEQ ID NO 2
<211> LENGTH: 1740
<212> TYPE: DNA
<213> ORGANISM: homo sapiens

<400> SEQUENCE: 2
tctcaaagga tgacacttct gtggtgtgta gtgagtctct acttttatgg aatcctgcaa      60
agtgatgcct cagaacgctg cgatgactgg ggactagaca ccatgaggca aatccaagtg     120
tttgaagatg agccagctcg catcaagtgc ccactctttg aacacttctt gaaattcaac     180
tacagcacag cccattcagc tggccttact ctgatctggt attggactag caggaccgg      240 gaccttgagg agccaattaa cttccgcctc cccgagaacc gcattagtaa ggagaaagat     300
gtgctgtggt tccggcccac tctcctcaat gacactggca actatacctg catgttaagg     360
aacactacat attgcagcaa agttgcattt cccttggaag ttgttcaaaa agacagctgt     420
ttcaattccc ccatgaaact cccagtgcat aaactgtata tagaatatgg cattcagagg     480
```

```
atcacttgtc caaatgtaga tggatatttt ccttccagtg tcaaaccgac tatcacttgg    540
tatatgggct gttataaaat acagaatttt aataatgtaa tacccgaagg tatgaacttg    600
agtttcctca ttgccttaat ttcaaataat ggaaattaca catgtgttgt tacatatcca    660
gaaaatggac gtacgtttca tctcaccagg actctgactg taaaggtagt aggctctcca    720
aaaaatgcag tgcccctgt gatccattca cctaatgatc atgtggtcta tgagaaagaa    780
ccaggagagg agctactcat tccctgtacg gtctatttta gttttctgat ggattctcgc    840
aatgaggttt ggtggaccat tgatggaaaa aaacctgatg acatcactat tgatgtcacc    900
attaacgaaa gtataagtca tagtagaaca gaagatgaaa caagaactca gattttgagc    960
atcaagaaag ttacctctga ggatctcaag cgcagctatg tctgtcatgc tagaagtgcc   1020
aaaggcgaag ttgccaaagc agccaaggtg aagcagaaag tgccagctcc aagatacaca   1080
gtggaactgg cttgtggttt tggagccaca gtcctgctag tggtgattct cattgttgtt   1140
taccatgttt actggctaga gatggtccta ttttaccggg ctcattttgg aacagatgaa   1200
accattttag atggaaaaga gtatgatatt tatgtatcct atgcaaggaa tgcggaagaa   1260 gaagaattg tattactgac cctccgtgga gttttggaga tgaatttgg atacaagctg   1320 tgcatctttg accgagacag tctgcctggg ggaattgtca cagatgagac tttgagcttc   1380
attcagaaaa gcagacgcct cctggttgtt ctaagcccca actacgtgct ccagggaacc   1440
caagccctcc tggagctcaa ggctggccta gaaaatatgg cctctcgggg caacatcaac   1500
gtcattttag tacagtacaa agctgtgaag gaaacgaagg tgaaagagct gaagagggct   1560
aagacggtgc tcacggtcat taaatggaaa ggggaaaaat ccaagtatcc acagggcagg   1620
ttctggaagc agctgcaggt ggccatgcca gtgaagaaaa gtcccaggcg gtctagcagt   1680
gatgagcagg gcctctcgta ttcatctttg aaaaatgtat gaaggaata atgaaaagga   1740
```

<210> SEQ ID NO 3
<211> LENGTH: 347
<212> TYPE: PRT
<213> ORGANISM: artificial
<220> FEATURE:
<223> OTHER INFORMATION: synthetic polypeptide

<400> SEQUENCE: 3

```
Ser Glu Arg Cys Asp Asp Trp Gly Leu Asp Thr Met Arg Gln Ile Gln
1               5                   10                  15

Val Phe Glu Asp Glu Pro Ala Arg Ile Lys Cys Pro Leu Phe Glu His
                20                  25                  30

Phe Leu Lys Phe Asn Tyr Ser Thr Ala His Ser Ala Gly Leu Thr Leu
            35                  40                  45

Ile Trp Tyr Trp Thr Arg Gln Asp Arg Asp Leu Glu Glu Pro Ile Asn
        50                  55                  60

Phe Arg Leu Pro Glu Asn Arg Ile Ser Lys Glu Lys Asp Val Leu Trp
65                  70                  75                  80

Phe Arg Pro Thr Leu Leu Asn Asp Thr Gly Asn Tyr Thr Cys Met Leu
                85                  90                  95

Arg Asn Thr Thr Tyr Cys Ser Lys Val Ala Phe Pro Leu Glu Val Val
                100                 105                 110

Gln Lys Asp Ser Cys Phe Asn Ser Pro Met Lys Leu Pro Val His Lys
            115                 120                 125

Leu Tyr Ile Glu Tyr Gly Ile Gln Arg Ile Thr Cys Pro Asn Val Asp
        130                 135                 140
```

```
Gly Tyr Phe Pro Ser Ser Val Lys Pro Thr Ile Thr Trp Tyr Met Gly
145                 150                 155                 160

Cys Tyr Lys Ile Gln Asn Phe Asn Asn Val Ile Pro Glu Gly Met Asn
                165                 170                 175

Leu Ser Phe Leu Ile Ala Leu Ile Ser Asn Asn Gly Asn Tyr Thr Cys
            180                 185                 190

Val Val Thr Tyr Pro Glu Asn Gly Arg Thr Phe His Leu Thr Arg Thr
        195                 200                 205

Leu Thr Val Lys Val Val Gly Ser Pro Lys Asn Ala Val Pro Pro Val
    210                 215                 220

Ile His Ser Pro Asn Asp His Val Val Tyr Glu Lys Glu Pro Gly Glu
225                 230                 235                 240

Glu Leu Leu Ile Pro Cys Thr Val Tyr Phe Ser Phe Leu Met Asp Ser
                245                 250                 255

Arg Asn Glu Val Trp Trp Thr Ile Asp Gly Lys Lys Pro Asp Asp Ile
                260                 265                 270

Thr Ile Asp Val Thr Ile Asn Glu Ser Ile Ser His Ser Arg Thr Glu
            275                 280                 285

Asp Glu Thr Arg Thr Gln Ile Leu Ser Ile Lys Lys Val Thr Ser Glu
        290                 295                 300

Asp Leu Lys Arg Ser Tyr Val Cys His Ala Arg Ser Ala Lys Gly Glu
305                 310                 315                 320

Val Ala Lys Ala Ala Lys Val Lys Gln Lys Val Pro Ala Pro Arg Tyr
                325                 330                 335

Thr Val Glu Leu Ala Cys Gly Phe Gly Ala Thr
            340                 345

<210> SEQ ID NO 4
<211> LENGTH: 113
<212> TYPE: PRT
<213> ORGANISM: artificial
<220> FEATURE:
<223> OTHER INFORMATION: synthetic polypeptide

<400> SEQUENCE: 4

Ser Glu Arg Cys Asp Asp Trp Gly Leu Asp Thr Met Arg Gln Ile Gln
1               5                   10                  15

Val Phe Glu Asp Glu Pro Ala Arg Ile Lys Cys Pro Leu Phe Glu His
                20                  25                  30

Phe Leu Lys Phe Asn Tyr Ser Thr Ala His Ser Ala Gly Leu Thr Leu
            35                  40                  45

Ile Trp Tyr Trp Thr Arg Gln Asp Arg Asp Leu Glu Glu Pro Ile Asn
    50                  55                  60

Phe Arg Leu Pro Glu Asn Arg Ile Ser Lys Glu Lys Asp Val Leu Trp
65                  70                  75                  80

Phe Arg Pro Thr Leu Leu Asn Asp Thr Gly Asn Tyr Thr Cys Met Leu
                85                  90                  95

Arg Asn Thr Thr Tyr Cys Ser Lys Val Ala Phe Pro Leu Glu Val Val
                100                 105                 110

Gln

<210> SEQ ID NO 5
<211> LENGTH: 217
<212> TYPE: PRT
<213> ORGANISM: artificial
<220> FEATURE:
```

<223> OTHER INFORMATION: synthetic polypeptide

<400> SEQUENCE: 5

Ser Glu Arg Cys Asp Asp Trp Gly Leu Asp Thr Met Arg Gln Ile Gln
1               5                   10                  15

Val Phe Glu Asp Glu Pro Ala Arg Ile Lys Cys Pro Leu Phe Glu His
            20                  25                  30

Phe Leu Lys Phe Asn Tyr Ser Thr Ala His Ser Ala Gly Leu Thr Leu
        35                  40                  45

Ile Trp Tyr Trp Thr Arg Gln Asp Arg Asp Leu Glu Glu Pro Ile Asn
50                  55                  60

Phe Arg Leu Pro Glu Asn Arg Ile Ser Lys Glu Lys Asp Val Leu Trp
65                  70                  75                  80

Phe Arg Pro Thr Leu Leu Asn Asp Thr Gly Asn Tyr Thr Cys Met Leu
            85                  90                  95

Arg Asn Thr Thr Tyr Cys Ser Lys Val Ala Phe Pro Leu Glu Val Val
            100                 105                 110

Gln Lys Asp Ser Cys Phe Asn Ser Pro Met Lys Leu Pro Val His Lys
        115                 120                 125

Leu Tyr Ile Glu Tyr Gly Ile Gln Arg Ile Thr Cys Pro Asn Val Asp
    130                 135                 140

Gly Tyr Phe Pro Ser Ser Val Lys Pro Thr Ile Thr Trp Tyr Met Gly
145                 150                 155                 160

Cys Tyr Lys Ile Gln Asn Phe Asn Asn Val Ile Pro Glu Gly Met Asn
            165                 170                 175

Leu Ser Phe Leu Ile Ala Leu Ile Ser Asn Asn Gly Asn Tyr Thr Cys
            180                 185                 190

Val Val Thr Tyr Pro Glu Asn Gly Arg Thr Phe His Leu Thr Arg Thr
        195                 200                 205

Leu Thr Val Lys Val Val Gly Ser Pro
    210                 215

<210> SEQ ID NO 6
<211> LENGTH: 130
<212> TYPE: PRT
<213> ORGANISM: artificial
<220> FEATURE:
<223> OTHER INFORMATION: synthetic polypeptide

<400> SEQUENCE: 6

Lys Asn Ala Val Pro Pro Val Ile His Ser Pro Asn Asp His Val Val
1               5                   10                  15

Tyr Glu Lys Glu Pro Gly Glu Glu Leu Leu Ile Pro Cys Thr Val Tyr
            20                  25                  30

Phe Ser Phe Leu Met Asp Ser Arg Asn Glu Val Trp Trp Thr Ile Asp
        35                  40                  45

Gly Lys Lys Pro Asp Asp Ile Thr Ile Asp Val Thr Ile Asn Glu Ser
50                  55                  60

Ile Ser His Ser Arg Thr Glu Asp Glu Thr Arg Thr Gln Ile Leu Ser
65                  70                  75                  80

Ile Lys Lys Val Thr Ser Glu Asp Leu Lys Arg Ser Tyr Val Cys His
            85                  90                  95

Ala Arg Ser Ala Lys Gly Glu Val Ala Lys Ala Ala Lys Val Lys Gln
            100                 105                 110

Lys Val Pro Ala Pro Arg Tyr Thr Val Glu Leu Ala Cys Gly Phe Gly
        115                 120                 125

Ala Thr
    130

<210> SEQ ID NO 7
<211> LENGTH: 336
<212> TYPE: PRT
<213> ORGANISM: artificial
<220> FEATURE:
<223> OTHER INFORMATION: synthetic polypeptide

<400> SEQUENCE: 7

Ser Glu Arg Cys Asp Asp Trp Gly Leu Asp Thr Met Arg Gln Ile Gln
1               5                   10                  15

Val Phe Glu Asp Glu Pro Ala Arg Ile Lys Cys Pro Leu Phe Glu His
            20                  25                  30

Phe Leu Lys Phe Asn Tyr Ser Thr Ala His Ser Ala Gly Leu Thr Leu
        35                  40                  45

Ile Trp Tyr Trp Thr Arg Gln Asp Arg Asp Leu Glu Glu Pro Ile Asn
    50                  55                  60

Phe Arg Leu Pro Glu Asn Arg Ile Ser Lys Glu Lys Asp Val Leu Trp
65                  70                  75                  80

Phe Arg Pro Thr Leu Leu Asn Asp Thr Gly Asn Tyr Thr Cys Met Leu
                85                  90                  95

Arg Asn Thr Thr Tyr Cys Ser Lys Val Ala Phe Pro Leu Glu Val Val
            100                 105                 110

Gln Lys Asp Ser Cys Phe Asn Ser Pro Met Lys Leu Pro Val His Lys
        115                 120                 125

Leu Tyr Ile Glu Tyr Gly Ile Gln Arg Ile Thr Cys Pro Asn Val Asp
    130                 135                 140

Gly Tyr Phe Pro Ser Ser Val Lys Pro Thr Ile Thr Trp Tyr Met Gly
145                 150                 155                 160

Cys Tyr Lys Ile Gln Asn Phe Asn Asn Val Ile Pro Glu Gly Met Asn
                165                 170                 175

Leu Ser Phe Leu Ile Ala Leu Ile Ser Asn Asn Gly Asn Tyr Thr Cys
            180                 185                 190

Val Val Thr Tyr Pro Glu Asn Gly Arg Thr Phe His Leu Thr Arg Thr
        195                 200                 205

Leu Thr Val Lys Val Val Gly Ser Pro Lys Asn Ala Val Pro Pro Val
    210                 215                 220

Ile His Ser Pro Asn Asp His Val Val Tyr Glu Lys Glu Pro Gly Glu
225                 230                 235                 240

Glu Leu Leu Ile Pro Cys Thr Val Tyr Phe Ser Phe Leu Met Asp Ser
                245                 250                 255

Arg Asn Glu Val Trp Trp Thr Ile Asp Gly Lys Lys Pro Asp Asp Ile
            260                 265                 270

Thr Ile Asp Val Thr Ile Asn Glu Ser Ile Ser His Ser Arg Thr Glu
        275                 280                 285

Asp Glu Thr Arg Thr Gln Ile Leu Ser Ile Lys Lys Val Thr Ser Glu
    290                 295                 300

Asp Leu Lys Arg Ser Tyr Val Cys His Ala Arg Ser Ala Lys Gly Glu
305                 310                 315                 320

Val Ala Lys Ala Ala Lys Val Lys Gln Lys Gly Asn Arg Cys Gly Gln
                325                 330                 335

<210> SEQ ID NO 8

```
<211> LENGTH: 347
<212> TYPE: PRT
<213> ORGANISM: artificial
<220> FEATURE:
<223> OTHER INFORMATION: synthetic polypeptide

<400> SEQUENCE: 8

Ser Glu Arg Cys Asp Asp Trp Gly Leu Asp Thr Met Arg Gln Ile Gln
1               5                   10                  15

Val Phe Glu Asp Glu Pro Ala Arg Ile Lys Cys Pro Leu Phe Glu His
            20                  25                  30

Phe Leu Lys Phe Asn Tyr Ser Thr Ala His Ser Ala Gly Leu Thr Leu
        35                  40                  45

Ile Trp Tyr Trp Thr Arg Gln Asp Arg Asp Leu Glu Glu Pro Ile Asn
50                  55                  60

Phe Arg Leu Pro Glu Asn Arg Ile Ser Lys Glu Lys Asp Val Leu Trp
65                  70                  75                  80

Phe Arg Pro Thr Leu Leu Asn Asp Thr Gly Asn Tyr Thr Cys Met Leu
            85                  90                  95

Arg Asn Thr Thr Tyr Cys Ser Lys Val Ala Phe Pro Leu Glu Val Val
            100                 105                 110

Gln Lys Asp Ser Cys Phe Asn Ser Pro Met Lys Leu Pro Val His Lys
        115                 120                 125

Leu Tyr Ile Glu Tyr Gly Ile Gln Arg Ile Thr Cys Pro Asn Val Asp
130                 135                 140

Gly Tyr Phe Pro Ser Ser Val Lys Pro Thr Ile Thr Trp Tyr Met Gly
145                 150                 155                 160

Cys Tyr Lys Ile Gln Asn Phe Asn Asn Val Ile Pro Glu Gly Met Asn
            165                 170                 175

Leu Ser Phe Leu Ile Ala Phe Ile Ser Asn Asn Gly Asn Tyr Thr Cys
            180                 185                 190

Val Val Thr Tyr Pro Glu Asn Gly Arg Thr Phe His Leu Thr Arg Thr
        195                 200                 205

Leu Thr Val Lys Val Val Gly Ser Pro Lys Asn Ala Val Pro Pro Val
210                 215                 220

Ile His Ser Pro Asn Asp His Val Val Tyr Glu Lys Glu Pro Gly Glu
225                 230                 235                 240

Glu Leu Leu Ile Pro Cys Thr Val Tyr Phe Ser Phe Leu Met Asp Ser
            245                 250                 255

Arg Asn Glu Val Trp Trp Thr Ile Asp Gly Lys Lys Pro Asp Asp Ile
            260                 265                 270

Pro Ile Asp Val Thr Ile Asn Glu Ser Ile Ser His Ser Arg Thr Glu
        275                 280                 285

Asp Glu Thr Arg Thr Gln Ile Leu Ser Ile Lys Lys Val Thr Ser Glu
290                 295                 300

Asp Leu Lys Arg Ser Tyr Val Cys His Ala Arg Ser Ala Lys Gly Glu
305                 310                 315                 320

Val Ala Lys Ala Ala Thr Val Lys Gln Lys Val Pro Ala Pro Arg Tyr
            325                 330                 335

Thr Val Glu Leu Ala Cys Gly Phe Gly Ala Thr
            340                 345

<210> SEQ ID NO 9
<211> LENGTH: 347
<212> TYPE: PRT
<213> ORGANISM: artificial
```

<220> FEATURE:
<223> OTHER INFORMATION: synthetic polypeptide

<400> SEQUENCE: 9

Ser Glu Arg Cys Asp Asp Trp Gly Leu Asp Thr Met Arg Gln Ile Gln
1               5                   10                  15

Val Phe Glu Asp Glu Pro Ala Arg Ile Lys Cys Pro Leu Phe Glu His
            20                  25                  30

Phe Leu Lys Tyr Asn Tyr Ser Thr Ala His Ser Ser Gly Leu Thr Leu
        35                  40                  45

Ile Trp Tyr Trp Thr Arg Gln Asp Arg Asp Leu Glu Glu Pro Ile Asn
    50                  55                  60

Phe Arg Leu Pro Glu Asn Arg Ile Ser Lys Glu Lys Asp Val Leu Trp
65                  70                  75                  80

Phe Arg Pro Thr Leu Leu Asn Asp Thr Gly Asn Tyr Thr Cys Met Leu
                85                  90                  95

Arg Asn Thr Thr Tyr Cys Ser Lys Val Ala Phe Pro Leu Glu Val Val
            100                 105                 110

Gln Lys Asp Ser Cys Phe Asn Ser Ala Met Arg Phe Pro Val His Lys
        115                 120                 125

Met Tyr Ile Glu His Gly Ile His Lys Ile Thr Cys Pro Asn Val Asp
    130                 135                 140

Gly Tyr Phe Pro Ser Ser Val Lys Pro Ser Val Thr Trp Tyr Lys Gly
145                 150                 155                 160

Cys Thr Glu Ile Val Asp Phe His Asn Val Leu Pro Glu Gly Met Asn
                165                 170                 175

Leu Ser Phe Phe Ile Pro Leu Val Ser Asn Asn Gly Asn Tyr Thr Cys
            180                 185                 190

Val Val Thr Tyr Pro Glu Asn Gly Arg Leu Phe His Leu Thr Arg Thr
        195                 200                 205

Val Thr Val Lys Val Val Gly Ser Pro Lys Asp Ala Leu Pro Pro Gln
    210                 215                 220

Ile Tyr Ser Pro Asn Asp Arg Val Val Tyr Glu Lys Glu Pro Gly Glu
225                 230                 235                 240

Glu Leu Val Ile Pro Cys Lys Val Tyr Phe Ser Phe Ile Met Asp Ser
                245                 250                 255

His Asn Glu Val Trp Trp Thr Ile Asp Gly Lys Lys Pro Asp Asp Val
            260                 265                 270

Thr Val Asp Ile Thr Ile Asn Glu Ser Val Ser Tyr Ser Ser Thr Glu
        275                 280                 285

Asp Glu Thr Arg Thr Gln Ile Leu Ser Ile Lys Lys Val Thr Pro Glu
    290                 295                 300

Asp Leu Arg Arg Asn Tyr Val Cys His Ala Arg Asn Thr Lys Gly Glu
305                 310                 315                 320

Ala Glu Gln Ala Ala Lys Val Lys Gln Lys Val Ile Pro Pro Arg Tyr
                325                 330                 335

Thr Val Glu Leu Ala Cys Gly Phe Gly Ala Thr
            340                 345

<210> SEQ ID NO 10
<211> LENGTH: 11
<212> TYPE: PRT
<213> ORGANISM: artificial
<220> FEATURE:
<223> OTHER INFORMATION: synthetic polypeptide
<220> FEATURE:

```
<221> NAME/KEY: VARIANT
<222> LOCATION: (7)..(7)
<223> OTHER INFORMATION: X is Y or W
<220> FEATURE:
<221> NAME/KEY: VARIANT
<222> LOCATION: (8)..(8)
<223> OTHER INFORMATION: X is S, H, K, L, M, N, Q, R, or Y
<220> FEATURE:
<221> NAME/KEY: VARIANT
<222> LOCATION: (10)..(10)
<223> OTHER INFORMATION: X is L, A, G, I, M, N, Q, S, T, V, or Y
<220> FEATURE:
<221> NAME/KEY: VARIANT
<222> LOCATION: (11)..(11)
<223> OTHER INFORMATION: X is A, G, N, S, or T

<400> SEQUENCE: 10

Arg Ala Ser Glu Asn Ile Xaa Xaa Asn Xaa Xaa
1               5                   10

<210> SEQ ID NO 11
<211> LENGTH: 11
<212> TYPE: PRT
<213> ORGANISM: artificial
<220> FEATURE:
<223> OTHER INFORMATION: synthetic polypeptide

<400> SEQUENCE: 11

Arg Ala Ser Glu Asn Ile Tyr Ser Asn Leu Ala
1               5                   10

<210> SEQ ID NO 12
<211> LENGTH: 11
<212> TYPE: PRT
<213> ORGANISM: artificial
<220> FEATURE:
<223> OTHER INFORMATION: synthetic polypeptide

<400> SEQUENCE: 12

Arg Ala Ser Glu Asn Ile Phe Ser Asn Leu Ala
1               5                   10

<210> SEQ ID NO 13
<211> LENGTH: 11
<212> TYPE: PRT
<213> ORGANISM: artificial
<220> FEATURE:
<223> OTHER INFORMATION: synthetic polypeptide

<400> SEQUENCE: 13

Arg Ala Ser Glu Asn Ile Trp Ser Asn Leu Ala
1               5                   10

<210> SEQ ID NO 14
<211> LENGTH: 11
<212> TYPE: PRT
<213> ORGANISM: artificial
<220> FEATURE:
<223> OTHER INFORMATION: synthetic polypeptide

<400> SEQUENCE: 14

Arg Ala Ser Glu Asn Ile Tyr His Asn Leu Ala
1               5                   10

<210> SEQ ID NO 15
<211> LENGTH: 11
<212> TYPE: PRT
<213> ORGANISM: artificial
<220> FEATURE:
```

```
<223> OTHER INFORMATION: synthetic polypeptide

<400> SEQUENCE: 15

Arg Ala Ser Glu Asn Ile Tyr Lys Asn Leu Ala
1               5                   10

<210> SEQ ID NO 16
<211> LENGTH: 11
<212> TYPE: PRT
<213> ORGANISM: artificial
<220> FEATURE:
<223> OTHER INFORMATION: synthetic polypeptide

<400> SEQUENCE: 16

Arg Ala Ser Glu Asn Ile Tyr Leu Asn Leu Ala
1               5                   10

<210> SEQ ID NO 17
<211> LENGTH: 11
<212> TYPE: PRT
<213> ORGANISM: artificial
<220> FEATURE:
<223> OTHER INFORMATION: synthetic polypeptide

<400> SEQUENCE: 17

Arg Ala Ser Glu Asn Ile Tyr Met Asn Leu Ala
1               5                   10

<210> SEQ ID NO 18
<211> LENGTH: 11
<212> TYPE: PRT
<213> ORGANISM: artificial
<220> FEATURE:
<223> OTHER INFORMATION: synthetic polypeptide

<400> SEQUENCE: 18

Arg Ala Ser Glu Asn Ile Tyr Asn Asn Leu Ala
1               5                   10

<210> SEQ ID NO 19
<211> LENGTH: 11
<212> TYPE: PRT
<213> ORGANISM: artificial
<220> FEATURE:
<223> OTHER INFORMATION: synthetic polypeptide

<400> SEQUENCE: 19

Arg Ala Ser Glu Asn Ile Tyr Gln Asn Leu Ala
1               5                   10

<210> SEQ ID NO 20
<211> LENGTH: 11
<212> TYPE: PRT
<213> ORGANISM: artificial
<220> FEATURE:
<223> OTHER INFORMATION: synthetic polypeptide

<400> SEQUENCE: 20

Arg Ala Ser Glu Asn Ile Tyr Arg Asn Leu Ala
1               5                   10

<210> SEQ ID NO 21
<211> LENGTH: 11
<212> TYPE: PRT
<213> ORGANISM: artificial
<220> FEATURE:
<223> OTHER INFORMATION: synthetic polypeptide
```

```
<400> SEQUENCE: 21

Arg Ala Ser Glu Asn Ile Tyr Tyr Asn Leu Ala
1               5                   10

<210> SEQ ID NO 22
<211> LENGTH: 11
<212> TYPE: PRT
<213> ORGANISM: artificial
<220> FEATURE:
<223> OTHER INFORMATION: synthetic polypeptide

<400> SEQUENCE: 22

Arg Ala Ser Glu Asn Ile Tyr Ser Asn Ala Ala
1               5                   10

<210> SEQ ID NO 23
<211> LENGTH: 11
<212> TYPE: PRT
<213> ORGANISM: artificial
<220> FEATURE:
<223> OTHER INFORMATION: synthetic polypeptide

<400> SEQUENCE: 23

Arg Ala Ser Glu Asn Ile Tyr Ser Asn Gly Ala
1               5                   10

<210> SEQ ID NO 24
<211> LENGTH: 11
<212> TYPE: PRT
<213> ORGANISM: artificial
<220> FEATURE:
<223> OTHER INFORMATION: synthetic polypeptide

<400> SEQUENCE: 24

Arg Ala Ser Glu Asn Ile Tyr Ser Asn Ile Ala
1               5                   10

<210> SEQ ID NO 25
<211> LENGTH: 11
<212> TYPE: PRT
<213> ORGANISM: artificial
<220> FEATURE:
<223> OTHER INFORMATION: synthetic polypeptide

<400> SEQUENCE: 25

Arg Ala Ser Glu Asn Ile Tyr Ser Asn Met Ala
1               5                   10

<210> SEQ ID NO 26
<211> LENGTH: 11
<212> TYPE: PRT
<213> ORGANISM: artificial
<220> FEATURE:
<223> OTHER INFORMATION: synthetic polypeptide

<400> SEQUENCE: 26

Arg Ala Ser Glu Asn Ile Tyr Ser Asn Asn Ala
1               5                   10

<210> SEQ ID NO 27
<211> LENGTH: 11
<212> TYPE: PRT
<213> ORGANISM: artificial
<220> FEATURE:
<223> OTHER INFORMATION: synthetic polypeptide
```

```
<400> SEQUENCE: 27

Arg Ala Ser Glu Asn Ile Tyr Ser Asn Gln Ala
1               5                   10

<210> SEQ ID NO 28
<211> LENGTH: 11
<212> TYPE: PRT
<213> ORGANISM: artificial
<220> FEATURE:
<223> OTHER INFORMATION: synthetic polypeptide

<400> SEQUENCE: 28

Arg Ala Ser Glu Asn Ile Tyr Ser Asn Ser Ala
1               5                   10

<210> SEQ ID NO 29
<211> LENGTH: 11
<212> TYPE: PRT
<213> ORGANISM: artificial
<220> FEATURE:
<223> OTHER INFORMATION: synthetic polypeptide

<400> SEQUENCE: 29

Arg Ala Ser Glu Asn Ile Tyr Ser Asn Thr Ala
1               5                   10

<210> SEQ ID NO 30
<211> LENGTH: 11
<212> TYPE: PRT
<213> ORGANISM: artificial
<220> FEATURE:
<223> OTHER INFORMATION: synthetic polypeptide

<400> SEQUENCE: 30

Arg Ala Ser Glu Asn Ile Tyr Ser Asn Val Ala
1               5                   10

<210> SEQ ID NO 31
<211> LENGTH: 11
<212> TYPE: PRT
<213> ORGANISM: artificial
<220> FEATURE:
<223> OTHER INFORMATION: synthetic polypeptide

<400> SEQUENCE: 31

Arg Ala Ser Glu Asn Ile Tyr Ser Asn Tyr Ala
1               5                   10

<210> SEQ ID NO 32
<211> LENGTH: 11
<212> TYPE: PRT
<213> ORGANISM: artificial
<220> FEATURE:
<223> OTHER INFORMATION: synthetic polypeptide

<400> SEQUENCE: 32

Arg Ala Ser Glu Asn Ile Tyr Ser Asn Leu Gly
1               5                   10

<210> SEQ ID NO 33
<211> LENGTH: 11
<212> TYPE: PRT
<213> ORGANISM: artificial
<220> FEATURE:
<223> OTHER INFORMATION: synthetic polypeptide

<400> SEQUENCE: 33
```

```
Arg Ala Ser Glu Asn Ile Tyr Ser Asn Leu Asn
1               5                   10

<210> SEQ ID NO 34
<211> LENGTH: 11
<212> TYPE: PRT
<213> ORGANISM: artificial
<220> FEATURE:
<223> OTHER INFORMATION: synthetic polypeptide

<400> SEQUENCE: 34

Arg Ala Ser Glu Asn Ile Tyr Ser Asn Leu Ser
1               5                   10

<210> SEQ ID NO 35
<211> LENGTH: 11
<212> TYPE: PRT
<213> ORGANISM: artificial
<220> FEATURE:
<223> OTHER INFORMATION: synthetic polypeptide

<400> SEQUENCE: 35

Arg Ala Ser Glu Asn Ile Tyr Ser Asn Leu Thr
1               5                   10

<210> SEQ ID NO 36
<211> LENGTH: 7
<212> TYPE: PRT
<213> ORGANISM: artificial
<220> FEATURE:
<223> OTHER INFORMATION: synthetic polypeptide
<220> FEATURE:
<221> NAME/KEY: VARIANT
<222> LOCATION: (2)..(2)
<223> OTHER INFORMATION: X is A, D, E, F, G, H, I, K, L, M, N, Q, R, S,
      T, V, W, or Y
<220> FEATURE:
<221> NAME/KEY: VARIANT
<222> LOCATION: (3)..(3)
<223> OTHER INFORMATION: X is K, G, or N
<220> FEATURE:
<221> NAME/KEY: VARIANT
<222> LOCATION: (5)..(5)
<223> OTHER INFORMATION: X is L, F, H, W, or Y

<400> SEQUENCE: 36

Gly Xaa Xaa Asn Xaa Ala Asp
1               5

<210> SEQ ID NO 37
<211> LENGTH: 7
<212> TYPE: PRT
<213> ORGANISM: artificial
<220> FEATURE:
<223> OTHER INFORMATION: synthetic polypeptide

<400> SEQUENCE: 37

Gly Ala Lys Asn Leu Ala Asp
1               5

<210> SEQ ID NO 38
<211> LENGTH: 7
<212> TYPE: PRT
<213> ORGANISM: artificial
<220> FEATURE:
<223> OTHER INFORMATION: synthetic polypeptide

<400> SEQUENCE: 38
```

Gly Asp Lys Asn Leu Ala Asp
1               5

<210> SEQ ID NO 39
<211> LENGTH: 7
<212> TYPE: PRT
<213> ORGANISM: artificial
<220> FEATURE:
<223> OTHER INFORMATION: synthetic polypeptide

<400> SEQUENCE: 39

Gly Glu Lys Asn Leu Ala Asp
1               5

<210> SEQ ID NO 40
<211> LENGTH: 7
<212> TYPE: PRT
<213> ORGANISM: artificial
<220> FEATURE:
<223> OTHER INFORMATION: synthetic polypeptide

<400> SEQUENCE: 40

Gly Phe Lys Asn Leu Ala Asp
1               5

<210> SEQ ID NO 41
<211> LENGTH: 7
<212> TYPE: PRT
<213> ORGANISM: artificial
<220> FEATURE:
<223> OTHER INFORMATION: synthetic polypeptide

<400> SEQUENCE: 41

Gly Gly Lys Asn Leu Ala Asp
1               5

<210> SEQ ID NO 42
<211> LENGTH: 7
<212> TYPE: PRT
<213> ORGANISM: artificial
<220> FEATURE:
<223> OTHER INFORMATION: synthetic polypeptide

<400> SEQUENCE: 42

Gly His Lys Asn Leu Ala Asp
1               5

<210> SEQ ID NO 43
<211> LENGTH: 7
<212> TYPE: PRT
<213> ORGANISM: artificial
<220> FEATURE:
<223> OTHER INFORMATION: synthetic polypeptide

<400> SEQUENCE: 43

Gly Ile Lys Asn Leu Ala Asp
1               5

<210> SEQ ID NO 44
<211> LENGTH: 7
<212> TYPE: PRT
<213> ORGANISM: artificial
<220> FEATURE:
<223> OTHER INFORMATION: synthetic polypeptide

<400> SEQUENCE: 44

Gly Lys Lys Asn Leu Ala Asp

```
1               5

<210> SEQ ID NO 45
<211> LENGTH: 7
<212> TYPE: PRT
<213> ORGANISM: artificial
<220> FEATURE:
<223> OTHER INFORMATION: synthetic polypeptide

<400> SEQUENCE: 45

Gly Leu Lys Asn Leu Ala Asp
1               5

<210> SEQ ID NO 46
<211> LENGTH: 7
<212> TYPE: PRT
<213> ORGANISM: artificial
<220> FEATURE:
<223> OTHER INFORMATION: synthetic polypeptide

<400> SEQUENCE: 46

Gly Met Lys Asn Leu Ala Asp
1               5

<210> SEQ ID NO 47
<211> LENGTH: 7
<212> TYPE: PRT
<213> ORGANISM: artificial
<220> FEATURE:
<223> OTHER INFORMATION: synthetic polypeptide

<400> SEQUENCE: 47

Gly Asn Lys Asn Leu Ala Asp
1               5

<210> SEQ ID NO 48
<211> LENGTH: 7
<212> TYPE: PRT
<213> ORGANISM: artificial
<220> FEATURE:
<223> OTHER INFORMATION: synthetic polypeptide

<400> SEQUENCE: 48

Gly Gln Lys Asn Leu Ala Asp
1               5

<210> SEQ ID NO 49
<211> LENGTH: 7
<212> TYPE: PRT
<213> ORGANISM: artificial
<220> FEATURE:
<223> OTHER INFORMATION: synthetic polypeptide

<400> SEQUENCE: 49

Gly Arg Lys Asn Leu Ala Asp
1               5

<210> SEQ ID NO 50
<211> LENGTH: 7
<212> TYPE: PRT
<213> ORGANISM: artificial
<220> FEATURE:
<223> OTHER INFORMATION: synthetic polypeptide

<400> SEQUENCE: 50

Gly Ser Lys Asn Leu Ala Asp
1               5
```

```
<210> SEQ ID NO 51
<211> LENGTH: 7
<212> TYPE: PRT
<213> ORGANISM: artificial
<220> FEATURE:
<223> OTHER INFORMATION: synthetic polypeptide

<400> SEQUENCE: 51

Gly Thr Lys Asn Leu Ala Asp
1               5

<210> SEQ ID NO 52
<211> LENGTH: 7
<212> TYPE: PRT
<213> ORGANISM: artificial
<220> FEATURE:
<223> OTHER INFORMATION: synthetic polypeptide

<400> SEQUENCE: 52

Gly Val Lys Asn Leu Ala Asp
1               5

<210> SEQ ID NO 53
<211> LENGTH: 7
<212> TYPE: PRT
<213> ORGANISM: artificial
<220> FEATURE:
<223> OTHER INFORMATION: synthetic polypeptide

<400> SEQUENCE: 53

Gly Trp Lys Asn Leu Ala Asp
1               5

<210> SEQ ID NO 54
<211> LENGTH: 7
<212> TYPE: PRT
<213> ORGANISM: artificial
<220> FEATURE:
<223> OTHER INFORMATION: synthetic polypeptide

<400> SEQUENCE: 54

Gly Tyr Lys Asn Leu Ala Asp
1               5

<210> SEQ ID NO 55
<211> LENGTH: 7
<212> TYPE: PRT
<213> ORGANISM: artificial
<220> FEATURE:
<223> OTHER INFORMATION: synthetic polypeptide

<400> SEQUENCE: 55

Gly Ala Gly Asn Leu Ala Asp
1               5

<210> SEQ ID NO 56
<211> LENGTH: 7
<212> TYPE: PRT
<213> ORGANISM: artificial
<220> FEATURE:
<223> OTHER INFORMATION: synthetic polypeptide

<400> SEQUENCE: 56

Gly Ala Asn Asn Leu Ala Asp
1               5
```

<210> SEQ ID NO 57
<211> LENGTH: 7
<212> TYPE: PRT
<213> ORGANISM: artificial
<220> FEATURE:
<223> OTHER INFORMATION: synthetic polypeptide

<400> SEQUENCE: 57

Gly Ala Lys Asn Phe Ala Asp
1               5

<210> SEQ ID NO 58
<211> LENGTH: 7
<212> TYPE: PRT
<213> ORGANISM: artificial
<220> FEATURE:
<223> OTHER INFORMATION: synthetic polypeptide

<400> SEQUENCE: 58

Gly Ala Lys Asn His Ala Asp
1               5

<210> SEQ ID NO 59
<211> LENGTH: 7
<212> TYPE: PRT
<213> ORGANISM: artificial
<220> FEATURE:
<223> OTHER INFORMATION: synthetic polypeptide

<400> SEQUENCE: 59

Gly Ala Lys Asn Trp Ala Asp
1               5

<210> SEQ ID NO 60
<211> LENGTH: 7
<212> TYPE: PRT
<213> ORGANISM: artificial
<220> FEATURE:
<223> OTHER INFORMATION: synthetic polypeptide

<400> SEQUENCE: 60

Gly Ala Lys Asn Tyr Ala Asp
1               5

<210> SEQ ID NO 61
<211> LENGTH: 7
<212> TYPE: PRT
<213> ORGANISM: artificial
<220> FEATURE:
<223> OTHER INFORMATION: synthetic polypeptide

<400> SEQUENCE: 61

Gly Arg Gly Asn Leu Ala Asp
1               5

<210> SEQ ID NO 62
<211> LENGTH: 9
<212> TYPE: PRT
<213> ORGANISM: artificial
<220> FEATURE:
<223> OTHER INFORMATION: synthetic polypeptide
<220> FEATURE:
<221> NAME/KEY: VARIANT
<222> LOCATION: (1)..(1)
<223> OTHER INFORMATION: X is Q or S
<220> FEATURE:
<221> NAME/KEY: VARIANT
<222> LOCATION: (2)..(2)

```
<223> OTHER INFORMATION: X is H or S
<220> FEATURE:
<221> NAME/KEY: VARIANT
<222> LOCATION: (4)..(4)
<223> OTHER INFORMATION: X is W, A, F, G, H, I, K, L, M, V, or Y
<220> FEATURE:
<221> NAME/KEY: VARIANT
<222> LOCATION: (6)..(6)
<223> OTHER INFORMATION: X is T, I, or V

<400> SEQUENCE: 62

Xaa Xaa Phe Xaa Thr Xaa Pro Arg Thr
1               5

<210> SEQ ID NO 63
<211> LENGTH: 9
<212> TYPE: PRT
<213> ORGANISM: artificial
<220> FEATURE:
<223> OTHER INFORMATION: synthetic polypeptide

<400> SEQUENCE: 63

Gln His Phe Trp Thr Thr Pro Arg Thr
1               5

<210> SEQ ID NO 64
<211> LENGTH: 9
<212> TYPE: PRT
<213> ORGANISM: artificial
<220> FEATURE:
<223> OTHER INFORMATION: synthetic polypeptide

<400> SEQUENCE: 64

Ser His Phe Trp Thr Thr Pro Arg Thr
1               5

<210> SEQ ID NO 65
<211> LENGTH: 9
<212> TYPE: PRT
<213> ORGANISM: artificial
<220> FEATURE:
<223> OTHER INFORMATION: synthetic polypeptide

<400> SEQUENCE: 65

Gln Ser Phe Trp Thr Thr Pro Arg Thr
1               5

<210> SEQ ID NO 66
<211> LENGTH: 9
<212> TYPE: PRT
<213> ORGANISM: artificial
<220> FEATURE:
<223> OTHER INFORMATION: synthetic polypeptide

<400> SEQUENCE: 66

Gln His Phe Ala Thr Thr Pro Arg Thr
1               5

<210> SEQ ID NO 67
<211> LENGTH: 9
<212> TYPE: PRT
<213> ORGANISM: artificial
<220> FEATURE:
<223> OTHER INFORMATION: synthetic polypeptide

<400> SEQUENCE: 67

Gln His Phe Phe Thr Thr Pro Arg Thr
1               5
```

```
<210> SEQ ID NO 68
<211> LENGTH: 9
<212> TYPE: PRT
<213> ORGANISM: artificial
<220> FEATURE:
<223> OTHER INFORMATION: synthetic polypeptide

<400> SEQUENCE: 68

Gln His Phe Gly Thr Thr Pro Arg Thr
1               5

<210> SEQ ID NO 69
<211> LENGTH: 9
<212> TYPE: PRT
<213> ORGANISM: artificial
<220> FEATURE:
<223> OTHER INFORMATION: synthetic polypeptide

<400> SEQUENCE: 69

Gln His Phe Ile Thr Thr Pro Arg Thr
1               5

<210> SEQ ID NO 70
<211> LENGTH: 9
<212> TYPE: PRT
<213> ORGANISM: artificial
<220> FEATURE:
<223> OTHER INFORMATION: synthetic polypeptide

<400> SEQUENCE: 70

Gln His Phe Lys Thr Thr Pro Arg Thr
1               5

<210> SEQ ID NO 71
<211> LENGTH: 9
<212> TYPE: PRT
<213> ORGANISM: artificial
<220> FEATURE:
<223> OTHER INFORMATION: synthetic polypeptide

<400> SEQUENCE: 71

Gln His Phe Leu Thr Thr Pro Arg Thr
1               5

<210> SEQ ID NO 72
<211> LENGTH: 9
<212> TYPE: PRT
<213> ORGANISM: artificial
<220> FEATURE:
<223> OTHER INFORMATION: synthetic polypeptide

<400> SEQUENCE: 72

Gln His Phe Met Thr Thr Pro Arg Thr
1               5

<210> SEQ ID NO 73
<211> LENGTH: 9
<212> TYPE: PRT
<213> ORGANISM: artificial
<220> FEATURE:
<223> OTHER INFORMATION: synthetic polypeptide

<400> SEQUENCE: 73

Gln His Phe Val Thr Thr Pro Arg Thr
1               5
```

```
<210> SEQ ID NO 74
<211> LENGTH: 9
<212> TYPE: PRT
<213> ORGANISM: artificial
<220> FEATURE:
<223> OTHER INFORMATION: synthetic polypeptide

<400> SEQUENCE: 74

Gln His Phe Tyr Thr Thr Pro Arg Thr
1               5

<210> SEQ ID NO 75
<211> LENGTH: 9
<212> TYPE: PRT
<213> ORGANISM: artificial
<220> FEATURE:
<223> OTHER INFORMATION: synthetic polypeptide

<400> SEQUENCE: 75

Gln His Phe Trp Thr Ile Pro Arg Thr
1               5

<210> SEQ ID NO 76
<211> LENGTH: 9
<212> TYPE: PRT
<213> ORGANISM: artificial
<220> FEATURE:
<223> OTHER INFORMATION: synthetic polypeptide

<400> SEQUENCE: 76

Gln His Phe Trp Thr Val Pro Arg Thr
1               5

<210> SEQ ID NO 77
<211> LENGTH: 7
<212> TYPE: PRT
<213> ORGANISM: artificial
<220> FEATURE:
<223> OTHER INFORMATION: synthetic polypeptide
<220> FEATURE:
<221> NAME/KEY: VARIANT
<222> LOCATION: (1)..(1)
<223> OTHER INFORMATION: X is F, A, D, E, G, H, I, K, M, N, P, Q, R, S,
      T, W, or Y
<220> FEATURE:
<221> NAME/KEY: VARIANT
<222> LOCATION: (2)..(2)
<223> OTHER INFORMATION: X is S, E, G, K, P, Q, R, or T
<220> FEATURE:
<221> NAME/KEY: VARIANT
<222> LOCATION: (3)..(3)
<223> OTHER INFORMATION: X is N, D, E, G, K, Q, or R
<220> FEATURE:
<221> NAME/KEY: VARIANT
<222> LOCATION: (4)..(4)
<223> OTHER INFORMATION: X is Y, A, D, E, H, S, or V
<220> FEATURE:
<221> NAME/KEY: VARIANT
<222> LOCATION: (5)..(5)
<223> OTHER INFORMATION: X is A, N, or S
<220> FEATURE:
<221> NAME/KEY: VARIANT
<222> LOCATION: (6)..(6)
<223> OTHER INFORMATION: X is M, V, or W
<220> FEATURE:
<221> NAME/KEY: VARIANT
<222> LOCATION: (7)..(7)
<223> OTHER INFORMATION: X is S, or G

<400> SEQUENCE: 77

Xaa Xaa Xaa Xaa Xaa Xaa Xaa
```

```
1               5

<210> SEQ ID NO 78
<211> LENGTH: 7
<212> TYPE: PRT
<213> ORGANISM: artificial
<220> FEATURE:
<223> OTHER INFORMATION: synthetic polypeptide

<400> SEQUENCE: 78

Phe Ser Asn Tyr Ala Met Ser
1               5

<210> SEQ ID NO 79
<211> LENGTH: 7
<212> TYPE: PRT
<213> ORGANISM: artificial
<220> FEATURE:
<223> OTHER INFORMATION: synthetic polypeptide

<400> SEQUENCE: 79

Ala Ser Asn Tyr Ala Met Ser
1               5

<210> SEQ ID NO 80
<211> LENGTH: 7
<212> TYPE: PRT
<213> ORGANISM: artificial
<220> FEATURE:
<223> OTHER INFORMATION: synthetic polypeptide

<400> SEQUENCE: 80

Asp Ser Asn Tyr Ala Met Ser
1               5

<210> SEQ ID NO 81
<211> LENGTH: 7
<212> TYPE: PRT
<213> ORGANISM: artificial
<220> FEATURE:
<223> OTHER INFORMATION: synthetic polypeptide

<400> SEQUENCE: 81

Glu Ser Asn Tyr Ala Met Ser
1               5

<210> SEQ ID NO 82
<211> LENGTH: 7
<212> TYPE: PRT
<213> ORGANISM: artificial
<220> FEATURE:
<223> OTHER INFORMATION: synthetic polypeptide

<400> SEQUENCE: 82

Gly Ser Asn Tyr Ala Met Ser
1               5

<210> SEQ ID NO 83
<211> LENGTH: 7
<212> TYPE: PRT
<213> ORGANISM: artificial
<220> FEATURE:
<223> OTHER INFORMATION: synthetic polypeptide

<400> SEQUENCE: 83

His Ser Asn Tyr Ala Met Ser
1               5
```

```
<210> SEQ ID NO 84
<211> LENGTH: 7
<212> TYPE: PRT
<213> ORGANISM: artificial
<220> FEATURE:
<223> OTHER INFORMATION: synthetic polypeptide

<400> SEQUENCE: 84

Ile Ser Asn Tyr Ala Met Ser
1               5

<210> SEQ ID NO 85
<211> LENGTH: 7
<212> TYPE: PRT
<213> ORGANISM: artificial
<220> FEATURE:
<223> OTHER INFORMATION: synthetic polypeptide

<400> SEQUENCE: 85

Lys Ser Asn Tyr Ala Met Ser
1               5

<210> SEQ ID NO 86
<211> LENGTH: 7
<212> TYPE: PRT
<213> ORGANISM: artificial
<220> FEATURE:
<223> OTHER INFORMATION: synthetic polypeptide

<400> SEQUENCE: 86

Leu Ser Asn Tyr Ala Met Ser
1               5

<210> SEQ ID NO 87
<211> LENGTH: 7
<212> TYPE: PRT
<213> ORGANISM: artificial
<220> FEATURE:
<223> OTHER INFORMATION: synthetic polypeptide

<400> SEQUENCE: 87

Met Ser Asn Tyr Ala Met Ser
1               5

<210> SEQ ID NO 88
<211> LENGTH: 7
<212> TYPE: PRT
<213> ORGANISM: artificial
<220> FEATURE:
<223> OTHER INFORMATION: synthetic polypeptide

<400> SEQUENCE: 88

Asn Ser Asn Tyr Ala Met Ser
1               5

<210> SEQ ID NO 89
<211> LENGTH: 7
<212> TYPE: PRT
<213> ORGANISM: artificial
<220> FEATURE:
<223> OTHER INFORMATION: synthetic polypeptide

<400> SEQUENCE: 89

Pro Ser Asn Tyr Ala Met Ser
1               5
```

<210> SEQ ID NO 90
<211> LENGTH: 7
<212> TYPE: PRT
<213> ORGANISM: artificial
<220> FEATURE:
<223> OTHER INFORMATION: synthetic polypeptide

<400> SEQUENCE: 90

Gln Ser Asn Tyr Ala Met Ser
1               5

<210> SEQ ID NO 91
<211> LENGTH: 7
<212> TYPE: PRT
<213> ORGANISM: artificial
<220> FEATURE:
<223> OTHER INFORMATION: synthetic polypeptide

<400> SEQUENCE: 91

Arg Ser Asn Tyr Ala Met Ser
1               5

<210> SEQ ID NO 92
<211> LENGTH: 7
<212> TYPE: PRT
<213> ORGANISM: artificial
<220> FEATURE:
<223> OTHER INFORMATION: synthetic polypeptide

<400> SEQUENCE: 92

Ser Ser Asn Tyr Ala Met Ser
1               5

<210> SEQ ID NO 93
<211> LENGTH: 7
<212> TYPE: PRT
<213> ORGANISM: artificial
<220> FEATURE:
<223> OTHER INFORMATION: synthetic polypeptide

<400> SEQUENCE: 93

Thr Ser Asn Tyr Ala Met Ser
1               5

<210> SEQ ID NO 94
<211> LENGTH: 7
<212> TYPE: PRT
<213> ORGANISM: artificial
<220> FEATURE:
<223> OTHER INFORMATION: synthetic polypeptide

<400> SEQUENCE: 94

Val Ser Asn Tyr Ala Met Ser
1               5

<210> SEQ ID NO 95
<211> LENGTH: 7
<212> TYPE: PRT
<213> ORGANISM: artificial
<220> FEATURE:
<223> OTHER INFORMATION: synthetic polypeptide

<400> SEQUENCE: 95

Trp Ser Asn Tyr Ala Met Ser
1               5

-continued

```
<210> SEQ ID NO 96
<211> LENGTH: 7
<212> TYPE: PRT
<213> ORGANISM: artificial
<220> FEATURE:
<223> OTHER INFORMATION: synthetic polypeptide

<400> SEQUENCE: 96

Tyr Ser Asn Tyr Ala Met Ser
1               5

<210> SEQ ID NO 97
<211> LENGTH: 7
<212> TYPE: PRT
<213> ORGANISM: artificial
<220> FEATURE:
<223> OTHER INFORMATION: synthetic polypeptide

<400> SEQUENCE: 97

Phe Glu Asn Tyr Ala Met Ser
1               5

<210> SEQ ID NO 98
<211> LENGTH: 7
<212> TYPE: PRT
<213> ORGANISM: artificial
<220> FEATURE:
<223> OTHER INFORMATION: synthetic polypeptide

<400> SEQUENCE: 98

Phe Gly Asn Tyr Ala Met Ser
1               5

<210> SEQ ID NO 99
<211> LENGTH: 7
<212> TYPE: PRT
<213> ORGANISM: artificial
<220> FEATURE:
<223> OTHER INFORMATION: synthetic polypeptide

<400> SEQUENCE: 99

Phe Lys Asn Tyr Ala Met Ser
1               5

<210> SEQ ID NO 100
<211> LENGTH: 7
<212> TYPE: PRT
<213> ORGANISM: artificial
<220> FEATURE:
<223> OTHER INFORMATION: synthetic polypeptide

<400> SEQUENCE: 100

Phe Pro Asn Tyr Ala Met Ser
1               5

<210> SEQ ID NO 101
<211> LENGTH: 7
<212> TYPE: PRT
<213> ORGANISM: artificial
<220> FEATURE:
<223> OTHER INFORMATION: synthetic polypeptide

<400> SEQUENCE: 101

Phe Gln Asn Tyr Ala Met Ser
1               5

<210> SEQ ID NO 102
```

```
<211> LENGTH: 7
<212> TYPE: PRT
<213> ORGANISM: artificial
<220> FEATURE:
<223> OTHER INFORMATION: synthetic polypeptide

<400> SEQUENCE: 102

Phe Arg Asn Tyr Ala Met Ser
1               5

<210> SEQ ID NO 103
<211> LENGTH: 7
<212> TYPE: PRT
<213> ORGANISM: artificial
<220> FEATURE:
<223> OTHER INFORMATION: synthetic polypeptide

<400> SEQUENCE: 103

Phe Thr Asn Tyr Ala Met Ser
1               5

<210> SEQ ID NO 104
<211> LENGTH: 7
<212> TYPE: PRT
<213> ORGANISM: artificial
<220> FEATURE:
<223> OTHER INFORMATION: synthetic polypeptide

<400> SEQUENCE: 104

Phe Ser Asp Tyr Ala Met Ser
1               5

<210> SEQ ID NO 105
<211> LENGTH: 7
<212> TYPE: PRT
<213> ORGANISM: artificial
<220> FEATURE:
<223> OTHER INFORMATION: synthetic polypeptide

<400> SEQUENCE: 105

Phe Ser Glu Tyr Ala Met Ser
1               5

<210> SEQ ID NO 106
<211> LENGTH: 7
<212> TYPE: PRT
<213> ORGANISM: artificial
<220> FEATURE:
<223> OTHER INFORMATION: synthetic polypeptide

<400> SEQUENCE: 106

Phe Ser Gly Tyr Ala Met Ser
1               5

<210> SEQ ID NO 107
<211> LENGTH: 7
<212> TYPE: PRT
<213> ORGANISM: artificial
<220> FEATURE:
<223> OTHER INFORMATION: synthetic polypeptide

<400> SEQUENCE: 107

Phe Ser Lys Tyr Ala Met Ser
1               5

<210> SEQ ID NO 108
<211> LENGTH: 7
```

```
<212> TYPE: PRT
<213> ORGANISM: artificial
<220> FEATURE:
<223> OTHER INFORMATION: synthetic polypeptide

<400> SEQUENCE: 108

Phe Ser Gln Tyr Ala Met Ser
1               5

<210> SEQ ID NO 109
<211> LENGTH: 7
<212> TYPE: PRT
<213> ORGANISM: artificial
<220> FEATURE:
<223> OTHER INFORMATION: synthetic polypeptide

<400> SEQUENCE: 109

Phe Ser Arg Tyr Ala Met Ser
1               5

<210> SEQ ID NO 110
<211> LENGTH: 7
<212> TYPE: PRT
<213> ORGANISM: artificial
<220> FEATURE:
<223> OTHER INFORMATION: synthetic polypeptide

<400> SEQUENCE: 110

Phe Ser Asn Ala Ala Met Ser
1               5

<210> SEQ ID NO 111
<211> LENGTH: 7
<212> TYPE: PRT
<213> ORGANISM: artificial
<220> FEATURE:
<223> OTHER INFORMATION: synthetic polypeptide

<400> SEQUENCE: 111

Phe Ser Asn Asp Ala Met Ser
1               5

<210> SEQ ID NO 112
<211> LENGTH: 7
<212> TYPE: PRT
<213> ORGANISM: artificial
<220> FEATURE:
<223> OTHER INFORMATION: synthetic polypeptide

<400> SEQUENCE: 112

Phe Ser Asn Glu Ala Met Ser
1               5

<210> SEQ ID NO 113
<211> LENGTH: 7
<212> TYPE: PRT
<213> ORGANISM: artificial
<220> FEATURE:
<223> OTHER INFORMATION: synthetic polypeptide

<400> SEQUENCE: 113

Phe Ser Asn His Ala Met Ser
1               5

<210> SEQ ID NO 114
<211> LENGTH: 7
<212> TYPE: PRT
```

```
<213> ORGANISM: artificial
<220> FEATURE:
<223> OTHER INFORMATION: synthetic polypeptide

<400> SEQUENCE: 114

Phe Ser Asn Ser Ala Met Ser
1               5

<210> SEQ ID NO 115
<211> LENGTH: 7
<212> TYPE: PRT
<213> ORGANISM: artificial
<220> FEATURE:
<223> OTHER INFORMATION: synthetic polypeptide

<400> SEQUENCE: 115

Phe Ser Asn Val Ala Met Ser
1               5

<210> SEQ ID NO 116
<211> LENGTH: 7
<212> TYPE: PRT
<213> ORGANISM: artificial
<220> FEATURE:
<223> OTHER INFORMATION: synthetic polypeptide

<400> SEQUENCE: 116

Phe Ser Asn Tyr Asn Met Ser
1               5

<210> SEQ ID NO 117
<211> LENGTH: 7
<212> TYPE: PRT
<213> ORGANISM: artificial
<220> FEATURE:
<223> OTHER INFORMATION: synthetic polypeptide

<400> SEQUENCE: 117

Phe Ser Asn Tyr Ser Met Ser
1               5

<210> SEQ ID NO 118
<211> LENGTH: 7
<212> TYPE: PRT
<213> ORGANISM: artificial
<220> FEATURE:
<223> OTHER INFORMATION: synthetic polypeptide

<400> SEQUENCE: 118

Phe Ser Asn Tyr Ala Val Ser
1               5

<210> SEQ ID NO 119
<211> LENGTH: 7
<212> TYPE: PRT
<213> ORGANISM: artificial
<220> FEATURE:
<223> OTHER INFORMATION: synthetic polypeptide

<400> SEQUENCE: 119

Phe Ser Asn Tyr Ala Trp Ser
1               5

<210> SEQ ID NO 120
<211> LENGTH: 7
<212> TYPE: PRT
<213> ORGANISM: artificial
```

```
<220> FEATURE:
<223> OTHER INFORMATION: synthetic polypeptide

<400> SEQUENCE: 120

Phe Ser Asn Tyr Ala Met Gly
1               5

<210> SEQ ID NO 121
<211> LENGTH: 5
<212> TYPE: PRT
<213> ORGANISM: artificial
<220> FEATURE:
<223> OTHER INFORMATION: synthetic polypeptide
<220> FEATURE:
<221> NAME/KEY: VARIANT
<222> LOCATION: (1)..(1)
<223> OTHER INFORMATION: X is N, D, E, G, K, Q, or R
<220> FEATURE:
<221> NAME/KEY: VARIANT
<222> LOCATION: (2)..(2)
<223> OTHER INFORMATION: X is Y, A, D, E, H, S, or V
<220> FEATURE:
<221> NAME/KEY: VARIANT
<222> LOCATION: (3)..(3)
<223> OTHER INFORMATION: X is A, N, or S
<220> FEATURE:
<221> NAME/KEY: VARIANT
<222> LOCATION: (4)..(4)
<223> OTHER INFORMATION: X is M, V, or W
<220> FEATURE:
<221> NAME/KEY: VARIANT
<222> LOCATION: (5)..(5)
<223> OTHER INFORMATION: X is S, or G

<400> SEQUENCE: 121

Xaa Xaa Xaa Xaa Xaa
1               5

<210> SEQ ID NO 122
<211> LENGTH: 5
<212> TYPE: PRT
<213> ORGANISM: artificial
<220> FEATURE:
<223> OTHER INFORMATION: synthetic polypeptide

<400> SEQUENCE: 122

Asn Tyr Ala Met Ser
1               5

<210> SEQ ID NO 123
<211> LENGTH: 5
<212> TYPE: PRT
<213> ORGANISM: artificial
<220> FEATURE:
<223> OTHER INFORMATION: synthetic polypeptide

<400> SEQUENCE: 123

Asp Tyr Ala Met Ser
1               5

<210> SEQ ID NO 124
<211> LENGTH: 5
<212> TYPE: PRT
<213> ORGANISM: artificial
<220> FEATURE:
<223> OTHER INFORMATION: synthetic polypeptide

<400> SEQUENCE: 124

Glu Tyr Ala Met Ser
1               5
```

```
<210> SEQ ID NO 125
<211> LENGTH: 5
<212> TYPE: PRT
<213> ORGANISM: artificial
<220> FEATURE:
<223> OTHER INFORMATION: synthetic polypeptide

<400> SEQUENCE: 125

Gly Tyr Ala Met Ser
1               5

<210> SEQ ID NO 126
<211> LENGTH: 5
<212> TYPE: PRT
<213> ORGANISM: artificial
<220> FEATURE:
<223> OTHER INFORMATION: synthetic polypeptide

<400> SEQUENCE: 126

Lys Tyr Ala Met Ser
1               5

<210> SEQ ID NO 127
<211> LENGTH: 5
<212> TYPE: PRT
<213> ORGANISM: artificial
<220> FEATURE:
<223> OTHER INFORMATION: synthetic polypeptide

<400> SEQUENCE: 127

Gln Tyr Ala Met Ser
1               5

<210> SEQ ID NO 128
<211> LENGTH: 5
<212> TYPE: PRT
<213> ORGANISM: artificial
<220> FEATURE:
<223> OTHER INFORMATION: synthetic polypeptide

<400> SEQUENCE: 128

Arg Tyr Ala Met Ser
1               5

<210> SEQ ID NO 129
<211> LENGTH: 5
<212> TYPE: PRT
<213> ORGANISM: artificial
<220> FEATURE:
<223> OTHER INFORMATION: synthetic polypeptide

<400> SEQUENCE: 129

Asn Ala Ala Met Ser
1               5

<210> SEQ ID NO 130
<211> LENGTH: 5
<212> TYPE: PRT
<213> ORGANISM: artificial
<220> FEATURE:
<223> OTHER INFORMATION: synthetic polypeptide

<400> SEQUENCE: 130

Asn Asp Ala Met Ser
1               5
```

<210> SEQ ID NO 131
<211> LENGTH: 5
<212> TYPE: PRT
<213> ORGANISM: artificial
<220> FEATURE:
<223> OTHER INFORMATION: synthetic polypeptide

<400> SEQUENCE: 131

Asn Glu Ala Met Ser
1               5

<210> SEQ ID NO 132
<211> LENGTH: 5
<212> TYPE: PRT
<213> ORGANISM: artificial
<220> FEATURE:
<223> OTHER INFORMATION: synthetic polypeptide

<400> SEQUENCE: 132

Asn His Ala Met Ser
1               5

<210> SEQ ID NO 133
<211> LENGTH: 5
<212> TYPE: PRT
<213> ORGANISM: artificial
<220> FEATURE:
<223> OTHER INFORMATION: synthetic polypeptide

<400> SEQUENCE: 133

Asn Ser Ala Met Ser
1               5

<210> SEQ ID NO 134
<211> LENGTH: 5
<212> TYPE: PRT
<213> ORGANISM: artificial
<220> FEATURE:
<223> OTHER INFORMATION: synthetic polypeptide

<400> SEQUENCE: 134

Asn Val Ala Met Ser
1               5

<210> SEQ ID NO 135
<211> LENGTH: 5
<212> TYPE: PRT
<213> ORGANISM: artificial
<220> FEATURE:
<223> OTHER INFORMATION: synthetic polypeptide

<400> SEQUENCE: 135

Asn Tyr Asn Met Ser
1               5

<210> SEQ ID NO 136
<211> LENGTH: 5
<212> TYPE: PRT
<213> ORGANISM: artificial
<220> FEATURE:
<223> OTHER INFORMATION: synthetic polypeptide

<400> SEQUENCE: 136

Asn Tyr Ser Met Ser
1               5

```
<210> SEQ ID NO 137
<211> LENGTH: 5
<212> TYPE: PRT
<213> ORGANISM: artificial
<220> FEATURE:
<223> OTHER INFORMATION: synthetic polypeptide

<400> SEQUENCE: 137

Asn Tyr Ala Val Ser
1               5

<210> SEQ ID NO 138
<211> LENGTH: 5
<212> TYPE: PRT
<213> ORGANISM: artificial
<220> FEATURE:
<223> OTHER INFORMATION: synthetic polypeptide

<400> SEQUENCE: 138

Asn Tyr Ala Trp Ser
1               5

<210> SEQ ID NO 139
<211> LENGTH: 5
<212> TYPE: PRT
<213> ORGANISM: artificial
<220> FEATURE:
<223> OTHER INFORMATION: synthetic polypeptide

<400> SEQUENCE: 139

Asn Tyr Ala Met Gly
1               5

<210> SEQ ID NO 140
<211> LENGTH: 17
<212> TYPE: PRT
<213> ORGANISM: artificial
<220> FEATURE:
<223> OTHER INFORMATION: synthetic polypeptide
<220> FEATURE:
<221> NAME/KEY: VARIANT
<222> LOCATION: (2)..(2)
<223> OTHER INFORMATION: X is V, A, N, or S
<220> FEATURE:
<221> NAME/KEY: VARIANT
<222> LOCATION: (3)..(3)
<223> OTHER INFORMATION: X is T or S
<220> FEATURE:
<221> NAME/KEY: VARIANT
<222> LOCATION: (4)..(4)
<223> OTHER INFORMATION: X is E, D, N, T, or V
<220> FEATURE:
<221> NAME/KEY: VARIANT
<222> LOCATION: (5)..(5)
<223> OTHER INFORMATION: X is G, I, P, T, or V
<220> FEATURE:
<221> NAME/KEY: VARIANT
<222> LOCATION: (6)..(6)
<223> OTHER INFORMATION: X is G, D, E, F, H, I, K, L, M, N, P, Q, R, T,
     V, W, or Y
<220> FEATURE:
<221> NAME/KEY: VARIANT
<222> LOCATION: (7)..(7)
<223> OTHER INFORMATION: X is D, A, E, G, H, K, N, P, Q, R, or S
<220> FEATURE:
<221> NAME/KEY: VARIANT
<222> LOCATION: (8)..(8)
<223> OTHER INFORMATION: X at 8 is Y or W
<220> FEATURE:
<221> NAME/KEY: VARIANT
<222> LOCATION: (9)..(9)
<223> OTHER INFORMATION: X is N, A, G, P, or R
<220> FEATURE:
```

```
<221> NAME/KEY: VARIANT
<222> LOCATION: (11)..(11)
<223> OTHER INFORMATION: X is C, A, D, F, R, S, T, V, or Y
<220> FEATURE:
<221> NAME/KEY: VARIANT
<222> LOCATION: (13)..(13)
<223> OTHER INFORMATION: X is D, S, or W

<400> SEQUENCE: 140

Thr Xaa Xaa Xaa Xaa Xaa Xaa Xaa Tyr Xaa Leu Xaa Asp Val Lys
1               5                   10                  15

Gly

<210> SEQ ID NO 141
<211> LENGTH: 17
<212> TYPE: PRT
<213> ORGANISM: artificial
<220> FEATURE:
<223> OTHER INFORMATION: synthetic polypeptide

<400> SEQUENCE: 141

Thr Val Thr Glu Gly Gly Asp Tyr Asn Tyr Cys Leu Asp Asp Val Lys
1               5                   10                  15

Gly

<210> SEQ ID NO 142
<211> LENGTH: 17
<212> TYPE: PRT
<213> ORGANISM: artificial
<220> FEATURE:
<223> OTHER INFORMATION: synthetic polypeptide

<400> SEQUENCE: 142

Thr Ala Thr Glu Gly Gly Asp Tyr Asn Tyr Cys Leu Asp Asp Val Lys
1               5                   10                  15

Gly

<210> SEQ ID NO 143
<211> LENGTH: 17
<212> TYPE: PRT
<213> ORGANISM: artificial
<220> FEATURE:
<223> OTHER INFORMATION: synthetic polypeptide

<400> SEQUENCE: 143

Thr Asn Thr Glu Gly Gly Asp Tyr Asn Tyr Cys Leu Asp Asp Val Lys
1               5                   10                  15

Gly

<210> SEQ ID NO 144
<211> LENGTH: 17
<212> TYPE: PRT
<213> ORGANISM: artificial
<220> FEATURE:
<223> OTHER INFORMATION: synthetic polypeptide

<400> SEQUENCE: 144

Thr Ser Thr Glu Gly Gly Asp Tyr Asn Tyr Cys Leu Asp Asp Val Lys
1               5                   10                  15

Gly

<210> SEQ ID NO 145
<211> LENGTH: 17
<212> TYPE: PRT
```

<213> ORGANISM: artificial
<220> FEATURE:
<223> OTHER INFORMATION: synthetic polypeptide

<400> SEQUENCE: 145

Thr Val Ser Glu Gly Gly Asp Tyr Asn Tyr Cys Leu Asp Asp Val Lys
1               5                   10                  15
Gly

<210> SEQ ID NO 146
<211> LENGTH: 17
<212> TYPE: PRT
<213> ORGANISM: artificial
<220> FEATURE:
<223> OTHER INFORMATION: synthetic polypeptide

<400> SEQUENCE: 146

Thr Val Thr Asp Gly Gly Asp Tyr Asn Tyr Cys Leu Asp Asp Val Lys
1               5                   10                  15
Gly

<210> SEQ ID NO 147
<211> LENGTH: 17
<212> TYPE: PRT
<213> ORGANISM: artificial
<220> FEATURE:
<223> OTHER INFORMATION: synthetic polypeptide

<400> SEQUENCE: 147

Thr Val Thr Asn Gly Gly Asp Tyr Asn Tyr Cys Leu Asp Asp Val Lys
1               5                   10                  15
Gly

<210> SEQ ID NO 148
<211> LENGTH: 17
<212> TYPE: PRT
<213> ORGANISM: artificial
<220> FEATURE:
<223> OTHER INFORMATION: synthetic polypeptide

<400> SEQUENCE: 148

Thr Val Thr Thr Gly Gly Asp Tyr Asn Tyr Cys Leu Asp Asp Val Lys
1               5                   10                  15
Gly

<210> SEQ ID NO 149
<211> LENGTH: 17
<212> TYPE: PRT
<213> ORGANISM: artificial
<220> FEATURE:
<223> OTHER INFORMATION: synthetic polypeptide

<400> SEQUENCE: 149

Thr Val Thr Val Gly Gly Asp Tyr Asn Tyr Cys Leu Asp Asp Val Lys
1               5                   10                  15
Gly

<210> SEQ ID NO 150
<211> LENGTH: 17
<212> TYPE: PRT
<213> ORGANISM: artificial
<220> FEATURE:
<223> OTHER INFORMATION: synthetic polypeptide

```
<400> SEQUENCE: 150

Thr Val Thr Glu Ile Gly Asp Tyr Asn Tyr Cys Leu Asp Asp Val Lys
1               5                   10                  15

Gly

<210> SEQ ID NO 151
<211> LENGTH: 17
<212> TYPE: PRT
<213> ORGANISM: artificial
<220> FEATURE:
<223> OTHER INFORMATION: synthetic polypeptide

<400> SEQUENCE: 151

Thr Val Thr Glu Pro Gly Asp Tyr Asn Tyr Cys Leu Asp Asp Val Lys
1               5                   10                  15

Gly

<210> SEQ ID NO 152
<211> LENGTH: 17
<212> TYPE: PRT
<213> ORGANISM: artificial
<220> FEATURE:
<223> OTHER INFORMATION: synthetic polypeptide

<400> SEQUENCE: 152

Thr Val Thr Glu Thr Gly Asp Tyr Asn Tyr Cys Leu Asp Asp Val Lys
1               5                   10                  15

Gly

<210> SEQ ID NO 153
<211> LENGTH: 17
<212> TYPE: PRT
<213> ORGANISM: artificial
<220> FEATURE:
<223> OTHER INFORMATION: synthetic polypeptide

<400> SEQUENCE: 153

Thr Val Thr Glu Val Gly Asp Tyr Asn Tyr Cys Leu Asp Asp Val Lys
1               5                   10                  15

Gly

<210> SEQ ID NO 154
<211> LENGTH: 17
<212> TYPE: PRT
<213> ORGANISM: artificial
<220> FEATURE:
<223> OTHER INFORMATION: synthetic polypeptide

<400> SEQUENCE: 154

Thr Val Thr Glu Gly Asp Asp Tyr Asn Tyr Cys Leu Asp Asp Val Lys
1               5                   10                  15

Gly

<210> SEQ ID NO 155
<211> LENGTH: 17
<212> TYPE: PRT
<213> ORGANISM: artificial
<220> FEATURE:
<223> OTHER INFORMATION: synthetic polypeptide

<400> SEQUENCE: 155

Thr Val Thr Glu Gly Glu Asp Tyr Asn Tyr Cys Leu Asp Asp Val Lys
1               5                   10                  15
```

Gly

<210> SEQ ID NO 156
<211> LENGTH: 17
<212> TYPE: PRT
<213> ORGANISM: artificial
<220> FEATURE:
<223> OTHER INFORMATION: synthetic polypeptide

<400> SEQUENCE: 156

Thr Val Thr Glu Gly Phe Asp Tyr Asn Tyr Cys Leu Asp Asp Val Lys
1               5                   10                  15

Gly

<210> SEQ ID NO 157
<211> LENGTH: 17
<212> TYPE: PRT
<213> ORGANISM: artificial
<220> FEATURE:
<223> OTHER INFORMATION: synthetic polypeptide

<400> SEQUENCE: 157

Thr Val Thr Glu Gly His Asp Tyr Asn Tyr Cys Leu Asp Asp Val Lys
1               5                   10                  15

Gly

<210> SEQ ID NO 158
<211> LENGTH: 17
<212> TYPE: PRT
<213> ORGANISM: artificial
<220> FEATURE:
<223> OTHER INFORMATION: synthetic polypeptide

<400> SEQUENCE: 158

Thr Val Thr Glu Gly Ile Asp Tyr Asn Tyr Cys Leu Asp Asp Val Lys
1               5                   10                  15

Gly

<210> SEQ ID NO 159
<211> LENGTH: 17
<212> TYPE: PRT
<213> ORGANISM: artificial
<220> FEATURE:
<223> OTHER INFORMATION: synthetic polypeptide

<400> SEQUENCE: 159

Thr Val Thr Glu Gly Lys Asp Tyr Asn Tyr Cys Leu Asp Asp Val Lys
1               5                   10                  15

Gly

<210> SEQ ID NO 160
<211> LENGTH: 17
<212> TYPE: PRT
<213> ORGANISM: artificial
<220> FEATURE:
<223> OTHER INFORMATION: synthetic polypeptide

<400> SEQUENCE: 160

Thr Val Thr Glu Gly Leu Asp Tyr Asn Tyr Cys Leu Asp Asp Val Lys
1               5                   10                  15

Gly

```
<210> SEQ ID NO 161
<211> LENGTH: 17
<212> TYPE: PRT
<213> ORGANISM: artificial
<220> FEATURE:
<223> OTHER INFORMATION: synthetic polypeptide

<400> SEQUENCE: 161

Thr Val Thr Glu Gly Met Asp Tyr Asn Tyr Cys Leu Asp Asp Val Lys
1               5                   10                  15
Gly

<210> SEQ ID NO 162
<211> LENGTH: 17
<212> TYPE: PRT
<213> ORGANISM: artificial
<220> FEATURE:
<223> OTHER INFORMATION: synthetic polypeptide

<400> SEQUENCE: 162

Thr Val Thr Glu Gly Asn Asp Tyr Asn Tyr Cys Leu Asp Asp Val Lys
1               5                   10                  15
Gly

<210> SEQ ID NO 163
<211> LENGTH: 17
<212> TYPE: PRT
<213> ORGANISM: artificial
<220> FEATURE:
<223> OTHER INFORMATION: synthetic polypeptide

<400> SEQUENCE: 163

Thr Val Thr Glu Gly Pro Asp Tyr Asn Tyr Cys Leu Asp Asp Val Lys
1               5                   10                  15
Gly

<210> SEQ ID NO 164
<211> LENGTH: 17
<212> TYPE: PRT
<213> ORGANISM: artificial
<220> FEATURE:
<223> OTHER INFORMATION: synthetic polypeptide

<400> SEQUENCE: 164

Thr Val Thr Glu Gly Gln Asp Tyr Asn Tyr Cys Leu Asp Asp Val Lys
1               5                   10                  15
Gly

<210> SEQ ID NO 165
<211> LENGTH: 17
<212> TYPE: PRT
<213> ORGANISM: artificial
<220> FEATURE:
<223> OTHER INFORMATION: synthetic polypeptide

<400> SEQUENCE: 165

Thr Val Thr Glu Gly Arg Asp Tyr Asn Tyr Cys Leu Asp Asp Val Lys
1               5                   10                  15
Gly

<210> SEQ ID NO 166
<211> LENGTH: 17
<212> TYPE: PRT
<213> ORGANISM: artificial
```

```
<220> FEATURE:
<223> OTHER INFORMATION: synthetic polypeptide

<400> SEQUENCE: 166

Thr Val Thr Glu Gly Thr Asp Tyr Asn Tyr Cys Leu Asp Asp Val Lys
1               5                   10                  15

Gly

<210> SEQ ID NO 167
<211> LENGTH: 17
<212> TYPE: PRT
<213> ORGANISM: artificial
<220> FEATURE:
<223> OTHER INFORMATION: synthetic polypeptide

<400> SEQUENCE: 167

Thr Val Thr Glu Gly Val Asp Tyr Asn Tyr Cys Leu Asp Asp Val Lys
1               5                   10                  15

Gly

<210> SEQ ID NO 168
<211> LENGTH: 17
<212> TYPE: PRT
<213> ORGANISM: artificial
<220> FEATURE:
<223> OTHER INFORMATION: synthetic polypeptide

<400> SEQUENCE: 168

Thr Val Thr Glu Gly Trp Asp Tyr Asn Tyr Cys Leu Asp Asp Val Lys
1               5                   10                  15

Gly

<210> SEQ ID NO 169
<211> LENGTH: 17
<212> TYPE: PRT
<213> ORGANISM: artificial
<220> FEATURE:
<223> OTHER INFORMATION: synthetic polypeptide

<400> SEQUENCE: 169

Thr Val Thr Glu Gly Tyr Asp Tyr Asn Tyr Cys Leu Asp Asp Val Lys
1               5                   10                  15

Gly

<210> SEQ ID NO 170
<211> LENGTH: 17
<212> TYPE: PRT
<213> ORGANISM: artificial
<220> FEATURE:
<223> OTHER INFORMATION: synthetic polypeptide

<400> SEQUENCE: 170

Thr Val Thr Glu Gly Gly Ala Tyr Asn Tyr Cys Leu Asp Asp Val Lys
1               5                   10                  15

Gly

<210> SEQ ID NO 171
<211> LENGTH: 17
<212> TYPE: PRT
<213> ORGANISM: artificial
<220> FEATURE:
<223> OTHER INFORMATION: synthetic polypeptide

<400> SEQUENCE: 171
```

```
Thr Val Thr Glu Gly Gly Glu Tyr Asn Tyr Cys Leu Asp Asp Val Lys
1               5                   10                  15

Gly

<210> SEQ ID NO 172
<211> LENGTH: 17
<212> TYPE: PRT
<213> ORGANISM: artificial
<220> FEATURE:
<223> OTHER INFORMATION: synthetic polypeptide

<400> SEQUENCE: 172

Thr Val Thr Glu Gly Gly Gly Tyr Asn Tyr Cys Leu Asp Asp Val Lys
1               5                   10                  15

Gly

<210> SEQ ID NO 173
<211> LENGTH: 17
<212> TYPE: PRT
<213> ORGANISM: artificial
<220> FEATURE:
<223> OTHER INFORMATION: synthetic polypeptide

<400> SEQUENCE: 173

Thr Val Thr Glu Gly Gly His Tyr Asn Tyr Cys Leu Asp Asp Val Lys
1               5                   10                  15

Gly

<210> SEQ ID NO 174
<211> LENGTH: 17
<212> TYPE: PRT
<213> ORGANISM: artificial
<220> FEATURE:
<223> OTHER INFORMATION: synthetic polypeptide

<400> SEQUENCE: 174

Thr Val Thr Glu Gly Gly Lys Tyr Asn Tyr Cys Leu Asp Asp Val Lys
1               5                   10                  15

Gly

<210> SEQ ID NO 175
<211> LENGTH: 17
<212> TYPE: PRT
<213> ORGANISM: artificial
<220> FEATURE:
<223> OTHER INFORMATION: synthetic polypeptide

<400> SEQUENCE: 175

Thr Val Thr Glu Gly Gly Asn Tyr Asn Tyr Cys Leu Asp Asp Val Lys
1               5                   10                  15

Gly

<210> SEQ ID NO 176
<211> LENGTH: 17
<212> TYPE: PRT
<213> ORGANISM: artificial
<220> FEATURE:
<223> OTHER INFORMATION: synthetic polypeptide

<400> SEQUENCE: 176

Thr Val Thr Glu Gly Gly Gln Tyr Asn Tyr Cys Leu Asp Asp Val Lys
1               5                   10                  15
```

Gly

```
<210> SEQ ID NO 177
<211> LENGTH: 17
<212> TYPE: PRT
<213> ORGANISM: artificial
<220> FEATURE:
<223> OTHER INFORMATION: synthetic polypeptide

<400> SEQUENCE: 177

Thr Val Thr Glu Gly Gly Pro Tyr Asn Tyr Cys Leu Asp Asp Val Lys
1               5                   10                  15

Gly

<210> SEQ ID NO 178
<211> LENGTH: 17
<212> TYPE: PRT
<213> ORGANISM: artificial
<220> FEATURE:
<223> OTHER INFORMATION: synthetic polypeptide

<400> SEQUENCE: 178

Thr Val Thr Glu Gly Gly Arg Tyr Asn Tyr Cys Leu Asp Asp Val Lys
1               5                   10                  15

Gly

<210> SEQ ID NO 179
<211> LENGTH: 17
<212> TYPE: PRT
<213> ORGANISM: artificial
<220> FEATURE:
<223> OTHER INFORMATION: synthetic polypeptide

<400> SEQUENCE: 179

Thr Val Thr Glu Gly Gly Ser Tyr Asn Tyr Cys Leu Asp Asp Val Lys
1               5                   10                  15

Gly

<210> SEQ ID NO 180
<211> LENGTH: 17
<212> TYPE: PRT
<213> ORGANISM: artificial
<220> FEATURE:
<223> OTHER INFORMATION: synthetic polypeptide

<400> SEQUENCE: 180

Thr Val Thr Glu Gly Gly Asp Tyr Ala Tyr Cys Leu Asp Asp Val Lys
1               5                   10                  15

Gly

<210> SEQ ID NO 181
<211> LENGTH: 17
<212> TYPE: PRT
<213> ORGANISM: artificial
<220> FEATURE:
<223> OTHER INFORMATION: synthetic polypeptide

<400> SEQUENCE: 181

Thr Val Thr Glu Gly Gly Asp Tyr Gly Tyr Cys Leu Asp Asp Val Lys
1               5                   10                  15

Gly

<210> SEQ ID NO 182
```

```
<211> LENGTH: 17
<212> TYPE: PRT
<213> ORGANISM: artificial
<220> FEATURE:
<223> OTHER INFORMATION: synthetic polypeptide

<400> SEQUENCE: 182

Thr Val Thr Glu Gly Gly Asp Tyr Pro Tyr Cys Leu Asp Asp Val Lys
1               5                   10                  15

Gly

<210> SEQ ID NO 183
<211> LENGTH: 17
<212> TYPE: PRT
<213> ORGANISM: artificial
<220> FEATURE:
<223> OTHER INFORMATION: synthetic polypeptide

<400> SEQUENCE: 183

Thr Val Thr Glu Gly Gly Asp Tyr Arg Tyr Cys Leu Asp Asp Val Lys
1               5                   10                  15

Gly

<210> SEQ ID NO 184
<211> LENGTH: 17
<212> TYPE: PRT
<213> ORGANISM: artificial
<220> FEATURE:
<223> OTHER INFORMATION: synthetic polypeptide

<400> SEQUENCE: 184

Thr Val Thr Glu Gly Gly Asp Tyr Asn Tyr Ala Leu Asp Asp Val Lys
1               5                   10                  15

Gly

<210> SEQ ID NO 185
<211> LENGTH: 17
<212> TYPE: PRT
<213> ORGANISM: artificial
<220> FEATURE:
<223> OTHER INFORMATION: synthetic polypeptide

<400> SEQUENCE: 185

Thr Val Thr Glu Gly Gly Asp Tyr Asn Tyr Asp Leu Asp Asp Val Lys
1               5                   10                  15

Gly

<210> SEQ ID NO 186
<211> LENGTH: 17
<212> TYPE: PRT
<213> ORGANISM: artificial
<220> FEATURE:
<223> OTHER INFORMATION: synthetic polypeptide

<400> SEQUENCE: 186

Thr Val Thr Glu Gly Gly Asp Tyr Asn Tyr Phe Leu Asp Asp Val Lys
1               5                   10                  15

Gly

<210> SEQ ID NO 187
<211> LENGTH: 17
<212> TYPE: PRT
<213> ORGANISM: artificial
<220> FEATURE:
```

<223> OTHER INFORMATION: synthetic polypeptide

<400> SEQUENCE: 187

Thr Val Thr Glu Gly Gly Asp Tyr Asn Tyr Arg Leu Asp Asp Val Lys
1               5                   10                  15
Gly

<210> SEQ ID NO 188
<211> LENGTH: 17
<212> TYPE: PRT
<213> ORGANISM: artificial
<220> FEATURE:
<223> OTHER INFORMATION: synthetic polypeptide

<400> SEQUENCE: 188

Thr Val Thr Glu Gly Gly Asp Tyr Asn Tyr Ser Leu Asp Asp Val Lys
1               5                   10                  15
Gly

<210> SEQ ID NO 189
<211> LENGTH: 17
<212> TYPE: PRT
<213> ORGANISM: artificial
<220> FEATURE:
<223> OTHER INFORMATION: synthetic polypeptide

<400> SEQUENCE: 189

Thr Val Thr Glu Gly Gly Asp Tyr Asn Tyr Thr Leu Asp Asp Val Lys
1               5                   10                  15
Gly

<210> SEQ ID NO 190
<211> LENGTH: 17
<212> TYPE: PRT
<213> ORGANISM: artificial
<220> FEATURE:
<223> OTHER INFORMATION: synthetic polypeptide

<400> SEQUENCE: 190

Thr Val Thr Glu Gly Gly Asp Tyr Asn Tyr Val Leu Asp Asp Val Lys
1               5                   10                  15
Gly

<210> SEQ ID NO 191
<211> LENGTH: 17
<212> TYPE: PRT
<213> ORGANISM: artificial
<220> FEATURE:
<223> OTHER INFORMATION: synthetic polypeptide

<400> SEQUENCE: 191

Thr Val Thr Glu Gly Gly Asp Tyr Asn Tyr Tyr Leu Asp Asp Val Lys
1               5                   10                  15
Gly

<210> SEQ ID NO 192
<211> LENGTH: 17
<212> TYPE: PRT
<213> ORGANISM: artificial
<220> FEATURE:
<223> OTHER INFORMATION: synthetic polypeptide

<400> SEQUENCE: 192

```
Thr Val Thr Glu Gly Gly Asp Tyr Asn Tyr Cys Leu Ser Asp Val Lys
1               5                   10                  15

Gly
```

<210> SEQ ID NO 193
<211> LENGTH: 17
<212> TYPE: PRT
<213> ORGANISM: artificial
<220> FEATURE:
<223> OTHER INFORMATION: synthetic polypeptide

<400> SEQUENCE: 193

```
Thr Val Thr Glu Gly Gly Asp Tyr Asn Tyr Cys Leu Trp Asp Val Lys
1               5                   10                  15

Gly
```

<210> SEQ ID NO 194
<211> LENGTH: 17
<212> TYPE: PRT
<213> ORGANISM: artificial
<220> FEATURE:
<223> OTHER INFORMATION: synthetic polypeptide

<400> SEQUENCE: 194

```
Thr Ser Thr Glu Gly His Asp Tyr Asn Tyr Cys Leu Asp Asp Val Lys
1               5                   10                  15

Gly
```

<210> SEQ ID NO 195
<211> LENGTH: 17
<212> TYPE: PRT
<213> ORGANISM: artificial
<220> FEATURE:
<223> OTHER INFORMATION: synthetic polypeptide

<400> SEQUENCE: 195

```
Thr Ser Thr Glu Gly Gly Asp Tyr Asn Tyr Tyr Leu Asp Asp Val Lys
1               5                   10                  15

Gly
```

<210> SEQ ID NO 196
<211> LENGTH: 17
<212> TYPE: PRT
<213> ORGANISM: artificial
<220> FEATURE:
<223> OTHER INFORMATION: synthetic polypeptide

<400> SEQUENCE: 196

```
Thr Val Thr Val Gly Gly Asp Tyr Asn Tyr Tyr Leu Asp Asp Val Lys
1               5                   10                  15

Gly
```

<210> SEQ ID NO 197
<211> LENGTH: 17
<212> TYPE: PRT
<213> ORGANISM: artificial
<220> FEATURE:
<223> OTHER INFORMATION: synthetic polypeptide

<400> SEQUENCE: 197

```
Thr Val Thr Glu Gly His Asp Tyr Asn Tyr Tyr Leu Asp Asp Val Lys
1               5                   10                  15

Gly
```

<210> SEQ ID NO 198
<211> LENGTH: 17
<212> TYPE: PRT
<213> ORGANISM: artificial
<220> FEATURE:
<223> OTHER INFORMATION: synthetic polypeptide

<400> SEQUENCE: 198

Thr Val Thr Glu Gly Val Asp Tyr Asn Tyr Tyr Leu Asp Asp Val Lys
1               5                   10                  15

Gly

<210> SEQ ID NO 199
<211> LENGTH: 17
<212> TYPE: PRT
<213> ORGANISM: artificial
<220> FEATURE:
<223> OTHER INFORMATION: synthetic polypeptide

<400> SEQUENCE: 199

Thr Val Thr Glu Gly Gly Gly Tyr Asn Tyr Tyr Leu Asp Asp Val Lys
1               5                   10                  15

Gly

<210> SEQ ID NO 200
<211> LENGTH: 17
<212> TYPE: PRT
<213> ORGANISM: artificial
<220> FEATURE:
<223> OTHER INFORMATION: synthetic polypeptide

<400> SEQUENCE: 200

Thr Val Thr Glu Gly Gly Asp Tyr Gly Tyr Tyr Leu Asp Asp Val Lys
1               5                   10                  15

Gly

<210> SEQ ID NO 201
<211> LENGTH: 17
<212> TYPE: PRT
<213> ORGANISM: artificial
<220> FEATURE:
<223> OTHER INFORMATION: synthetic polypeptide

<400> SEQUENCE: 201

Thr Ser Thr Glu Gly His Asp Tyr Asn Tyr Tyr Leu Asp Asp Val Lys
1               5                   10                  15

Gly

<210> SEQ ID NO 202
<211> LENGTH: 11
<212> TYPE: PRT
<213> ORGANISM: artificial
<220> FEATURE:
<223> OTHER INFORMATION: synthetic polypeptide
<220> FEATURE:
<221> NAME/KEY: VARIANT
<222> LOCATION: (1)..(1)
<223> OTHER INFORMATION: X is A, G, S, or T
<220> FEATURE:
<221> NAME/KEY: VARIANT
<222> LOCATION: (2)..(2)
<223> OTHER INFORMATION: X is H, I, L, M, N, Q, or V
<220> FEATURE:
<221> NAME/KEY: VARIANT
<222> LOCATION: (4)..(4)

```
<223> OTHER INFORMATION: X is R, A, D, E, I, M, N, Q, or S
<220> FEATURE:
<221> NAME/KEY: VARIANT
<222> LOCATION: (5)..(5)
<223> OTHER INFORMATION: X at 5 is W, or F
<220> FEATURE:
<221> NAME/KEY: VARIANT
<222> LOCATION: (9)..(9)
<223> OTHER INFORMATION: X is F, L, M, or W

<400> SEQUENCE: 202

Xaa Xaa Asp Xaa Xaa Pro Tyr Phe Xaa Asp Tyr
1               5                   10

<210> SEQ ID NO 203
<211> LENGTH: 11
<212> TYPE: PRT
<213> ORGANISM: artificial
<220> FEATURE:
<223> OTHER INFORMATION: synthetic polypeptide

<400> SEQUENCE: 203

Ala Arg Asp Arg Trp Pro Tyr Phe Phe Asp Tyr
1               5                   10

<210> SEQ ID NO 204
<211> LENGTH: 11
<212> TYPE: PRT
<213> ORGANISM: artificial
<220> FEATURE:
<223> OTHER INFORMATION: synthetic polypeptide

<400> SEQUENCE: 204

Gly Arg Asp Arg Trp Pro Tyr Phe Phe Asp Tyr
1               5                   10

<210> SEQ ID NO 205
<211> LENGTH: 11
<212> TYPE: PRT
<213> ORGANISM: artificial
<220> FEATURE:
<223> OTHER INFORMATION: synthetic polypeptide

<400> SEQUENCE: 205

Ser Arg Asp Arg Trp Pro Tyr Phe Phe Asp Tyr
1               5                   10

<210> SEQ ID NO 206
<211> LENGTH: 11
<212> TYPE: PRT
<213> ORGANISM: artificial
<220> FEATURE:
<223> OTHER INFORMATION: synthetic polypeptide

<400> SEQUENCE: 206

Thr Arg Asp Arg Trp Pro Tyr Phe Phe Asp Tyr
1               5                   10

<210> SEQ ID NO 207
<211> LENGTH: 11
<212> TYPE: PRT
<213> ORGANISM: artificial
<220> FEATURE:
<223> OTHER INFORMATION: synthetic polypeptide

<400> SEQUENCE: 207

Ala His Asp Arg Trp Pro Tyr Phe Phe Asp Tyr
1               5                   10
```

```
<210> SEQ ID NO 208
<211> LENGTH: 11
<212> TYPE: PRT
<213> ORGANISM: artificial
<220> FEATURE:
<223> OTHER INFORMATION: synthetic polypeptide

<400> SEQUENCE: 208

Ala Ile Asp Arg Trp Pro Tyr Phe Phe Asp Tyr
1               5                   10

<210> SEQ ID NO 209
<211> LENGTH: 11
<212> TYPE: PRT
<213> ORGANISM: artificial
<220> FEATURE:
<223> OTHER INFORMATION: synthetic polypeptide

<400> SEQUENCE: 209

Ala Leu Asp Arg Trp Pro Tyr Phe Phe Asp Tyr
1               5                   10

<210> SEQ ID NO 210
<211> LENGTH: 11
<212> TYPE: PRT
<213> ORGANISM: artificial
<220> FEATURE:
<223> OTHER INFORMATION: synthetic polypeptide

<400> SEQUENCE: 210

Ala Met Asp Arg Trp Pro Tyr Phe Phe Asp Tyr
1               5                   10

<210> SEQ ID NO 211
<211> LENGTH: 11
<212> TYPE: PRT
<213> ORGANISM: artificial
<220> FEATURE:
<223> OTHER INFORMATION: synthetic polypeptide

<400> SEQUENCE: 211

Ala Asn Asp Arg Trp Pro Tyr Phe Phe Asp Tyr
1               5                   10

<210> SEQ ID NO 212
<211> LENGTH: 11
<212> TYPE: PRT
<213> ORGANISM: artificial
<220> FEATURE:
<223> OTHER INFORMATION: synthetic polypeptide

<400> SEQUENCE: 212

Ala Gln Asp Arg Trp Pro Tyr Phe Phe Asp Tyr
1               5                   10

<210> SEQ ID NO 213
<211> LENGTH: 11
<212> TYPE: PRT
<213> ORGANISM: artificial
<220> FEATURE:
<223> OTHER INFORMATION: synthetic polypeptide

<400> SEQUENCE: 213

Ala Val Asp Arg Trp Pro Tyr Phe Phe Asp Tyr
1               5                   10
```

```
<210> SEQ ID NO 214
<211> LENGTH: 11
<212> TYPE: PRT
<213> ORGANISM: artificial
<220> FEATURE:
<223> OTHER INFORMATION: synthetic polypeptide

<400> SEQUENCE: 214

Ala Arg Asp Ala Trp Pro Tyr Phe Phe Asp Tyr
1               5                   10

<210> SEQ ID NO 215
<211> LENGTH: 11
<212> TYPE: PRT
<213> ORGANISM: artificial
<220> FEATURE:
<223> OTHER INFORMATION: synthetic polypeptide

<400> SEQUENCE: 215

Ala Arg Asp Asp Trp Pro Tyr Phe Phe Asp Tyr
1               5                   10

<210> SEQ ID NO 216
<211> LENGTH: 11
<212> TYPE: PRT
<213> ORGANISM: artificial
<220> FEATURE:
<223> OTHER INFORMATION: synthetic polypeptide

<400> SEQUENCE: 216

Ala Arg Asp Glu Trp Pro Tyr Phe Phe Asp Tyr
1               5                   10

<210> SEQ ID NO 217
<211> LENGTH: 11
<212> TYPE: PRT
<213> ORGANISM: artificial
<220> FEATURE:
<223> OTHER INFORMATION: synthetic polypeptide

<400> SEQUENCE: 217

Ala Arg Asp Ile Trp Pro Tyr Phe Phe Asp Tyr
1               5                   10

<210> SEQ ID NO 218
<211> LENGTH: 11
<212> TYPE: PRT
<213> ORGANISM: artificial
<220> FEATURE:
<223> OTHER INFORMATION: synthetic polypeptide

<400> SEQUENCE: 218

Ala Arg Asp Met Trp Pro Tyr Phe Phe Asp Tyr
1               5                   10

<210> SEQ ID NO 219
<211> LENGTH: 11
<212> TYPE: PRT
<213> ORGANISM: artificial
<220> FEATURE:
<223> OTHER INFORMATION: synthetic polypeptide

<400> SEQUENCE: 219

Ala Arg Asp Asn Trp Pro Tyr Phe Phe Asp Tyr
1               5                   10
```

```
<210> SEQ ID NO 220
<211> LENGTH: 11
<212> TYPE: PRT
<213> ORGANISM: artificial
<220> FEATURE:
<223> OTHER INFORMATION: synthetic polypeptide

<400> SEQUENCE: 220

Ala Arg Asp Gln Trp Pro Tyr Phe Phe Asp Tyr
1               5                   10

<210> SEQ ID NO 221
<211> LENGTH: 11
<212> TYPE: PRT
<213> ORGANISM: artificial
<220> FEATURE:
<223> OTHER INFORMATION: synthetic polypeptide

<400> SEQUENCE: 221

Ala Arg Asp Ser Trp Pro Tyr Phe Phe Asp Tyr
1               5                   10

<210> SEQ ID NO 222
<211> LENGTH: 11
<212> TYPE: PRT
<213> ORGANISM: artificial
<220> FEATURE:
<223> OTHER INFORMATION: synthetic polypeptide

<400> SEQUENCE: 222

Ala Arg Asp Arg Phe Pro Tyr Phe Phe Asp Tyr
1               5                   10

<210> SEQ ID NO 223
<211> LENGTH: 11
<212> TYPE: PRT
<213> ORGANISM: artificial
<220> FEATURE:
<223> OTHER INFORMATION: synthetic polypeptide

<400> SEQUENCE: 223

Ala Arg Asp Arg Trp Pro Tyr Phe Leu Asp Tyr
1               5                   10

<210> SEQ ID NO 224
<211> LENGTH: 11
<212> TYPE: PRT
<213> ORGANISM: artificial
<220> FEATURE:
<223> OTHER INFORMATION: synthetic polypeptide

<400> SEQUENCE: 224

Ala Arg Asp Arg Trp Pro Tyr Phe Met Asp Tyr
1               5                   10

<210> SEQ ID NO 225
<211> LENGTH: 11
<212> TYPE: PRT
<213> ORGANISM: artificial
<220> FEATURE:
<223> OTHER INFORMATION: synthetic polypeptide

<400> SEQUENCE: 225

Ala Arg Asp Arg Trp Pro Tyr Phe Trp Asp Tyr
1               5                   10

<210> SEQ ID NO 226
```

```
<211> LENGTH: 9
<212> TYPE: PRT
<213> ORGANISM: artificial
<220> FEATURE:
<223> OTHER INFORMATION: synthetic polypeptide
<220> FEATURE:
<221> NAME/KEY: VARIANT
<222> LOCATION: (2)..(2)
<223> OTHER INFORMATION: X is R, A, D, E, I, M, N, Q, or S
<220> FEATURE:
<221> NAME/KEY: VARIANT
<222> LOCATION: (3)..(3)
<223> OTHER INFORMATION: X is W, or F
<220> FEATURE:
<221> NAME/KEY: VARIANT
<222> LOCATION: (7)..(7)
<223> OTHER INFORMATION: X is F, L, M, or W

<400> SEQUENCE: 226

Asp Xaa Xaa Pro Tyr Phe Xaa Asp Tyr
1               5

<210> SEQ ID NO 227
<211> LENGTH: 9
<212> TYPE: PRT
<213> ORGANISM: artificial
<220> FEATURE:
<223> OTHER INFORMATION: synthetic polypeptide

<400> SEQUENCE: 227

Asp Arg Trp Pro Tyr Phe Phe Asp Tyr
1               5

<210> SEQ ID NO 228
<211> LENGTH: 9
<212> TYPE: PRT
<213> ORGANISM: artificial
<220> FEATURE:
<223> OTHER INFORMATION: synthetic polypeptide

<400> SEQUENCE: 228

Asp Ala Trp Pro Tyr Phe Phe Asp Tyr
1               5

<210> SEQ ID NO 229
<211> LENGTH: 9
<212> TYPE: PRT
<213> ORGANISM: artificial
<220> FEATURE:
<223> OTHER INFORMATION: synthetic polypeptide

<400> SEQUENCE: 229

Asp Asp Trp Pro Tyr Phe Phe Asp Tyr
1               5

<210> SEQ ID NO 230
<211> LENGTH: 9
<212> TYPE: PRT
<213> ORGANISM: artificial
<220> FEATURE:
<223> OTHER INFORMATION: synthetic polypeptide

<400> SEQUENCE: 230

Asp Glu Trp Pro Tyr Phe Phe Asp Tyr
1               5

<210> SEQ ID NO 231
<211> LENGTH: 9
<212> TYPE: PRT
```

```
<213> ORGANISM: artificial
<220> FEATURE:
<223> OTHER INFORMATION: synthetic polypeptide

<400> SEQUENCE: 231

Asp Ile Trp Pro Tyr Phe Phe Asp Tyr
1               5

<210> SEQ ID NO 232
<211> LENGTH: 9
<212> TYPE: PRT
<213> ORGANISM: artificial
<220> FEATURE:
<223> OTHER INFORMATION: synthetic polypeptide

<400> SEQUENCE: 232

Asp Met Trp Pro Tyr Phe Phe Asp Tyr
1               5

<210> SEQ ID NO 233
<211> LENGTH: 9
<212> TYPE: PRT
<213> ORGANISM: artificial
<220> FEATURE:
<223> OTHER INFORMATION: synthetic polypeptide

<400> SEQUENCE: 233

Asp Asn Trp Pro Tyr Phe Phe Asp Tyr
1               5

<210> SEQ ID NO 234
<211> LENGTH: 9
<212> TYPE: PRT
<213> ORGANISM: artificial
<220> FEATURE:
<223> OTHER INFORMATION: synthetic polypeptide

<400> SEQUENCE: 234

Asp Gln Trp Pro Tyr Phe Phe Asp Tyr
1               5

<210> SEQ ID NO 235
<211> LENGTH: 9
<212> TYPE: PRT
<213> ORGANISM: artificial
<220> FEATURE:
<223> OTHER INFORMATION: synthetic polypeptide

<400> SEQUENCE: 235

Asp Ser Trp Pro Tyr Phe Phe Asp Tyr
1               5

<210> SEQ ID NO 236
<211> LENGTH: 9
<212> TYPE: PRT
<213> ORGANISM: artificial
<220> FEATURE:
<223> OTHER INFORMATION: synthetic polypeptide

<400> SEQUENCE: 236

Asp Arg Phe Pro Tyr Phe Phe Asp Tyr
1               5

<210> SEQ ID NO 237
<211> LENGTH: 9
<212> TYPE: PRT
<213> ORGANISM: artificial
```

```
<220> FEATURE:
<223> OTHER INFORMATION: synthetic polypeptide

<400> SEQUENCE: 237

Asp Arg Trp Pro Tyr Phe Leu Asp Tyr
1               5

<210> SEQ ID NO 238
<211> LENGTH: 9
<212> TYPE: PRT
<213> ORGANISM: artificial
<220> FEATURE:
<223> OTHER INFORMATION: synthetic polypeptide

<400> SEQUENCE: 238

Asp Arg Trp Pro Tyr Phe Met Asp Tyr
1               5

<210> SEQ ID NO 239
<211> LENGTH: 9
<212> TYPE: PRT
<213> ORGANISM: artificial
<220> FEATURE:
<223> OTHER INFORMATION: synthetic polypeptide

<400> SEQUENCE: 239

Asp Arg Trp Pro Tyr Phe Trp Asp Tyr
1               5

<210> SEQ ID NO 240
<211> LENGTH: 23
<212> TYPE: PRT
<213> ORGANISM: artificial
<220> FEATURE:
<223> OTHER INFORMATION: synthetic polypeptide

<400> SEQUENCE: 240

Asp Ile Gln Met Thr Gln Ser Pro Ala Ser Leu Ser Val Ser Val Gly
1               5                   10                  15

Glu Thr Val Thr Ile Thr Cys
            20

<210> SEQ ID NO 241
<211> LENGTH: 15
<212> TYPE: PRT
<213> ORGANISM: artificial
<220> FEATURE:
<223> OTHER INFORMATION: synthetic polypeptide

<400> SEQUENCE: 241

Trp Tyr Gln Gln Lys Gln Gly Arg Ser Pro Gln Leu Leu Val Tyr
1               5                   10                  15

<210> SEQ ID NO 242
<211> LENGTH: 32
<212> TYPE: PRT
<213> ORGANISM: artificial
<220> FEATURE:
<223> OTHER INFORMATION: synthetic polypeptide

<400> SEQUENCE: 242

Gly Val Pro Ser Arg Phe Ser Gly Ser Gly Ser Gly Thr Gln Tyr Ser
1               5                   10                  15

Leu Asn Ile Asn Ser Leu Gln Ser Glu Asp Phe Gly Thr Tyr Tyr Cys
            20                  25                  30
```

<210> SEQ ID NO 243
<211> LENGTH: 10
<212> TYPE: PRT
<213> ORGANISM: artificial
<220> FEATURE:
<223> OTHER INFORMATION: synthetic polypeptide

<400> SEQUENCE: 243

Phe Gly Gly Gly Thr Lys Leu Glu Ile Lys
1               5                   10

<210> SEQ ID NO 244
<211> LENGTH: 23
<212> TYPE: PRT
<213> ORGANISM: artificial
<220> FEATURE:
<223> OTHER INFORMATION: synthetic polypeptide

<400> SEQUENCE: 244

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 245
<211> LENGTH: 15
<212> TYPE: PRT
<213> ORGANISM: artificial
<220> FEATURE:
<223> OTHER INFORMATION: synthetic polypeptide

<400> SEQUENCE: 245

Trp Tyr Gln Gln Lys Pro Gly Lys Ala Pro Lys Leu Leu Val Tyr
1               5                   10                  15

<210> SEQ ID NO 246
<211> LENGTH: 15
<212> TYPE: PRT
<213> ORGANISM: artificial
<220> FEATURE:
<223> OTHER INFORMATION: synthetic polypeptide

<400> SEQUENCE: 246

Trp Tyr Gln Gln Lys Pro Gly Lys Ser Pro Lys Leu Leu Val Tyr
1               5                   10                  15

<210> SEQ ID NO 247
<211> LENGTH: 32
<212> TYPE: PRT
<213> ORGANISM: artificial
<220> FEATURE:
<223> OTHER INFORMATION: synthetic polypeptide

<400> SEQUENCE: 247

Gly Val Pro Ser Arg Phe Ser Gly Ser Gly Ser Gly Thr Asp Tyr Thr
1               5                   10                  15

Leu Thr Ile Ser Ser Leu Gln Pro Glu Asp Phe Ala Thr Tyr Tyr Cys
            20                  25                  30

<210> SEQ ID NO 248
<211> LENGTH: 10
<212> TYPE: PRT
<213> ORGANISM: artificial
<220> FEATURE:
<223> OTHER INFORMATION: synthetic polypeptide

```
<400> SEQUENCE: 248

Phe Gly Gly Gly Thr Lys Val Glu Ile Lys
1               5                   10

<210> SEQ ID NO 249
<211> LENGTH: 28
<212> TYPE: PRT
<213> ORGANISM: artificial
<220> FEATURE:
<223> OTHER INFORMATION: synthetic polypeptide

<400> SEQUENCE: 249

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr
            20                  25

<210> SEQ ID NO 250
<211> LENGTH: 14
<212> TYPE: PRT
<213> ORGANISM: artificial
<220> FEATURE:
<223> OTHER INFORMATION: synthetic polypeptide

<400> SEQUENCE: 250

Trp Val Arg Gln Thr Pro Glu Lys Arg Leu Glu Trp Val Ala
1               5                   10

<210> SEQ ID NO 251
<211> LENGTH: 32
<212> TYPE: PRT
<213> ORGANISM: artificial
<220> FEATURE:
<223> OTHER INFORMATION: synthetic polypeptide

<400> SEQUENCE: 251

Arg Phe Thr Ile Ser Arg Asp Asn Ala Asn Asp Asn Leu Tyr Leu Gln
1               5                   10                  15

Met Ser His Leu Lys Ser Glu Asp Ser Ala Arg Tyr Tyr Cys Ala Arg
            20                  25                  30

<210> SEQ ID NO 252
<211> LENGTH: 12
<212> TYPE: PRT
<213> ORGANISM: artificial
<220> FEATURE:
<223> OTHER INFORMATION: synthetic polypeptide

<400> SEQUENCE: 252

Tyr Trp Gly Gln Gly Thr Thr Leu Thr Val Ser Ser
1               5                   10

<210> SEQ ID NO 253
<211> LENGTH: 28
<212> TYPE: PRT
<213> ORGANISM: artificial
<220> FEATURE:
<223> OTHER INFORMATION: synthetic polypeptide

<400> SEQUENCE: 253

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr
            20                  25
```

```
<210> SEQ ID NO 254
<211> LENGTH: 14
<212> TYPE: PRT
<213> ORGANISM: artificial
<220> FEATURE:
<223> OTHER INFORMATION: synthetic polypeptide

<400> SEQUENCE: 254

Trp Val Arg Gln Ala Pro Gly Lys Gly Leu Glu Trp Val Ala
1               5                   10

<210> SEQ ID NO 255
<211> LENGTH: 32
<212> TYPE: PRT
<213> ORGANISM: artificial
<220> FEATURE:
<223> OTHER INFORMATION: synthetic polypeptide

<400> SEQUENCE: 255

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 256
<211> LENGTH: 12
<212> TYPE: PRT
<213> ORGANISM: artificial
<220> FEATURE:
<223> OTHER INFORMATION: synthetic polypeptide

<400> SEQUENCE: 256

Tyr Trp Gly Gln Gly Thr Leu Val Thr Val Ser Ser
1               5                   10

<210> SEQ ID NO 257
<211> LENGTH: 107
<212> TYPE: PRT
<213> ORGANISM: artificial
<220> FEATURE:
<223> OTHER INFORMATION: synthetic polypeptide

<400> SEQUENCE: 257

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Arg Ser Pro Gln Leu Leu Val
        35                  40                  45

Tyr Gly Ala Lys Asn Leu Ala Asp Gly Val Pro Ser Arg Phe Ser Gly
    50                  55                  60

Ser Gly Ser Gly Thr Gln Tyr Ser Leu Asn Ile Asn Ser Leu Gln Ser
65                  70                  75                  80

Glu Asp Phe Gly Thr Tyr Tyr Cys Gln His Phe Trp Thr Thr Pro Arg
                85                  90                  95

Thr Phe Gly Gly Gly Thr Lys Leu Glu Ile Lys
            100                 105

<210> SEQ ID NO 258
<211> LENGTH: 107
<212> TYPE: PRT
<213> ORGANISM: artificial
<220> FEATURE:
```

<223> OTHER INFORMATION: synthetic polypeptide

<400> SEQUENCE: 258

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Val
        35                  40                  45

Tyr Gly Ala Lys Asn Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Thr Thr Pro Arg
                85                  90                  95

Thr Phe Gly Gly Gly Thr Lys Val Glu Ile Lys
            100                 105

<210> SEQ ID NO 259
<211> LENGTH: 107
<212> TYPE: PRT
<213> ORGANISM: artificial
<220> FEATURE:
<223> OTHER INFORMATION: synthetic polypeptide

<400> SEQUENCE: 259

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ser Pro Lys Leu Leu Val
        35                  40                  45

Tyr Gly Ala Lys Asn Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Thr Thr Pro Arg
                85                  90                  95

Thr Phe Gly Gly Gly Thr Lys Val Glu Ile Lys
            100                 105

<210> SEQ ID NO 260
<211> LENGTH: 107
<212> TYPE: PRT
<213> ORGANISM: artificial
<220> FEATURE:
<223> OTHER INFORMATION: synthetic polypeptide

<400> SEQUENCE: 260

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Trp Ser Asn
            20                  25                  30

Leu Ala Trp Tyr Gln Gln Lys Pro Gly Lys Ser Pro Lys Leu Leu Val
        35                  40                  45

Tyr Gly Ala Lys Asn Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro

```
                65                  70                  75                  80
Glu Asp Phe Ala Thr Tyr Tyr Cys Gln His Phe Trp Thr Thr Pro Arg
                    85                  90                  95
Thr Phe Gly Gly Gly Thr Lys Val Glu Ile Lys
            100                 105
```

<210> SEQ ID NO 261
<211> LENGTH: 107
<212> TYPE: PRT
<213> ORGANISM: artificial
<220> FEATURE:
<223> OTHER INFORMATION: synthetic polypeptide

<400> SEQUENCE: 261

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Glu Asn Ile Trp Ser Asn
                20                  25                  30
Leu Ala Trp Tyr Gln Gln Lys Pro Gly Lys Ser Pro Lys Leu Leu Val
            35                  40                  45
Tyr Gly Ala Lys Asn Leu Ala Asp Gly Val Pro Ser Arg Phe Ser Gly
50                  55                  60
Ser Gly Ser Gly Thr Asp Tyr Thr Leu Thr Ile Ser Ser Leu Gln Pro
65                  70                  75                  80
Glu Asp Phe Ala Thr Tyr Tyr Cys Gln His Phe Leu Thr Thr Pro Arg
                85                  90                  95
Thr Phe Gly Gly Gly Thr Lys Val Glu Ile Lys
            100                 105
```

<210> SEQ ID NO 262
<211> LENGTH: 107
<212> TYPE: PRT
<213> ORGANISM: artificial
<220> FEATURE:
<223> OTHER INFORMATION: synthetic polypeptide

<400> SEQUENCE: 262

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Glu Asn Ile Trp Ser Asn
                20                  25                  30
Leu Ala Trp Tyr Gln Gln Lys Pro Gly Lys Ser Pro Lys Leu Leu Val
            35                  40                  45
Tyr Gly Ala Lys Asn Leu Ala Asp Gly Val Pro Ser Arg Phe Ser Gly
50                  55                  60
Ser Gly Ser Gly Thr Asp Tyr Thr Leu Thr Ile Ser Ser Leu Gln Pro
65                  70                  75                  80
Glu Asp Phe Ala Thr Tyr Tyr Cys Gln His Phe Phe Thr Thr Pro Arg
                85                  90                  95
Thr Phe Gly Gly Gly Thr Lys Val Glu Ile Lys
            100                 105
```

<210> SEQ ID NO 263
<211> LENGTH: 107
<212> TYPE: PRT
<213> ORGANISM: artificial
<220> FEATURE:
<223> OTHER INFORMATION: synthetic polypeptide

<400> SEQUENCE: 263

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Gly Ala Trp Tyr Gln Gln Lys Pro Gly Lys Ser Pro Lys Leu Leu Val
        35                  40                  45

Tyr Gly Ala Lys Asn Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Thr Thr Pro Arg
                85                  90                  95

Thr Phe Gly Gly Gly Thr Lys Val Glu Ile Lys
            100                 105
```

<210> SEQ ID NO 264
<211> LENGTH: 107
<212> TYPE: PRT
<213> ORGANISM: artificial
<220> FEATURE:
<223> OTHER INFORMATION: synthetic polypeptide

<400> SEQUENCE: 264

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Gly Ala Trp Tyr Gln Gln Lys Pro Gly Lys Ser Pro Lys Leu Leu Val
        35                  40                  45

Tyr Gly Tyr Lys Asn Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Thr Thr Pro Arg
                85                  90                  95

Thr Phe Gly Gly Gly Thr Lys Val Glu Ile Lys
            100                 105
```

<210> SEQ ID NO 265
<211> LENGTH: 107
<212> TYPE: PRT
<213> ORGANISM: artificial
<220> FEATURE:
<223> OTHER INFORMATION: synthetic polypeptide

<400> SEQUENCE: 265

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ser Pro Lys Leu Leu Val
        35                  40                  45

Tyr Gly Asp Lys Asn Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Thr Thr Pro Arg
```

```
                85                  90                  95

Thr Phe Gly Gly Gly Thr Lys Val Glu Ile Lys
            100                 105

<210> SEQ ID NO 266
<211> LENGTH: 107
<212> TYPE: PRT
<213> ORGANISM: artificial
<220> FEATURE:
<223> OTHER INFORMATION: synthetic polypeptide

<400> SEQUENCE: 266

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ser Pro Lys Leu Leu Val
        35                  40                  45

Tyr Gly Leu Lys Asn Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Thr Thr Pro Arg
                85                  90                  95

Thr Phe Gly Gly Gly Thr Lys Val Glu Ile Lys
            100                 105

<210> SEQ ID NO 267
<211> LENGTH: 107
<212> TYPE: PRT
<213> ORGANISM: artificial
<220> FEATURE:
<223> OTHER INFORMATION: synthetic polypeptide

<400> SEQUENCE: 267

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ser Pro Lys Leu Leu Val
        35                  40                  45

Tyr Gly Arg Lys Asn Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Thr Thr Pro Arg
                85                  90                  95

Thr Phe Gly Gly Gly Thr Lys Val Glu Ile Lys
            100                 105

<210> SEQ ID NO 268
<211> LENGTH: 107
<212> TYPE: PRT
<213> ORGANISM: artificial
<220> FEATURE:
<223> OTHER INFORMATION: synthetic polypeptide

<400> SEQUENCE: 268

Asp Ile Gln Met Thr Gln Ser Pro Ser Ser Leu Ser Ala Ser Val Gly
1               5                   10                  15
```

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ser Pro Lys Leu Leu Val
        35                  40                  45

Tyr Gly Tyr Lys Asn Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Thr Thr Pro Arg
                85                  90                  95

Thr Phe Gly Gly Gly Thr Lys Val Glu Ile Lys
            100                 105

<210> SEQ ID NO 269
<211> LENGTH: 107
<212> TYPE: PRT
<213> ORGANISM: artificial
<220> FEATURE:
<223> OTHER INFORMATION: synthetic polypeptide

<400> SEQUENCE: 269

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ser Pro Lys Leu Leu Val
        35                  40                  45

Tyr Gly Tyr Lys Asn Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Ile Thr Thr Pro Arg
                85                  90                  95

Thr Phe Gly Gly Gly Thr Lys Val Glu Ile Lys
            100                 105

<210> SEQ ID NO 270
<211> LENGTH: 107
<212> TYPE: PRT
<213> ORGANISM: artificial
<220> FEATURE:
<223> OTHER INFORMATION: synthetic polypeptide

<400> SEQUENCE: 270

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ser Pro Lys Leu Leu Val
        35                  40                  45

Tyr Gly Tyr Lys Asn Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Lys Thr Thr Pro Arg
                85                  90                  95

Thr Phe Gly Gly Gly Thr Lys Val Glu Ile Lys

```
<210> SEQ ID NO 271
<211> LENGTH: 107
<212> TYPE: PRT
<213> ORGANISM: artificial
<220> FEATURE:
<223> OTHER INFORMATION: synthetic polypeptide

<400> SEQUENCE: 271

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ser Pro Lys Leu Leu Val
        35                  40                  45

Tyr Gly Ala Gly Asn Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Thr Thr Pro Arg
                85                  90                  95

Thr Phe Gly Gly Gly Thr Lys Val Glu Ile Lys
            100                 105

<210> SEQ ID NO 272
<211> LENGTH: 107
<212> TYPE: PRT
<213> ORGANISM: artificial
<220> FEATURE:
<223> OTHER INFORMATION: synthetic polypeptide

<400> SEQUENCE: 272

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ser Pro Lys Leu Leu Val
        35                  40                  45

Tyr Gly Arg Gly Asn Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Thr Thr Pro Arg
                85                  90                  95

Thr Phe Gly Gly Gly Thr Lys Val Glu Ile Lys
            100                 105

<210> SEQ ID NO 273
<211> LENGTH: 107
<212> TYPE: PRT
<213> ORGANISM: artificial
<220> FEATURE:
<223> OTHER INFORMATION: synthetic polypeptide

<400> SEQUENCE: 273

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30
```

```
Leu Ala Trp Tyr Gln Gln Lys Pro Gly Lys Ser Pro Lys Leu Leu Val
            35                  40                  45

Tyr Gly Ala Lys Asn Leu Ala Asp Gly Val Pro Ser Arg Phe Ser Gly
         50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln His Phe Phe Thr Thr Pro Arg
                 85                  90                  95

Thr Phe Gly Gly Gly Thr Lys Val Glu Ile Lys
                100                 105

<210> SEQ ID NO 274
<211> LENGTH: 107
<212> TYPE: PRT
<213> ORGANISM: artificial
<220> FEATURE:
<223> OTHER INFORMATION: synthetic polypeptide

<400> SEQUENCE: 274

Asp Ile Gln Met Thr Gln Ser Pro Ser Ser Leu Ser Ala Ser Val Gly
 1               5                  10                  15

Asp Arg Val Thr Ile Thr Cys Arg Ala Ser Glu Asn Ile Tyr Ser Asn
             20                  25                  30

Leu Ala Trp Tyr Gln Gln Lys Pro Gly Lys Ser Pro Lys Leu Leu Val
            35                  40                  45

Tyr Gly Ala Lys Asn Leu Ala Asp Gly Val Pro Ser Arg Phe Ser Gly
         50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln His Phe Ile Thr Thr Pro Arg
                 85                  90                  95

Thr Phe Gly Gly Gly Thr Lys Val Glu Ile Lys
                100                 105

<210> SEQ ID NO 275
<211> LENGTH: 107
<212> TYPE: PRT
<213> ORGANISM: artificial
<220> FEATURE:
<223> OTHER INFORMATION: synthetic polypeptide

<400> SEQUENCE: 275

Asp Ile Gln Met Thr Gln Ser Pro Ser Ser Leu Ser Ala Ser Val Gly
 1               5                  10                  15

Asp Arg Val Thr Ile Thr Cys Arg Ala Ser Glu Asn Ile Tyr Ser Asn
             20                  25                  30

Leu Ala Trp Tyr Gln Gln Lys Pro Gly Lys Ser Pro Lys Leu Leu Val
            35                  40                  45

Tyr Gly Ala Lys Asn Leu Ala Asp Gly Val Pro Ser Arg Phe Ser Gly
         50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln His Phe Lys Thr Thr Pro Arg
                 85                  90                  95

Thr Phe Gly Gly Gly Thr Lys Val Glu Ile Lys
                100                 105
```

```
<210> SEQ ID NO 276
<211> LENGTH: 107
<212> TYPE: PRT
<213> ORGANISM: artificial
<220> FEATURE:
<223> OTHER INFORMATION: synthetic polypeptide

<400> SEQUENCE: 276

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ser Pro Lys Leu Leu Val
        35                  40                  45

Tyr Gly Ala Lys Asn Leu Ala Asp Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Leu Thr Thr Pro Arg
                85                  90                  95

Thr Phe Gly Gly Gly Thr Lys Val Glu Ile Lys
            100                 105

<210> SEQ ID NO 277
<211> LENGTH: 107
<212> TYPE: PRT
<213> ORGANISM: artificial
<220> FEATURE:
<223> OTHER INFORMATION: synthetic polypeptide

<400> SEQUENCE: 277

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ser Pro Lys Leu Leu Val
        35                  40                  45

Tyr Gly Ala Lys Asn Leu Ala Asp Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Thr Ile Pro Arg
                85                  90                  95

Thr Phe Gly Gly Gly Thr Lys Val Glu Ile Lys
            100                 105

<210> SEQ ID NO 278
<211> LENGTH: 107
<212> TYPE: PRT
<213> ORGANISM: artificial
<220> FEATURE:
<223> OTHER INFORMATION: synthetic polypeptide

<400> SEQUENCE: 278

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ser Pro Lys Leu Leu Val
        35                  40                  45
```

```
Tyr Gly Ala Lys Asn Leu Ala Asp Gly Val Pro Ser Arg Phe Ser Gly
            50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Thr Val Pro Arg
                85                  90                  95

Thr Phe Gly Gly Gly Thr Lys Val Glu Ile Lys
                100                 105
```

<210> SEQ ID NO 279
<211> LENGTH: 118
<212> TYPE: PRT
<213> ORGANISM: artificial
<220> FEATURE:
<223> OTHER INFORMATION: synthetic polypeptide

<400> SEQUENCE: 279

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asn Tyr
            20                  25                  30

Ala Met Ser Trp Val Arg Gln Thr Pro Glu Lys Arg Leu Glu Trp Val
        35                  40                  45

Ala Thr Val Thr Glu Gly Gly Asp Tyr Asn Tyr Cys Leu Asp Asp Val
    50                  55                  60

Lys Gly Arg Phe Thr Ile Ser Arg Asp Asn Ala Asn Asp Asn Leu Tyr
65                  70                  75                  80

Leu Gln Met Ser His Leu Lys Ser Glu Asp Ser Ala Arg Tyr Tyr Cys
                85                  90                  95

Ala Arg Asp Arg Trp Pro Tyr Phe Phe Asp Tyr Trp Gly Gln Gly Thr
                100                 105                 110

Thr Leu Thr Val Ser Ser
        115
```

<210> SEQ ID NO 280
<211> LENGTH: 118
<212> TYPE: PRT
<213> ORGANISM: artificial
<220> FEATURE:
<223> OTHER INFORMATION: synthetic polypeptide

<400> SEQUENCE: 280

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asn Tyr
            20                  25                  30

Ala Met Ser Trp Val Arg Gln Thr Pro Glu Lys Arg Leu Glu Trp Val
        35                  40                  45

Ala Thr Val Thr Glu Gly Gly Asp Tyr Asn Tyr Ala Leu Asp Asp Val
    50                  55                  60

Lys Gly Arg Phe Thr Ile Ser Arg Asp Asn Ala Asn Asp Asn Leu Tyr
65                  70                  75                  80

Leu Gln Met Ser His Leu Lys Ser Glu Asp Ser Ala Arg Tyr Tyr Cys
                85                  90                  95

Ala Arg Asp Arg Trp Pro Tyr Phe Phe Asp Tyr Trp Gly Gln Gly Thr
                100                 105                 110

Thr Leu Thr Val Ser Ser
```

<210> SEQ ID NO 281
<211> LENGTH: 118
<212> TYPE: PRT
<213> ORGANISM: artificial
<220> FEATURE:
<223> OTHER INFORMATION: synthetic polypeptide

<400> SEQUENCE: 281

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asn Tyr
            20                  25                  30

Ala Met Ser Trp Val Arg Gln Thr Pro Glu Lys Arg Leu Glu Trp Val
        35                  40                  45

Ala Thr Val Thr Glu Gly Gly Asp Tyr Asn Tyr Ser Leu Asp Asp Val
    50                  55                  60

Lys Gly Arg Phe Thr Ile Ser Arg Asp Asn Ala Asn Asp Asn Leu Tyr
65                  70                  75                  80

Leu Gln Met Ser His Leu Lys Ser Glu Asp Ser Ala Arg Tyr Tyr Cys
                85                  90                  95

Ala Arg Asp Arg Trp Pro Tyr Phe Phe Asp Tyr Trp Gly Gln Gly Thr
            100                 105                 110

Thr Leu Thr Val Ser Ser
        115

<210> SEQ ID NO 282
<211> LENGTH: 118
<212> TYPE: PRT
<213> ORGANISM: artificial
<220> FEATURE:
<223> OTHER INFORMATION: synthetic polypeptide

<400> SEQUENCE: 282

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asn Tyr
            20                  25                  30

Ala Met Ser Trp Val Arg Gln Thr Pro Glu Lys Arg Leu Glu Trp Val
        35                  40                  45

Ala Thr Val Thr Glu Gly Gly Asp Tyr Asn Tyr Thr Leu Asp Asp Val
    50                  55                  60

Lys Gly Arg Phe Thr Ile Ser Arg Asp Asn Ala Asn Asp Asn Leu Tyr
65                  70                  75                  80

Leu Gln Met Ser His Leu Lys Ser Glu Asp Ser Ala Arg Tyr Tyr Cys
                85                  90                  95

Ala Arg Asp Arg Trp Pro Tyr Phe Phe Asp Tyr Trp Gly Gln Gly Thr
            100                 105                 110

Thr Leu Thr Val Ser Ser
        115

<210> SEQ ID NO 283
<211> LENGTH: 118
<212> TYPE: PRT
<213> ORGANISM: artificial
<220> FEATURE:
<223> OTHER INFORMATION: synthetic polypeptide

<400> SEQUENCE: 283

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asn Tyr
            20                  25                  30

Ala Met Ser Trp Val Arg Gln Thr Pro Glu Lys Arg Leu Glu Trp Val
        35                  40                  45

Ala Thr Val Thr Glu Gly Gly Asp Tyr Asn Tyr Val Leu Asp Asp Val
    50                  55                  60

Lys Gly Arg Phe Thr Ile Ser Arg Asp Asn Ala Asn Asp Asn Leu Tyr
65                  70                  75                  80

Leu Gln Met Ser His Leu Lys Ser Glu Asp Ser Ala Arg Tyr Tyr Cys
            85                  90                  95

Ala Arg Asp Arg Trp Pro Tyr Phe Phe Asp Tyr Trp Gly Gln Gly Thr
            100                 105                 110

Thr Leu Thr Val Ser Ser
            115
```

<210> SEQ ID NO 284
<211> LENGTH: 118
<212> TYPE: PRT
<213> ORGANISM: artificial
<220> FEATURE:
<223> OTHER INFORMATION: synthetic polypeptide

<400> SEQUENCE: 284

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asn Tyr
            20                  25                  30

Ala Met Ser Trp Val Arg Gln Thr Pro Glu Lys Arg Leu Glu Trp Val
        35                  40                  45

Ala Thr Val Thr Glu Gly Gly Asp Tyr Asn Tyr Leu Asp Asp Val
    50                  55                  60

Lys Gly Arg Phe Thr Ile Ser Arg Asp Asn Ala Asn Asp Asn Leu Tyr
65                  70                  75                  80

Leu Gln Met Ser His Leu Lys Ser Glu Asp Ser Ala Arg Tyr Tyr Cys
            85                  90                  95

Ala Arg Asp Arg Trp Pro Tyr Phe Phe Asp Tyr Trp Gly Gln Gly Thr
            100                 105                 110

Thr Leu Thr Val Ser Ser
            115
```

<210> SEQ ID NO 285
<211> LENGTH: 118
<212> TYPE: PRT
<213> ORGANISM: artificial
<220> FEATURE:
<223> OTHER INFORMATION: synthetic polypeptide

<400> SEQUENCE: 285

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ala Thr Val Thr Glu Gly Gly Asp Tyr Asn Tyr Cys Leu Asp Asp Val
```

```
            50                  55                  60
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Arg Trp Pro Tyr Phe Phe Asp Tyr Trp Gly Gln Gly Thr
            100                 105                 110

Leu Val Thr Val Ser Ser
        115
```

<210> SEQ ID NO 286
<211> LENGTH: 118
<212> TYPE: PRT
<213> ORGANISM: artificial
<220> FEATURE:
<223> OTHER INFORMATION: synthetic polypeptide

<400> SEQUENCE: 286

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
         35                  40                  45

Ala Thr Val Thr Glu Gly Gly Asp Tyr Asn Tyr Ala Leu Asp Asp Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Arg Trp Pro Tyr Phe Phe Asp Tyr Trp Gly Gln Gly Thr
            100                 105                 110

Leu Val Thr Val Ser Ser
        115
```

<210> SEQ ID NO 287
<211> LENGTH: 118
<212> TYPE: PRT
<213> ORGANISM: artificial
<220> FEATURE:
<223> OTHER INFORMATION: synthetic polypeptide

<400> SEQUENCE: 287

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
         35                  40                  45

Ala Thr Val Thr Glu Gly Gly Asp Tyr Asn Tyr Ser Leu Asp Asp Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Arg Trp Pro Tyr Phe Phe Asp Tyr Trp Gly Gln Gly Thr
            100                 105                 110
```

Leu Val Thr Val Ser Ser
        115

<210> SEQ ID NO 288
<211> LENGTH: 118
<212> TYPE: PRT
<213> ORGANISM: artificial
<220> FEATURE:
<223> OTHER INFORMATION: synthetic polypeptide

<400> SEQUENCE: 288

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ala Thr Val Thr Glu Gly Gly Asp Tyr Asn Tyr Thr Leu Asp Asp Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Trp Pro Tyr Phe Phe Asp Tyr Trp Gly Gln Gly Thr
            100                 105                 110

Leu Val Thr Val Ser Ser
        115

<210> SEQ ID NO 289
<211> LENGTH: 118
<212> TYPE: PRT
<213> ORGANISM: artificial
<220> FEATURE:
<223> OTHER INFORMATION: synthetic polypeptide

<400> SEQUENCE: 289

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ala Thr Val Thr Glu Gly Gly Asp Tyr Asn Tyr Val Leu Asp Asp Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Trp Pro Tyr Phe Phe Asp Tyr Trp Gly Gln Gly Thr
            100                 105                 110

Leu Val Thr Val Ser Ser
        115

<210> SEQ ID NO 290
<211> LENGTH: 118
<212> TYPE: PRT
<213> ORGANISM: artificial
<220> FEATURE:
<223> OTHER INFORMATION: synthetic polypeptide

<400> SEQUENCE: 290

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ala Thr Val Thr Glu Gly Gly Asp Tyr Asn Tyr Leu Asp Asp Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Asp Arg Trp Pro Tyr Phe Phe Asp Tyr Trp Gly Gln Gly Thr
            100                 105                 110

Leu Val Thr Val Ser Ser
        115

<210> SEQ ID NO 291
<211> LENGTH: 118
<212> TYPE: PRT
<213> ORGANISM: artificial
<220> FEATURE:
<223> OTHER INFORMATION: synthetic polypeptide

<400> SEQUENCE: 291

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Glu Ser Asn Tyr
            20                  25                  30

Ala Met Ser Trp Val Arg Gln Ala Pro Gly Lys Gly Leu Glu Trp Val
        35                  40                  45

Ala Thr Val Thr Glu Gly Gly Asp Tyr Asn Tyr Leu Asp Asp Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Asp Arg Trp Pro Tyr Phe Phe Asp Tyr Trp Gly Gln Gly Thr
            100                 105                 110

Leu Val Thr Val Ser Ser
        115

<210> SEQ ID NO 292
<211> LENGTH: 118
<212> TYPE: PRT
<213> ORGANISM: artificial
<220> FEATURE:
<223> OTHER INFORMATION: synthetic polypeptide

<400> SEQUENCE: 292

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Glu Ser Asn Tyr
            20                  25                  30

Ala Met Ser Trp Val Arg Gln Ala Pro Gly Lys Gly Leu Glu Trp Val
        35                  40                  45

Ala Thr Val Thr Glu Gly Gly Asp Tyr Gly Tyr Tyr Leu Asp Asp Val
            50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Ala Trp Pro Tyr Phe Phe Asp Tyr Trp Gly Gln Gly Thr
            100                 105                 110

Leu Val Thr Val Ser Ser
            115

<210> SEQ ID NO 293
<211> LENGTH: 118
<212> TYPE: PRT
<213> ORGANISM: artificial
<220> FEATURE:
<223> OTHER INFORMATION: synthetic polypeptide

<400> SEQUENCE: 293

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Ser Asn Tyr
            20                  25                  30

Ala Met Ser Trp Val Arg Gln Ala Pro Gly Lys Gly Leu Glu Trp Val
            35                  40                  45

Ala Thr Val Thr Glu Gly Gly Asp Tyr Asn Tyr Tyr Leu Asp Asp Val
            50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Arg Trp Pro Tyr Phe Phe Asp Tyr Trp Gly Gln Gly Thr
            100                 105                 110

Leu Val Thr Val Ser Ser
            115

<210> SEQ ID NO 294
<211> LENGTH: 118
<212> TYPE: PRT
<213> ORGANISM: artificial
<220> FEATURE:
<223> OTHER INFORMATION: synthetic polypeptide

<400> SEQUENCE: 294

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Ser Ser Asn Tyr
            20                  25                  30

Ala Met Ser Trp Val Arg Gln Ala Pro Gly Lys Gly Leu Glu Trp Val
            35                  40                  45

Ala Thr Val Thr Glu Gly Gly Asp Tyr Asn Tyr Tyr Leu Asp Asp Val
            50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Arg Trp Pro Tyr Phe Phe Asp Tyr Trp Gly Gln Gly Thr
            100                 105                 110

```
Leu Val Thr Val Ser Ser
        115

<210> SEQ ID NO 295
<211> LENGTH: 118
<212> TYPE: PRT
<213> ORGANISM: artificial
<220> FEATURE:
<223> OTHER INFORMATION: synthetic polypeptide

<400> SEQUENCE: 295

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ser Ser Asn Tyr
            20                  25                  30

Ala Met Ser Trp Val Arg Gln Ala Pro Gly Lys Gly Leu Glu Trp Val
        35                  40                  45

Ala Thr Val Thr Val Gly Gly Asp Tyr Asn Tyr Tyr Leu Asp Asp Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Trp Pro Tyr Phe Phe Asp Tyr Trp Gly Gln Gly Thr
            100                 105                 110

Leu Val Thr Val Ser Ser
        115

<210> SEQ ID NO 296
<211> LENGTH: 118
<212> TYPE: PRT
<213> ORGANISM: artificial
<220> FEATURE:
<223> OTHER INFORMATION: synthetic polypeptide

<400> SEQUENCE: 296

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ser Ser Asn Tyr
            20                  25                  30

Ala Met Ser Trp Val Arg Gln Ala Pro Gly Lys Gly Leu Glu Trp Val
        35                  40                  45

Ala Thr Val Thr Glu Gly Gly Tyr Asn Tyr Tyr Leu Asp Asp Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Trp Pro Tyr Phe Phe Asp Tyr Trp Gly Gln Gly Thr
            100                 105                 110

Leu Val Thr Val Ser Ser
        115

<210> SEQ ID NO 297
<211> LENGTH: 118
<212> TYPE: PRT
<213> ORGANISM: artificial
<220> FEATURE:
<223> OTHER INFORMATION: synthetic polypeptide
```

-continued

<400> SEQUENCE: 297

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Val Ser Trp Val Arg Gln Ala Pro Gly Lys Gly Leu Glu Trp Val
        35                  40                  45

Ala Thr Val Thr Glu Gly Gly Asp Tyr Asn Tyr Tyr Leu Asp Asp Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Trp Pro Tyr Phe Phe Asp Tyr Trp Gly Gln Gly Thr
            100                 105                 110

Leu Val Thr Val Ser Ser
        115

<210> SEQ ID NO 298
<211> LENGTH: 118
<212> TYPE: PRT
<213> ORGANISM: artificial
<220> FEATURE:
<223> OTHER INFORMATION: synthetic polypeptide

<400> SEQUENCE: 298

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ala Thr Ser Thr Glu Gly Gly Asp Tyr Asn Tyr Tyr Leu Asp Asp Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Trp Pro Tyr Phe Phe Asp Tyr Trp Gly Gln Gly Thr
            100                 105                 110

Leu Val Thr Val Ser Ser
        115

<210> SEQ ID NO 299
<211> LENGTH: 118
<212> TYPE: PRT
<213> ORGANISM: artificial
<220> FEATURE:
<223> OTHER INFORMATION: synthetic polypeptide

<400> SEQUENCE: 299

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

```
Ala Thr Val Thr Val Gly Gly Asp Tyr Asn Tyr Tyr Leu Asp Asp Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Asp Arg Trp Pro Tyr Phe Phe Asp Tyr Trp Gly Gln Gly Thr
                100                 105                 110

Leu Val Thr Val Ser Ser
        115

<210> SEQ ID NO 300
<211> LENGTH: 118
<212> TYPE: PRT
<213> ORGANISM: artificial
<220> FEATURE:
<223> OTHER INFORMATION: synthetic polypeptide

<400> SEQUENCE: 300

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
                20                  25                  30

Ala Met Ser Trp Val Arg Gln Ala Pro Gly Lys Gly Leu Glu Trp Val
            35                  40                  45

Ala Thr Val Thr Glu Gly His Asp Tyr Asn Tyr Tyr Leu Asp Asp Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Asp Arg Trp Pro Tyr Phe Phe Asp Tyr Trp Gly Gln Gly Thr
                100                 105                 110

Leu Val Thr Val Ser Ser
        115

<210> SEQ ID NO 301
<211> LENGTH: 118
<212> TYPE: PRT
<213> ORGANISM: artificial
<220> FEATURE:
<223> OTHER INFORMATION: synthetic polypeptide

<400> SEQUENCE: 301

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
                20                  25                  30

Ala Met Ser Trp Val Arg Gln Ala Pro Gly Lys Gly Leu Glu Trp Val
            35                  40                  45

Ala Thr Val Thr Glu Gly Val Asp Tyr Asn Tyr Tyr Leu Asp Asp Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Asp Arg Trp Pro Tyr Phe Phe Asp Tyr Trp Gly Gln Gly Thr
```

```
Leu Val Thr Val Ser Ser
        115

<210> SEQ ID NO 302
<211> LENGTH: 118
<212> TYPE: PRT
<213> ORGANISM: artificial
<220> FEATURE:
<223> OTHER INFORMATION: synthetic polypeptide

<400> SEQUENCE: 302

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ala Thr Val Thr Glu Gly Val Asp Tyr Asn Tyr Tyr Leu Asp Asp Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Trp Pro Tyr Phe Phe Asp Tyr Trp Gly Gln Gly Thr
            100                 105                 110

Leu Val Thr Val Ser Ser
        115

<210> SEQ ID NO 303
<211> LENGTH: 118
<212> TYPE: PRT
<213> ORGANISM: artificial
<220> FEATURE:
<223> OTHER INFORMATION: synthetic polypeptide

<400> SEQUENCE: 303

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ala Thr Val Thr Glu Gly Gly Gly Tyr Asn Tyr Tyr Leu Asp Asp Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Trp Pro Tyr Phe Phe Asp Tyr Trp Gly Gln Gly Thr
            100                 105                 110

Leu Val Thr Val Ser Ser
        115

<210> SEQ ID NO 304
<211> LENGTH: 118
<212> TYPE: PRT
<213> ORGANISM: artificial
<220> FEATURE:
```

<223> OTHER INFORMATION: synthetic polypeptide

<400> SEQUENCE: 304

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ala Thr Val Thr Glu Gly Gly Asp Tyr Gly Tyr Tyr Leu Asp Asp Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Trp Pro Tyr Phe Phe Asp Tyr Trp Gly Gln Gly Thr
            100                 105                 110

Leu Val Thr Val Ser Ser
            115

<210> SEQ ID NO 305
<211> LENGTH: 118
<212> TYPE: PRT
<213> ORGANISM: artificial
<220> FEATURE:
<223> OTHER INFORMATION: synthetic polypeptide

<400> SEQUENCE: 305

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ala Thr Ser Thr Glu Gly His Asp Tyr Asn Tyr Tyr Leu Asp Asp Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Trp Pro Tyr Phe Phe Asp Tyr Trp Gly Gln Gly Thr
            100                 105                 110

Leu Val Thr Val Ser Ser
            115

<210> SEQ ID NO 306
<211> LENGTH: 118
<212> TYPE: PRT
<213> ORGANISM: artificial
<220> FEATURE:
<223> OTHER INFORMATION: synthetic polypeptide

<400> SEQUENCE: 306

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val

```
                35                  40                  45
Ala Thr Val Thr Glu Gly Gly Asp Tyr Asn Tyr Tyr Leu Asp Asp Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Ala Trp Pro Tyr Phe Phe Asp Tyr Trp Gly Gln Gly Thr
            100                 105                 110

Leu Val Thr Val Ser Ser
        115

<210> SEQ ID NO 307
<211> LENGTH: 118
<212> TYPE: PRT
<213> ORGANISM: artificial
<220> FEATURE:
<223> OTHER INFORMATION: synthetic polypeptide

<400> SEQUENCE: 307

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
                 20                  25                  30

Ala Met Ser Trp Val Arg Gln Ala Pro Gly Lys Gly Leu Glu Trp Val
             35                  40                  45

Ala Thr Val Thr Glu Gly Gly Asp Tyr Asn Tyr Tyr Leu Asp Asp Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Asp Trp Pro Tyr Phe Phe Asp Tyr Trp Gly Gln Gly Thr
            100                 105                 110

Leu Val Thr Val Ser Ser
        115

<210> SEQ ID NO 308
<211> LENGTH: 118
<212> TYPE: PRT
<213> ORGANISM: artificial
<220> FEATURE:
<223> OTHER INFORMATION: synthetic polypeptide

<400> SEQUENCE: 308

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
                 20                  25                  30

Ala Met Ser Trp Val Arg Gln Ala Pro Gly Lys Gly Leu Glu Trp Val
             35                  40                  45

Ala Thr Val Thr Glu Gly Gly Asp Tyr Asn Tyr Tyr Leu Asp Asp Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95
```

```
Ala Arg Asp Gln Trp Pro Tyr Phe Phe Asp Tyr Trp Gly Gln Gly Thr
            100                 105                 110

Leu Val Thr Val Ser Ser
        115

<210> SEQ ID NO 309
<211> LENGTH: 118
<212> TYPE: PRT
<213> ORGANISM: artificial
<220> FEATURE:
<223> OTHER INFORMATION: synthetic polypeptide

<400> SEQUENCE: 309

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ala Thr Val Thr Glu Gly Gly Asp Tyr Asn Tyr Tyr Leu Asp Asp Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Trp Pro Tyr Phe Phe Asp Tyr Trp Gly Gln Gly Thr
            100                 105                 110

Leu Val Thr Val Ser Ser
        115

<210> SEQ ID NO 310
<211> LENGTH: 118
<212> TYPE: PRT
<213> ORGANISM: artificial
<220> FEATURE:
<223> OTHER INFORMATION: synthetic polypeptide

<400> SEQUENCE: 310

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ala Thr Val Thr Glu Gly Gly Asp Tyr Asn Tyr Tyr Leu Asp Asp Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Phe Pro Tyr Phe Phe Asp Tyr Trp Gly Gln Gly Thr
            100                 105                 110

Leu Val Thr Val Ser Ser
        115

<210> SEQ ID NO 311
<211> LENGTH: 107
<212> TYPE: PRT
<213> ORGANISM: artificial
```

```
<220> FEATURE:
<223> OTHER INFORMATION: synthetic polypeptide

<400> SEQUENCE: 311

Asp Ile Gln Met Thr Gln Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Thr Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys His Gln Tyr Ser Lys Phe Pro Pro
                85                  90                  95

Thr Phe Gly Ser Gly Thr Lys Leu Glu Ile Lys
            100                 105

<210> SEQ ID NO 312
<211> LENGTH: 121
<212> TYPE: PRT
<213> ORGANISM: artificial
<220> FEATURE:
<223> OTHER INFORMATION: synthetic polypeptide

<400> SEQUENCE: 312

Glu Val Gln Leu Gln Gln Ser Gly Ala Glu Leu Val Lys Pro Gly Ala
1               5                   10                  15

Ser Val Arg Leu Ser Cys Thr Ser Ser Gly Phe Asn Ile Lys Asp Tyr
            20                  25                  30

Phe Met His Trp Val Lys Gln Arg Thr Glu Gln Gly Leu Glu Trp Val
        35                  40                  45

Gly Arg Ile Asp Pro Glu Asp Gly Glu Thr Gln Tyr Ala Pro Asn Phe
    50                  55                  60

Gln Asp Lys Ala Thr Ile Thr Val Asp Thr Ser Ser Asn Thr Val Tyr
65                  70                  75                  80

Leu Gln Leu Ser Ser Leu Thr Ser Glu Asp Thr Ala Val Tyr Tyr Cys
                85                  90                  95

Phe Arg Pro Leu Tyr Tyr Gly Asn Ser Pro Trp Phe Ala Tyr Trp Gly
            100                 105                 110

Gln Gly Thr Leu Val Thr Val Ser Pro
        115                 120

<210> SEQ ID NO 313
<211> LENGTH: 107
<212> TYPE: PRT
<213> ORGANISM: artificial
<220> FEATURE:
<223> OTHER INFORMATION: synthetic polypeptide

<400> SEQUENCE: 313

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Thr Tyr
            20                  25                  30

Leu Ser Trp Phe Leu Gln Lys Pro Gly Lys Ser Pro Lys Thr Leu Ile
        35                  40                  45
```

```
Tyr Arg Ala Asp Arg Leu Val Asp Gly Val Pro Ser Arg Phe Ser Gly
 50                  55                  60

Gly Gly Ser Gly Gln Asp Tyr Ser Leu Thr Ile Ser Ser Leu Glu Tyr
 65                  70                  75                  80

Glu Asp Leu Gly Ile Tyr Tyr Cys Leu Gln Tyr Asp Glu Phe Pro Tyr
                 85                  90                  95

Thr Phe Gly Ser Gly Thr Lys Leu Glu Ile Lys
            100                 105
```

<210> SEQ ID NO 314
<211> LENGTH: 119
<212> TYPE: PRT
<213> ORGANISM: artificial
<220> FEATURE:
<223> OTHER INFORMATION: synthetic polypeptide

<400> SEQUENCE: 314

```
Gln Val Gln Leu Gln Gln Ser Gly Ala Glu Leu Ala Arg Pro Gly Ala
 1               5                   10                  15

Ser Val Lys Phe Ser Cys Lys Ala Ser Gly Tyr Thr Phe Thr Ser Tyr
                 20                  25                  30

Trp Met Gln Trp Val Lys Gln Arg Pro Gly Gln Gly Leu Glu Trp Ile
             35                  40                  45

Gly Thr Ile Tyr Pro Gly Asp Gly Asn Thr Arg Tyr Thr Gln Lys Phe
 50                  55                  60

Lys Gly Lys Ala Thr Leu Thr Ala Asp Lys Ser Ser Ser Thr Ala Tyr
 65                  70                  75                  80

Met Gln Leu Ser Gly Leu Ala Ser Glu Asp Ser Ala Val Tyr Tyr Cys
                 85                  90                  95

Ala Arg Gly Tyr Phe Gly Asn Leu Val Phe Asp Val Trp Gly Ala Gly
                100                 105                 110

Thr Thr Val Thr Val Ser Ser
            115
```

<210> SEQ ID NO 315
<211> LENGTH: 107
<212> TYPE: PRT
<213> ORGANISM: artificial
<220> FEATURE:
<223> OTHER INFORMATION: synthetic polypeptide

<400> SEQUENCE: 315

```
Asn Ile Val Met Thr Gln Thr Pro Lys Phe Leu Pro Val Ala Ala Glu
 1               5                   10                  15

Asp Arg Val Ile Ile Thr Cys Lys Ala Ser Gln Asp Val Ser Asn Glu
                 20                  25                  30

Val Ala Trp Tyr Gln Gln Lys Pro Gly Gln Ser Pro Lys Leu Leu Met
             35                  40                  45

Tyr Tyr Ala Ser Asn Arg Tyr Thr Gly Val Pro Asp Arg Phe Thr Gly
 50                  55                  60

Ser Gly Ser Gly Thr Asp Phe Thr Phe Thr Ile Ser Ser Val Gln Val
 65                  70                  75                  80

Glu Asp Leu Ala Val Tyr Phe Cys Gln Gln His Tyr Ser Ser Pro Leu
                 85                  90                  95

Thr Phe Gly Ala Gly Thr Lys Leu Glu Leu Lys
            100                 105
```

<210> SEQ ID NO 316

```
<211> LENGTH: 118
<212> TYPE: PRT
<213> ORGANISM: artificial
<220> FEATURE:
<223> OTHER INFORMATION: synthetic polypeptide

<400> SEQUENCE: 316

Gln Val Gln Leu Gln Gln Ser Gly Pro Glu Leu Val Lys Ser Gly Ala
1               5                   10                  15

Ser Val Arg Ile Ser Cys Lys Ala Ser Gly Tyr Ala Phe Ser Gly Ser
            20                  25                  30

Trp Met Asn Trp Val Lys Gln Arg Pro Gly Lys Gly Leu Glu Trp Ile
        35                  40                  45

Gly Arg Ile Tyr Pro Gly Asp Gly Asn Thr Asn Tyr Asn Gly Lys Phe
    50                  55                  60

Lys Asp Lys Ala Thr Leu Thr Ala Asp Lys Ser Ser Thr Ala Phe
65                  70                  75                  80

Met Gln Leu Ser Ser Leu Thr Ser Glu Asp Ser Ala Val Tyr Phe Cys
                85                  90                  95

Ala Arg Asp Tyr Tyr Leu Phe Tyr Phe Asp Tyr Trp Gly Gln Gly Thr
            100                 105                 110

Thr Leu Thr Val Ser Ser
            115

<210> SEQ ID NO 317
<211> LENGTH: 107
<212> TYPE: PRT
<213> ORGANISM: artificial
<220> FEATURE:
<223> OTHER INFORMATION: synthetic polypeptide

<400> SEQUENCE: 317

Asp Ile Gln Met Thr Gln Ser Pro Ala Ser Leu Ser Val Ser Val Gly
1               5                   10                  15

Glu Thr Val Thr Ile Thr Cys Arg Ala Ser Asp Asn Ile Tyr Ser Asn
            20                  25                  30

Leu Ala Trp Tyr Gln Glu Lys Gln Gly Lys Ser Pro Gln Leu Leu Val
        35                  40                  45

Tyr Gly Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Thr Thr Pro Arg
                85                  90                  95

Ser Phe Gly Gly Gly Thr Lys Leu Glu Leu Lys
            100                 105

<210> SEQ ID NO 318
<211> LENGTH: 118
<212> TYPE: PRT
<213> ORGANISM: artificial
<220> FEATURE:
<223> OTHER INFORMATION: synthetic polypeptide

<400> SEQUENCE: 318

Glu Val Gln Leu Val Glu Ser Gly Gly Gly Leu Val Lys Pro Gly Gly
1               5                   10                  15

Ser Leu Lys Leu Ser Cys Thr Ala Ser Gly Phe Thr Phe Ser Asn Tyr
            20                  25                  30
```

```
Ala Met Ser Trp Val Arg Gln Thr Pro Glu Lys Arg Leu Glu Trp Val
             35                  40                  45
Ala Thr Ile Ser Asp Gly Gly Asn Tyr Thr Tyr Tyr Pro Asp Asn Val
 50                  55                  60
Lys Gly Arg Phe Thr Ile Ser Arg Asp Ile Ala Lys Asn Asn Leu Tyr
 65                  70                  75                  80
Leu Gln Met Ser His Leu Lys Ser Glu Asp Thr Ala Met Tyr Tyr Cys
             85                  90                  95
Ala Arg Asp Arg Trp Pro Tyr Phe Phe Asp Phe Trp Gly Gln Gly Thr
            100                 105                 110
Thr Leu Thr Val Ser Ser
            115

<210> SEQ ID NO 319
<211> LENGTH: 24
<212> TYPE: PRT
<213> ORGANISM: artificial
<220> FEATURE:
<223> OTHER INFORMATION: synthetic polypeptide

<400> SEQUENCE: 319

Gly Gly Gly Ser Gly Lys Pro Ile Pro Asn Pro Leu Leu Gly Leu Asp
 1               5                  10                  15
Ser Thr His His His His His His
             20

<210> SEQ ID NO 320
<211> LENGTH: 39
<212> TYPE: PRT
<213> ORGANISM: artificial
<220> FEATURE:
<223> OTHER INFORMATION: synthetic polypeptide

<400> SEQUENCE: 320

Gly Gly Gly Ser Gly Lys Pro Ile Pro Asn Pro Leu Leu Gly Leu Asp
 1               5                  10                  15
Ser Thr Gly Leu Asn Asp Ile Phe Glu Ala Gln Lys Ile Glu Trp His
             20                  25                  30
Glu His His His His His His
             35

<210> SEQ ID NO 321
<211> LENGTH: 28
<212> TYPE: DNA
<213> ORGANISM: artificial
<220> FEATURE:
<223> OTHER INFORMATION: synthetic oligonucleotide

<400> SEQUENCE: 321
tcttgtccac cttggtgctg ctggccgg                                       28

<210> SEQ ID NO 322
<211> LENGTH: 28
<212> TYPE: DNA
<213> ORGANISM: artificial
<220> FEATURE:
<223> OTHER INFORMATION: synthetic oligonucleotide

<400> SEQUENCE: 322
tttgtccacc gtggtgctgc tggctggt                                       28

<210> SEQ ID NO 323
```

```
<211> LENGTH: 25
<212> TYPE: DNA
<213> ORGANISM: artificial
<220> FEATURE:
<223> OTHER INFORMATION: synthetic oligonucleotide

<400> SEQUENCE: 323
gatcagtcca actgttcagg acgcc                                           25

<210> SEQ ID NO 324
<211> LENGTH: 33
<212> TYPE: DNA
<213> ORGANISM: artificial
<220> FEATURE:
<223> OTHER INFORMATION: synthetic oligonucleotide

<400> SEQUENCE: 324
acactcagca cgggacaaac tcttctccac agt                                  33

<210> SEQ ID NO 325
<211> LENGTH: 33
<212> TYPE: DNA
<213> ORGANISM: artificial
<220> FEATURE:
<223> OTHER INFORMATION: synthetic oligonucleotide

<400> SEQUENCE: 325
acactctgca ggagacagac tcttttccac agt                                  33

<210> SEQ ID NO 326
<211> LENGTH: 33
<212> TYPE: DNA
<213> ORGANISM: artificial
<220> FEATURE:
<223> OTHER INFORMATION: synthetic oligonucleotide

<400> SEQUENCE: 326
acactcagca cgggacaaac tcttctccac atg                                  33

<210> SEQ ID NO 327
<211> LENGTH: 330
<212> TYPE: PRT
<213> ORGANISM: artificial
<220> FEATURE:
<223> OTHER INFORMATION: synthetic polypeptide

<400> SEQUENCE: 327
```

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

-continued

Lys Pro Lys Asp Thr Leu Tyr Ile Thr Arg Glu Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Gly Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 328
<211> LENGTH: 214
<212> TYPE: PRT
<213> ORGANISM: artificial
<220> FEATURE:
<223> OTHER INFORMATION: synthetic polypeptide

<400> SEQUENCE: 328

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Val
            35                  40                  45

Tyr Gly Ala Lys Asn Leu Ala Asp Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Thr Thr Pro Arg
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 329
<211> LENGTH: 214
<212> TYPE: PRT
<213> ORGANISM: artificial
<220> FEATURE:
<223> OTHER INFORMATION: synthetic polypeptide

<400> SEQUENCE: 329

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ser Pro Lys Leu Leu Val
        35                  40                  45

Tyr Gly Tyr Lys Asn Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Thr Thr Pro Arg
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 330
<211> LENGTH: 214
<212> TYPE: PRT
<213> ORGANISM: artificial
<220> FEATURE:
<223> OTHER INFORMATION: synthetic polypeptide

<400> SEQUENCE: 330

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
```

```
                    20                  25                  30

Leu Ala Trp Tyr Gln Gln Lys Pro Gly Lys Ser Pro Lys Leu Leu Val
                35                  40                  45

Tyr Gly Tyr Lys Asn Leu Ala Asp Gly Val Pro Ser Arg Phe Ser Gly
            50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Ile Thr Thr Pro Arg
                85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
                130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210
```

<210> SEQ ID NO 331
<211> LENGTH: 214
<212> TYPE: PRT
<213> ORGANISM: artificial
<220> FEATURE:
<223> OTHER INFORMATION: synthetic polypeptide

<400> SEQUENCE: 331

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
                20                  25                  30

Leu Ala Trp Tyr Gln Gln Lys Pro Gly Lys Ser Pro Lys Leu Leu Val
                35                  40                  45

Tyr Gly Tyr Lys Asn Leu Ala Asp Gly Val Pro Ser Arg Phe Ser Gly
            50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Lys Thr Thr Pro Arg
                85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
                130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

Ser Thr Leu Thr Leu Ser Lys Ala Asp Tyr Glu Lys His Lys Val Tyr
            165                 170                 175

Ala Cys Glu Val Thr His Gln Gly Leu Ser Ser Pro Val Thr Lys Ser
        180                 185                 190

Phe Asn Arg Gly Glu Cys
    195                 200                 205

210

<210> SEQ ID NO 332
<211> LENGTH: 447
<212> TYPE: PRT
<213> ORGANISM: artificial
<220> FEATURE:
<223> OTHER INFORMATION: synthetic polypeptide

<400> SEQUENCE: 332

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ala Thr Val Thr Glu Gly Gly Asp Tyr Asn Tyr Cys Leu Asp Asp Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Trp Pro Tyr Phe Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Gly Ser Thr Tyr Arg Val Val
    290                 295                 300

Ser Val Leu Thr Val Leu His Gln Asp Trp Leu Asn Gly Lys Glu Tyr

```
305                 310                 315                 320
Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
                355                 360                 365

Leu Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly
                435                 440                 445

<210> SEQ ID NO 333
<211> LENGTH: 447
<212> TYPE: PRT
<213> ORGANISM: artificial
<220> FEATURE:
<223> OTHER INFORMATION: synthetic polypeptide

<400> SEQUENCE: 333

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
                20                  25                  30

Ala Met Ser Trp Val Arg Gln Ala Pro Gly Lys Gly Leu Glu Trp Val
                35                  40                  45

Ala Thr Ser Thr Glu Gly Gly Asp Tyr Asn Tyr Tyr Leu Asp Asp Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Trp Pro Tyr Phe Phe Asp Tyr Trp Gly Gln Gly Thr
                100                 105                 110

Leu Val Thr Val Ser Ser Ala Ser Thr Lys Gly Pro Ser Val Phe Pro
                115                 120                 125

Leu Ala Pro Ser Ser Lys Ser Thr Ser Gly Gly Thr Ala Ala Leu Gly
                130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Lys Val Glu Pro Lys Ser Cys Asp Lys Thr
                210                 215                 220

His Thr Cys Pro Pro Cys Pro Ala Pro Glu Leu Leu Gly Gly Pro Ser
```

```
            225                 230                 235                 240
Val Phe Leu Phe Pro Pro Lys Pro Lys Asp Thr Leu Met Ile Ser Arg
                245                 250                 255

Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Gly Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 334
<211> LENGTH: 448
<212> TYPE: PRT
<213> ORGANISM: artificial
<220> FEATURE:
<223> OTHER INFORMATION: synthetic polypeptide

<400> SEQUENCE: 334

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
                20                  25                  30

Ala Met Ser Trp Val Arg Gln Ala Pro Gly Lys Gly Leu Glu Trp Val
            35                  40                  45

Ala Thr Ser Thr Glu Gly Gly Asp Tyr Asn Tyr Tyr Leu Asp Asp Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Trp Pro Tyr Phe Phe Asp Tyr Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
```

-continued

```
            145                 150                 155                 160
        Ser Gly Ala Leu Thr Ser Gly Val His Thr Phe Pro Ala Val Leu Gln
                        165                 170                 175
        Ser Ser Gly Leu Tyr Ser Leu Ser Ser Val Val Thr Val Pro Ser Ser
                        180                 185                 190
        Ser Leu Gly Thr Gln Thr Tyr Ile Cys Asn Val Asn His Lys Pro Ser
                        195                 200                 205
        Asn Thr Lys Val Asp Lys Lys Val Glu Pro Lys Ser Cys Asp Lys Thr
                        210                 215                 220
        His Thr Cys Pro Pro Cys Pro Ala Pro Glu Leu Leu Gly Gly Pro Ser
        225                 230                 235                 240
        Val Phe Leu Phe Pro Pro Lys Pro Lys Asp Thr Leu Tyr Ile Thr Arg
                        245                 250                 255
        Glu Pro Glu Val Thr Cys Val Val Val Asp Val Ser His Glu Asp Pro
                        260                 265                 270
        Glu Val Lys Phe Asn Trp Tyr Val Asp Gly Val Glu Val His Asn Ala
                        275                 280                 285
        Lys Thr Lys Pro Arg Glu Glu Gln Tyr Gly Ser Thr Tyr Arg Val Val
                        290                 295                 300
        Ser Val Leu Thr Val Leu His Gln Asp Trp Leu Asn Gly Lys Glu Tyr
        305                 310                 315                 320
        Lys Cys Lys Val Ser Asn Lys Ala Leu Pro Ala Pro Ile Glu Lys Thr
                        325                 330                 335
        Ile Ser Lys Ala Lys Gly Gln Pro Arg Glu Pro Gln Val Tyr Thr Leu
                        340                 345                 350
        Pro Pro Ser Arg Asp Glu Leu Thr Lys Asn Gln Val Ser Leu Thr Cys
                        355                 360                 365
        Leu Val Lys Gly Phe Tyr Pro Ser Asp Ile Ala Val Glu Trp Glu Ser
                        370                 375                 380
        Asn Gly Gln Pro Glu Asn Asn Tyr Lys Thr Thr Pro Pro Val Leu Asp
        385                 390                 395                 400
        Ser Asp Gly Ser Phe Phe Leu Tyr Ser Lys Leu Thr Val Asp Lys Ser
                        405                 410                 415
        Arg Trp Gln Gln Gly Asn Val Phe Ser Cys Ser Val Met His Glu Ala
                        420                 425                 430
        Leu His Asn His Tyr Thr Gln Lys Ser Leu Ser Leu Ser Pro Gly Lys
                        435                 440                 445

<210> SEQ ID NO 335
<211> LENGTH: 447
<212> TYPE: PRT
<213> ORGANISM: artificial
<220> FEATURE:
<223> OTHER INFORMATION: synthetic polypeptide

<400> SEQUENCE: 335

Glu Val Gln Leu Val Glu Ser Gly Gly Gly Leu Val Gln Pro Gly Gly
        1                   5                   10                  15
        Ser Leu Arg Leu Ser Cys Ala Ala Ser Gly Phe Thr Phe Ser Asn Tyr
                        20                  25                  30
        Ala Met Ser Trp Val Arg Gln Ala Pro Gly Lys Gly Leu Glu Trp Val
                        35                  40                  45
        Ala Thr Val Thr Glu Gly Gly Asp Tyr Asn Tyr Tyr Leu Asp Asp Val
                        50                  55                  60
        Lys Gly Arg Phe Thr Ile Ser Arg Asp Asn Ala Lys Asn Ser Leu Tyr
```

```
                65                  70                  75                  80
Leu Gln Met Asn Ser Leu Arg Ala Glu Asp Thr Ala Val Tyr Tyr Cys
                    85                  90                  95
Ala Arg Asp Asp Trp Pro Tyr Phe Phe Asp Tyr Trp Gly Gln Gly Thr
                100                 105                 110
Leu Val Thr Val Ser Ser Ala Ser Thr Lys Gly Pro Ser Val Phe Pro
                115                 120                 125
Leu Ala Pro Ser Ser Lys Ser Thr Ser Gly Gly Thr Ala Ala Leu Gly
            130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Val Val Thr Val Pro Ser Ser
                180                 185                 190
Ser Leu Gly Thr Gln Thr Tyr Ile Cys Asn Val Asn His Lys Pro Ser
                195                 200                 205
Asn Thr Lys Val Asp Lys Lys Val Glu Pro Lys Ser Cys Asp Lys Thr
            210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
                260                 265                 270
Glu Val Lys Phe Asn Trp Tyr Val Asp Gly Val Glu Val His Asn Ala
                275                 280                 285
Lys Thr Lys Pro Arg Glu Glu Gln Tyr Gly Ser Thr Tyr Arg Val Val
            290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
                340                 345                 350
Pro Pro Ser Arg Asp Glu Leu Thr Lys Asn Gln Val Ser Leu Thr Cys
                355                 360                 365
Leu Val Lys Gly Phe Tyr Pro Ser Asp Ile Ala Val Glu Trp Glu Ser
            370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
                420                 425                 430
Leu His Asn His Tyr Thr Gln Lys Ser Leu Ser Leu Ser Pro Gly
            435                 440                 445

<210> SEQ ID NO 336
<211> LENGTH: 448
<212> TYPE: PRT
<213> ORGANISM: artificial
<220> FEATURE:
<223> OTHER INFORMATION: synthetic polypeptide
```

<400> SEQUENCE: 336

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ala Thr Val Thr Glu Gly Gly Asp Tyr Asn Tyr Tyr Leu Asp Asp Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Asp Trp Pro Tyr Phe Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Tyr Ile Thr Arg
                245                 250                 255

Glu Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Gly Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415
```

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
            435                 440                 445

<210> SEQ ID NO 337
<211> LENGTH: 130
<212> TYPE: PRT
<213> ORGANISM: artificial
<220> FEATURE:
<223> OTHER INFORMATION: synthetic polypeptide

<400> SEQUENCE: 337

Lys Asp Ala Leu Pro Pro Gln Ile Tyr Ser Pro Asn Asp Arg Val Val
1               5                   10                  15

Tyr Glu Lys Glu Pro Gly Glu Glu Leu Val Ile Pro Cys Lys Val Tyr
            20                  25                  30

Phe Ser Phe Ile Met Asp Ser His Asn Glu Val Trp Trp Thr Ile Asp
        35                  40                  45

Gly Lys Lys Pro Asp Asp Val Thr Val Asp Ile Thr Ile Asn Glu Ser
    50                  55                  60

Val Ser Tyr Ser Ser Thr Glu Asp Glu Thr Arg Thr Gln Ile Leu Ser
65                  70                  75                  80

Ile Lys Lys Val Thr Pro Glu Asp Leu Arg Arg Asn Tyr Val Cys His
                85                  90                  95

Ala Arg Asn Thr Lys Gly Glu Ala Glu Gln Ala Ala Lys Val Lys Gln
            100                 105                 110

Lys Val Ile Pro Pro Arg Tyr Thr Val Glu Leu Ala Cys Gly Phe Gly
        115                 120                 125

Ala Thr
    130

<210> SEQ ID NO 338
<211> LENGTH: 217
<212> TYPE: PRT
<213> ORGANISM: artificial
<220> FEATURE:
<223> OTHER INFORMATION: synthetic polypeptide

<400> SEQUENCE: 338

Ser Glu Arg Cys Asp Asp Trp Gly Leu Asp Thr Met Arg Gln Ile Gln
1               5                   10                  15

Val Phe Glu Asp Glu Pro Ala Arg Ile Lys Cys Pro Leu Phe Glu His
            20                  25                  30

Phe Leu Lys Tyr Asn Tyr Ser Thr Ala His Ser Ser Gly Leu Thr Leu
        35                  40                  45

Ile Trp Tyr Trp Thr Arg Gln Asp Arg Asp Leu Glu Glu Pro Ile Asn
    50                  55                  60

Phe Arg Leu Pro Glu Asn Arg Ile Ser Lys Glu Lys Asp Val Leu Trp
65                  70                  75                  80

Phe Arg Pro Thr Leu Leu Asn Asp Thr Gly Asn Tyr Thr Cys Met Leu
                85                  90                  95

Arg Asn Thr Thr Tyr Cys Ser Lys Val Ala Phe Pro Leu Glu Val Val
            100                 105                 110

Gln Lys Asp Ser Cys Phe Asn Ser Ala Met Arg Phe Pro Val His Lys
        115                 120                 125

Met Tyr Ile Glu His Gly Ile His Lys Ile Thr Cys Pro Asn Val Asp

```
                130               135               140
Gly Tyr Phe Pro Ser Ser Val Lys Pro Ser Val Thr Trp Tyr Lys Gly
145               150               155               160

Cys Thr Glu Ile Val Asp Phe His Asn Val Leu Pro Glu Gly Met Asn
                165               170               175

Leu Ser Phe Phe Ile Pro Leu Val Ser Asn Asn Gly Asn Tyr Thr Cys
                180               185               190

Val Val Thr Tyr Pro Glu Asn Gly Arg Leu Phe His Leu Thr Arg Thr
            195               200               205

Val Thr Val Lys Val Val Gly Ser Pro
            210               215
```